(12) United States Patent
Han et al.

(10) Patent No.: US 12,091,671 B2
(45) Date of Patent: Sep. 17, 2024

(54) CONSTITUTIVELY ACTIVE FORM OF MYB46

(71) Applicant: Board of Trustees of Michigan State University, East Lansing, MI (US)

(72) Inventors: Kyung-Hwan Han, Okemos, MI (US); Jong Hee Im, Jeju-do (KR)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 236 days.

(21) Appl. No.: 17/256,441

(22) PCT Filed: Jun. 28, 2019

(86) PCT No.: PCT/US2019/039903
§ 371 (c)(1),
(2) Date: Dec. 28, 2020

(87) PCT Pub. No.: WO2020/006465
PCT Pub. Date: Jan. 2, 2020

(65) Prior Publication Data
US 2022/0340924 A1    Oct. 27, 2022

Related U.S. Application Data

(60) Provisional application No. 62/692,269, filed on Jun. 29, 2018.

(51) Int. Cl.
| | | |
|---|---|---|
| *C12N 15/82* | (2006.01) | |
| *C07K 1/107* | (2006.01) | |
| *C07K 14/415* | (2006.01) | |
| *C12N 15/09* | (2006.01) | |
| *C12N 15/10* | (2006.01) | |

(52) U.S. Cl.
CPC ........ *C12N 15/8261* (2013.01); *C07K 1/1075* (2013.01); *C07K 14/415* (2013.01); *C12N 15/102* (2013.01); *C12N 15/09* (2013.01)

(58) Field of Classification Search
CPC ..... C07K 1/1075; C12N 15/102; C12N 15/09
See application file for complete search history.

(56) References Cited

U.S. PATENT DOCUMENTS

| | | |
|---|---|---|
| 7,223,904 B2 | 5/2007 | Heard et al. |
| 7,598,429 B2 | 10/2009 | Heard et al. |
| 8,173,866 B1 | 5/2012 | Bao et al. |
| 8,937,219 B2 | 1/2015 | Hertzberg et al. |
| 9,650,643 B2 | 5/2017 | Han et al. |
| 9,944,939 B2 | 4/2018 | Han et al. |
| 10,837,025 B2 | 11/2020 | Han et al. |
| 2003/0088057 A1 | 5/2003 | Traugh et al. |
| 2010/0107279 A1 | 4/2010 | Ratcliffe et al. |
| 2015/0052641 A1 | 2/2015 | Han et al. |
| 2015/0133651 A1 | 5/2015 | Han et al. |
| 2017/0298375 A1 | 10/2017 | Han et al. |

FOREIGN PATENT DOCUMENTS

| | | |
|---|---|---|
| EP | 2410060 A1 | 1/2012 |
| WO | WO-2012103555 A2 | 8/2012 |
| WO | WO-2013130456 A2 | 9/2013 |
| WO | WO-2013130456 A3 | 9/2013 |
| WO | WO-2020006465 A1 | 1/2020 |

OTHER PUBLICATIONS

Kim et al. "Phosphorylation of the transcriptional repressor MYB15 by mitogen-activated protein kinase 6 is required for freezing tolerance in *Arabidopsis*". Nucleic acids research. 45(11) 6613-6627. (Year: 2017).*
Zhong et al. "The MYB46 Transcription Factor Is a Direct Target of SND1 and Regulates Secondary Wall Biosynthesis in *Arabidopsis*". Plant cell. 19(9): 2776-2792. (Year: 2007).*
Kim S et al. Nucleic Acids Res. Jun. 20, 2017;45(11):6613-6627 (Year: 2017).*
Dephoure N et al. Mol Biol Cell. Mar. 2013;24(5):535-42 (Year: 2013).*
"U.S. Appl. No. 14/381,040, Non-Final Office Action mailed Apr. 22, 2016", 6 pgs.
"U.S. Appl. No. 14/381,040, Notice of Allowance mailed Jan. 9, 2017", 7 pgs.
"U.S. Appl. No. 14/381,040, Notice of Allowance mailed Oct. 5, 2016", 7 pgs.
"U.S. Appl. No. 14/381,040, Preliminary Amendment filed Aug. 26, 2014", 3 pgs.
"U.S. Appl. No. 14/381,040, Response filed Mar. 15, 2016 to Restriction Requirement mailed Jan. 15, 2016", 6 pgs.
"U.S. Appl. No. 14/381,040, Response filed Sep. 22, 2016 to Non-Final Office Action mailed Apr. 22, 2016", 8 pgs.
"U.S. Appl. No. 14/381,040, Restriction Requirement mailed Jan. 15, 2016", 4 pgs.
"U.S. Appl. No. 14/540,320, Advisory Action mailed Oct. 26, 2016", 3 pgs.
"U.S. Appl. No. 14/540,320, Final Office Action mailed Jul. 7, 2017", 4 pgs.
"U.S. Appl. No. 14/540,320, Final Office Action mailed Aug. 8, 2016", 9 pgs.
"U.S. Appl. No. 14/540,320, Non-Final Office Action mailed Feb. 25, 2016", 7 pgs.
"U.S. Appl. No. 14/540,320, Non-Final Office Action mailed Dec. 28, 2016", 5 pgs.
"U.S. Appl. No. 14/540,320, Notice of Allowance mailed Nov. 9, 2017", 8 pgs.
"U.S. Appl. No. 14/540,320, Preliminary Amendment filed Dec. 17, 2014", 3 pgs.
"U.S. Appl. No. 14/540,320, Response filed Mar. 28, 2017 to Non-Final Office Aciton mailed Dec. 28, 2016", 6 pgs.

(Continued)

*Primary Examiner* — Nancy J Leith
*Assistant Examiner* — Douglas Charles Ryan
(74) *Attorney, Agent, or Firm* — McKee, Voorhees & Sease, PLC

(57) ABSTRACT

Described herein are modified MYB46 transcription factors that are more stable and less prone to degradation than corresponding unmodified MYB46 transcription factors. Expression of the modified MYB46 transcription factors within plants improves the structural strength, increases biomass, and enhances fiber strength of the plants.

22 Claims, 22 Drawing Sheets
Specification includes a Sequence Listing.

(56) References Cited

OTHER PUBLICATIONS

"U.S. Appl. No. 14/540,320, Response filed May 25, 2016 to Non-Final Office Action mailed Feb. 25, 2016", 10 pgs.
"U.S. Appl. No. 14/540,320, Response filed Sep. 20, 2017 to Final Office Action mailed Jul. 7, 2017", 5 pgs.
"U.S. Appl. No. 14/540,320, Response Filed Oct. 10, 2016 to Final Office Action Mailed Aug. 8, 2016", 7 pgs.
"U.S. Appl. No. 14/540,320, Response filed Nov. 8, 2016 to Non-Final Office Action mailed Apr. 22, 2016", 12 pgs.
"U.S. Appl. No. 15/478,661, Advisory Action mailed Dec. 9, 2019", 3 pgs.
"U.S. Appl. No. 15/478,661, Advisory Action mailed Dec. 19, 2018", 3 pgs.
"U.S. Appl. No. 15/478,661, Final Office Action mailed Aug. 31, 2018", 10 pgs.
"U.S. Appl. No. 15/478,661, Final Office Action mailed Sep. 20, 2019", 10 pgs.
"U.S. Appl. No. 15/478,661, Non Final Office Action mailed Jan. 24, 2020", 6 pgs.
"U.S. Appl. No. 15/478,661, Non Final Office Action mailed Mar. 15, 2019", 8 pgs.
"U.S. Appl. No. 15/478,661, Non Final Office Action mailed Mar. 27, 2018", 8 pgs.
"U.S. Appl. No. 15/478,661, Notice of Allowance mailed Jun. 23, 2020", 10 pgs.
"U.S. Appl. No. 15/478,661, Preliminary Amendment filed May 4, 2017", 6 pgs.
"U.S. Appl. No. 15/478,661, Response filed Apr. 24, 2020 to Non-Final Office Action mailed Jan. 24, 2020", 10 pgs.
"U.S. Appl. No. 15/478,661, Response filed Jun. 14, 2019 to Non Final Office Action mailed Mar. 15, 2019", 11 pgs.
"U.S. Appl. No. 15/478,661, Response filed Jun. 22, 2018 to Non Final Office Action mailed Mar. 27, 2018", 7 pgs.
"U.S. Appl. No. 15/478,661, Response filed Nov. 20, 2019 to Final Office Action mailed Sep. 20, 2019", 10 pgs.
"U.S. Appl. No. 15/478,661, Response filed Nov. 30, 2018 to Final Office Action mailed Aug. 31, 2018", 8 pgs.
"*Arabidopsis thaliana* MYB transcription factor (At5g12870) mRNA, complete cds", XP002714414, accession No. EM_STD:AY519621 Database accession No. AY519621 sequence, (Feb. 7, 2004), 1 pg.
"Canadian Application Serial No. 2,865,787, Office Action mailed Jan. 7, 2021", 5 pgs.
"Canadian Application Serial No. 2,865,787, Office Action mailed Jan. 27, 2020", 3 pgs.
"Canadian Application Serial No. 2,865,787, Office Action mailed Nov. 8, 2018", 5 pgs.
"Canadian Application Serial No. 2,865,787, Response filed May 4, 2021 to Office Action mailed Jan. 7, 2021", 10 pgs.
"Canadian Application Serial No. 2,865,787, Response filed May 8, 2019 to Office Action mailed Nov. 8, 2018", 13 pgs.
"Canadian Application Serial No. 2,865,787, Response filed May 27, 2020 to Office Action mailed Jan. 27, 2020", 8 pgs.
"International Application Serial No. PCT/US2013/027777, International Preliminary Report on Patentability mailed Sep. 12, 2014", 11 pgs.
"International Application Serial No. PCT/US2013/027777, International Search Report mailed Feb. 11, 2014", 9 pgs.
"International Application Serial No. PCT/US2013/027777, Invitation to Pay Additional Fees and Partial Search Report mailed Nov. 20, 2013", 6 pgs.
"International Application Serial No. PCT/US2013/027777, Written Opinion mailed Feb. 11, 2014", 9 pgs.
"International Application Serial No. PCT/US2019/039903, International Preliminary Report on Patentability mailed Jan. 7, 2021", 7 pgs.
"International Application Serial No. PCT/US2019/039903, International Search Report mailed Sep. 24, 2019", 3 pgs.
"International Application Serial No. PCT/US2019/039903, Written Opinion mailed Sep. 24, 2019", 5 pgs.
"International Application Serial No. PCT/US2013/027777, Corrected International Search Report mailed Mar. 24, 2014", 9 pgs.
Bosca, S., et al., "Interactions between MUR10/CesA7-Dependent Secondary Cellulose Biosynthesis and Cell Wall Structure", Plant Physiology, 142(4), (2006), 1353-1363.
Kim, W.-C., et al., "Transcription factors that directly regulate the expression of CSLA9 encoding mannan synthase in *Arabidopsis thaliana*", Plant Mol Biol, 84(4-5), (2014), 577-587.
Ko, J.-H., et al., "Ectopic expression of MYB46 identifies transcriptional regulatory genes involve din secondary wall biosynthesis in *Arabidopsis*", The Plant Journal, 60(4), (2009), 649-665.
Ko, J.-H., et al., "MYB46-Mediated Transcriptional Regulation of Secondary Wall Biosynthesis", Molecular Plant, 5(5), (Sep. 2012), 961-963.
Li, L., et al., "Combinatorial modification of multiple lignin traits in trees through multigene cotransformation", Proc. Natl. Acad. Sci. USA, 100(8), (2003), 4939-4944.
Zhong, R., et al., "The MYB46 Transcription Factor Is a Direct Target of SND1 and Regulates Secondary Wall Biosynthesis in *Arabidopsis*", The Plant Cell, 19(9), (2007), 2776-2792.
"Canadian Application Serial No. 2,865,787, Response filed Apr. 29, 2022 to Non Final Office Action mailedDec. 30, 2021", 10 pgs.

\* cited by examiner

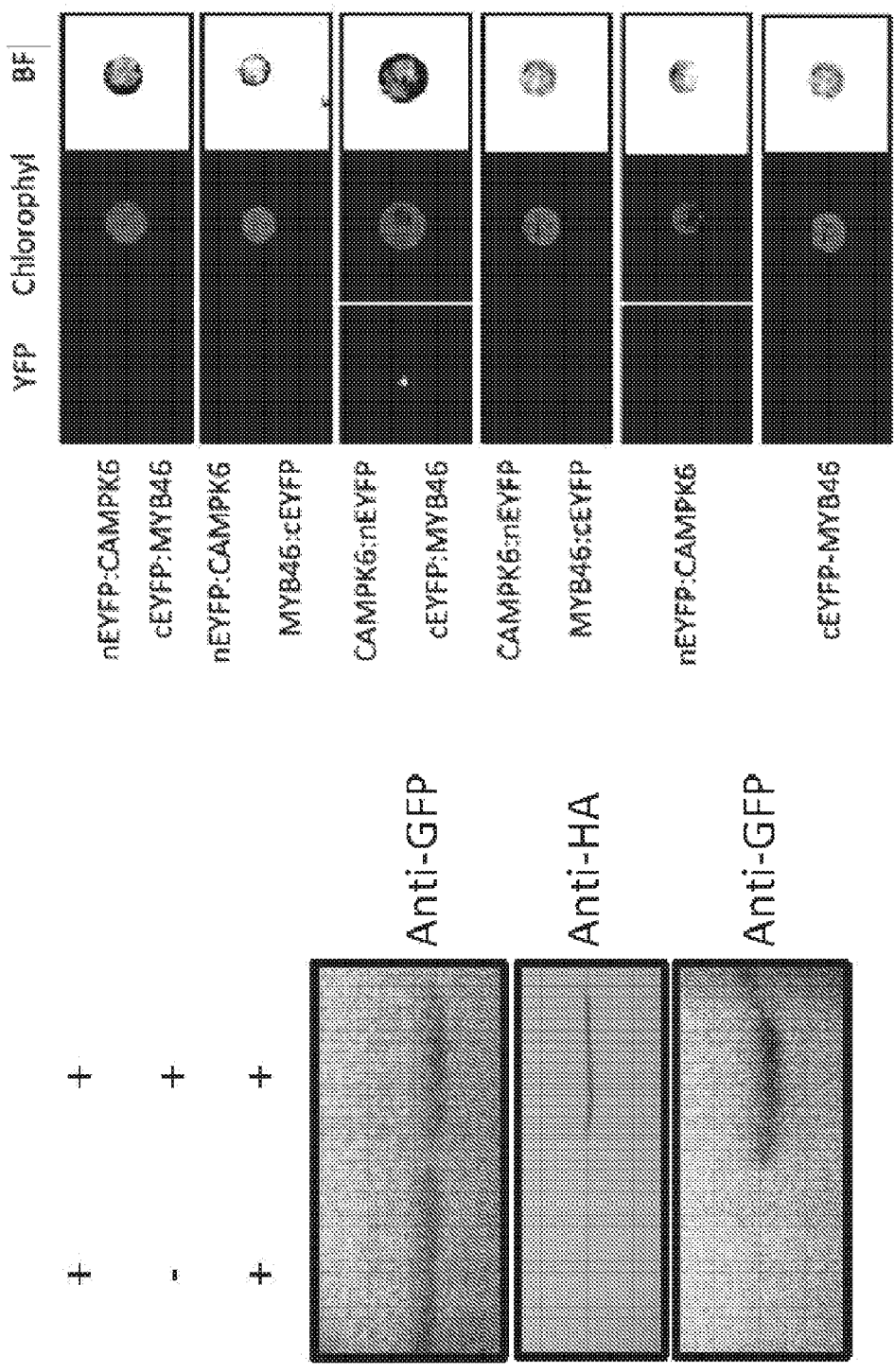

Fig. 6A

```
M83  MMMRKPDITTIRDKGKPNHACGGNNNKPKLRKGLWSPDEDEKLIRYMLTNGQGCWSDIAR
M46  --MRKPEVAI--------------AASTHQVKKMKKGLWSPEEDSKLMQYMLSNGQGCWSDVAK
       ****              . :. :    * .:.*****:.**:*****:*

M83  NAGLLRCGKSCRLRWINYLRPDLKRGSFSPQEEDLIFHLHSILGNRWSQIATRLPGRTDN
M46  NAGLQRCGKSCRLRWINYLRPDLKRGAFSPQEEDLIIRFHSILGNRWSQIAARLPGRTDN
     **** ********************:********:  ********:**: ********

M83  EIKNFWNSTLKKRLKNNS---------NNNTSSGS[S]PNNSNSNSLDPRDQHVDMGGNSTSLMD
M46  EIKNFWNSTIKKRLKKMSDTSNLINNSSS[S]PNTASDSSSNSASSLDIK-DIIGSFMSL---
     ********:*****::.        .  : ***  ::**. .* :..**:.  .  :**

M83  DYHHDENMMTVGNTMRMDSS[S]PFNVGPMVNSGLNQLYDPLMISVPDNGYHQMGNTVNVF
M46  ----QEQGFVNPSLTHIQTNNPFPTGNMI-SHPCNDDF[T]PYV------DG------IY
         :: :.: .* : : ::  *.  .*: *  . *  :  *         .*   :  :**

M83  SVNGLGDYGNTILDPISKRVSVEGDDWFIPPSENTNVIACSTSNNLNLQALDPCFNSKNL
M46  GVNA-GVQGELYFPPL------ECEEGDWY-----NANI-----NNHLDELN-------
     .**. *  * : :* :      * ..**:      *.:.     *::*::*:

M83  CHSESFKVGNVLGIENGSW----EIENPKIGDWDLDGLIDNN-SSFPFLDFQVD
M46  -------------------TNGSGNAPEGMRPVEEFWDLDQLMNTEVPSFYFNFKQSI
                            :.. . : : :***.:::* . .**: *:  *

☐ MPK BINDING MOTIF IN MYB46
☐ PHOSPHORYLATION CANDIDATE SITE       MYB83:S147 AND S195
                                       MYB846:S138 AND T199
```

CONSTITUTIVELY ACTIVE FORM OF MYB46

This application is a U.S. national stage filing under 35 U.S.C. 371 from International Application No. PCT/US2019/039903, filed on 28 Jun. 2019, and published as WO 2020/006465 A1 on 2 Jan. 2020, which claims benefit of priority to the filing date of U.S. Provisional Application Ser. No. 62/692,269, filed Jun. 29, 2018, the contents of which are specifically incorporated herein by reference in their entity.

BACKGROUND OF THE INVENTION

Secondary cell walls, located between plasma membrane and primary cell wall, are a defining feature of xylem fibers and vessels that provide mechanical ti support for plants and serve as a conduit for long-distance transport of water and solutes, Xylem fibers and vessels constitute most of the plant's biomass and are of economic importance to humans as fiber, pulp for paper manufacture, animal feed, and as an environmentally cost-effective renewable source of energy. The biosynthesis of secondary walls occurs in a highly-coordinated manner by successive encrustation and deposition of cellulose fibrils, hemicelluloses and lignin as soon as the cell has stopped growth (Lerouxel et al., 2006; Zhong and Ye, 2007). Although this process requires a coordinated transcriptional activation of the biosynthetic genes for the components, the regulation of the involved transcriptional factors is not understood.

Due to wood's potential for large-scale commercial production of biofuels, a rapid increase in the use of wood as a source of energy may occur as policies promoting greater use of renewable energy are adopted globally. However, the economics of purpose-grown tree feedstocks for energy show that these production systems are not financially viable without improvement in the base growth rate. Conventional breeding programs have produced willow and poplar clones that show potential for rapid growth, but current top-performing clones do not grow fast enough for profitable biofuel production.

SUMMARY

Described herein are modified MYB46 transcription factors that are more stable and more resistant to degradation than wild type, unmodified MYB46 transcription factors. Such modified MYB46 transcription factors have one or more serine and threonine residues replaced by another amino acid. For example, serine and threonine residues that act as phosphorylation sites can be replaced by another amino acid that is not a serine, threonine, aspartic acid, or glutamic acid.

Also described herein are plants, plant cells, plant seeds, and nucleic acids encoding the modified MYB46 transcription factors. Plants that express the modified MYB46 transcription factors exhibit increased biomass, increased structural strength, and increased fiber content. Hence, such plants are useful for improving fiber and biomass yields per acre of plant cultivation.

DESCRIPTION OF THE FIGURES

FIG. 1A-1E illustrate that MYB46 directly interacts with and is phosphorylated by CAMPK6. FIG. 1A is a schematic drawing of mitogen-activated protein kinase (MPK) binding motif and phosphorylation target sites in MYB46 as predicted by Eukaryotic Linear Motif. FIG. 1B shows results of yeast two hybrid assays illustrating binary interaction between MYB46 and CAMPK6. A standard spot assay was carried out using the designated selective media condition (-Leu, -Trp, -His in the presence of 1 mM 3-amino-1,2,4-triazole (3-AT)). FIG. 1C illustrates coimmunoprecipitation of MYB46 and CAMPK6. Green fluorescent protein (GFP) conjugated MYB46 and hemagglutinin (HA) conjugated CAMPK6 were co-expressed in Arabidopsis mesophyll protoplasts (AMPs) with proteasome inhibitor MG132 treatment. After expression, immunoprecipitation was carried out with anti-HA antibody and then protein blot analysis was carried out with anti-GFP antibody. FIG. 1D illustrates bimolecular fluorescence complementation (BiFC) of MYB46 and CAMPK6. BiFC was carried out with designated combinations in the Arabidopsis mesophyll protoplast transient expression system (AMPs) with MG-132 treatment. FIG. 1E shows results of an immunocomplex kinase assay of MYB46 and CAMPK6. GFP-conjugated MYB46 and hemagglutinin (HA)-conjugated CAMPK6 were expressed respectively in the Arabidopsis mesophyll protoplast transient expression system (AMPs). After the expression, immunoprecipitation was carried out with anti-HA antibody and in vitro kinase assay was carried out with anti-GPF antibody.

FIG. 2A shows that the GET signal of MYB46 conjugated GPF disappears when co-expressed with CAMPK6. MYB46-GFP fusion protein was expressed in AMPs with/without YFP conjugated CAMPK6. Images were taken after incubation for 10 hr with fluorescence microscopy. FIG. 2B shows a protein blot of MYB46. GFP conjugated MYB46 was expressed in AMPs with and without hemagglutinin-conjugated MPK6 or CAMPK6 for 10 hr. After expression, the cells were harvested for protein blot analysis with anti-HA antibody or anti-GPF antibody. FIG. 2C shows a protein blot of MYB46 with or without the MG132 inhibitor. GFP conjugated MYB46 was expressed in AMPs with or without CAMPK6. For MG132 treatment, 1 ul of 5 mM of MG132 was added to the reaction and the mixture was incubated for additional 9 hr. The harvested cells were used for protein blot analysis with anti-GFP antibody or anti-HA antibody, DMSO was used as control of MG132, FIG. 2D shows a protein blot of MYB46. Using total protein extracted from transgenic Arabidopsis plants overexpressing MYB46 (MYB46OX), CAMPK6 (CAMPK6OX), or both (MYB46OX/CAMPK6OX), MYB46 protein was detected with anti-MYb46 antibody. FIG. 2E-2F show that the active form of MPK6 (CAMPK6) negatively regulates MYB46 transcriptional activity. FIG. 2E shows an in-gel kinase assay of MPK6. Hemagglutinin (HA) conjugated MPK6 and CAMPK6 were coexpressed in AMPs. Immunoprecipitation was carried out using anti-HA antibody and followed by In-gel kinase assay. Myelin Basic Protein (MBP) was used as substrate. As illustrated, CAMPK6 exhibits much more kinase activity than MPK2. FIG. 2F illustrates that MYB46-induced activation of CESA8 promoter activity was reduced by CAMPK6 coexpression. After six hours of incubation, the AMP cells were harvested, for GUS activity measurement. NAN was used as expression control.

FIG. 3A illustrates that the promoter activities of MYB46 target genes were decreased by CAMPK6 co-expression. The promoter::GUS fusion constructs were expressed in AMPs with MYB46 alone, or with MYB46 and CAMPK6,NAN was used as expression control. FIG. 3B illustrates the expression levels of MYB46 and two direct targets (4CL1 and PAL/4) of MYB46. Relative expression over Acting gene was measured by Real-Time PCR analysis using 3-weeks-old wild-type (Col-0) or transgenic *Arabidopsis* plants overexpressing MYB46 (MYB46OX), CAMPK6 (CAMPK6OX) or both (MYB46OX/CAMPK6OX). Statistical analysis and standard errors were performed on three biological repeats. ***P<0.001. FIG. 3C illustrates the phenotypes of 3-weeks-old Col-0 plants, and plants that overexpress MYB46OX, CAMPK6OX or MYB46OX/CAMPK6OX (upper panel). Phloroglucinol-HCl staining was used to illustrate wherein lignin was in the stems of 8-weeks-old Col-0 plants, and plants that overexpress MYB46OX, CAMPK6OX or MYB46OX/CAMPK6OX (lower panel). FIG. 3D illustrates that Dexamethasone (DEX) inducible expression of CAMPK6 in the background of myb83 stunts plant growth. FIG. 3E illustrates that expression of MYB46 target genes in a myb83 background was significantly reduced by DEX inducible expression of CAMPK6.

FIG. 4A shows protein blots of GFP-fused MYB46 and its non-phosphorable, mutants. The GFP-fused MYB46 and its non-phosphorable mutants were expressed with or without CAMPK6-HA fusion in AMPs and incubated for 10 hrs. Protein blot analysis was carried out with anti-GFP antibody for MYB46 and anti-HA antibody for CAMPK6. FIG. 4B illustrates GFP signals from GFP conjugated MYB46 and its non-phosphorable mutants were expressed with YFP conjugated CAMPK6. After 10 hours of incubation, images were taken by fluorescence microscopy. FIG. 4C shows protein blots of HA-fused MYB46 and its phospho-mimics with or without proteasome inhibitor MG132. The protein blot analysis was carried out with anti-HA antibody. FIG. 4D illustrates GUS expression driven by CESA8 promoter was expressed with MYB46 or its nonphosphorable mutants with or without CAMPK6 in AMPs. After six hours of incubation, the cells were harvested for GUS activity measurement, NAN was used as expression control. FIG. 4E illustrates relative GUS expression driven by the CESA8 promoter in AMPs that also express MYB46 or its phospho-mimic mutants. After six hours of incubation, GUS activity was measured. NAN was used as expression control. FIG. 4F illustrates phloroglucinol-HCl staining of lignin in 8-week-old *Arabidopsis* Col-0 plant stems and in transgenic plant stems that overexpress MYB46 (MYB46OX), MYB46 and CAMPK6 (MYB46OX/CAMPK6OX nonphosphorable mutant (MYB46S138R/T199ROX), or MYB46S138R/T199R and CAMPK6 (MYB46S138R/T199ROX/CAMPK6OX). Scale bar, 100 μm. FIG. 4G illustrates that mutation of putative ubiquitination site increases the stability of phosphormimic mutant MYB46$^{S138D}$ and MYB46$^{T199E}$ proteins, A ubiquitination site was predicted from UbPred (see website at uhpred.org) and Lys156 was identified as a putative ubiquitination site. Lys156 to Arg replacements were made in two phosphormimic mutant MYB46$^{S138D}$ or MYB46$^{T199E}$ proteins, and protein blot analysis was performed.

FIG. 5A illustrates phenotypes of a 3-week-old *Arabidopsis* Col-0 plant, and 3-week-old transgenic plants that overexpress MYB46 (MYB46OX), 3-week-old plants with MPK6 knockout mutant (mpk6-4), and 3-week-old plants that overexpress MYB46 (MYB46OX) in mpk6-4 plants (upper panel) and phloroglucinol-HO (i.e., lignin) staining of the stems of 8-weeks-old the plants (lower panel), FIG. 5B shows phloroglucinol-HCl (lignin) staining of salt stress treated roots of 2-week-old seedlings of Col-0, MYB46OX, mpk6-4 and MYB46OXlmpk6-4 plants. The plants were treated with MS medium or MS+100 mM NaCl for 72 hr before the phloroglucinol-HCl staining. FIG. 5C graphically illustrates MYB46 and PAM expression levels from the plants described in FIG. 5B as quantified by real-time PCR analysis of whole plants. Statistics and standard error means are from three biological replicates, *P<0.001, P<0.01, and *P<0.05. FIG. 5D shows protein blots illustrating expression of MYB46 in the plants described in FIG. 5B. MYB46 protein was detected with anti-MYB46 antibody. FIG. 5E shows that salt stress negatively affects MYB46 protein stability in the roots of *Arabidopsis* plants MYB46, Transgenic plants overexpressing MYB46-GFP fusion construct (35S::MYB46-GFP) were treated with MS medium alone or with 0.1 M NaCl for 72 hr before fluorescence microscopic imaging. Scale bar, 100 μm.

FIG. 6A-6E illustrate that MYB83, which is a functional homolog of MYB46, is not regulated by CAMPK6. FIG. 6A shows an amino acid sequence alignment of MYB46 (SEQ ID NO:1) and MYB83 (SEQ ID NO:87). FIG. 6B shows protein blot analysis of MYB83. HA conjugated MYB46 and MYB83 was transfected with CAMPK6 with designated combination in AMPs. After 10 hr incubation protein blot analysis was carried out with anti-HA antibodies. FIG. 6C illustrates GFP signal from MYB83 conjugated with GFP and expressed in AMPs with or without co-expression of YFP-conjugated CAMPK6. The image was taken with fluorescence microscopy after incubation for 10 hr. FIG. 6D graphically illustrates CCoAOMT promoter activities. GUS conjugated CCoAOMT promoter was transfected to AMPs with MYB46, MYB83 and CAMPK6 with designated combination. After 6 hr incubation the cells were harvested and GUS activities were measured. NAN was used as expression control. FIG. 6E shows a schematic drawing of phosphorylation target sites in MYB83 as predicted by Eukaryotic Linear Motif. The MPK docking domain was not identified.

DETAILED DESCRIPTION

Figure 1A:
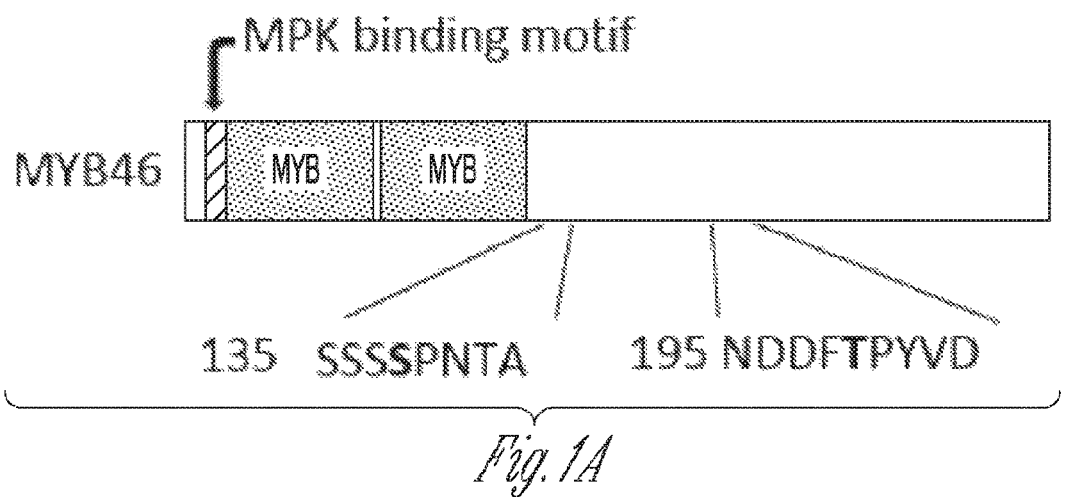

Described herein are modified MYB46 transcription factors that are ore stable and more resistant to degradation than wild type, unmodified MYB46 transcription factors, Such modified MYB46 transcription factors have one or more serine and threonine residues replaced by another amino acid. For example, serine and threonine residues can function as phosphorylation sites. Replacement of such serine and threonine with an amino acid that is not serine, threonine, aspartic acid, or glutamic acid can improve the stability of the modified MYB46 transcription factor.

Transcription factor MYB46 is a master regulator in secondary wall formation in plants. Plants produce two distinct types of cell walls, the primary and secondary walls. The outer primary cell wall provides the rigidity necessary for cells to hold their shape, and also acts as a filter to external factors entering the cell. Secondary cell walls are deposited after the cell is fully grown. The secondary wall provides the strength needed for support of larger plants, and provide a water-proofed environment for water transport in the xylem. Secondary walls are comprised mainly of cellulose and lignin, which gives the cells the additional protection and strength as they mature.

The secondary cell wall is a defining feature of xylem cells and allows them to resist both gravitational forces and the tension forces associated with the transpirational pull on their internal columns of water. Secondary walls also constitute most of plant biomass. Formation of secondary walls requires coordinated transcriptional regulation of the genes involved in the biosynthesis of cellulose, hemicellulose and lignin. This coordinated control involves a multifaceted and multilayered transcriptional regulatory program that is controlled by the MYB46 master regulator. MYB46 directly regulates the biosynthesis genes for all three major components of the secondary wall as well as the transcription factors in the biosynthesis pathway. As provided herein, plants that express the highly stable MYB46 transcription factors described herein can have stronger secondary cell walls and increased biomass.

MYB46 transcription factor sequences are available from the National Center for Biotechnology Information (NCBI) database (see, e.g., the website at ncbi.nlm.nih.gov), For example, a wild type amino acid sequence for an *Arabidopsis thaliana* MYB46 transcription factor is available as accession number 0.4095045.1, and reproduced below as SEQ ID NO:1.

```
  1  MRKPEVAIAA  STHQVKKMKK  GLWSPEEDSK  LMQYMLSNGQ
 41  GCWSDVAKNA  GLQRCGKSCR  LRWINYLRPD  LKRGAFSPQE
 81  EDLIIRFHSI  LGNRWSQIAA  RLPGRTDNEI  KNFWNSTIKK
121  RLKKMSDTSN  LINNSSSSPN  TASDSSSNSA  SSLDIKDIIG
161  SFMSLQEQGF  VNPSLTHIQT  NNPFPTGNMI  SHPCNDDFTP
201  YVDGIYGVNA  GVQGELYFPP  LECEEGDWYN  ANINNHLDEL
241  NTNGSGNAPE  GMRPVEEFWD  LDQLMNTEVP  SFYFNFKQSI
```

As illustrated herein, near its N-terminus the *Arabidopsis thaliana* MYB46 has a mitogen-activated protein kinase (MPK) binding or docking motif ($^2$RKPEVAI$^8$, SEQ ID NO:9, underlined above). The *Arabidopsis thaliana* MYB46 also has two mitogen-activated protein kinase (MPK) phosphorylation sites, a serine at position 138 (S138) and a threonine at position 199 (T199). These two sites are highlighted in bold and with underlining in the SEQ ID NO:1 sequence above. These two sites, the serine at position 138 (S138) and the threonine at position 199 (T199) can be modified to improve the stability of the *Arabidopsis thaliana* MYB46. Such modifications can include replacement of the serine and/or the threonine with an amino acid that is not a serine, threonine, aspartic acid, or glutamic acid.

A nucleic acid sequence for the *Arabidopsis thaliana* MYB46 transcription factor with SEQ ID NO:1 is available as cDNA accession number NM 121290, and is reproduced below as SEQ ID NO:2.

```
  1  CATCATTCTC  CCTTCATCAA  GTCTTCTCTC  TTTTCTCTCT
 41  CTATTATAAA  ACAAACTTCA  CTCGTTCACA  TCAATGGATC
 81  CTTGAGAAAG  ACAAACAAAT  TGAAGAGAAA  TAATAACAAT
121  TAACTCAACC  AAAAATATGA  GGAAGCCAGA  GGTAGCCATT
161  GCAGCTAGTA  CTCACCAAGT  AAAGAAGATG  AAGAAGGGAC
201  TTTGGTCTCC  TGAGGAAGAC  TCAAAGCTGA  TGCAATACAT
241  GTTAAGCAAT  GGACAAGGAT  GTTGGAGTGA  TGTTGCGAAA
281  AACGCAGGAC  TTCAAAGATG  TGGCAAAAGC  TGCCGTCTTC
321  GTTGGATCAA  CTATCTTCGT  CCTGACCTCA  AGCGTGGCGC
361  TTTCTCTCCT  CAAGAAGAGG  ATCTCATCAT  TCGCTTTCAT
401  TCCATCCTCG  GCAACAGGTG  GTCTCAGATT  GCAGCACGAT
441  TGCCTGGTCG  GACCGATAAC  GAGATCAAGA  ATTTCTGGAA
481  CTCAACAATA  AAGAAAAGGC  TAAAGAAGAT  GTCCGATACC
521  TCCAACTTAA  TCAACAACTC  ATCCTCATCA  CCCAACACAG
561  CAAGCGATTC  CTCTTCTAAT  TCCGCATCTT  CTTTGGATAT
601  TAAAGACATT  ATAGGAAGCT  TCATGTCCTT  ACAAGAACAA
641  GGCTTCGTCA  ACCCTTCCTT  GACCCACATA  CAAACCAACA
681  ATCCATTTCC  AACGGGAAAC  ATGATCAGCC  ACCCGTGCAA
721  TGACGATTTT  ACCCCTTATG  TAGATGGTAT  CTATGGAGTA
761  AACGCAGGGG  TACAAGGGGA  ACTCTACTTC  CCACCTTTGG
801  AATGTGAAGA  AGGTGATTGG  TACAATGCAA  ATATAAACAA
841  CCACTTAGAC  GAGTTGAACA  CTAATGGATC  CGGAAACGCA
881  CCTGAGGGTA  TGACACCAGT  GGAAGAATTT  TGGGACCTTG
921  ACCAGTTGAT  GAACACTGAG  GTTCCTTCGT  TTTACTTCAA
961  CTTCAAACAA  AGCATATGAA  TATTTTTACG  TCATCTTATT
1001 CTTTTTTCTA  TTGCGGTTTA  TACTCAAGAT  TCTTAGCCAC
1041 ACACACATAA  ATGCAAATAT  ATATACATTG  TTAGAGAGTA
1081 TTTTGTATTT  CGAATAATCT  TTTCGTACTA  GGGCTTGAGC
1121 CTTGAGGTGC  CATGTAATGA  TTAGTCAATG  TAAAACATAT
1161 ATCCTATAAT  AAATAAATAA  AAGAAATAAT  AAGCACATAC
1201 ATTCTTTAAT  ATAACAGGGG  CAAACACTTG  AAGAATTTTG
1241 TAATCAAGTA  GC
```

An MYB46 transcription factor from *Gossypium hirsutum* (cotton) has the following sequence (SEQ 1D NO:3), with potential phosphorylation sites highlighted in bold with underlining.

```
  1  MMRKPNNGST  ITTTNNKLRK  GLWSPEEDDK  LINYMLTNGQ
 41  GCWSDVARNA  GLQRCGKSCR  LRWINYLRPD  LKRGAISPEE
 81  EELIVHLHSI  LGNRWSQIAA  RLPGRTDNEI  KNFWNSTIKK
121  RLKNSSPNTI  GSSTSNFNKD  SNPVGFITME  QQGVLLPTYI
161  DLSSTSSNSS  LQSTVTNPGT  AFGATVGYFA  TNVNCMYGEN
201  EMLCGEELYM  PPLETVRENL  KIENTFESDI  TTTTTTNNNN
241  NVDCSMKSEN  VMTGAAVGNF  WLGEEIKVGD  WNLEDLMKDV
281  SSFPFLDFQS
```

A comparison between the N-terminal portion of the *Arabidopsis thaliana* MYB46 amino acid sequence with SEQ ID NO:1 and the N-terminal portion of the *Gossypium hirsutum* (cotton) amino acid sequence with SEQ ID NO:3 is shown below, indicating that these two sequences have at least 73% sequence identity.

```
Seq1    1  MRKPEVAIAASTHQVKKMKKGLWSPEEDSKLMQYMLSNGQGCWSDVAKNAGLQRCGKSCR
Seq3    2  MRKPNNGSTITTTN-NKLRKGLWSPEEDDKLINYMLTNGQGCWSDVARNAGLQRCGKSCR
           ****     *    *  ********* **  *** ********** ************

Seq1   61  LRWINYLRPDLKRGAFSPQEEDLIIRFHSILGNRWSQIAARLPGRTDNEIKNFWNSTIKK
Seq3   61  LRWINYLRPDLKRGAISPEEEELIVHLHSILGNRWSQIAARLPGRTDNEIKNFWNSTIKK
           ***************  ** ** **  *********************************

Seq1  121  RLKKMSDTSNLINNSSSSPNTASD
Seq3  121  RLKNSS--PNTIGSSTSNFNKDSN
           ***  *    *  * *  *   *
```

As illustrated, the *Gossypium hirsutum* (cotton) MYB46 with SEQ ID NO:3 has a potential MPK binding site (underlined above) and a serine at about position 135 that can be phosphorylated (in bold and underlined above). A comparison between the portion of the relating to the second phosphorylation site of *Arabidopsis thaliana* MYB46 amino acid sequence (SEQ ID NO: and the homologous portion of the *Gossypium hirsutum* (cotton) amino acid sequence with SEQ ID NO:3 is shown below, indicating that these two sequences have at least 50% sequence identity in this region.

```
Seq1  198  FTPYVDGIYGVNAGVQGE-LYFPPLE  (SEQ ID NO: 4)
Seq3  189  FATNVNCMYGENEMLCGEELYMPPLE  (SEQ ID NO: 5)
           * *   * **     ** ** ****
```

As illustrated, the *Gossypium hirsutism* (cotton) MYB46 with SEQ ID NO:3 has a threonine at about position 191 (in bold and underlined above) that can be phosphorylated. Such phosphorylation sites, for example the serine at position 135 (S135) and the threonine at position 191 (T191), can be modified to improve the stability of this *Gossypium hirsutum* (cotton) MYB46. Such modifications can include replacement of the serine and/or the threonine with an amino acid that is not a serine, threonine, aspartic acid, or glutamic acid.

A nucleotide sequence for the *Gossypium hirsutum* (cotton) with SEQ 1D NO:3 is shown below as SEQ ID NO:6.

```
   1  TCATCACCAC CATTTCCCCC ACCATGAAGC CTCCTCCTCC
  41  CTTCTTCTAT AAAATCTCCA CTAATTTCCT TATGACCAAA
  81  AAAAAACTCG TTTATAATAT CAACAAAAAT AAACCCAAGT
 121  CTTTAGTTAG TTCTTAAATT TTCATCTCTT AGGAGATTTT
 141  TTATTATTTT ACATGATGAG GAAGCCTAAC AATGGTAGCA
 181  CTATTACTAC TACTAACAAT AAGCTTAGGA AAGGGTTATG
 241  GTCACCCGAA GAAGATGATA AGCTCATCAA CTATATGTTA
 281  ACCAATGGCC AAGGTTGTTG GAGTGACGTA GCTCGGAACG
 321  CCGGCTTGCA ACGGTGCGGC AAGAGTTGCC GTCTCCGTTG
 361  GATCAATTAC TTGAGACCCG ATCTCAAACG AGGTGCCATT
 401  TCGCCAGAAG AAGAAGAACT AATCGTCCAT TTACATTCTA
 441  TTCTCGGCAA TAGGTGGTCT CAAATTGCGG CTCGCTTGCC
 481  TGGTCGTACC GACAATGAAA TAAAGAACTT TTGGAATTCG
 521  ACGATAAAGA AAAGGCTCAA AAATTCTTCA CCAAACACCA
 561  TCGGTTCATC AACATCAAAC TTTAACAAAG ATTCCAATCC
 601  AGTCGGCTTC ATTACAATGG AACAACAAGG TGTTCTTTTG
 641  CCTACGTACA TCGATTTATC GTCGACTTCA TCCAATTCTT
 681  CCTTGCAATC AACCGTCACG AACCCCGGGA CTGCATTCGG
 721  TGCCACCGTC GGGTACTTTG CGACAAACGT CAACTGTATG
 761  TACGGTGAAA ACGAGATGTT ATGTGGGGAG GAACTATACA
 801  TGCCTCCTTT AGAAACTGTT AGAGAAAACC TTAAAATCGA
 841  GAATACATTC GAAAGCGACA TCACCACCAC CACCACCACA
 881  AACAACAACA ATAACGTAGA TTGCAGTATG AAATCGGAGA
 921  ACGTAATGAC CGGTGCGGCT GTCGGGAATT TTTGGTTAGG
 961  TGAAGAGATT AAAGTTGGAG ACTGGAATTT GGAGGATTTG
1001  ATGAAAGATG TTTCTTCTTT TCCATTTCTT GATTTTCAAA
1041  GTTAAATATA ATTAAAACAT TTTAGGTCAA AATTAAAACA
1081  TTAAAAAAAA ACCCTAGAGT CCATTACCAA AAAAAAAAAC
1121  CCTTAAAACC TTGTTTGTTT GATAGTGAAA AAAGGACTAC
1161  AAAATTCTCA TAGATTCGA CAATACTTAC AAAAAA
```

Another MYB46 transcription factor from *Gossypium hirsutum* (cotton) has the following sequence (SEQ ID NO:7) with potential phosphorylation sites highlighted in bold with underlining.

```
   1  MMRKPPSMKG NNSNGTNKHK KGLWSPEEDD KLVTYMLTNG
  41  RGCWSDVARN AGLQRCGKSC RLRWINYLRP DLKRGAFSPQ
  81  EQELIVHLHS ILGNRWSQIA ARLPGRTDNE IKNFWNSTIK
 121  KRLKHSSSTA SHNASDSSSE PNKDAMAAGF MTMLEQEVPP
 161  IYLDLSSAWS NSFLQSMVLN HSGNSLPMLQ HGRNVVGAVG
 201  YFDPAGSCVT QAEVNGDSSL GTSEIFGSVD NGIERELYVP
 241  PLESIGKDLK TENSVDGNIN NGFNIINTSG VRSDNNNNMS
 281  KNMDSDDVGS FWIGEELKVG EWDMENLMKD VSSFPFLDFQ
 321  S
```

For example, a comparison between the N-terminal portion of the *Arabidopsis thaliana* MYB46 amino acid sequence with SEQ ID NO:1 and the N-terminal portion of the *Gossypium hirsutum* (cotton) amino acid sequence with SEQ ID NO:7 is shown below, indicating that these two sequences have at least 75% sequence identity.

```
Seq1    1   MRKPEVAIAASTHQVKKMKKGLWSPEEDSKLMQYMLSNGQGCWSDVAKNAGLQRCGKSCR
Seq7    2   MRKPPSMKGNNSNGTNKHKKGLWSPEEDDKLVTYMLTNGRGCWSDVARNAGLQRCGKSCR
            ****         * ********** **  *** ** ****** ************

Seq1   61   LRWINYLRPDLKRGAFSPQEEDLIIRFHSILGNRWSQIAARLPGRTDNEIKNFWNSTIKK
Seq7   62   LRWINYLRPDLKRGAFSPQEQELIVHLHSILGNRWSQIAARLPGRTDNEIKNFWNSTIKK
            ********************  **   **********************************

Seq1  121   RLKKMSDT-SNLINNSSSSPN
Seq7  122   RLKHSSSTASHNASDSSSEPN
            *** *  *        **  **
```

The *Gossypium hirsutum* (cotton) MYB46 with SEQ ID NO:7 has a potential MPK binding site (underlined above). The *Gossypium hirsutum* (cotton) MYB46 with SEQ ID NO:7 also has, for example, a serine at about position 139 (in bold and underlined above) that in some cases can be phosphorylated. This *Gossypium hirsutum* (cotton) MYB46 with SEQ ID NO:7 also has a glutamic acid at position 140 that, like MYB46$^{S138D}$, may be unstable and prone to degradation. Hence, the serine at position 139 and/or the glutamic acid at position 140 can be modified to improve the stability of the *Gossypium hirsutum* (cotton) MYB46 with SEQ ID NO:7. Such modifications can include replacement of the serine, threonine and/or the glutamic acid with an amino acid that is not a serine, threonine, aspartic acid, or glutamic acid. In other cases, the *Gossypium hirsutum* (cotton) MYB46 with SEQ ID NO:7 is not used. For example, the *Gossypium hirsutum* (cotton) MYB46 with SEQ 1D NO:3 may be used instead of the MYB46 with SEQ ID NO:7.

A nucleotide sequence for the *Gossypium hirsutum* (cotton) with SEQ ID NO:7 is shown below as SEQ ID NO:8.

```
   1   CGTTGTCTAC TTAGACCCAT CAACCAACTC TCTTTCTCTC
  41   TCCTTTCTTC CCTGTATTCT AAGCAAACCC CACAACCATC
  81   AGCATCATCA TGAGCACCAT TTCCGCTCCA TGAAGCCTTC
 121   TCCTTTCTCT CTCTTTTCCT CTTTTAGTTC CAATCTATAA
 161   AGCGTGCCCA CTAATCTATA TGATCAAACT AGTTAGGATC
 201   AACAAAAATA ACCCACCAAG ATTATTTATT GTGGTTGTTG
 241   GATAGGATCC AAGGCTTATC TCTCAATTAA TTTCTCCCTT
 281   AGGAGATATT GGTTTGATGA TGAGGAAGCC TCCATCCATG
 321   AAGGGTAACA ATAGTAATGG GACCAATAAG CATAAGAAAG
 361   GGTTATGGTC GCCAGAGGAA GACGACAAGC TCGTCACCTA
 401   TATGCTAACA AATGGCCGGG GTTGTTGGAG TGACGTGGCT
 441   AGAAATGCTG GCCTGCAGAG GTGTGGCAAG AGCTGCCGGC
 481   TTCGATGGAT AAATTATCTC AGACCCGATC TCAAACGAGG
 521   CGCGTTTTCG CCTCAGGAAC AAGAGCTTAT CGTCCATTTA
 561   CACTCCATTC TTGGCAACAG GTGGTCTCAA ATAGCGGCTC
 601   GCCTACCTGG TCGTACGGAC AATGAAATAA AGAACTTTTG
 641   GAATTCAACA ATAAAGAAAA GGCTAAAGCA TTCATCATCT
 681   ACTGCCTCAC ATAACGCCAG TGATTCATCG TCGGAGCCTA
 721   ACAAAGATGC CATGGCGGCA GGGTTCATGA CGATGCTTGA
 761   ACAAGAGGTT CCGCCAATTT ACCTGGATTT ATCATCGGCT
 801   TGGTCGAATT CTTTCTTGCA ATCCATGGTC CTTAACCATT
 841   CCGGCAACTC TTTACCGATG CTCCAGCATG GCAGAAACGT
 881   TGTTGGGGCT GTCGGATACT TTGATCCGGC AGGCTCATGC
 921   GTGACACAGG CTGAGGTGAA CGGGGACAGT TCCTTGGGTG
 961   AAAGTGAGAT ATTTGGAAGT GTTGATAATG GGATAGAAAG
1001   GGAGTTATAT GTGCCTCCGT TAGAAAGCAT TGGGAAAGAC
1041   CTTAAAACTG AAAACTCAGT TGATGGGAAC ATCAACAACG
1081   GTTTCAATAT CATAAATACT AGCGGTGTTA GAAGCGACAA
1121   CAATAATAAC ATGTCGAAAA ACATGGACAG CGACGACGTT
1161   GGGAGTTTTT GGATAGGAGA GGAGCTAAAA GTTGGAGAAT
1201   GGGACATGGA AAATTTGATG AAAGATGTTT CTTCCTTTCC
1241   TTTTCTTGAT TTCCAAAGCT GAAAATAGTT AATTCTAAAC
1281   TTTAGTTATA ATTATAAACC TCCAATATAT ATATATATCC
1321   ATGTATTTGA ACAACTTTTG GAAAGGAACA TCTCAAGGAA
1361   TGTTATTGA
```

An MYB46 transcription factor from *Populus trichocarpa* (poplar) has the following sequence (SEQ ID NO:11) with potential phosphorylation sites highlighted in bold with underlining.

```
  1   MRKPEASGKN NVNNINKFRK GLWSPEEDDK LMNYMLNNGQ
 41   GCWSDVARNA GLQRCGKSCR LRWINYLRPD LKRGAFSPQE
 81   EEMIIHLHSL LGNRWSQIAA RLPGRTDNEI KNFWNSTIKK
121   RLKNLQSSNA SPNTSDSSSE PSKDVMGGLM STMQEQGIFS
161   MNMDPSMSSS SSLATSMKAM ILNTMMDPLL PMLDYDHGLN
201   MYGGASGYES ITAPPCMAQV GVLNSGDHGF YGEGIFEGIN
241   VEIPPLESVS CMEENAKTQN IQDNNTDKYS YSSPVNSLYH
281   KNCNITSNNK TDSIAADQMG NLWHGSEELK VGEWDLEELM
321   KDVSAFPFLD FQ
```

For example, a comparison between the N-terminal portion of the *Arabidopsis thaliana* MYB46 amino acid sequence with SEQ ID NO:1 and the N-terminal portion of the *Populus trichocarpa* (poplar) amino acid sequence with SEQ ID NO:11 is shown below, indicating that these two sequences have at least 66% sequence identity.

```
Seq1   1 MRKPEVAIAASTHQVKKMKKGLWSPEEDSKLMQYMLSNGQGCWSDVAKNAGLQRCGKSCR
Seq11  1 MRKPEASGKNNVNNINKFRKGLWSPEEDDKLMNYMLNNGQGCWSDVARNAGLQRCGKSCR
         *****      *   *********  ***  ***  *********  ************

Seq1  61 LRWINYLRPDLKRGAFSPQEEDLIIRFHSILGNRWSQIAARLPGRTDNEIKNFWNSTIKK
Seq11 61 LRWINYLRPDLKRGAFSPQEEEMIIHLHSLLGNRWSQIAARLPGRTDNEIKNFWNSTIKK
         *********************  **  ** ******************************

Seq1  121 RLKKMSDTSNLINNSSSSPNTASDSSSNSASSLDIKDIIGSFM
Seq11 121 RLKNLQSSNASPNTSDSSSEPSKDVMGGLMSTMQEQGIFSMNM
          ***   *  *  **       *    *     *    *   *
```

As illustrated, the *Populus trichocarpa* (poplar) MYB46 with SEQ ID NO:11 has a potential MPK binding site (underlined above) and a serine at about position 138, that can be phosphorylated. Hence, in some cases the serine at position 138 of the *Populus trichocarpa* (poplar) MYB46 with SEQ ID NO:11 can be modified. Such modifications can include replacement of the serine and/or the threonine with an amino acid that is not a serine, threonine, aspartic acid, or glutamic acid.

A nucleotide sequence for the *Populus trichocarpa* (poplar) with SEQ ID NO:11 is shown below as SEQ ID NO:12.

```
   1 CTCTCTCTTT CTTTCCTATA TTCTAAGCAA TACCCCACAA
  41 CCATCATCAA AATCATGATC ATCAAGCCCA CTCTACCAAG
  81 CCTCCTCTTT CTCTTTCTTA TAATCTGCCA CTCTATAAAG
 121 TCTTAACTAA TCGACATCAA ACCAGTTGGG AAGAGATATA
 161 GATCACCTTT CTAGTGACAG GATCCAAAGG CTCTCAGAAT
 201 GAGGAAGCCA GAGGCCTCTG GGAAGAACAA CGTTAATAAC
 241 ATTAACAAGT TCAGAAAGGG CTTGTGGTCA CCAGAGGAAG
 281 ATGACAAGCT CATGAACTAC ATGCTAAACA ATGGACAAGG
 321 TTGCTGGAGT GATGTGGCAA GGAATGCTGG TTTGCAGCGA
 361 TGCGGCAAGA GTTGCCGGCT TCGTTGGATT AATTACTTGA
 401 GGCCTGATCT CAAGAGAGGT GCATTTTCAC CCCAAGAAGA
 441 AGAGATGATC ATCCATTTGC ATTCCCTTCT CGGCAATAGG
 481 TGGTCTCAAA TTGCGGCTCG CTTGCCAGGA AGAACGGACA
 521 ATGAAATCAA GAATTTTTGG AATTCAACAA TAAAGAAGAG
 561 ATTAAAGAAT CTGCAGTCAT CCAACGCATC ACCAAACACA
 601 AGTGATTCCT CCTCGGAGCC TAGCAAAGAT GTCATGGGAG
 641 GGTTGATGTC GACCATGCAA GAACAAGGCA TTTTCTCCAT
 681 GAACATGGAT CCTTCAATGT CATCTTCGTC ATCGTTAGCA
 721 ACCTCCATGA AAGCAATGAT TCTAAATACC ATGATGGATC
 761 CATTACTACC TATGCTTGAT TATGATCATG GCCTAAACAT
 801 GTATGGCGGT GCAAGTGGGT ACGAATCCAT TACCGCACCA
 841 CCATGCATGG CTCAAGTTGG AGTCCTTAAC AGTGGTGATC
 881 ATGGTTTTTA TGGGGAAGGG ATCTTTGAAG GTATTAATGT
 921 TGAGATTCCT CCTTTAGAGA GTGTAAGCTG CATGGAGGAA
 961 AATGCAAAAA CCCAGAATAT ACAGGATAAC AACACTGACA
1001 AGTACTCATA TAGTAGTCCT GTGAATAGTC TTTACCACAA
1041 AAACTGCAAC ATCACTAGTA ATAACAAGAC AGATAGCATA
1081 GCTGCTGATC AGATGGGGAA CTTATGGCAC GGATCAGAAG
1121 AGTTAAAAGT GGGGGAGTGG GACTTGGAAG AGTTGATGAA
1161 AGATGTTTCG GCCTTTCCAT TCCTTGATTT CCAATGATCG
1201 TTGAATAAAT GGTTTCCCAA TACACATAAT TTTTCAAGTT
1241 TAGATCGGCC TTGCCACATA TTCACCCTTC AAATACTGTT
1281 ATCACTCAAC CCTTGTATTG ATCTATCCTT TTTCGTCAAG
1321 AAACTTAGCA ATTTCATGTA TAGTTCCGAT GAGGTACAGG
1361 AAGCATGGAA TAAAGGTCAG GAGAGTTATA CATTAATTAG
1401 TGACCAAACA TTTCTTGTAC GTAAATTTAT GTACCTTATG
1441 ATATTATTGC AATTTCGATC GCCATTAATT A
```

An MYB46 transcription factor from *Arabidopsis lyrata* has the following sequence (SEQ ID NO:13) with potential phosphorylation sites highlighted in bold with underlining, and a MPK binding site (underlined).

```
  1 MRKPEVAIAA STHQVKKMKK GLWSPEEDSK LMQYMLSNGQ
 41 GCWSDVAKNA GLQRCGKSCR LRWINYLRPD LKRGAFSPQE
 81 EDLIIRFHSI LGNRWSQIAA RLPGRTDNEI KNFWNSTIKK
121 RLKKMSDTSN LINNSSSSPN TTSDTSSNSA SSLDLKDIIG
161 SFMSLQEQGF VNPSLTHIPS NNPFPAANMT SHPCNDDFTP
201 YVDGIYGVNA GVQGDLYFPP LECEEGDWYN ANINNHLDEL
241 NTNGSGNAPD SMRPVEEFWD LDQLMNTEVP SFYFNFKQSI
```

For example, a comparison between the *Arabidopsis thaliana* MYB46 amino acid sequence with SEQ ID NO:1 and the *Arabidopsis lyrata* amino acid sequence with SEQ ID NO:13 is shown below, indicating that these two sequences have at least 96% sequence identity.

```
Seq1     1  MRKPEVAIAASTHQVKKMKKGLWSPEEDSKLMQYMLSNGQGCWSDVAKNAGLQRCGKSCR
Seq13    1  MRKPEVAIAASTHQVKKMKKGLWSPEEDSKLMQYMLSNGQGCWSDVAKNAGLQRCGKSCR
            ************************************************************

Seq1    61  LRWINYLRPDLKRGAFSPQEEDLIIRFHSILGNRWSQIAARLPGRTDNEIKNFWNSTIKK
Seq13   61  LRWINYLRPDLKRGAFSPQEEDLIIRFHSILGNRWSQIAARLPGRTDNEIKNFWNSTIKK
            ************************************************************

Seq1   121  RLKKMSDTSNLINNSSSSPNTASDSSSNSASSLDIKDIIGSFMSLQEQGFVNPSLTHIQT
Seq13  121  RLKKMSDTSNLINNSSSSPNTTSDTSSNSASSLDLKDIIGSFMSLQEQGFVNPSLTHIPS
            ******************* ** ********* ***************************

Seq1   181  NNPFPTGNMISHPCNDDFTPYVDGIYGVNAGVQGELYFPPLECEEGDWYNANINNHLDEL
Seq13  181  NNPFPAANMTSHPCNDDFTPYVEGIYGVNAGVQGDLYFPPLECEEGDWYNANINNHLDEL
            *****  ** *********** ************ *************************

Seq1   241  NTNGSGNAPEGMRPVEEFWDLDQLMNTEVPSFYFNFKQSI
Seq13  241  NTNGSGNAPDSMRPVEEFWDLDQLMNTEVPSFYFNFKQSI
            *********  *****************************
```

As illustrated in this example, this *Arabidopsis lyrata* MYB46 has two mitogen-activated protein kinase (MPK) phosphorylation sites, a serine at position 138 (S138) and a threonine at position 199 (T199), which are highlighted in bold and with underlining in the SEQ ID NO:13 sequence above. These two sites, or other sites within this this *Arabidopsis lyrata* MYB46, can be modified to improve the stability of the *Arabidopsis lyrata* MYB46. Such modifications can include replacement of the serine and/or the threonine with an amino acid that is not a serine, threonine, aspartic acid, or glutamic acid.

A nucleotide sequence for the *Arabidopsis lyrata* with SEQ ID NO:13 is shown below as SEQ ID NO:14.

```
   1  AAACCATACA ACCATCCCTT TCTCATCATC ATCATTCTCC
  41  CTTCATCAAG TCTTCTCTCT TTTCTCTCCC TATTATAAAA
  81  TAAACTTCAC TCGTTCACAT CAATGGATCC TTGCAGAAAT
 121  ACAAACACAT TGAAGAGAAA TAATAACAAT TAACTCAACT
 161  AAAAAAATGA GGAAACCAGA GGTAGCCATT GCAGCTAGTA
 201  CTCATCAAGT AAAGAAGATG AAGAAGGGTC TTTGGTCTCC
 241  GGAGGAAGAC TCAAAGCTTA TGCAATACAT GTTAAGCAAT
 281  GGACAAGGAT GTTGGAGCGA TGTTGCGAAA AACGCAGGTC
 321  TTCAAAGATG TGGCAAAAGC TGCCGTCTTC GTTGGATCAA
 361  CTATCTTCGT CCTGACCTCA AGCGTGGTGC TTTCTCTCCT
 401  CAAGAAGAGG ATCTCATCAT TCGCTTTCAT TCCATCCTCG
 441  GCAACAGGTG GTCTCAGATT GCAGCACGAT TGCCTGGTCG
 481  GACCGACAAT GAGATCAAGA ATTTTTGGAA CTCAACAATA
 521  AAGAAAAGGC TAAAGAAGAT GTCTGATACA TCCAATCTCA
 561  TCAACAACTC ATCCTCATCA CCCAACACAA CAAGTGACAC
 601  CTCTTCTAAT TCCGCCTCTT CTTTGGATCT TAAAGACATT
 641  ATAGGAAGCT TCATGTCTTT ACAAGAACAA GGCTTCGTCA
 681  ACCCTTCCTT GACCCACATA CCAAGCAACA ATCCATTTCC
 721  AGCGGCAAAC ATGACCAGCC ACCCGTGCAA TGACGATTTC
 761  ACACCTTATG TAGATGGTAT CTATGGAGTA AACGCAGGGG
 801  TACAAGGGGA CCTCTATTTT CCACCTTTGG AATGTGAAGA
 841  AGGTGATTGG TACAATGCAA ATATTAACAA CCACTTAGAC
 881  GAGTTGAACA CTAATGGATC TGGAAACGCA CCTGACAGTA
 921  TGAGACCAGT GGAAGAATTT TGGGACCTTG ACCAGTTGAT
 961  GAACACTGAG GTTCCTTCGT TTTACTTCAA CTTCAAACAA
1001  AGCATATGAA TTTTTACATC ATCTTATTTT TTTTTCTGCT
1041  GCTGATTTAT ACTCAAGATT CTTAGCCACA CACATAAATG
1081  CAAATATATA TACATTGTTA TTGATAGATG AAAGCTTAGA
1121  GAGTATTTTG TATTTCGAAT AACGTTTTCG CACTAGGGCT
1161  TGAGGTGCCG TGTGTAATGA TAGTCAATGT AAAACATATA
1201  TAATATAATA AAAAAGAAAT AATAATAATA AACACATA
```

An MYB46 transcription factor from *Camelina sativa* (false flax) has the following sequence (SEQ ID NO:15) with potential phosphorylation sites highlighted in bold with underlining, and a MPK binding site (underlined).

```
   1  MRKPEVAIAA ATTHQVKKMK KGLWSPEEDS KLMQYMLSNG
  41  QGCWSDVAKN AGLQRCGKSC RLRWINYLRP DLKRGAFSPQ
  81  EEDLIIRFHS ILGNRWSQIA ARLPGRTDNE IKNFWNSTIK
 121  KRLKKMSDTS NLINNSSSSP NTTSDSSSNS TSSLELKDII
 161  GSFMTLQEQG FINPSLTQIP TNNPFPAPNM ISHPCNDDFT
 201  PYLDGIYGVN TGVQGELYFP PLECEEGDWY NTNINNNHLD
 241  ELNTNGSGNA PESMIRPVEE LWDLDQLMMN TEVPSFYFNE
 281  KQSI
```

A comparison between the *Arabidopsis thaliana* MYB46 amino acid sequence with SEQ ID NO:1 and the *Camelina sativa* (false flax) amino acid sequence with SEQ ID NO:15 is shown below, indicating that these two sequences have at least 93% sequence identity.

```
Seq1    1   MRKPEVAIAAST-HQVKKMKKGLWSPEEDSKLMQYMLSNGQGCWSDVAKNAGLQRCGKSC
Seq15   1   MRKPEVAIAAATTHQVKKMKKGLWSPEEDSKLMQYMLSNGQGCWSDVAKNAGLQRCGKSC
            ********** * ***********************************************

Seq1    60  RLRWINYLRPDLKRGAFSPQEEDLIIRFHSILGNRWSQIAARLPGRTDNEIKNFWNSTIK
Seq15   61  RLRWINYLRPDLKRGAFSPQEEDLIIRFHSILGNRWSQIAARLPGRTDNEIKNFWNSTIK
            ************************************************************

Seq1    120 KRLKKMSDTSNLINNSSSSPNTASDSSSNSASSLDIKDIIGSFMSLQEQGFVNPSLTHIQ
Seq15   121 KRLKKMSDTSNLINNSSSSPNTTSDSSSNSTSSLELKDIIGSFMTLQEQGFINPSLTQIP
            ******************** ******* *** ******** ****** ***** *

Seq1    180 TNNPFPTGNMISHPCNDDFTPYVDGIYGVNAGVQGELYFPPLECEEGDWYNANINN-HLD
Seq15   181 TNNPFPAPNMISHPCNDDFTPYLDGIYGVNTGVQGELYFPPLECEEGDWYNTNINNNHLD
            ****** ************** ******* ****************** **** ****

Seq1    239 ELNTNGSGNAPEGM-RPVEEFWDLDQLM-NTEVPSFYFNFKQSI
Seq15   241 ELNTNGSGNAPESMIRPVEELWDLDQLMMNTEVPSFYFNFKQSI
            ************ * **** ******* ***************
```

This *Camelina sativa* (false flax) MYB46 with SEQ ID NO:15 has a potential MPK binding site (underlined above). This *Camelina sativa* (false flax) MYB46 with SEQ ID NO:15 also, for example, has at least two mitogen-activated protein kinase (MPK) phosphorylation sites, a serine at position 139 (S139) and a threonine at position 200 (T200), which are highlighted in bold and with underlining in the SEQ ID NO:15 sequence above. Such phosphorylation sites can be modified to improve the stability of the *Camelina sativa* (false flax) MYB46, for example, by replacement of the serine and/or the threonine with an amino acid that is not a serine, threonine, aspartic acid, or glutamic acid.

A nucleotide sequence for the *Camelina sativa* (false flax) with SEQ ID NO:15 is shown below as SEQ ID NO:16.

```
  1  AATGGAGCCT TGAGAAAGAC AAACAAATCA AAGAGAAACA
 41  ATTAACTCAA CCAAAAAAAA AAAATGAGGA AACCAGAGGT
 81  AGCCATTGCA GCAGCCACTA CTCATCAAGT AAAGAAGATG
121  AAGAAAGGAC TTTGGTCTCC GGAGGAAGAC TCAAAGCTGA
161  TGCAATACAT GCTAAGCAAT GGGCAAGGAT GTTGGAGCGA
201  TGTCGCGAAA AACGCAGGCC TTCAAAGATG TGGCAAAAGC
241  TGCCGTCTTC GTTGGATCAA CTATCTTCGT CCTGACCTCA
281  AGCGTGGAGC TTTCTCTCCT CAAGAAGAGG ATCTCATCAT
321  TCGCTTTCAT TCCATCCTCG GCAACAGGTG GTCTCAGATT
361  GCAGCACGAT TGCCTGGTCG GACTGACAAC GAGATCAAGA
401  ATTTTTGGAA CTCAACAATA AAGAAAAGGC TAAAGAAGAT
441  GTCGGATACA TCCAATCTCA TCAACAACTC ATCTTCATCG
481  CCCAACACAA CAAGCGACTC TCTTCTAAT TCGACCTCCT
521  CTTTGGAGCT TAAAGACATT ATAGGAAGCT TCATGACCTT
561  ACAAGAACAA GGATTCATCA ACCCTTCCTT GACTCAGATA
601  CCAACCAACA ATCCATTCCC CGCGCCAAAC ATGATCAGCC
641  ACCCGTGCAA TGATGATTTT ACCCCATACC TAGATGGTAT
681  CTATGGTGTA AACACAGGGG TACAAGGGGA ACTTTACTTT
721  CCACCGTTGG AATGTGAAGA AGGTGATTGG TACAATACAA
761  ATATTAACAA CAACCACTTA GACGAGTTGA ACACTAATGG
801  ATCTGGAAAC GCACCTGAGA GTATGATCAG ACCAGTGGAA
841  GAATTATGGG ACCTTGACCA GTTGATGATG AACACTGAGG
881  TTCCTTCGTT TTACTTCAAC TTCAAACAAA GCATATGAAA
921  TTTTTACGTC ATCTTATTCT TTTTTTCTTC TGTTGCGGAT
961  TTATACTCAA GAGTCAGCAT GCACACTCAC ACACACATAA
1001 ATGCAAATAT ATATATACAT TGTTATA
```

Another MYB46 transcription factor from *Camelina sativa* (false flax) has the following sequence (SEQ ID NO:17) with potential phosphorylation sites highlighted in bold with underlining, and a MPK binding site (underlined).

```
  1  MRKPEVAIAA ATTHQVKKMK KGLWSPEEDS KLMQYMLSNG
 41  QGCWSDVAKN AGLQRCGKSC RLRWINYLRP DLKRGAFSPQ
 81  EEDLIIRFHS ILGNRWSQIA ARLPGRTDNE IKNFWNSTIK
121  KRLKKMSDTS NLINNSSSSP NNTTSDSSSN STSSLELKDI
161  IGSFMSLQEQ GFINPSLTQI PTNNPFPAPN MISHPCNDDF
201  TPYVDGIYGV NTGVQGELYF PPLECEEGDW YNTNINNNHL
241  DELNTNGSGN APESMIRPVE ELWDLDQLMM NTEVPSFYFN
281  FKQSI
```

A comparison between the *Arabidopsis thaliana* MYB46 amino acid sequence with SEQ ID NO:1 and the *Camelina sativa* (false flax) amino acid sequence with SEQ ID NO:17 is shown below, indicating that these two sequences have at least 93% sequence identity.

```
Seq1    1   MRKPEVAIAAST-HQVKKMKKGLWSPEEDSKLMQYMLSNGQGCWSDVAKNAGLQRCGKSC
Seq17   1   MRKPEVAIAAATTHQVKKMKKGLWSPEEDSKLMQYMLSNGQGCWSDVAKNAGLQRCGKSC
            ********** * ***********************************************
```

```
                              -continued
Seq1    60 RLRWINYLRPDLKRGAFSPQEEDLIIRFHSILGNRWSQIAARLPGRTDNEIKNFWNSTIK
Seq17   61 RLRWINYLRPDLKRGAFSPQEEDLIIRFHSILGNRWSQIAARLPGRTDNEIKNFWNSTIK
           ************************************************************

Seq1   120 KRLKKMSDTSNLINNSSSSPN-TASDSSSNSASSLDIKDIIGSFMSLQEQGFVNPSLTHI
Seq17  121 KRLKKMSDTSNLINNSSSSPNNTTSDSSSNSTSSLELKDIIGSFMSLQEQGFINPSLTQI
           ****************** *  ******* *** *************** ***** *

Seq1   179 QTNNPFPTGNMISHPCNDDFTPYVDGIYGVNAGVQGELYFPPLECEEGDWYNANINN-HL
Seq17  181 PTNNPFPAPNMISHPCNDDFTPYVDGIYGVNTGVQGELYFPPLECEEGDWYNTNINNNHL
            ****** *********************** ****************** * *** **

Seq1   238 DELNTNGSGNAPEGM-RPVEEFWDLDQLM-NTEVPSFYFNFKQSI
Seq17  241 DELNTNGSGNAPESMIRPVEELWDLDQLMMNTEVPSFYFNFKQSI
           ************* * ***** ******  **************
```

As illustrated, this *Camelina sativa* (false flax) MYB46 with SEQ ID NO:17 has a MPK binding site (underlined above). This *Camelina sativa* (false flax) MYB46 with SEQ ID NO:17 also, for example, has two mitogen-activated protein kinase (MPK) phosphorylation sites, a serine at position 139 (S139) and a threonine at position 201 (T201), highlighted in bold and with underlining in the SEQ ID NO:17 sequence above. These two sites, and/or other sites within the Camelina swim (false flax) MYB46 with SEQ ID NO:17 can be modified to improve the stability of the *Camelina sativa* (false flax) MYB46. Such modifications can include replacement of the serine and/or the threonine with an amino acid that is not a serine, threonine, aspartic acid, or glutamic acid.

A nucleotide sequence for the *Camelina sativa* (false flax) with SEQ ID NO:17 is shown below as SEQ ID NO:18.

```
   1 AAGACAAAAC AAAACAAAGA GAAACAATCA ACTTAACCAA
  41 AAAAAAAATA TGAGGAAACC AGAGGTAGCC ATTGCAGCAG
  81 CCACTACTCA TCAAGTAAAG AAGATGAAGA AGGGACTTTG
 121 GTCTCCAGAG GAAGACTCAA AGCTGATGCA ATACATGCTA
 161 AGCAATGGGC AAGGATGTTG GAGCGATGTC GCAAAAAACG
 201 CAGGCCTTCA AAGATGTGGC AAAAGCTGCC GTCTTCGTTG
 241 GATTAACTAT CTTCGTCCTG ACCTCAAGCG TGGAGCTTTC
 281 TCTCCTCAAG AAGAGGATCT CATCATTCGC TTTCATTCCA
 321 TCCTCGGCAA CAGGTGGTCT CAGATTGCAG CACGATTGCC
 361 TGGTCGGACT GACAACGAGA TCAAGAATTT TTGGAACTCA
 401 ACAATAAAGA AAAGGCTAAA GAAGATGTCG GATACATCCA
 441 ATCTCATCAA CAACTCATCT TCATCGCCCA ATAACACAAC
 481 AAGCGACTCC TCTTCTAATT CCACCTCTTC TTTGGAGCTT
 521 AAAGACATTA TAGGAAGCTT CATGTCCTTA CAAGAACAAG
 561 GATTCATCAA CCCTTCCTTA ACTCAGATAC CAACCAACAA
 601 TCCATTCCCC GCGCCAAACA TGATCAGCCA CCCGTGCAAC
 641 GATGATTTTA CCCCATATGT AGATGGTATC TATGGTGTAA
 681 ACACAGGGGT ACAAGGGGAA CTTTACTTTC CACCACTGGA
 721 ATGTGAAGAA GGTGATTGGT ACAATACAAA TATTAACAAC
 761 AACCACTTAG ACGAGTTGAA CACTAATGGA TCTGGAAACG
 801 CACCTGAGAG TATGATCAGA CCAGTGGAAG AATTATGGGA
 841 CCTTGACCAG TTGATGATGA ACACTGAGGT TCCTTCGTTT
 881 TACTTCAACT TCAAACAAAG CATATGAAAT TTTTACGTCA
 921 TCTTATTCTT TTTTTCTTCT GTTGCGGATT TATACTCAAG
 961 AGTCAGCATG CACACTCACA CACACATAAA TGCAAATATA
1001 TATATACATT GTTATA
```

An MYB46 transcription factor from *Hevea brasiliensis* (rubber tree) has the following sequence (SEQ ID NO:19) with potential phosphorylation sites highlighted in bold with underlining, and a MPK binding site (underlined).

```
   1 MRKPEASGKN NNNNNKLRKG LWSPEEDDKL MNYMINNGQG
  41 CWSDVARNAG LQRCGKSCRL RWINYLRPDL KRGAFSPQEE
  81 ELIIHLHSLL GNRWSQIAAR LPGRTDNEIK NFWNSTIKKR
 121 LKNLSSSASP NTSNSSSEPS KEVAAALGEG FISMQEQSMT
 161 PMYIYPSLSS SSSSNTSMQA MTLNQMMDPL PTFDHGLSTC
 201 GASVYFNNDA PPCMTHIGVS GDDIYGNQGI LGGVNIGIEG
 241 ELHIPPLESI SIEENAKTED MYGSNNNKYP YSNVRINSN
 281 CNNNTKAESM TTGVGRQGEE LKVGDWDLEE LMKDVSSFPF
 321 LDIFQAE
```

For example, a comparison between the *Arabidopsis thaliana* MYB46 amino acid sequence with SEQ ID NO:1 and the *Hevea brasiliensis* (rubber tree) amino acid sequence with SEQ ID NO:19 is shown below, indicating that these two sequences have at least 93% sequence identity.

```
Seq1     1  MRKPEVAIAASTHQVKKMKKGLWSPEEDSKLMQYMLSNGQGCWSDVAKNAGLQRCGKSCR
Seq19    1  MRKPE-ASGKNNNNNNKLRKGLWSPEEDDKLMNYMLNNGQGCWSDVARNAGLQRCGKSCR
            ***** *      *  ********* *** *** ********** ************

Seq1    51  LRWINYLRPDLKRGAFSPQEEDLIIRFHSILGNRWSQIAARLPGPTDNEIKNFWNSTIKK
Seq19   60  LRWINYLRPDLKRGAFSPQEEELIIHLHSLLGNRWSQIAARLPGRTDNEIKNFWNSTIKK
            ********************* *** ** *******************************

Seq1   121  RLKKMSDTSNLINNSSSS
Seq19  120  RLKNLSSSASPNTSNSSS
            *** *         ***
```

As illustrated by this example, the *Hevea brasiliensis* (rubber tree) MYB46 with SEQ ID NO:19 has a potential MPK binding site (underlined above) and a serine at about position 137 that in some cases can be phosphorylated. However, the *Hevea brasiliensis* (rubber tree) MYB46 with SEQ ID NO:19 also has a glutamic acid at position 138. In some cases, the MYB46 with SEQ ID NO:19 may be like MYB46$^{S138D}$, which is unstable and prone to degradation. Hence, in some cases the *Hevea brasiliensis* (rubber tree) with SEQ ID NO:19 is modified at positions 137 and/or 138 to improve the stability of the *Hevea brasiliensis* (rubber tree) MYB46. Such modifications can include replacement of the serine, glutamic acid, and/or the threonine with an amino acid that is not a serine, threonine, aspartic acid, or glutamic acid. In other cases, a modified *Arabidopsis thaliana* MYB46 such as one with SEQ ID NO:1 may be used instead of the MYB46 with SEQ ID NO:19.

An MYB4 transcription factor from *Pinus taeda* (pine) has the following sequence (SEQ ID NO:20) with potential phosphorylation sites highlighted in bold with underlining.

```
  1  MSCTTGGLSS  PVSKPKLRKG  LWSPEEDDKL  INYMMKNGQG
 41  CWSDVAKQAG  LQRCGKSCRL  RWINYLRPDL  KRGAFSPQEE
 81  HWIIHLHSIL  GNRWSQIAAR  LPGRTDNEIK  NFWNSCIKKK
121  LKHLSASTNN  SKSISAPNRT  STMNSSITPF  SESSAEPLEV
161  MATRYQPSNA  FNHEVPTAEN  QFCIPDVLAL  RHEQVQSQNQ
201  FSIDQDSATN  NLISHLWNSN  STAVSSHESF  SHAFMSPGLQ
241  TQGHVVKTPI  KPCDQISWST  PLTREAAGSH  ACNYSLGCNI
281  PALVESETLK  EKFKNDAGDQ  INENEIMYLP  RHLL
```

A comparison between the *Arabidopsis thaliana* MYB46 amino acid sequence with SEQ ID NO:1 and the *Pinus taeda* (pine) amino acid sequence with SEQ ID NO:20 is shown below, indicating that these two sequences have at least 75% sequence identity.

As illustrated, the *Pinus taeda* (pine) MYB4 with SEQ ID NO:20 has a serine at about position 135 that in some cases can be phosphorylated. However, the *Pinus taeda* (pine) MYB4 with SEQ 1D NO:20 also has an alanine at position 136. In some cases, the *Pinus taeda* (pine) with SEQ ID NO:20 is modified at position 135, or at other positions, to improve the stability of the *Pinus taeda* (pine) MYB4.

Another comparison between the portion of the relating to the second phosphorylation site of *Arabidopsis thaliana* MYB46 amino acid sequence (SEQ ID NO:1) and the homologous portion of the *Pinus taeda* (pine) amino acid sequence with SEQ ID NO:20 is shown below, indicating that these two sequences have at least 50% sequence identity in this region.

```
SEQ1    186    TGNMISHPCNDDFT    (SEQ ID NO: 22)
SEQ20   209    TNNLISHLWNSNST    (SEQ ID NO: 23)
               * * ***    *  *
```

As illustrated, the *Pinus taeda* (pine) MYB4 protein with SEQ ID NO:20 has a threonine at about position 222 (in bold and underlined above) that can be phosphorylated. These two sites, the serine at position 135 (S135) and the threonine at position 222 (1222), as well as other sites can be modified to improve the stability of this *Pinus taeda* (pine) MYB4. Such modifications can include replacement of the serine and/or the threonine with an amino acid that is not a serine, threonine, aspartic acid, or glutamic acid. In other cases, a modified *Arabidopsis thaliana* MYB46 such as one with SEQ ID NO:1 may be used instead of the MYB4 with SEQ ID NO:20.

A nucleotide sequence for the *Pinus taeda* (pine) with SEQ ID NO:20 is shown below as SEQ ID NO:21:

```
  1  ATGAGCTGCA  CAACAGGAGG  ACTCTCCTCT  CCCGTCTCCA
 41  AACCCAAGCT  AAGGAAAGGC  CTCTGGTCGC  CTGAGGAGGA
 81  TGATAAACTC  ATCAACTACA  TGATGAAAAA  CGGCCAGGGT
```

```
Seq1    17  KMKKGLWSPEEDSKLMQYMLSNGQGCWSDVAKNAGLQRCGKSCRLRWINYLRPDLKRGAF
Seq20   16  KLRKGLWSPEEDDKLINYMMKNGQGCWSDVAKQAGLQRCGKSCRLRWINYLRPDLKRGAF
            *   ********  **  ***********   ******************************

Seq1    77  SPQEEDLIIRFHSILGNRWSQIAARLPGRTDNEIKNFWNSTIKKRLKKMSDTSNLINNSS
Seq20   76  SPQEEHWIIHLHSILGNRWSQIAARLPGRTDNEIKNFWNSCIKKKLKHLSASTNNSKSIS
            *****  **  ******************************* ** *    *       *

Seq1   137  SSPNTASDSSS
Seq20  136  APNRTSTMNSS
              *  **
```

```
121  TGCTGGAGCG ATGTCGCCAA GCAAGCTGGT CTGCAGAGAT
161  GCGGAAAAAG CTGTAGGCTG AGGTGGATTA ACTATTTAAG
201  GCCCGACCTC AAACGCGGTG CATTTTCACC CCAGGAAGAA
241  CATTGGATCA TACACTTGCA TTCCATTCTC GGCAACAGGT
281  GGTCTCAGAT TGCAGCCCGG TTGCCCGGAC GTACGGACAA
321  CGAGATCAAG AATTTCTGGA ACTCCTGCAT AAAGAAGAAG
361  TTGAAACACC TTTCGGCCTC CACCAACAAC AGTAAATCTA
401  TCTCTGCACC TAATCGTACC AGTACCATGA ATTCATCGAT
441  CACGCCCTTT TCTGAATCGT CTGCCGAGCC ATTGGAGGTC
481  ATGGCAACAA GGTATCAGCC ATCGAATGCT TTTAATCATG
521  AAGTGCCCAC TGCAGAAAAT CAGTTTTGTA TTCCGGATGT
561  ATTGGCGTTA AGACATGAGC AAGTACAGAG TCAGAATCAA
601  TTTTCAATTG ATCAGGACTC GGCCACCAAC AACCTCATTT
641  CCCACCTGTG GAATTCCAAT TCTACAGCTG TTTCTTCTCA
681  TGAGAGCTTC TCCCATGCCT TCATGTCTCC GGGTCTGCAA
721  ACGCAAGGCC ATGTTGTAAA GACTCCAATT AAACCATGCG
761  ATCAAATCTC GTGGAGTACA CCACTGACTC GTGAAGCTGC
801  TGGGTCTCAT GCCTGCAATT ACTCTCTTGG CTGCAACATC
841  CCTGCTCTTG TTGAGAGCGA GACACTGAAA GAAAAATTCA
881  AGAATGATGC AGGCGATCAG ATTAATGAAA ATGAGATCAT
921  GTATCTTCCA CGGCATCTTC TGTGA
```

An MYB2 transcription factor from *Eucalyptus grandis* (eucalyptus) has the following sequence (SEQ ID NO:24) with potential phosphorylation sites highlighted in bold with underlining.

```
  1  MARSSCNQKL RKGLWSPEED EKLFNYISRH GLGCWSSVPK
 41  LAGLQRCGKS CRLRWINYLR PDLKRGMFSQ QEEDLIITLH
 81  AALGNRWAQI ATQLPGRTDN EIKNFWNSYV RKKLTKQGID
121  PVTHKPLREL NSMSENCVEI EAAQALQEFK GSRDISSLRA
161  KEPAFPIDGM HGGPMESPVG EVFLNRALFD PSSSLEFHNA
201  INPVLHGAKS RLVDPGYFEM NAAPFSSVSS SMEIDHENKN
241  TSGNLVSRMS CLFFHEAKKY CSNSSNNISN NTEFQLNSAA
281  ENKDLPWADD EELDPLHQFQ VNVTGSEDLK SISWQEEHLL
321  ABAAVDFHGN HPSMSLSDDQ ILQAHFNIF
```

A comparison between a portion of the *Arabidopsis thaliana* MYB2 amino acid sequence with SEQ ID NO:1 and a portion of the *Eucalyptus grandis* (eucalyptus) amino acid sequence with SEQ ID NO:24 is shown below, indicating that these two sequences have at least 29% sequence identity in this region.

```
Seq1  135 SSSSPNTASDSSSNSASSLDIKDI  SEQ ID NO: 25
Seq24 262 SNSSNNISNNTEFQLNSAAENKDL  SEQ ID NO: 26
          * **  *         *    **
```

As illustrated, the *Eucalyptus grandis* (eucalyptus) MYB2 protein with SEQ ID NO:24 has a serine at about position 265 (in bold and underlined above) that can be phosphorylated. This serine at position 265 (S265), or other serines or threonines, can be modified to improve the stability of this *Eucalyptus grandis* (eucalyptus) MYB2. Such modifications can include replacement of the serine(s) and/or threonine(s) with amino acids that are not a serine, threonine, aspartic acid, or glutamic acid. In other cases, a modified *Arabidopsis thaliana* MYB46 such as one with SEQ ID NO:1 may be used instead of the MYB2 with SEQ ID NO:24.

An MYB46 transcription factor from *Oryza sativa* (rice) has the following sequence (SEQ ID NO:27) with potential phosphorylation sites highlighted in bold with underlining.

```
  1  MRKPDCGGGG GAAKGGGVLG VAGGNNAAVV GGKVRKGLWS
 41  PEEDEKLVAY MLRSGQGSWS DVARNAGLQR CGKSCRLRWI
 81  NYLRPDLKRG AFSPQEEDLI VNLHAILGNR WSQIAARLPG
121  RTDNEIKNFW NSTIKKRLKI SSSSASPATT TDCASPPEHK
161  LGAVVDLAGG GGATDDVVVG TANAAMKSMW VDSSSSSSSS
201  SSSMQSRPSI MAAAAAGRSY GGLLPLPDQV CGVDTSPPPP
241  FFHDHSISIK QAYYGSTGAH HHHHAIATMD GSSLIGDHHH
281  HSSSILFGGA SVPPLLDHQT ILDDDDDHPN KTGSNTTAAT
321  LSSNITDNSN SNKNNSDNNN NISSSCCISL MNSSSNMIYW
361  EGHHQQQQQQ HQMLQQQQQH MSRNVMGEWD LEELMKDVSS
401  LPFLDFQVE
```

For example, a comparison between a portion of the *Arabidopsis thaliana* MYB46 amino acid sequence with SEQ ID NO:1 and a portion of the *Oryza sativa* (rice) amino acid sequence with SEQ ID NO:27 is shown below, indicating that these two sequences have at least 50% sequence identity in this region.

```
Seq1  132 INNSSSSPNTASDSSS  SEQ ID NO: 28
Seq27 140 ISSSSASPATTTDCAS  SEQ ID NO: 29
          *  ** **  *   *
```

As illustrated, the *Oryza sativa* (rice) MYB46 protein with SEQ ID NO:27 has a serine at about position 146 (in bold and underlined above) that can be phosphorylated. This serine at position 146 (S146), or other sites within this *Oryza sativa* (rice) MYB46 protein, can be modified to improve the stability of this *Oryza sativa* (rice) MYB46. Such modifications can include replacement of the serine(s) and/or threonine(s) with an amino acid that is not a serine, threonine, aspartic acid, or glutamic acid. In other cases, a modified *Arabidopsis thaliana* MYB46 such as one with SEQ ID NO:1 may be used instead of the MYB46 with SEQ ID NO:27.

An MYB46 transcription factor from *Zea mays* (corn) has the following sequence (SEQ ID NO:30) with potential phosphorylation sites highlighted in bold with underlining.

```
  1  MRKPDCGGGG GAAKGGGVLG VAGGNNAAVV GGKVRKGLWS
 41  PEEDEKLVAY MLRSGQGSWS DVARNAGLQR CGKSCRLRWI
 81  NYLRPDLKRG AFSPQEEDLI VNLHAILGNR WSQIAARLPG
```

-continued

```
121  RTDNEIKNFW  NSTIKKRLKI  SSSSASPATT  TDCASPPEHK

161  LGAVVDLAGG  GGATDDVVVG  TANAAMKSMW  VDSSSSSSSS

201  SSSMQSRPSI  MAAAAAGRSY  GGLLPLPDQV  CGVDTSPPPP

241  FFHDHSISIK  QAYYGSTGAH  HHHHAIATMD  GSSLIGDHHH

281  HSSSILFGGA  SVPPLLDHQT  ILDDDDDHPN  KTGSNTTAAT

321  LSSNITDNSN  SNKNNSDNNN  NISSSCCISL  MNSSSNMIYW

361  EGHHQQQQQQ  HQMLQQQQQH  MSRNVMGEWD  LEELMKDVSS

401  LPFLDFQVE
```

For example, a comparison between a portion of the *Arabidopsis thaliana* MYB46 amino acid sequence with SEQ ID NO:1 and a portion of the *Zea mays* (corn) amino acid sequence with SEQ ID NO:30 is shown below, indicating that these two sequences have at least 50% sequence identity in this region.

```
Seq1   132 INNSSSSPNTASDSSS  SEQ ID NO: 31
Seq30  140 ISSSSASPATTTDCAS  SEQ ID NO: 32
           *  ** **  *   *  *
```

As illustrated, the *Zea mays* (corn) MYB46 protein with SEQ ID NO:30 has a serine at about position 146 (in bold and underlined above) that can be phosphorylated.

Another comparison between a portion of the *Arabidopsis thaliana* MYB46 amino acid sequence with SEQ ID NO: 1 and a portion of the *Zea mays* (corn) amino acid sequence with SEQ ID NO:30 is shown below, indicating that these two sequences have at least 37% sequence identity in this region.

```
Seq1   132 INNSSSSPNTASDSSS  SEQ ID NO: 33
Seq30  191 VDSSSSSSSSSSSMQS  SEQ ID NO: 34
           ****     *     *
```

As illustrated, the *Zea mays* (corn) MYB46 protein with SEQ ID NO:30 has a serine at about position 197 (in bold and underlined above) that can be phosphorylated.

These two sites in the SEQ ID NO:30 MYB46, the serine at position 146 (S146) and the serine at position 197 (S197), and/or other sites can be modified to improve the stability of this *Zea mays* (corn) MYB46. Such modifications can include replacement of these amino acids with an amino acid that is not a serine, threonine, aspartic acid, or glutamic acid. In other cases, a modified *Arabidopsis thaliana* MYB46 such as one with SEQ ID NO:1 may be used instead of the MYB46 with SEQ ID NO:30.

An MYB2 transcription factor from *Populus trichocarpa* (poplar) has the following sequence (SEQ ID NO:35).

```
  1  MSWGVMAGQL  AWGGLIEEGW  RKGPWTAEED  RLLIEYVRLH

41  GDGRWSSVAR  LAGLKRNGKS  CRLRWVNYLR  PDLKRGQITP

81  HEESIIVELH  ARWGNRWSTI  ARSLPGRTDN  EIKNYWRTHF

121  KKKAKLSPDN  SDKARTRHLK  RQQFQQQQQQ  LQRQQQQTQH

161  QQPLQINQLD  MRKIVSLLDE  NEDKAPCTPQ  MRQEMAPHAI

201  YPNTIEEHVL  LYNMFNVNNA  SVPEASNEDI  LWDGLWNLDD

241  LHGNLGVACA  TSKASMQNLV  APFC
```

For example, a comparison between a portion of the *Arabidopsis thaliana* MYB2 amino acid sequence with SEQ ID NO:1 and a portion of the *Populus trichocarpa* (poplar) amino acid sequence with SEQ ID NO:35 is shown below, indicating that these two sequences have at least 50% sequence identity in this region.

```
Seq1   130 NLINNSSSSPNTASD  SEQ ID NO: 36
Seq35  213 NMFNVNNASVPEASN  SEQ ID NO: 37
             *    *     **
```

As illustrated, the *Populus trichocarpa* (poplar) MYB2 protein with SEQ 1D NO:35 has a serine at about position 221 (in bold and underlined above) that can be phosphorylated.

This serine at position 221 (S221), or other serine/threonine positions, can be modified to improve the stability of this *Populus trichocarpa* (poplar) MYB2. Such modifications can include replacement of the serine and/or threonine residues with an amino acid that is not a serine, threonine, aspartic acid, or glutamic acid. In other cases, a modified *Arabidopsis thaliana* MYB46 such as one with SEQ ID NO:1 may be used instead of the MYB2 with SEQ ID NO:35.

An MYB3 transcription factor from *Populus trichocarpa* (poplar) has the following sequence (SEQ ID NO:38), with potential phosphorylation sites identified in bold with underlining.

```
  1  MRKPCCDKQY  TNKGAWSQQE  DQKLIDYIQK  HGEGCWRSLP

41  QAAGLLRCGK  SCRLRWRNYL  RPDLKRDGFG  EDEEDLIIRL

81  HALLGNRWSL  IAGRLPGRTD  NEVKNYWNSH  IRKKLESSHR

121  NTGFTRLRAE  ISSAARSKRQ  ANVPETQVFD  SNGGKPEPSN

161  KSSSDINLDL  TLSIPSKKLE  SSDEN
```

An MYB20 transcription factor from *Populus trichocarpa* (poplar) has the following sequence (SEQ ID NO:39), with potential phosphorylation sites that can be modified identified in bold with underlining.

```
  1  MGRQPCCDKV  GLKKGPWTSD  EDKKLITFIL  ANGQCCWRAV

41  PKLAGLLRCG  KSCRLRWTNY  LRPDLKRGLL  SEYEEKMVID

81  LHAQLGNRWS  KIASHLPGRT  DNEIKNHWNT  HIKKKLRKMG

121  IDPLTHKPLS  TIETPPSPPP  QQEVQVQEKI  QEIEQQAVQQ

161  SCSPNIVSEL  DQNKEPETSL  RSTVTQEEEI  NNMAASTYGT

201  MEQTDGFCID  EVPLIEPHEI  LVPCGLSPSS  TPAPTSSSSS

241  STSSSSSSYG  SNNILEDLLL  PDFEWPINNV  DIGLWGDYLN

281  SWDVLISDAV  GDWKQTTMFD  PPLNQCSRMI  LDQDSWTNGL

321  L
```

An MYB21 transcription factor from *Populus trichocarpa* (poplar) has the following sequence (SEQ ID NO:40), with potential phosphorylation sites that can be modified identified in bold with underlining.

```
  1  MRKPEASGKN NVNNINKFRK GLWSPEEDDK LMNYMLNNGQ
 41  GCWSDVARNA GLQRCGKSCR LRWINYLRPD LKRGAFSPQE
 81  EEMIIHLHSL LGNRWSQIAA RLPGRTDNEI KNFWNSTIKK
121  RLKNLQSSNA SPNTSDSSSE PSKDVMGGLM STMQEQGIFS
161  MNMDPSMSSS SSLATSMKAM ILNTMMDPLL PMLDYDHGLN
201  MYGGASGYES ITAPPCMAQV GVLNSGDHGF YGEGIFEGIN
241  VEIPPLESVS CMEENAKTQN IQDNNTDKYS YSSPVNSLYH
281  KNCNITSNNK TDSIAADQMG NLWHGSEELK VGEWDLEELM
321  KDVSAFPFLD FQ
```

For example, a comparison between a portion of the *Arabidopsis thaliana* MYB46 amino acid sequence with SEQ ID NO:1 and a portion of the from *Populus trichocarpa* (poplar) amino acid sequence with SEQ ID NO:40 is shown below, indicating that these two sequences have at least 66% sequence identity in this region.

```
Seq1    1  MRKPEVAIAASTHQVKKMKKGLWSPEEDSKLMQYMLSNGQGCWSDVAKNAGLQRCGKSCR
Seq40   1  MRKPEASGKNNVNNINKFRKGLWSPEEDDKLMNYMLNNGQGCWSDVARNAGLQRCGKSCR
           *****        *  ********* ***  ***  ********** ************

Seq1   61  LRWINYLRPDLKRGAFSPQEEDLIIRFHSILGNRWSQIAARLPGRTDNEIKNFWNSTIKK
Seq40  51  LRWINYLRPDLKRGAFSPQEEEMIIHLHSLLGNRWSQIAARLPGRTDNEIKNFWNSTIKK
           *********************  **  ** **********************************

Seq1  121  RLKKMSDTSNLINNSSSSPNTASDSSSNSASSLDIKDIIGSFM
Seq40 121  RLKNLQSSNASPNTSDSSSEPSKDVMGGLMSTMQEQGIFSMNM
           ***           * * **       *      *    *  *
```

As illustrated for example, the *Populus trichocarpa* (poplar) MYB21 protein with SEQ ID NO:40 has a serine at about position 138 (in bold and underlined above) that can be phosphorylated. This serine at position 138 (S138) can be modified to improve the stability of this *Populus trichocarpa* (poplar) MYB21. Such a modification can include replacement of the serine with an amino acid that is not a serine, threonine, aspartic acid, or glutamic acid. In other cases, a modified *Arabidopsis thaliana* MYB46 such as one with SEQ ID NO:1 may be used instead of the MYB21 with SEQ ID NO:40.

An MYB46 transcription factor from *Vitis vinifera* (grapevine) has the following sequence (SEQ ID NO:41), with potential phosphorylation sites that can be modified identified in bold with underlining.

```
  1  MRKPDLMGKD RVLINNNIAN NNNKNNNNKL RKGLWSPEED
 41  EKLMSYMLRN GQGCWSDIAR NAGLQRCGKS CRLRWINYLR
 81  PDLKRGAFSP QEEELIIHLH SILGNRWSQI AARLPGRTDN
121  EIKNFWNSTI KKRLKNSLQT HSPNDCHDSS LEPRVVVDNI
161  NAMGMGVGGS SGMLLSMHEH EMMNMYMDSS SSSFSSMNTM
201  LTSNHLDNPF PLLDNRHDQM VFSLPNCMAK PEMTDEFDGR
241  YGVTGGGNMG VEREISIPGS QSNSTTEENN GATQNEYYTI
281  DMKNNNSKVE ESDNIFGVGN HWQGENMGIG EWDLEGLLEN
321  ASSFPFLDFQ LQ
```

For example, a comparison between a portion of the *Arabidopsis thaliana* MYB46 amino acid sequence with SEQ ID NO:1 and a portion of the from *Vitis vinifera* (grapevine) amino acid sequence with SEQ ID NO:41 is shown below, indicating that these two sequences have at least 67% sequence identity in this region.

```
Seq1  17  KMKKGLWSPEEDSKLMQYMLSNGQGCWSDVAKNAGLQRCGKSCRLRWINYLRPDLKRGAF
Seq41 29  KLRKGLWSPEEDEKLMSYMLRNGQGCWSDIARNAGLQRCGKSCRLRWINYLRPDLKRGAF
          *  *********  *** *** *******  *************************** 
```

```
Seq1   77  SPQEEDLIIRFHSILGNRWSQIAARLPGRTDNEIKNFWNSTIKKRLKKMSDTSNLINNSS
Seq41  89  SPQEEELIIHLHSILGNRWSQIAARLPGRTDNEIKNFWNSTIKKRLKNSLQTHSPNDCHD
           *****  ***  ****************************       *

Seq1   137 SSPNTASDSSSNSASSLDIKDIIGSFMSLQEQGFVN
Seq41  149 SSLEPRVVVDNINAMGMGVGGSSGMLLSMHEHEMNN
           **         *      *    *  *   *
```

As illustrated by this example, the *Vitis vinifera* (grapevine) MYB46 protein with SEQ ID NO:41 has a serine at about position 150 (in bold and underlined above) that can be phosphorylated. This serine at position 150 (S150) can be modified to improve the stability of this *Vitis vinifera* (grapevine) MYB46. Such a modification can include replacement of the serine with an amino acid that is not a serine, threonine, aspartic acid, or glutamic acid. In other cases, a modified *Arabidopsis thaliana* MYB46 such as one with SEQ ID NO: 1 may be used instead of the MYB46 with SEQ ID NO:41.

An MYB46 transcription factor from *Medicago truncatula* (alfalfa) has the following sequence (SEQ ID NO:42), with potential phosphorylation sites that can be modified identified in bold with underlining.

```
  1 MRKPDIASGK NNTNNKLRKG LWSPEEDEKL MNYMLNSGQG

41 CWSDVARNAG LQRCGKSCRL RWINYLRPDL KRGAFSPQEE

81 EHIIHLHSLL GNRWSQIAAR LPGRTDNEIK NFWNSTIKKR

121 LKNMSLNTSP NASDESSYDP NKDHNMGGFI TSSTQDQQHI

161 DNHFMPMFNT SSPSPPTMQN TVFNTIMSGS GCGFFNNSTT

201 GTYLSQNNHD SKSFYLEKVF GSVNIINGVE GDEMEIYNVP

241 PLESVNSTIT SEHSVKMENA CNGEDGNYNS SYNFDDINNI

281 VINNCNVVSK RSENRVDDEV ENLFHGDLSV GDWNLEDLMK

321 DVSSFPFLDF SN
```

For example, a comparison between a portion of the *Arabidopsis thaliana* MYB46 amino acid sequence with SEQ ID NO:1 and a portion of the from *Medicago truncatula* (alfalfa) amino acid sequence with SEQ ID NO:42 is shown below, indicating that these two sequences have at least 75% sequence identity in this region.

```
Seq1    1 MRKPEVAIAASTHQVKKMKKGLWSPEEDSKLMQYMLSNGQGCWSDVAKNAGLQRCGKSCR
Seq42   1 MRKPDIA-SGKNNTNNKLRKGLWSPEEDEKLMNYMLNSGQGCWSDVARNAGLQRCGKSCR
          ****  *       *  ********* ***  ********  ************

Seq1   61 LRWINYLRPDLKRGAFSPQEEDLIIRFHSILGNRWSQIAARLPGRTDNEIKNFWNSTIKK
Seq42  60 LRWINYLRPDLKRGAFSPQEEEHIIHLHSLLGNRWSQIAARLPGRTDNEIKNFWNSTIKK
          *********************  **  ** *****************************

Seq1  121 RLKKMS--DTSNLINNSSSSPN
Seq42 120 RLKNMSLNTSPNASDESSYDPN
          *** **    *    ** **
```

As illustrated by this example, the *Medicago truncatula* (alfalfa) MYB46 protein with SEQ ID NO:42 has serines at about positions 136 and 137 (in bold and underlined above) that can be phosphorylated.

Another comparison between a portion of the *Arabidopsis thaliana* MYB46 amino acid sequence with SEQ ID NO:1 and a portion of the *Medicago truncatula* (alfalfa) amino acid sequence with SEQ ID NO:42 is shown below, indicating that these two sequences have at least 26% sequence identity in this region.

```
Seq1  182 NPFPTGNMISHPCNDDFTPYVDGIYG SEQ ID NO: 43
Seq42 196 NNSTTGTYLSQNNHDSKSFYLEKVFG SEQ ID NO: 44
            *  **   *    *   *      *
```

As illustrated by this example, the *Medicago truncatula* (alfalfa) MYB46 protein with SEQ ID NO:42 has a serine at about position 213 (in bold and underlined above) that can be phosphorylated.

The serines at positions 136, 137 and 213 (S136, S137, and S213) can be modified to improve the stability of this *Medicago truncatula* (alfalfa) MYB46. Such a modification can include replacement of the serines with amino acids that are not serine, threonine, aspartic acid, or glutamic acid. In other cases, a modified *Arabidopsis thaliana* MYB46 such as one with SEQ ID NO:1 may be used instead of the MYB46 with SEQ ID NO:42.

An MYB46 transcription factor from *Glycine max* (soybean) has the following sequence (SEQ ID NO:45), with potential phosphorylation sites that can be modified identified in bold with underlining.

```
  1 MRKPEVSGNN NNNNNINNKL RKGLWSPEED DKLMNYMLNS

41 GQGCWSDVAR NAGLQRCGKS CRLRWINYLR PDLKRGAFSQ

81 QEEELIIHLH SLLGNRWSQI AARLPGRTDN EIKNFWNSTI

121 KKRLKNMSSN TSPNGSESSY EPNNRDLNMA GFTTSNTQDQ

161 QHADFMPMFN SSSQSPSMHA MVLNSIIDRL PMLEHGLNMP

201 CSGGFFNSTG PCFSSSQSGV DNKGIYLENG GVFGSVNIGA

241 EGDVYVPPLE SVSTTSDHNL KVESTCNTDT NNSYFDDINS
```

-continued
```
281 ILLNNCNINS NNKRAENRAG GVENLFQEEL TIGEWDLEEL

321 MKDVSSFPFL DFSNIQ
```

For example, a comparison between a portion of the *Arabidopsis thaliana* MYB46 amino acid sequence with SEQ ID NO:1 and a portion of the from *Glycine max* (soybean) amino acid sequence with SEQ ID NO:45 is shown below, indicating that these two sequences have at least 59% sequence identity in this region.

```
Seq1      1  MRKPEVAIAASTHQV--KKMKKGLWSPEEDSKLMQYMLSNGQGCWSDVAKNAGLQRCGKS
Seq45     1  MPKPEVSGNNNNNNNINNKLRKGLWSPEEDDKLMNYMLNSGQGCWSDVARNAGLQRCGKS
             ******         * ********* *** *** ********* **********

Seq1     59  CRLRWINYLRPDLKRGAFSPQEEDLIIRFHSILGNRWSQIAARLPGRTDNEIKNFWNSTI
Seq45    61  CRLRWINYLRPDLKRGAFSQQEEELIIHLHSLLGNRWSQIAARLPGRTDNEIKNFWNSTI
             ******************  *** ***  ** ****************************

Seq1    119  KKRLKKMS-DTSNLINNSSSSPNTASDSSSNSASSLDIKDIIGSFMSLQEQGFVNPSLTH
Seq45   121  KKRLKNMSSNTSPNGSESSYEPNNRDLNMAGFTTSNTQDQQHADFMPMFNSSSQSPSMHA
             ***** **  **    ** **        *         **         **     **

Seq1    178  IQTNNPFPTGNMISHPCN
Seq45   181  MVLNSIIDRLPMLEHGLN
                *       *   *
```

As illustrated, the *Glycine max* (soybean) MYB46 with SEQ ID NO: 45 has a potential MPK binding site (underlined above) and serines at about positions 138 and 139, and it has a glutamic acid at position 141, where position 141 appears to correspond to position 138 in the *Arabidopsis* MYB46 (SEQ ID NO:1). However, like the *Arabidopsis* mutant MYB46$138D, the *Glycine max* (soybean) MYB46 with a glutamic acid at position 141 in SEQ ID NO:45 may be unstable and prone to degradation. Hence, in some cases positions 138, 139 and/or 141 of the *Glycine max* (soybean) MYB46 with SEQ ID NO: 45 can be modified. Such a modification can include replacement of the serines with amino acids that are not serine, threonine, aspartic acid, or glutamic acid. In other cases, the *Glycine max* (soybean) MYB46 with SEQ ID NO:45 is not used. For example, a modified *Arabidopsis thaliana* MYB46 with SEQ ID NO:1 may be used instead of the MYB46 with SEQ ID NO:45, An MYB46 transcription factor from *Sorghum bicolor* has the following sequence (SEQ ID NO:46), with potential phosphorylation sites that can be modified identified in bold with underlining.

```
  1 MRKPECPAAA NSGNAGGAAA ATKLRKGLWS PEEDERLVAY
 41 MLRSGQGSWS DVARNAGLQR CGKSCRLRWI NYLRPDLKRG
 81 AFSPQEEELI VSLHAILGNR WSQIAARLPG RTDNEIKNFW
121 NSTIKKRLKN TSATSSPAAT ECASPEPNNK VAAGSCPDLA
161 GLDHQDGGHH HHHHLMTTTT TGLWMVDSSS SCTSSTSPMH
201 QRQPPPTTAI MAAAAVAATR SYGGLVPFPD QLRGVMADAS
241 PPGRFFHGHA APPFKHQVAA LHHGGFYGST PPHHHGMMAT
281 MEGGGCFMRG EDMFVGVVPP LLDPMSAAAQ EQEQGQQGLM
321 ASSGSNNAKN NNNSNNTTET TTTTTLSNNE SNITENNTNT
361 KDNINTISQV NNGSNVAAVF WEGAHQQYMS RNVMHGEWDL
401 EELMKDVSSL PFLDFQVE
```

For example, a comparison between a portion of the *Arabidopsis thaliana* MYB46 amino acid sequence with SEQ ID NO: I and a portion of the from *Sorghum bicolor* amino acid sequence with SEQ ID NO:46 is shown below, indicating that these two sequences have at least 72% sequence identity in this region.

```
Seq1    17  KMKKGLWSPEEDSKLMQYMLSNGQGCWSDVAKNAGLQRCGKSCRLPWINYLRPDLKRGAF
Seq46   23  KLRKGLWSPEEDERLVAYMLRSGQGSWSDVARNAGLQRCGKSCRLRWINYLRPDLKRGAF
            * *********  *** *** ***** ***** ********** **************

Seq1    77  SPQEEDLIIRFHSILGNRWSQIAARLPGRTDNEIKNFWNSTIKKRLKKMSDTSNLINNSS
Seq46   83  SPQEELIVSLHAILGNRWSQIAARLPGRTDNEIKNFWNSTIKKRLKNTSATSSPAATEC
            ***** **   * ******************************** *  **

Seq1   137  SSPNTASDSSSNSASSL
Seq46  143  ASPEPNNKVAAGSCPDL
             **       *   *
```

As illustrated by this example, the *Sorghum bicolor* MYB46 protein with SEQ ID NO:46 has a serine at about position 144 (in bold and underlined above) that can be phosphorylated. Such a modification can include replacement of the serine with an amino acid that are not serine, threonine, aspartic acid, or glutamic acid.

An MYB46 transcription factor from *Hordeum vulgare* (barley) has the following sequence (SEQ ID NO:47), with potential phosphorylation sites that can be modified identified in bold with underlining.

```
  1 MRKPVECPAT KCSGGVAPGN SNVAAAAAKL RKGLWSPEED
 41 ERLVAYMLRS GQGSWSDVAR NAGLQRCGKS CRLRWINYLR
 81 PDLKRGAFSP HEEDLIVNLH AILGNRWSQI AARLPGRTDN
121 EIKNFWNSTI KKRLKMNSAA SSPATTECAS PPEPNLDGGS
161 ASCLDLTSQE DGSHHAMKSM WMDSSSSSSS SSSMQQGSRP
201 STMAPAANRG YGGLLLPLPD QVCGVAPSTH TSLPPFFQDH
241 SSFKQVSPLR TGGYYPHGMA MEGAGGCFMG EEAVGGGGER
281 SVVFNVPPLL TPMAVALQDQ TLMASTGNSN NNHRNTNSTA
321 EGTTLSSKNG CNINDDNTSK NNINSVVSYW EQHGQQQHMS
361 RNVVMGEWDL EELMKDVSCL PFLDFQVE
```

For example, a comparison between a portion of the *Arabidopsis thaliana* MYB46 amino acid sequence with SEQ ID NO:1 and a portion of the from *Hordeum vulgare* (barley) amino acid sequence with SEQ ID NO:47 is shown below, indicating that these two sequences have at least 72% sequence identity in this region.

```
Seq1    17  KMKKGLWSPEEDSKLMQYMLSNGQGCWSDVAKNAGLQRCGKSCRLRWINYLRPDLKRGAF
Seq47   29  KLRKGLWSPEEDERLVAYMLRSGQGSWSDVARNAGLQRCGKSCRLRWINYLRPDLKRGAF
            * ********* * *** *** ***** ********************************

Seq1    77  SPQEEDLIIRFHSILGNRWSQIAARLPGRTDNEIKNFWNSTIKKRLKKMSDTSNLINNSS
Seq47   89  SPHEEDLIVNLHAILGNRWSQIAARLPGRTDNEIKNFWNSTIKKRLKMNSAASSPATTEC
            ** *****  * ***********************************  *   *

Seq1   137  SSPNTASDSSSNSASSLDI
Seq47  149  ASP-PEPNLDGGSASCLDL
            **       ***  **
```

As illustrated by this example, the *Hordeum vulgare* (barley) MYB46 protein with SEQ ID NO:47 has a serine at about position 150 (in bold and underlined above) that can be phosphorylated. Such a modification can include replacement of the serine with an amino acid that are not serine, threonine, aspartic acid, or glutamic acid.

An MYB46 transcription factor from *Brachypodium distachyon* has the following sequence (SEQ ID NO:48), with potential phosphorylation sites that can be modified identified in bold with underlining.

```
  1  MGAEAECDRI  KGPWSPEEDE  ALRRLVERHG  ARNWTAIGRG
 41  IPGRSGKSCR  LRWCNQLSPQ  VERRPFTAEE  DASILRAHAR
 81  LGNRWAAIAR  LLPGRTDNAV  KNHWNSSLKR  KLATATAAWE
121  GDAVSGDGSG  SGGESTPPRP  CKRASPGPGP  ESPTGSDRSE
161  LSHGSGQVFR  PVPRAGGFDA  IISADVVRPP  PPRPEEDPLT
201  STSLSLPGLD  QGFHHDSARS  HFQELSPSPR  SPSPPPAQPA
241  YPFSGDLVAA  MQEMIRAEVR  YYLLSSDEVG  MG
```

For example, a comparison between a portion of the *Arabidopsis thaliana* MYB46 amino acid sequence with SEQ ID NO:1 and a portion of the from *Brachypodium distachyon* amino acid sequence with SEQ ID NO:48 is shown below, indicating that these two sequences have at least 31% sequence identity in this region.

```
Seq1   137  SSPNTASDSSSNSASS   (SEQ ID NO: 49)
Seq48  144  ASPGPGPESPTGSDRS   (SEQ ID NO: 50)
            **       *  *  *
```

As illustrated by this example, the *Brachypodium distachyon* MYB46 protein with SEQ ID NO:48 has a serine at about position 145 (in bold and underlined above) that can be phosphorylated. Such a modification can include replacement of the serine with an amino acid that are not serine, threonine, aspartic acid, or glutamic acid.

The nucleic acids, polypeptides, promoters, plants, and seeds, can encode or include transcription factors and promoters that have sequences related to any of the sequences described herein. For example, related nucleic acids can be isolated and identified by mutation of the SEQ ID NO:2, 6, 8, 12, 14, 16, 18, or 21 nucleic acids and/or by examination and modification of amino acid sequence SEQ ID NO:1, 3, 7, 11, 13, 15, 17, 19, 20, 24, 27, 30, 35, 38, 39, 40, 41, 42, 45, 46, 47, or 48. In addition, related nucleic acids can be isolated and identified by hybridization to DNA and/or RNA isolated from other plant species using any of the SEQ ID NO:2, 6, 8, 12, 14, 16, 18, or 21 nucleic acids (or portions thereof) as probes.

In some embodiments, the related nucleic acids and proteins are identified by hybridization of any of SEQ ID NO:2, 6, 8, 12, 14, 16, 18, or 21 nucleic acids (or portions thereof) as probes under stringent hybridization conditions. The terms "stringent conditions" or "stringent hybridization conditions" include conditions under which a probe will hybridize to its target sequence to a detectably greater degree than other sequences (e.g., at least 2-fold over background). Stringent conditions are somewhat sequence-dependent and can vary in different circumstances. By controlling the stringency of the hybridization and/or washing conditions, target sequences can be identified with up to 100% complementarity to the probe (homologous probing). Alternatively, stringency conditions can be adjusted to allow some mismatching in sequences so that lower degrees of sequence similarity are detected (heterologous probing). The probe can be approximately 20-500 nucleotides in length, but can vary greatly in length from about 18 nucleotides to equal to the entire length of the target sequence. In some embodiments, the probe is about 10-50 nucleotides in length, or about 18-25 nucleotides in length, or about 18-50 nucleotides in length, or about 18-100 nucleotides in length.

Typically, stringent conditions will be those where the salt concentration is less than about 1.5 M Na ion (or salts thereof), typically about 0.01 to 1.0 M Na (sodium) ion concentration (or salts thereof), at pH 7.0 to 8.3 and the temperature is at least about 30° C. for shorter probes (e.g., 10 to 50 nucleotides), and at least about 60° C. for longer probes (e.g., greater than 50 nucleotides). Stringent conditions may also be achieved with the addition of destabilizing agents such as formamide or Denhardt's solution. Exemplary low stringency conditions include hybridization with a buffer solution of 30 to 35% formamide, 1M NaCl, 1% SDS (sodium dodecyl sulfate) at 37° C., and a wash in 1×SSC to 2×SSC (where 20×SSC is 0.0 M NaCl, 0.3 M trisodium citrate) at 50 to 55° C. Exemplary moderate stringency conditions include hybridization in 40 to 45% formamide, 1M NaCl, 1% SDS at 37° C., and a wash in 0.5×SSC to 1×SSC at 55 to 60° C. Exemplary high stringency conditions include hybridization in 50% formamide, 1M NaCl, 1% SDS at 37° C., and a wash in 0.1×SSC at 60 to 65° C. Specificity is typically a function of post-hybridization washes, where the factors controlling hybridization include the ionic strength and temperature of the final wash solution.

For DNA-DNA hybrids, the $T_m$ can be approximated from the equation of Meinkoth and Wahl (Anal. Biochem. 138: 267-84 (1984));

$$T_m = 81.5° C. + 16.6(\log M) + 0.41(\% \text{ GC}) - 0.61(\% \text{ formamide}) - 500/L$$

where M is the molarity of monovalent cations; % GC is the percentage of guanosine and cytosine nucleotides in the DNA, % formamide is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. The $T_m$ is reduced by about 1° C. for each 1% of mismatching. Thus, the $T_m$, hybridization and/or wash conditions can be adjusted to hybridize to sequences of the desired sequence identity. For example, if sequences with greater than or equal to 90% sequence identity are sought, the $T_m$ can be decreased 10° C. Generally, stringent conditions are selected to be about 5° C. lower than the thermal melting point $(T_m)$ for the specific sequence and its complement at a defined ionic strength and pH. However, severely stringent conditions can include hybridization and/or a wash at 1, 2, 3 or 4° C. lower than the thermal melting point $(T_m)$. Moderately stringent conditions can include hybridization and/or a wash at 6, 7, 8, 9 or 10° C. lower than the thermal melting point $(T_m)$. Low stringency conditions can include hybridization and/or a wash at 11, 12, 13, 14, 15 or 20° C. lower than the thermal melting point $(T_m)$. Using the equation, hybridization and wash compositions, and a desired $T_m$, those of ordinary skill can identify and isolate nucleic acids with sequences related to any of SEQ ID NO:2, 6, 8, 12, 14, 16, 18, or 21 nucleic acids.

Those of skill in the art also understand how to vary the hybridization and/or wash solutions to isolate desirable nucleic acids. For example, if the desired degree of mismatching results in a $T_m$ of less than 45° C. (aqueous solution) or 32° C. (formamide solution) it is preferred to increase the SSC concentration so that a higher temperature can be used.

An extensive guide to the hybridization of nucleic acids is found in Tijssen, LABORATORY TECHNIQUES IN BIOCHEMISTRY AND MOLECULAR BIOLOGY—HYBRIDIZATION WITH NUCLEIC ACID PROBES, part I, chapter 2, "Overview of principles of hybridization and the strategy of nucleic acid probe assays," Elsevier, N.Y. (1993); and in CURRENT PROTOCOLS IN MOLECULAR BIOLOGY, chapter 2, Ausubel, et al., eds, Greene Publishing and Wiley-Interscience, New York (1995).

For example, high stringency can be defined as hybridization in 4×SSC, 5×Denhardt's (5 g Ficoll, 5 g polyvinylpyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C. However, the stringency of hybridization is actually determined by the wash conditions. Thus, wash conditions in 0.1×SSC, 0.1% SDS at 65° C. are a sufficient definition of stringent hybridization conditions.

Such selective hybridization substantially excludes non-target nucleic acids. Selectively hybridizing sequences typically have about at least 40% sequence identity, at least about 50% sequence identity, at least 55% sequence identity, at least about 60% sequence identity, at least 70% sequence identity, at least about 80% sequence identity, at least about 90% sequence identity, at least about 95% sequence identity, at least 96% sequence identity, at least about 97% sequence identity, at least 98% sequence identity, at least about 99% sequence identity, or 40-95% sequence identity, or 50-95% sequence identity, or 60-90% sequence identity, or 90-95% sequence identity, or 95-97% sequence identity, or 98-99% sequence identity, or 100% sequence identity or complementarity with any of the SEQ ID NO:2, 6, 8, 12, 14, 16, 18, or 21 nucleic acids.

The nucleic acids of the invention include those with about 500 of the same nucleotides as any of SEQ ID NO:2, 6, 8, 12, 14, 16, 18, or 21 nucleic acids, or about 600 of the same nucleotides, or about 700 of the same nucleotides, or about 800 of the same nucleotides, or about 900 of the same nucleotides, or about 1000 of the same nucleotides, or about 1100 of the same nucleotides, or about 1200 of the same nucleotides, or about 500-1200 of the same nucleotides. The identical nucleotides or amino acids can be distributed throughout the nucleic acid, and need not be contiguous.

The transcription factor polypeptides of the invention include those with about 50 of the same amino acids as any of SEQ ID NO:1, 3, 7, 11, 13, 15, 17, 19, 20, 24, 27, 30, 35, 38, 39, 40, 41, 42, 45, 46, 47, or 48 polypeptides, or about 60 of the same amino acids, or about 70 of the same amino acids, or about 80 of the same amino acids, or about 90 of the same amino acids, or about 100 of the same amino acids, or about 110 of the same amino acids, or about 120 of the same amino acids, or about 130 of the same amino acids, or about 140 of the same amino acids, or about 150 of the same amino acids, or about 50-80 of the same amino acids, or about 150-300 of the same amino acids as any of any of SEQ ID NO:1, 3, 7, 11, 13, 15, 17, 19, 20, 24, 27, 30, 35, 38, 39, 40, 41, 42, 45, 46, 47, or 48 polypeptides. The identical amino acids can be distributed throughout the nucleic acid, and need not be contiguous.

The transcription factor polypeptides have about at least 40% sequence identity, at least about 50% sequence identity, at least 50% sequence identity, at least about 60% sequence identity, at least 70% sequence identity, at least about 80% sequence identity, at least 90% sequence identity, at least about 95% sequence identity, at least about 96% sequence identity, at least 97% sequence identity, at least about 98% sequence identity, at least 99% sequence identity, or 40-95% sequence identity, or 50-95% sequence identity, or 60-90% sequence identity, or 90-95% sequence identity, or 90-99% sequence identity, or 95-97% sequence identity, or 98-99% sequence identity, or 100% sequence identity with any of the SEQ ID NO:1, 3, 7, 11, 13, 15, 17, 19, 20, 24, 27, 30, 35, 38, 39, 40, 41, 42, 45, 46, 47, or 48 polypeptides.

Note that if a value of a variable that is necessarily an integer, e.g., the number of nucleotides or amino acids in a nucleic acid or protein, is described as a range, e.g., or 90-99% sequence identity, what is meant is that the value can be any integer between 90 and 99 inclusive, i.e., 90-99% sequence identity means any of 90, 91, 92, 93, 94, 95, 96, 97, 98 or 99% sequence identity.

Plants Modified to Contain Transcription Factors

To engineer plants that express stable MYB46 transcription factors, one of skill in the art can introduce transcription factors or nucleic acids encoding transcription factors into the plants. Any of the MYB46 and related nucleic acid sequences described herein can be incorporated into the expression cassettes, plants and seeds described herein.

In some embodiments, one of skill in the art could inject transcription factors or nucleic acids encoding such transcription factors into young plants, or into selected regions of plants. Alternatively, one of skill in the art can generate genetically-modified plants that contain nucleic acids encoding transcription factors within their somatic and/or germ cells. For example, any of the transcription factors nucleic acids described herein can be operably linked to a selected promoter (e.g., a heterologous promoter), to generate an expression cassette that can be used to generate transgenic plants and/or seeds. Examples of transcription factor coding regions that can be used in such expression cassettes include any nucleic acid with a sequence such SEQ ID NO:2, 6, 8, 12, 14, 16, 18, 21, or any combination thereof. The expression cassettes can be introduced into plants to increase the stability of MYB46 within the plant's tissues.

To facilitate expression of a coding region of interest, a separate expression cassette can be made that encodes any of the MYB46 and related transcription factors. Expression of any of these transcription factors can increase the expression of the selected MYB46. The genetic modifications involved can be accomplished by any convenient procedure. For example, one of skill in the art can prepare an expression cassette or expression vector that can express one or more encoded transcription factors.

Plant cells can be transformed by the expression cassettes or expression vector, and whole plants (and their seeds) can be generated from the plant cells that were successfully transformed with an expression cassette or expression vector that includes a promoter operably linked to a nucleic acid encoding the transcription factor. Some procedures for making such genetically modified plants and their seeds are described in more detail below.

Heterologous Promoters: The transcription factor nucleic acids (e.g., any of those encoding MYB46 or related proteins) can be operably linked to a promoter, such as a heterologous promoter, which provides for expression of snRNA encoding the transcription factors. The heterologous promoter employed is typically a promoter functional in plants and/or seeds, and can be a promoter functional during plant growth and development. The heterologous promoter is a promoter that is not operably linked to MYB46 or a related protein in nature. A transcription factor nucleic acid is operably linked to the promoter when it is located downstream from the promoter, so that the promoter is configured to express the transcription factor.

Promoters regulate gene expression. Promoter regions are typically found in the flanking DNA upstream from the coding sequence in both prokaryotic and eukaryotic cells. A promoter sequence provides for regulation of transcription of the downstream gene sequence and typically includes from about 50 to about 2,000 nucleotide base pairs. Promoter sequences can also contain regulatory sequences such as enhancer sequences that can influence the level of gene expression. Some isolated promoter sequences can provide for gene expression of heterologous DNAs, that is a DNA different from the native or homologous DNA.

Promoter sequences can be strong or weak, or inducible. A strong promoter provides for a high level of gene expression, whereas a weak promoter provides for a very low level of gene expression. An inducible promoter is a promoter that provides for the turning on and off gene expression in response to an exogenously added agent, or to an environmental or developmental stimulus. For example, expression can be stimulated from an inducible promoter by factors such as alcohol, acetaldehyde, antibiotics (e.g., tetracycline), steroids, metals and other compounds. An environmentally inducible promoter can induce expression of a gene in response to environmental stimuli such as drought, cold, heat, longer exposure to light, or shorter exposure to light. A bacterial promoter such as the $P_{tac}$ promoter can be induced to vary levels of gene expression depending on the level of isothiopropylgalactoside added to the transformed cells. Steroid inducible promoters have also been employed in plants. Dexamethasone-inducible promoters are activated by introduction of dexamethasone to a cell, tissue, cell culture, or tissue culture. The alc promoter system from the filamentous fungi *Aspergillus nidulans* can be induced by alcohol (e.g., ethanol) or acetaldehyde (see, e.g., Schaarschinidt et al., Plant & Cell Physiol 45(11): 1566-77 (2004). The nopaline synthase (nos) promoter is inducible by hydrogen peroxide and/or methyl jasmonate (see, e.g., Sai & An, *Plant Physiol.* 109(4): 1191-97 (1995)).

Examples of developing xylem-specific (DX) promoter sequences include the following.

```
>DX15 PromoTer (1025 bp)
                                                  (SEQ ID NO: 51)
TTCCCCCTTTTGGTTCAATGCCTTTTATTCTTCCAAAATTATTTCATATTTTGTATC

CGGAGGACATATTTGTTTCAAAAGGTGTCAGAAAATCAAAGCCCATTGAAAATATAT

AAACATATATAGATATAAAAACTCAAGGGTTCATTCCAAAATATAAGAACAAACTGA

TTGAATTAATTTGTTATTTTAAGAACACTGTCTATATGTTTATATAGTGGGAGGTAG

TGTTTTTTAAATCATATACTAACTTATTATAAAAATAAATCATAAAAAAGGAACCTC

AAGCATCCCCTGGTAAGCTCGTATGTAGGAATACTCGGAGATCAAATGTCCGAATGT

CAAATGTTAAGGCAAGTGAAATATCCCTGACTTTTTAGCAAGCAAATTGTTGAGTAG

CTAAAATGAATTATTTTAATATTTTTAAATCATTTTAATATATTAATATTAAAAAAA

ATTAAATATTTTTTTAATACATTTTCAATAACAAACACTTTAAAATATAATCTTTG

TCACACTCTTAAACAGTAACAGCAGAAAGCATATGTGAGTGATATAGCTATAGTTGC

TGTTTGACACGGACAATCTCCATCTAAATTCATGAATAATAAAGTTTTGCCTACACA

CCCACTTGAAATCTCCTCCTAGTTTTCCTGATTTGCCATGCTAACTACAAGAACAAG

ATGCTAGCTAGTATCTTGTTCTGTCTCTCGCTCTCTCTATCTCTCCAGTTGATAG

TTGATAGTTGATAGTTGATAGCTGATACCCTCCCACCTTTCCCAGAAAGATGATTGA

GGAACTAGTCACTGTGTTCGTGTAACTAATACTGTTCATGGCACCTAACTTGATCCT

CTCTTCACCAGACCACTATAAAAACCCTATCTGTCCTCCTCATAATCATATCACTAC

ACCCAACACTTCTGCAAGCACAACTCCATTCAAGAACATCAAGAGTATAGGCCGCCG

CTGCAACAAAACAGCACTCCTAGCTACTTCAAGATGAGGCCACAATCTTTCATCTT
```

>DX5PromoTer (1940 bp)

(SEQ ID NO: 52)

<u>GGGGCAGATGATACCTTGATACTT</u>GGACTAGGAATATTCAAAGGAGAAAATATTGAT

GTGTATATTTGTACTTAATTATGCACATCTCTTTCACTTTATGCTGTAAGCTGGCAG

TATACAACACAAGAACGGTCTTTATACTTTGATTTTCTTTTCTCATAAGAAGGTAGA

TAATTGGCTTTTAACTGAAATGAATATTGCTTCAGTTAGAGAATATATCAAGTATCG

TAAAGGGCACCCCAAATTCTTACAGCCTCGTGATGCACGTTTTGTTCTTCAAAATCT

AGGGGAAATTCATTAATTTGAAGGTCGGATCTGTAGGTAGAGTTTCCTTTTTCTTTT

TAATGGAATTTGATGAAAGATACTGTAGCAATAATTTAAAAGGAAATTAAGGAAGTT

CCCGGGTTTTGATGGGGTTTTTCTCGAACTAATTGCGGATTAACCTGAGTTTTTGAA

CGGATTATACCAAATAAATTTCTTCTTATATTTATTGAAATTTAGTCTAATCTAAAT

CCCGGGTTATTCTATCCATTAAATAATGAAGTAAGTTTAAAAAAAAAGAGTAATAAA

AGACATTAAAGACGAACTATTTATGTGGGAAGTAGACAATTCCATGTAAGAAATTTG

TGTTGTCATTTTTTTTATTAAATTGCTCTCTCTTTTTTAACAGGAATGCTATAATAC

AGGGACATTTATTAATTCAGCTCAATAATCTTTTGGATTTAATTTATTTTTCTTGGA

ACAAGGGGCTGTTACCAAATATGGAGCACTGTGCTTGTGTCATGCATGTAGGTAAGG

GGGGAAAAAACTAAGGAATTTAGCTGAGAAAGAGGTTGTCAATTTACTGTGATAGAT

AGGTTCCTTGCTTTACATGAGAAGTCTACGTGAAGAAATGGAATTATATATTTGGTT

GGACATTGGCTCTCTTAATATTTATTAATTATTATTCCATTTTATCCTGTGATATTA

A<u>ACCTAAC</u>TCCTCTTGAATAATCGGGTTGAATTGATATTTAATTAACTTGATATATC

AAGTATCAAAACTTAATTTGATATTTTTAAAAATAATATTGTTTTGATTTTTTTAA

ATATTGATTTAGATTATTTTTTATAATTTGAATCATAGTTAGATAAATTTTGA<u>GTTA</u>

<u>GG</u>TTTATAATTATTATTTTATTAGTTTCTTTCTTATTTATGTTTTTCAATATTAAG

GAGTTTATACATTAGCTTTGTTCACACTCTAGGTTGACATTGGAGCTGAAATATCTC

TCTCTATGAGGTGGTGAAATAGCTCTCACGCATCAGATTGCCCCATCTCCACTCAAC

CCTAACTAGCCATGATTAATATTTTATTTCTTTTTTTAAAAAAAAATTATTAATCTT

TAAAACTTATTTCAAGAAGAAAAACATGACTTTGGACGGAGTAAAAAGGACCCTAAA

ACTACATTTATTGTCCTACGAGTTTTCATAAGCATCCCATTTACATAAGCACACC<u>AC</u>

<u>CAAAC</u>TTAAGATCCAAGCAACCCTAAAATTTTCCTTTCTTTGCAACATACTACTACT

ACTGCATTTTTGGAAATTACACCATATTTTGATTTTTTAGGTATACTTTTCTCTCTC

TCTCTCTCTCTCTCTCCTGAGAAAGGACAAAGAGGTGGTAGGGGGAGGGGGG

AGGAGAGGAGAGGAGAGTGTGCATGTTGTCTCATGCAAAAGTGGAGGAGAATTTAAT

TCCTTCCCTACCCTAAAGATCAAGAGCTATCTATGTCTTGAAGAGAGACAATACATG

CTTTAGAAGGAGACAAATTGCTTTTCCTTCTTTTCTTTTAAGCCCTTCGTGTCTCTC

TTCCACACACACACACGCATCATACATAGTCTTTGTCTATTTTTGGAGTAGCAGTTG

TCGAGGGAGAGAGCAAGAAAGAAAGGTGTGCAATATAT<u>GGGCATAAGAGGAAACCAA</u>

<u>AG</u>

Promoters can therefore also provide for tissue specific or developmental regulation. In some embodiments, an isolated promoter sequence that is a strong promoter for heterologous DNAs is advantageous because it provides for a sufficient level of gene expression for easy detection and selection of transformed cells and provides for a high level of gene expression when desired.

Expression cassettes encoding a transcription factor can include, but are not limited to, a plant promoter such as the CaMV 35S promoter (Odell et al., *Nature*. 313:810-812 (1985)), or others such as CaMV 19S (Lawton et al., *Plant Molecular Biology*. 9:315-324 (1987)), nos (Ebert et al., *Proc. Natl. Acad. Sci. USA*. 84:5745-5749 (1987)), Adh1 (Walker et al., *Proc. Natl. Acad Sci. USA*. 84:6624-6628 (1987)), sucrose synthase (Yang et al., *Proc. Natl. Acad. Sci. USA*. 87:4144-4148 (1990)), α-tubulin, ubiquitin, actin (Wang et al., *Ma Cell. Biol.* 12:3399 (1992)), cab (Sullivan et al., *Mot. Gen. Genet.* 215:431 (1989)), PEPCase (Hudspeth et al., *Plant Molecular Biology*. 12:579-589 (1989)), drought-inducible promoters (e.g., as in U.S. Ser. Nos. 13/821,095 and 14/617,061, which are each incorporated by reference herein in their entireties), GAL4/UAS (Brand & Perrimon, Development 118: 401-15 (1993); and/or those associated with the R gene complex (Chandler et al., *The Plant Cell*. 1:1175-1183 (1989)). Cellulose synthase promoters can also be employed such as CESA4 (cellulose synthase A4), CESA7, CESA8, or a combination thereof. Further suitable promoters include xylem or secondary cell wall promoters such as the poplar xylem-specific secondary cell wall specific cellulose synthase 8 promoter. Other suitable promoters include the cauliflower mosaic virus promoter, the Z10 promoter from a gene encoding a 10 kD zein protein, a Z27 promoter from a gene encoding a 27 kD zein protein, inducible promoters, such as the light inducible promoter derived from the pea rbcS gene (Coruzzi et al., *EMBO J.* 3:1671 (1971)) and the actin promoter from rice (McElroy et al., *The Plant Cell*. 2:163-171 (1990)). Seed specific promoters, such as the phaseolin promoter from beans, may also be used (Sengupta-Gopalan, *Proc. Natl. Acad. Sci. USA*. 83:3320-3324 (1985). Other promoters useful in the practice of the invention are available to those of skill in the art.

Alternatively, novel tissue specific promoter sequences may be employed for the expression of the transcription factor(s). cDNA clones from a particular tissue can be isolated and those clones that are expressed specifically in a tissue of interest are identified, for example, using Northern blotting, quantitative PCR and other available methods. In some embodiments, the gene isolated is not present in a high copy number, but is relatively abundant in specific tissues. The promoter and control elements of corresponding genomic clones can then be identified, isolated and utilized using techniques well known to those of skill in the at.

A transcription factor nucleic acid can be combined with a selected promoter by available methods to yield an expression cassette, for example, as described in Sambrook et al. (MOLECULAR CLONING: A LABORATORY MANUAL, Second Edition (Cold Spring Harbor, NY: Cold Spring Harbor Press (1989); MOLECULAR CLONING: A LABORATORY MANUAL, Third Edition (Cold Spring Harbor, NY: Cold Spring Harbor Press (2000)). Briefly, a plasmid containing a promoter such as the 35S CaMV promoter can be constructed as described in Jefferson (*Plant Molecular Biology Reporter* 5:387-405 (1987)) or obtained from Clontech Lab in Palo Alto, California (e.g., pBI121 or pB1221). Typically, these plasmids are constructed to have multiple cloning sites having specificity for different restriction enzymes downstream from the promoter. The transcription factor nucleic acids can be subcloned downstream from the promoter using restriction enzymes and positioned to ensure that the transcription factor DNA is inserted in proper orientation with respect to the promoter so that the DNA can be expressed. Once the transcription factor nucleic acid is operably linked to a promoter, the expression cassette so formed can be subcloned into a plasmid or other vector (e.g., an expression vector).

In some embodiments, a cDNA encoding a protein with at least 60% sequence identity to any of SEQ ID NO:1, 3, 7, 11, 13, 15, 17, 19, 20, 24, 27, 30, 35, 38, 39, 40, 41, 42, 45, 46, 47, or 48 is obtained or isolated from a selected plant species, and operably linked to a heterologous promoter. The cDNA can be a transcription factor with at least 90% sequence identity to any of SEQ ID NO:1, 3, 7, 11, 13, 15, 17, 19, 20, 24, 27, 30, 35, 38, 39, 40, 41, 42, 45, 46, 47, or 48, A nucleic acid encoding the transcription factor can, for example, be from a fiber-producing species. In some cases, the nucleic acid encoding the transcription factor can be an Arabidopsis, cotton, grass (e.g., miscanthus, switchgrass, and the like), flax, or tree (e.g., poplar, aspen, willow, and the like) species nucleic acid. In other embodiments, cDNA from other species that encode transcription factor proteins are isolated from selected plant tissues, or a nucleic acid encoding a mutant or modified transcription factor protein is prepared by available methods or as described herein. For example, the nucleic acid encoding a mutant or modified transcription factor protein can be any nucleic acid with a coding region that hybridizes to SEQ ID NO:2, 6, 8, 12, 14, 16, 18, or 21 nucleic acids that has been modified to increase the stability of the encoded transcription factor. Using restriction endonucleases, the entire coding sequence for the transcription factor can be subcloned downstream of the promoter in a 5' to 3' sense orientation.

Targeting Sequences: Additionally, expression cassettes can be constructed and employed to target the transcription factors or polypeptides of interest to intracellular compartments within plant cells, or to target the transcription factors or polypeptides of interest for extracellular secretion.

In general, transcription factors bind to plant chromosomal DNA within the nucleus, Therefore, the transcription factor is preferably targeted to the nucleus and not directed to other plant organelles or the extracellular environment. A nuclear localization signal or sequence can be used that includes an amino acid sequences that 'tags' a protein for import into the cell nucleus by nuclear transport. Transcription factors may naturally have such a nuclear localization signal or sequence. Alternatively, a nuclear localization signal or sequence can be operably linked to the transcription factor sequence. Transit peptides act by facilitating the transport of proteins through intracellular membranes, e.g., vacuole, vesicle, plastid and mitochondrial membranes, whereas signal peptides direct proteins through the extracellular membrane. Polypeptides of interest can be operably linked to nuclear localization signals/sequences, to transit peptides or to signal peptides.

Targeting to selected intracellular regions can generally be achieved by joining a DNA sequence encoding a nuclear localization sequence, or a transit peptide or a signal peptide sequence to the coding sequence of the transcription factor or the polypeptide of interest. The resultant nuclear localization sequence (or transit, or signal, peptide) will transport the transcription factor or protein to a particular intracellular (or extracellular) destination. Such sequences (nuclear localization sequences, transit peptides or signal peptides) may be post-translationally removed by cellular enzymes. By facilitating transport of the protein into compartments inside or outside the cell, these sequences can increase the accumulation of a particular gene product in a particular location.

3' Sequences: The expression cassette can also optionally include 3' nontranslated plant regulatory DNA sequences that act as a signal to terminate transcription and allow for the polyadenylation of the resultant mRNA. The 3' nontranslated regulatory DNA sequence preferably includes from about 300 to 1,000 nucleotide base pairs and contains plant transcriptional and translational termination sequences. For example, 3' elements that can be used include those derived from the nopaline synthase gene of *Agrobacterium tumefaciens* (Bevan et al., *Nucleic Acid Research.* 11:369-385 (1983)), or the terminator sequences for the T7 transcript from the octopine synthase gene of *Agrobacterium tumefaciens*, and/or the 3' end of the protease inhibitor I or II genes from potato or tomato. Other 3' elements known to those of skill in the art can also be employed. These 3' nontranslated regulatory sequences can be obtained as described in An (*Methods in Enzymology.* 153:292 (1987)). Many such 3' nontranslated regulatory sequences are already present in plasmids available from commercial sources such as Clontech, Palo Alto, California The 3' nontranslated regulatory sequences can be operably linked to the 3' terminus of the transcription factor or other polypeptide nucleic acids by standard methods.

Selectable and Screenable Marker Sequences: To improve identification of transformants, a selectable or screenable marker gene can be employed with the expressible transcription factor or other polypeptide nucleic acids. "Marker genes" are genes that impart a distinct phenotype to cells expressing the marker gene and thus allow such transformed cells to be distinguished from cells that do not have the marker, Such genes may encode either a selectable or screenable marker, depending on whether the marker confers a trait which one can 'select' for the marker by chemical means, i.e., through use of a selective agent (e.g., an herbicide, antibiotic, or the like), or whether marker is simply a trait that one can identify through observation or testing, i.e., by 'screening' the R-locus trait). Many examples of suitable marker genes are known to the art and can be employed in the practice of the invention.

Included within the terms selectable or screenable marker genes are also genes which encode a "secretable marker" whose secretion can be detected as a means of identifying or selecting for transformed cells. Examples include markers which encode a secretable antigen that can be identified by antibody interaction, or secretable enzymes that can be detected by their catalytic activity. Secretable proteins fall into several classes, including small, diffusible proteins detectable, e.g., by ELISA; and proteins that are inserted or trapped in the cell wall (e.g., proteins that include a leader sequence such as that found in the expression unit of extensin or tobacco PR-S).

Regarding selectable secretable markers, the use of a gene that encodes a polypeptide that becomes sequestered in the cell wall, where the polypeptide includes a unique epitope may be advantageous. Such a secreted antigen marker can employ an epitope sequence that would provide low background in plant tissue, a promoter-leader sequence that imparts efficient expression and targeting across the plasma membrane, and can produce protein that is bound in the cell wall and yet is accessible to antibodies. A normally secreted wall protein modified to include a unique epitope would satisfy such requirements.

Examples of marker proteins suitable for modification in this manner include extensor or hydroxyproline rich glycoprotein (HPRG). For example, the maize HPRG (Stiefel et al., *The Plant Cell.* 2:785-793 (1990)) is well characterized in terms of molecular biology, expression, and protein structure and therefore can readily be employed. However, any one of a variety of extensins and/or glycine-rich wall proteins (Keller et al., *EMBO J.* 8:1309-1314 (1989)) could be modified by the addition of an antigenic site to create a screenable marker.

Numerous other possible selectable and/or screenable marker genes will be apparent to those of skill in the art in addition to the one set forth herein. Therefore, it will be understood that the following discussion is exemplary rather than exhaustive. In light of the techniques disclosed herein and the general recombinant techniques that are known in the art, the present invention readily allows the introduction of any gene, including marker genes, into a recipient cell to generate a transformed plant cell, e.g., a monocot cell or dicot cell.

Possible selectable markers for use in connection with expression cassettes include, but are not limited to, a neo gene (Potrykus et al., *Mol. Gen. Genet.* 199:183-188 (1985)) which codes for kanamycin resistance and can be selected for using kanamycin, G418, and the like; a bar gene which codes for bialaphos resistance; a gene which encodes an altered EPSP synthase protein (Hinchee et at, *Bio/Technology.* 6:915-922 (1988)) thus conferring glyphosate resistance; a nitrilase gene such as bxn from *Klebsiella ozaenae* which confers resistance to bromoxvnil (Stalker et al., Science. 242:419-423 (1988)); a mutant acetolactate synthase gene (ALS) which confers resistance to imidazolinone, sulfonylurea or other ALS-inhibiting chemicals (European Patent Application 154,204 (1985)); a methotrexate-resistant DHFR gene (Thillet et al., *J. Biol. Chem.* 263:12500-12508 (1988)); a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable chloroplast transit peptide, CTP (European Patent Application 0 218 571 (1987)).

Another selectable marker gene capable of being used in for selection of transformants is the gene that encodes the enzyme phosphinothricin acetyltransferase, such as the bar gene from *Streptomyces hygroscopicus* or the pat gene from *Streptomyces viridochromogenes* (U.S. Pat. No. 5,550,318). The enzyme phosphinothricin acetyl transferase (PAT) inactivates the active ingredient in the herbicide bialaphos, phosphinothricin (PPT). PPT inhibits glutamine synthetase, (Murakami et al., *Mol. Gen. Genet.* 205:42-50 (1986); Twell et al., *Plant Physiol.* 91:1270-1274 (1989)) causing rapid accumulation of ammonia and cell death. The success in using this selective system in conjunction with monocots was surprising because of the major difficulties that have been reported in transformation of cereals (Potrykus, *Trends Biotech.* 7:269-273 (1989)).

Screenable markers that may be employed include, but are not limited to, a β-glucuronidase or uidA gene (GUS) that encodes an enzyme for which various chromogenic substrates are known; an R-locus gene, which encodes a product that regulates the production of anthocyanin pigments (red color) in plant tissues (Dellaporta et al., In: *Chromosome Structure and Function: Impact of New Concepts,* 18th Stadler Genetics Symposium, J. P. Gustafson and R. Appels, eds. (New York: Plenum Press) pp. 263-282 (1988)); a β-lactamase gene (Sutcliffe, *Proc. Natl. Acad. Sci. USA.* 75:3737-3741 (1978)), which encodes an enzyme for which various chromogenic substrates are known (e.g., PAD AC, a chromogenic cephalosporin); a xylE gene (Zukowsky et al., *Proc. Natl. Acad. Sci. USA.* 80:1101 (1983)) which encodes a catechol dioxygenase that can convert chromogenic catechols; an α-amylase gene (Ikuta et al., *Bio/technology* 8:241-242 (1990)); a tyrosinase gene (Katz et al., *J. Gen. Microbiol.* 129:2703-2714 (1983)) which encodes an enzyme capable of oxidizing tyrosine to DOPA and dopaquinone which in turn condenses to form the easily detectable compound melanin; a 3-galactosidase gene, which encodes an enzyme for which there are chromogenic substrates; a luciferase (lux) gene (Ow et al., *Science.* 234:856-859.1986), which allows for bioluminescence detection; or an aequorin gene (Prasher et al., *Biochem. Biophys. Res. Comm.* 126:1259-1268 (1985)), which may be employed in calcium-sensitive bioluminescence detection, or a green or yellow fluorescent protein gene (Niedz et al., *Plant Cell Reports.* 14:403 (1995).

For example, genes from the maize R gene complex can be used as screenable markers. The R gene complex in maize encodes a protein that acts to regulate the production of anthocyanin pigments in most seed and plant tissue. Maize strains can have one, or as many as four, R alleles that combine to regulate pigmentation in a developmental and tissue specific manner. A gene from the R gene complex does not harm the transformed cells. Thus, an R gene introduced into such cells will cause the expression of a red pigment and, if stably incorporated, can be visually scored as a red sector. If a maize line carries dominant alleles for genes encoding the enzymatic intermediates in the anthocyanin biosynthetic pathway (C2, A1, A2, Bz1 and Bz2), but carries a recessive allele at the R locus, transformation of any cell from that line with R will result in red pigment formation. Exemplary lines include Wisconsin 22 that contains the rg-Stadler allele and TR112, a K55 derivative that is r-g, b, Pl. Alternatively any genotype of maize can be utilized if the C1 and R alleles are introduced together.

The R gene regulatory regions can be employed in chimeric constructs to facilitate control of the expression of chimeric genes. More diversity of phenotypic expression is known at the R locus than at any other locus (Coe et al., in *Corn and Corn Improvement*, eds. Sprague, G. F. & Dudley, J. W. (Am. Soc. Agron., Madison, WI), pp. 81-258 (1988)). It is contemplated that regulatory regions obtained from regions 5' to the structural R gene can be useful in directing the expression of genes, e.g., insect resistance, drought resistance, herbicide tolerance or other protein coding regions. For the purposes of the present invention, it is believed that any of the various R gene family members may be successfully employed (e.g., P, S, Lc, etc.). However, one that can be used is Sn (particularly Sn:bol3). Sn is a dominant member of the R gene complex and is functionally similar to the R and B loci in that Sn controls the tissue specific deposition of anthocyanin pigments in certain seedling and plant cells, therefore, its phenotype is similar to R.

A further screenable marker contemplated for use in the present invention is firefly luciferase, encoded by the lux gene. The presence of the lux gene in transformed cells may be detected using, for example, X-ray film, scintillation counting, fluorescent spectrophotometry, low-light video cameras, photon counting cameras or multiwell luminometry. It is also envisioned that this system may be developed for population screening for bioluminescence, such as on tissue culture plates, or even for whole plant screening.

Other Optional Sequences: An expression cassette of the invention can also further comprise plasmid DNA. Plasmid vectors include additional DNA sequences that provide for easy selection, amplification, and transformation of the expression cassette in prokaryotic and eukaryotic cells, e.g., pUC-derived vectors such as pUC8, pUC9, pUC18, pUC19, pUC23, pUC119, and pUC120, pSK-derived vectors, pGEM-derived vectors, pSP-derived vectors, or pBS-derived vectors. The additional DNA sequences include origins of replication to provide for autonomous replication of the vector, additional selectable marker genes (e.g., antibiotic or herbicide resistance),unique multiple cloning sites providing for multiple sites to insert DNA sequences or genes encoded in the expression cassette and sequences that enhance transformation of prokaryotic and eukaryotic cells.

Another vector that is useful for expression in both plant and prokaryotic cells is the binary Ti plasmid (as disclosed in Schilperoort et al., U.S. Pat. No. 4,940,838) as exemplified by vector pGA582. This binary Ti plasmid vector has been previously characterized by An (*Methods in Enzymology.* 153:292 (1987)) and is available from Dr. An. This binary Ti vector can be replicated in prokaryotic bacteria such as *E. coli* and *Agrobacterium*. The *Agrobacterium* plasmid vectors can be used to transfer the expression cassette to dicot plant cells, and under certain conditions to monocot cells, such as rice cells. The binary Ti vectors preferably include the nopaline T DNA right and left borders to provide for efficient plant cell transformation, a selectable marker gene, unique multiple cloning sites in the T border regions, the colE1 replication of origin and a wide host range replicon. The binary Ti vectors carrying an expression cassette of the invention can be used to transform both prokaryotic and eukaryotic cells, but is preferably used to transform dicot plant cells.

In Vitro Screening of Expression Cassettes: Once the expression cassette is constructed and subcloned into a suitable plasmid, it can be screened for the ability to express the transcription factor or the polypeptide of interest. For example, an expression cassette encoding a transcription factor can be screened to ascertain whether it can promote expression of a stable MYB46 protein by methods described herein or other available methods. An expression cassette encoding other polypeptides of interest can be screened to ascertain whether it can promote expression of the polypeptide, for example, by immunological detection of the polypeptide of interest, by detection of the activity of the polypeptide, by hybridization or PCR detection of transcripts encoding the polypeptide, or by other procedures available to those of skill in the art.

DNA Delivery of the DNA Molecules into Host Cells: Transcription factor or other polypeptide encoding nucleic acids can be introduced into host cells by a variety of methods. For example, a preselected cDNA encoding the selected transcription factor or other polypeptide can be introduced into a recipient cell to create a transformed cell by available procedures. The frequency of occurrence of cells taking up exogenous (foreign) DNA may be low. Moreover, it is most likely that not all recipient cells receiving DNA segments or sequences will result in a transformed cell wherein the DNA is stably integrated into the plant genome and/or expressed. Some may show only initial and transient gene expression. However, certain cells from virtually any dicot or monocot species may be stably transformed, and these cells can be regenerated into transgenic plants, through the application of the techniques disclosed herein.

Another aspect of the invention is an isolated plant or plant cell that has one of the transcription factors introduced into the cell, e.g., as a nucleic acid encoding the transcription factor as a protein product. The plant can be a monocotyledon or a dicotyledon. Another aspect of the invention includes plant cells (e.g., embryonic cells or other cell lines) that can regenerate fertile transgenic plants and/or seeds. The cells can be derived from either monocotyledons or dicotyledons. Suitable examples of plant species include fiber producing plants such as cotton, flax, grasses (e.g., miscanthus, switchgrass, and the like), as well as trees such as poplar, aspen, willow, and the like. In some embodiments, the plant or cell is a monocotyledon plant or cell. In some cases, the plant or cell can be a maize plant or cell. The cell(s) may be in a suspension cell culture or may be in an intact plant part, such as an immature embryo, or in a specialized plant tissue, such as callus, such as Type I or Type II callus.

Transformation of the cells of the plant tissue source can be conducted by any one of a number of methods known to those of skill in the art. Examples are: Transformation by direct DNA transfer into plant cells by electroporation (U.S. Pat. Nos. 5,384,253 and 5,472,869, Dekeyser et al., *The Plant Cell.* 2:591-602 (1990)); direct DNA transfer to plant cells by PEG precipitation (Hayashimoto et al., *Plant Physiol.* 93:857-863 (1990)); direct DNA transfer to plant cells by microprojectile bombardment (McCabe et al., *Bio/Technology.* 6:923-926 (1988); Gordon-Kamm et al., *The Plant Cell.* 2:603-618 (1990); U.S. Pat. Nos. 5,489,520; 5,538,877; and 5,538,880) and DNA transfer to plant cells via infection with *Agrobacterium*. Methods such as microprojectile bombardment or electroporation can be carried out with "naked" DNA where the expression cassette may be simply carried on any *E. coli*-derived plasmid cloning vector. In the case of viral vectors, it is desirable that the system retain replication functions, but lack functions for disease induction.

One method for dicot transformation, for example, involves infection of plant cells with *Agrobacterium tumefaciens* using the leaf-disk protocol (Horsch et al., *Science* 227:1229-1231 (1985). Monocots such as *Zea mays* can be transformed via microprojectile bombardment of embryogenic callus tissue or immature embryos, or by electroporation following partial enzymatic degradation of the cell wall with a pectinase-containing enzyme (U.S. Pat. Nos. 5,384,253; and 5,472,869). For example, embryogenic cell lines derived from immature *Zea mays* embryos can be transformed by accelerated particle treatment as described by Gordon-Kamm et al. (*The Plant Cell.* 2:603-618 (1990)) or U.S. Pat. Nos. 5,489,520; 5,538,877 and 5,538,880, cited above. Excised immature embryos can also be used as the target for transformation prior to tissue culture induction, selection and regeneration as described in U.S. application Ser. No. 08/112,245 and PCT publication WO 95/06128. Furthermore, methods for transformation of monocotyledonous plants utilizing *Agrobacterium tumefaciens* have been described by Hiei et al. (European Patent 0 604 662, 1994) and Saito et al. (European Patent 0 672 752, 1995).

Methods such as microprojectile bombardment or electroporation e carried out with "naked" DNA where the expression cassette may be simply carried on any *E. coli*-derived plasmid cloning vector. In the case of viral vectors, it is desirable that the system retain replication functions, but eliminate functions for disease induction.

The choice of plant tissue source for transformation will depend on the nature of the host plant and the transformation protocol. Useful tissue sources include callus, suspension culture cells, protoplasts, leaf segments, stem segments, tassels, pollen, embryos, hypocotyls, tuber segments, meristematic regions, and the like. The tissue source is selected and transformed so that it retains the ability to regenerate whole, fertile plants following transformation, i.e., contains totipotent cells. Type I or Type II embryonic maize callus and immature embryos are preferred *Zea mays* tissue sources. Selection of tissue sources for transformation of monocots is described in detail in U.S. application Ser. No. 08/112,245 and PCT publication WO 95/06128.

The transformation is carried out under conditions directed to the plant tissue of choice. The plant cells or tissue are exposed to the DNA or RNA carrying the transcription factor nucleic acids for an effective period of time. This may range from a less than one second pulse of electricity for electroporation to a 2-3 day co-cultivation in the presence of plasmid-bearing *Agrobacterium* cells. Buffers and media used will also vary with the plant tissue source and transformation protocol. Many transformation protocols employ a feeder layer of suspended culture cells (tobacco or Black Mexican Sweet corn, for example) on the surface of solid media plates, separated by a sterile filter paper disk from the plant cells or tissues being transformed.

Electroporation: Where one wishes to introduce DNA by means of electroporation, it is contemplated that the method of Krzyzek et al. (U.S. Pat. No. 5,384,253) may be advantageous. In this method, certain cell wall-degrading enzymes, such as pectin-degrading enzymes, are employed to render the target recipient cells more susceptible to transformation by electroporation than untreated cells. Alternatively, recipient cells can be made more susceptible to transformation, by mechanical wounding.

To effect transformation by electroporation, one may employ either friable tissues such as a suspension cell cultures, or embryogenic callus, or alternatively, one may transform immature embryos or other organized tissues directly. The cell walls of the preselected cells or organs can be partially degraded by exposing them to pectin-degrading enzymes (pectinases or pectolyases) or mechanically wounding them in a controlled manner. Such cells would then be receptive to DNA uptake by electroporation, which may be carried out at this stage, and transformed cells then identified by a suitable selection or screening protocol dependent on the nature of the newly incorporated DNA.

Microprojectile Bombardment: A further advantageous method for delivering transforming DNA segments to plant cells is microprojectile bombardment. In this method, microparticles may be coated with DNA and delivered into cells by a propelling force. Exemplary particles include those comprised of tungsten, gold, platinum, and the like.

It is contemplated that in some instances DNA precipitation onto metal particles would not be necessary for DNA delivery to a recipient cell using microprojectile bombardment. For example, non-embryogenic Black Mexican Sweet maize cells can be bombarded with intact cells of the bacteria *E. coli* or *Agrobacterium tumefaciens* containing plasmids with either the β-glucuronidase or bar gene engineered for expression in maize. Bacteria can be inactivated by ethanol dehydration prior to bombardment. A low level of transient expression of the β-glucuronidase gene may be observed 24-48 hours following DNA delivery. In addition, stable transformants containing the bar gene can be recovered following bombardment with either *E. coli* or *Agrobacterium tumefaciens* cells. It is contemplated that particles may contain DNA rather than be coated with DNA. The particles may increase the level of DNA delivery but may not be, in and of themselves, necessary to introduce DNA into plant cells.

An advantage of microprojectile bombardment, in addition to being an effective means of reproducibly stably transforming monocots, is that the isolation of protoplasts (Christou et al., *PNAS.* 84:3962-3966 (1987)), the formation of partially degraded cells, or the susceptibility to *Agrobacterium* infection is not required. An illustrative embodiment of a method for delivering DNA into maize cells by acceleration is a Biolistics Particle Delivery System, which can be used to propel particles coated with DNA or cells through a screen, such as a stainless steel or Nytex screen, onto a filter surface covered with maize cells cultured in suspension (Gordon-Kamm et al., *The Plant Cell.* 2:603-618 (1990)). The screen disperses the particles so that they are not delivered to the recipient cells in large aggregates. It is believed that a screen intervening between the projectile apparatus and the cells to be bombarded reduces the size of projectile aggregate and may contribute to a higher frequency of transformation, by reducing damage inflicted on the recipient cells by an aggregated projectile.

For bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of such techniques one may obtain up to 1000 or more foci of cells transiently expressing a marker gene. The number of cells in a focus which express the exogenous gene product 48 hours post-bombardment often range from about 1 to 10 and average about 1 to 3.

In bombardment transformation, one may optimize the prebombardment culturing conditions and the bombardment parameters to yield the maximum numbers of stable transformants Both the physical and biological parameters for bombardment can influence transformation frequency. Physical factors are those that involve manipulating the DNA/microprojectile precipitate or those that affect the path and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmid DNA.

One may wish to adjust various bombardment parameters in small scale studies to fully optimize the conditions and/or to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. Execution of such routine adjustments will be known to those of skill in the art.

An Example of Production and Characterization of Stable Transgenic Maize: After effecting delivery of a transcription factor nucleic acid (or other nucleic acid encoding a desirable polypeptide) to recipient cells by any of the methods discussed above, the transformed cells can be identified for further culturing and plant regeneration. As mentioned above, to improve the ability to identify transformants, one may employ a selectable or screenable marker gene as, or in addition to, the expressible transcription factor nucleic acids. In this case, one would then generally assay the potentially transformed cell population by exposing the cells to a selective agent or agents, or one would screen the cells for the desired marker gene trait.

Selection: An exemplary embodiment of methods for identifying transformed cells involves exposing the bombarded cultures to a selective agent, such as a metabolic inhibitor, an antibiotic, herbicide or the like. Cells that have been transformed and have stably integrated a marker gene conferring resistance to the selective agent used, will grow and divide in culture. Sensitive cells will not be amenable to further culturing.

To use the bar-bialaphos or the EPSPS-glyphosate selective system, bombarded tissue is cultured for about 0-28 days on nonselective medium and subsequently transferred to medium containing from about 1-3 mg/l bialaphos or about 1-3 mM glyphosate, as appropriate. While ranges of about 1-3 mg/l bialaphos or about 1-3 mM glyphosate can be employed, it is proposed that ranges of at least about 0.1-50 mg/l bialaphos or at least about 0.1-50 mM glyphosate will find utility in the practice of the invention. Tissue can be placed on any porous, inert, solid or semi-solid support for bombardment, including but not limited to filters and solid culture medium. Bialaphos and glyphosate are provided as examples of agents suitable for selection of transformants, but the technique of this invention is not limited to them.

An example of a screenable marker trait is the red pigment produced under the control of the R-locus in maize This pigment may be detected by culturing cells on a solid support containing nutrient media capable of supporting growth at this stage and selecting cells from colonies (visible aggregates of cells) that are pigmented. These cells may be cultured further, either in suspension or on solid media. The R-locus is useful for selection of transformants from bombarded immature embryos. In a similar fashion, the introduction of the C1 and B genes will result in pigmented cells and/or tissues.

The enzyme luciferase is also useful as a screenable marker in the context of the present invention. In the presence of the substrate luciferin, cells expressing luciferase emit light which can be detected on photographic or X-ray film, in a luminometer (or liquid scintillation counter), by devices that enhance night vision, or by a highly light sensitive video camera, such as a photon counting camera. All of these assays are nondestructive and transformed cells may be cultured further following identification. The photon counting camera is especially valuable as it allows one to identify specific cells or groups of cells which are expressing luciferase and manipulate those in real time.

It is further contemplated that combinations of screenable and selectable markers may be useful for identification of transformed cells. For example, selection with a growth inhibiting compound, such as bialaphos or glyphosate at concentrations below those that cause 100% inhibition followed by screening of growing tissue for expression of a screenable marker gene such as luciferase would allow one to recover transformants from cell or tissue types that are not amenable to selection alone. In an illustrative embodiment embryogenic Type II callus of *Zea mays* L. can be selected with sub-lethal levels of bialaphos. Slowly growing tissue was subsequently screened for expression of the luciferase gene and transformants can be identified.

Regeneration and Seed Production: Cells that survive the exposure to the selective agent, or cells that have been scored positive in a screening assay, are cultured in media that supports regeneration of plants. One example of a growth regulator that can be used for such purposes is dicamba or 2,4-D. However, other growth regulators may be employed, including NAA, NAA+2,4-D or perhaps even picloram. Media improvement in these and like ways can facilitate the growth of cells at specific developmental stages. Tissue can be maintained on a basic media with growth regulators until sufficient tissue is available to begin plant regeneration efforts, or following repeated rounds of manual selection, until the morphology of the tissue is suitable for regeneration, at least two weeks, then transferred to media conducive to maturation of embryoids. Cultures are typically transferred every two weeks on this medium. Shoot development signals the time to transfer to medium lacking growth regulators.

The transformed cells, identified by selection or screening and cultured in an appropriate medium that supports regeneration, can then be allowed to mature into plants. Developing plantlets are transferred to soil-less plant growth mix, and hardened, e.g., in an environmentally controlled chamber at about 85% relative humidity, about 600 ppm $CO_2$, and at about 25-250 microeinsteins/sec·m$^2$ of light. Plants can be matured either in a growth chamber or greenhouse. Plants are regenerated from about 6 weeks to 10 months after a transformant is identified, depending on the initial tissue. During regeneration, cells are grown on solid media in tissue culture vessels. Illustrative embodiments of such vessels are petri dishes and Plant Con™. Regenerating plants can be grown at about 19° C. to 28° C. After the regenerating plants have reached the stage of shoot and root development, they may be transferred to a greenhouse for further growth and testing.

Mature plants are then obtained from cell lines that are known to express the trait. In some embodiments, the regenerated plants are self-pollinated. In addition, pollen obtained from the regenerated plants can be crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture can facilitate development of traits that are commercially useful.

Regenerated plants can be repeatedly crossed to inbred plants to introgress the transcription factor nucleic acids into the genome of the inbred plants. This process is referred to as backcross conversion. When a sufficient number of crosses to the recurrent inbred parent have been completed in order to produce a product of the backcross conversion process that is substantially isogenic with the recurrent inbred parent except for the presence of the introduced transcription factor or other promoter-polypeptide encoding nucleic acids, the plant is self-pollinated at least once in order to produce a homozygous backcross converted inbred containing the transcription factor or other promoter-polypeptide nucleic acids. Progeny of these plants are true breeding.

Alternatively, seed from transformed monocot plants regenerated from transformed tissue cultures is grown in the field and self-pollinated to generate true breeding plants.

Seed from the fertile transgenic plants can then be evaluated for the presence and/or expression of the transcription factor or other polypeptide nucleic acids (or the encoded transcription factor or other polypeptide). Transgenic plant and/or seed tissue can be analyzed for transcription factor expression using standard methods such as SUS polyacrylamide gel electrophoresis, liquid chromatography (e.g., HPLC) or other means of detecting a product of transcription factor activity (e.g., increased biomass, increased fiber content, increased structural strength to the plant or to fibers in the plant) or a product of the polypeptide of interest.

Once a transgenic seed expressing the transcription factor or other polypeptide sequence is identified, the seed can be used to develop true breeding plants. The true breeding plants are used to develop a line of plants that express the transcription factor described herein and/or contain a nucleic acid that includes an expression cassette with a promoter linked to a polypeptide of interest, while still maintaining other desirable functional agronomic traits. Adding the trait of increased transcription factor or other polypeptide expression to the plant can be accomplished by back-crossing with this trait with plants that do not exhibit this trait and by studying the pattern of inheritance in segregating generations. Those plants expressing the target trait in a dominant fashion are preferably selected. Back-crossing is carried out by crossing the original fertile transgenic plants with a plant from an inbred line exhibiting desirable functional agronomic characteristics while not necessarily expressing the trait of expression of a transcription factor and/or other desired polypeptide in the plant. The resulting progeny are then crossed back to the parent that expresses the trait. The progeny from this cross will also segregate so that some of the progeny carry the trait and some do not. This back-crossing is repeated until an inbred line with the desirable functional agronomic traits, and with expression of the desired trait within the plant. The transcription factor or other polypeptide in plant can be expressed in a dominant fashion.

After back-crossing, the new transgenic plants can be evaluated for expression of the transcription factor or other polypeptide. For example, when the transcription factor is expressed the biomass, fiber content, and/or structural strength of a plant is increased. Detection of increased fiber or structural strength can be done, for example, by observing whether the tensile strength of plant fibers is increased or otherwise modulated relative to a plant that does not contain the exogenously added transcription factor. The biomass, structural (e.g., tensile) strength, or fiber content can be increased in plants expressing the modified transcription factor(s) by at least at least 5%, at least 7%, at least 10%, at least 15%, at least 20%, at least 25 at least 30%, at least 40%, at least 50%, at least 60%, at least 70%, at least 80%, at least 85%, at least 95%, or at least 100%. In some cases, the biomass, structural (e.g., tensile) strength, or fiber content can be increased in plants expressing the modified transcription factor(s) by at least 2-fold, or at least 3-fold, or at least 4-fold, or at least 5-fold, or at least 7-fold, or at least 10-fold.

The new transgenic plants can also be evaluated for a battery of functional agronomic characteristics such as lodging, kernel hardness, yield, resistance to disease and insect pests, drought resistance, and/or herbicide resistance.

Plants that may be improved by these methods (incorporation of nucleic acids encoding transcription factors) include but are not limited to fiber-containing plants, trees, flax, grains (maize, wheat, barley, oats, rice, sorghum, millet and rye), grasses (switchgrass, prairie grass, wheat grass, sudangrass, sorghum, straw-producing plants), softwood, hardwood and other woody plants (e.g., those used for paper production such as poplar species, pine species, and eucalyptus), oil and/or starch plants (canola, potatoes, lupins, sunflower and cottonseed), and forage plants (alfalfa, clover and fescue). In some embodiments the plant is a gymnosperm. Examples of plants useful for pulp and paper production include most pine species such as loblolly pine, Jack pine, Southern pine, Radiata pine, spruce, Douglas fir and others. Hardwoods that can be modified as described herein include aspen, poplar, eucalyptus, and others. Plants useful for making biofuels and ethanol include corn, grasses (e.g., miscanthus, switchgrass, and the like), as well as trees such as poplar, aspen, pine, oak, maple, walnut, rubber tree, willow, and the like. Plants useful for generating dairy forage include legumes such as alfalfa, as well as forage grasses such as bromegrass, and bluestem.

Determination of Stably Transformed Plant Tissues: To confirm the presence of the transcription factor or other promoter-polypeptide-encoding nucleic acids in the regenerating plants, or seeds or progeny derived from the regenerated plant, a variety of assays may be performed. Such assays include, for example, molecular biological assays available to those of skill in the art, such as Southern and Northern blotting and PCR; biochemical assays, such as detecting the presence of a protein product, e.g., by immunological means (ELISAs and Western blots) or by enzymatic function; plant part assays, such as leaf, seed or root assays; and also, by analyzing the phenotype of the whole regenerated plant.

Whereas DNA analysis techniques may be conducted using DNA isolated from any part of a plant, RNA may only be expressed in particular cells or tissue types, and so RNA for analysis can be obtained from those tissues. PCR techniques may also be used for detection and quantification of RNA produced from introduced transcription factor nucleic acids. PCR also be used to reverse transcribe RNA into DNA, using enzymes such as reverse transcriptase, and then this DNA can be amplified, for example, by use of PCR techniques. Further information about the nature of the RNA product may be obtained by Northern blotting. This technique will demonstrate the presence of an RNA species and give information about the integrity of that RNA. The presence or absence of an RNA species can also be determined using dot or slot blot Northern hybridizations. These techniques are modifications of Northern blotting and also demonstrate the presence or absence of an RNA species.

While Southern blotting and PCR may be used to detect the transcription factor nucleic acid in question, they do not provide information as to whether the preselected DNA segment is being expressed. Expression may be evaluated by specifically identifying the protein products of the introduced transcription factor nucleic acids or evaluating the phenotypic changes brought about by their expression.

Assays for the production and identification of specific proteins may make use of physical-chemical, structural, functional, or other properties of the proteins. Unique physical-chemical or structural properties allow the proteins to be separated and identified by electrophoretic procedures, such as native or denaturing gel electrophoresis or isoelectric focusing, or by chromatographic techniques such as ion exchange, liquid chromatography or gel exclusion chromatography. The unique structures of individual proteins offer opportunities for use of specific antibodies to detect their presence in formats such as an ELISA assay. Combinations of approaches may be employed with even greater specificity such as Western blotting in which antibodies are used to locate individual gene products that have been separated by electrophoretic techniques. Additional techniques may be employed to absolutely confirm the identity of the transcription factor or other polypeptide such as evaluation by amino acid sequencing following purification. The Examples of this application also provide assay procedures for detecting and quantifying transcription factor or other polypeptide or enzyme activities. Other procedures may be additionally used.

The expression of a gene product can also be determined by evaluating the phenotypic results of its expression. These assays also may take many forms including but not limited to analyzing changes in the chemical composition, morphology, or physiological properties of the plant.

Definitions

As used herein, the term "exogenous promoter" refers to a promoter in operable combination with a coding region wherein the promoter is not the promoter naturally associated with the coding region in the genome of an organism. The promoter which is naturally associated or linked to a coding region in the genome is referred to as the "endogenous promoter" for that coding region.

As used herein, the term "expression" when used in reference to a nucleic acid sequence, such as a coding region or protein, refers to the process of converting genetic information encoded in a coding region into RNA (e.g., mRNA, rRNA, tRNA, or snRNA) through "transcription" of a gene or expression cassette (i.e., via the enzymatic action of an RNA polymerase), and into protein where applicable (as when a coding region encodes a protein), through "translation" of mRNA. Gene expression can be regulated at many stages in the process. "Up-regulation" or "activation" or "increased expression" refers to regulation that increases the production of gene expression products (i.e., RNA or protein), while "down-regulation" or "repression" or "decreased expression" refers to regulation that decreases production. Molecules (e.g., transcription factors) that are involved in up-regulation or down-regulation can also be called "activators" and "repressors," respectively.

As used herein, the term "heterologous" when used in reference to a gene, promoter, or nucleic acid refers to a gene, promoter, or nucleic acid that has been manipulated in some way. For example, a heterologous nucleic acid or a heterologous promoter includes a nucleic acid or promoter from one species that is introduced into another species. A heterologous nucleic acid or promoter also includes a nucleic acid or promoter that is native to an organism but that has been altered in some way (e.g., placed in a different chromosomal location, mutated, added in multiple copies, linked to a non-native promoter or enhancer sequence, etc.). Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous coding regions can be distinguished from endogenous plant coding regions, for example, when the heterologous coding regions are joined to nucleotide sequences comprising regulatory elements such as promoters that are not found naturally associated with the coding region, or when the heterologous coding regions are associated with portions of a chromosome not found in nature (e.g., genes expressed in loci where the protein encoded by the coding region is not normally expressed). Similarly, heterologous promoters can be promoters that at linked to a coding region to which they are not linked in nature.

As used herein, "isolated" means a nucleic acid or polypeptide has been removed from its natural or native cell. Thus, the nucleic acid or polypeptide can be physically isolated from the cell or the nucleic acid or polypeptide can be present or maintained in another cell where it is not naturally present or synthesized.

As used herein, the terms "leaf" and "leaves" refer to a usually flat, green structure of a plant where photosynthesis and transpiration take place and attached to a stem or branch.

As used herein, a "native" nucleic acid or polypeptide means a DNA, RNA or amino acid sequence or segment that has not been manipulated in vitro, i.e., has not been isolated, purified, and/or amplified.

As used herein, the term "naturally linked" or "naturally located" when used in reference to the relative positions of nucleic acid sequences means that the nucleic acid sequences exist in nature in those positions.

As used herein, the terms "operably linked" or "in operable combination" or "in operable order" refers to the linkage of nucleic acids in such a manner that a nucleic acid molecule capable of directing the transcription of a given coding region and/or the synthesis of a desired, protein molecule is produced. As used herein, the term also refers to the linkage of amino acid sequences in such a manner so that a functional protein is produced.

As used herein, the term "plant" is used, in its broadest sense. It includes, but is not limited to, any species of fiber-producing plant, grass (e.g. turf grass), sedge, rush, ornamental or decorative, crop or cereal, fodder or forage, fruit or vegetable, fruit plant or vegetable plant, woody, flower or tree. It is not meant to limit a plant to any particular structure. Such structures include, but are not limited to, stomata, a seed, a tiller, a sprig, a stolon, a plug, a rhizome, a shoot, a stem, a leaf, a flower petal, a fruit, etc.

As used herein, the terms "protein," "polypeptide," "peptide," "encoded product," "amino acid sequence," are used interchangeably to refer to compounds comprising amino acids joined via peptide bonds and. A "protein" encoded by a gene is not limited to the amino acid sequence encoded by the gene, but includes post-translational modifications of the protein. Where the term "amino acid sequence" is recited herein to refer to an amino acid sequence of a protein molecule, the term "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein. The deduced amino acid sequence from a coding nucleic acid sequence includes sequences which are derived from the deduced amino acid sequence and modified by post-translational processing, where modifications include but not limited to glycosylation, hydroxylations, phosphorylations, and amino acid deletions, substitutions, and additions. Thus, an amino acid sequence comprising a deduced amino acid sequence can include post-translational modifications of the encoded and deduced amino acid sequence.

As used herein, "seed" refers to a ripened ovule, consisting of the embryo and a casing.

As used herein, "stem" refers to a main ascending axis of a plant.

As used herein, the term "transfection" refers to the introduction of foreign DNA into cells. Transfection may be accomplished by a variety of means known to the art including calcium phosphate-DNA co-precipitation, DEAF-dextran-mediated transfection, polybrene-mediated transfection, glass beads, electroporation, microinjection, liposome fusion, lipofection, protoplast fusion, viral infection, biolistics (i.e., particle bombardment), Agrobacterium infection, and the like. Methods of transfection are described herein.

As used herein, the term "transgene" refers to a foreign gene (e.g., an expression cassette) that is placed into an organism by the process of transfection.

As used herein, the term. "vector" refers to nucleic acid molecules that transfer DNA segment(s). Transfer can be into a cell, cell-to-cell, etc.

As used herein, the term "wild-type" when made in reference to a nucleic acid or gene refers to a functional nucleic acid or gene common throughout an outbred population. As used herein, the term "wild-type" when made in reference to a gene product refers to a functional gene product common throughout an outbred population. A functional wild-type gene is that which is most frequently observed in a population and is thus arbitrarily designated the "normal" or "wild-type" form of the gene.

The following non-limiting Examples illustrate how aspects of the invention have been developed and can be made and used.

Example 1: MYB46 Directly Interacts with and is Phosphorylated by MPK6

This Example illustrates that MYB46 interacts with MPK6 and is phosphorylated by MPK6.

Figure 1B:
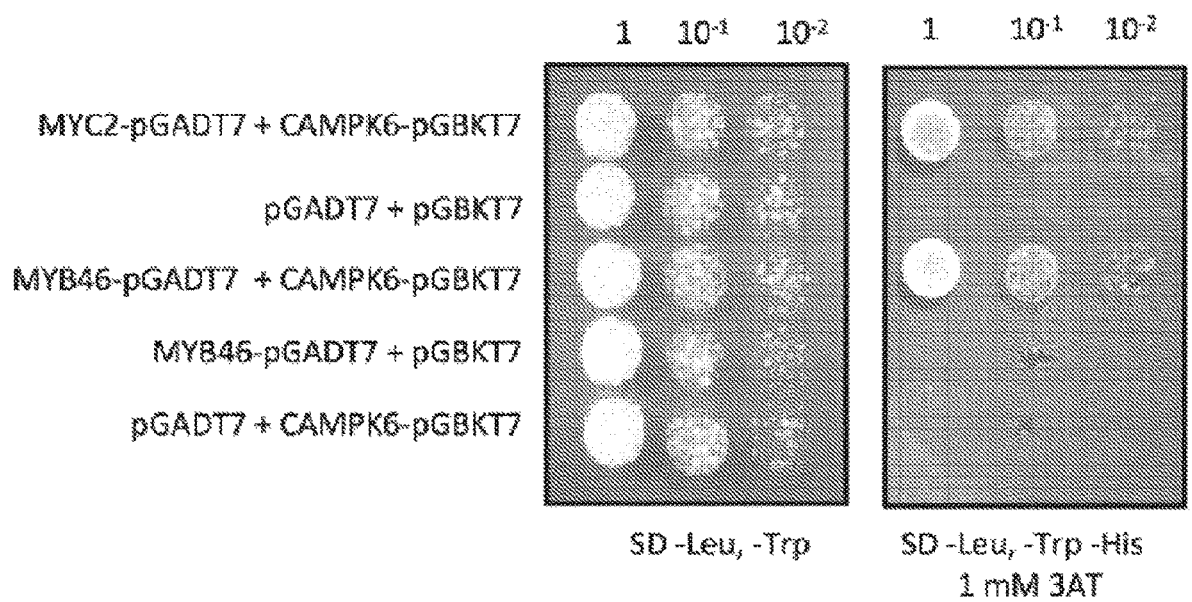
Figure 1E:
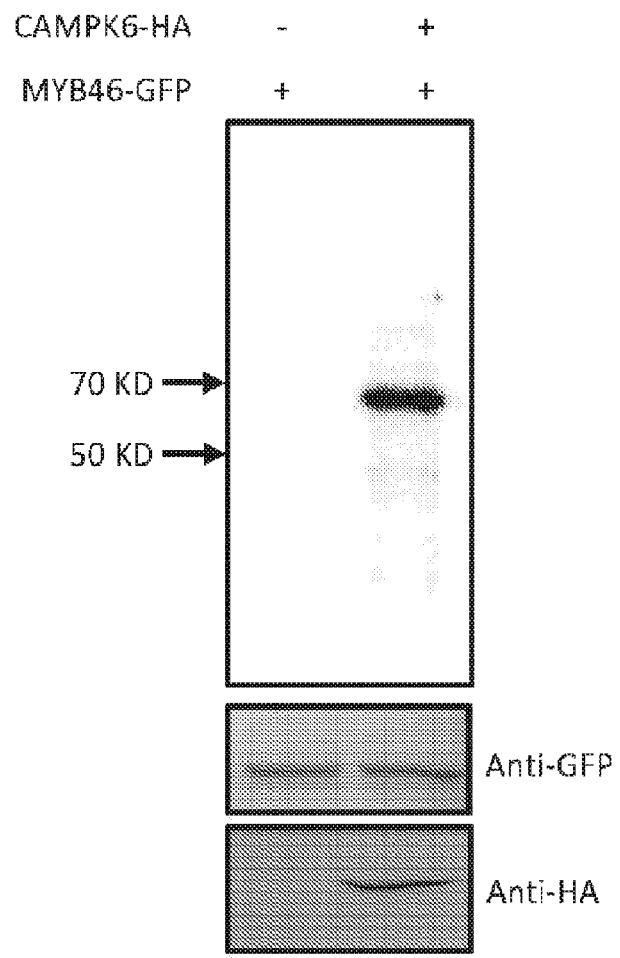

Functional sites analysis using the Eukaryotic Linear Motif (ELM; see website at elm.eu.org) prediction tool showed that MYB46 contains a mitogen-activated protein kinases (MPK)-docking domain ($^{2}$RKPEVAI$^{8}$, SEQ ID NO:9) and two potential phosphorylation sites ($137^{Ser}$ and $199^{Thr}$) (FIG. 1A). In MPK signaling, docking domains act as substrate determinants, recruiting the kinases to the correct substrates and thereby enhancing their fidelity and efficiency of action (Sharrocks et al., 2000). In addition to the docking domains, phosphorylation targeting sites (i.e., phosphoacceptor motifs) on substrates contribute to MPK specify. The presence of the docking domain and targeting sites suggests that MYB46 may be subject to post-translational regulation. To test the hypothesis, MYB46 was first investigated to determine whether it interacts with a MPK associated with stress responses. For this test, MPK6 was used, which has been shown to be activated by salt stress (Yu et al., 2010). Yeast 2-hybrid (Y2H) experiments using MYB46 as bait and constitutively activate a form of MPK6 having a glycine at position 218 instead of an aspartic acid and an alanine instead of a glutamic acid (MPK6$^{D218G,}$ $_{E222A}$; CAMPK6) as prey showed that MYB46 interacts with CAMPK6 (FIG. 1B). To confirm the Y21 res co-immunoprecipitation assays were performed using Arabidopsis mesophyll protoplast (AMP) transient expression system (Im et al., 2014). For this, a MYB46-GFP fusion construct and CAMPK6-11A construct were transiently co-expressed in AMPs in the presence of proteasome inhibitor MG132. CAMPK6 interacting protein was immunoprecipitated using anti-HA antibodies followed by protein blot analysis with anti-GFP antibody. The result showed direct interaction of these two proteins (FIG. 1C). To further confirm the interaction and gain insight into the interacting position of the proteins, BiFC (Bimolecular Fluorescence Complementation) experiments were carried out in AMPs. As shown in FIG. 1D, the C-terminal part of CAMPK6 interacted with the N-terminal part of MYB46. The interaction of MYB46 and CAMPK6 was investigated to ascertain such interaction results in MYB46 phosphorylation. Assays that identified an immunocomplex with CAMPK6 showed that CAMPK6 directly phosphorylates MYB46 (JIG. 1E).

Example 2: MYB46 Protein is Degraded by MPK6 Through Proteasomal Degradation Pathway Printers were used to clone, mutagenize, and detect various proteins. The sequences of these primers are provided in Table 1.

TABLE 1

Primer Sequences

| Purpose | Name | Sequence 5' to 3' |
|---|---|---|
| Cloning | MYB46-F | CATGCCATGGCAAGGAAGCCAGAGGTAGC (SEQ ID NO: 53) |
| | MYB46-R | GAAGGCCTTATGCTTTGTTTGAAGTTGA (SEQ ID NO: 54) |
| | MPK6-F | CGGGATCCATGGACGGTGGTTCAGGTCA (SEQ ID NO: 55) |
| | MPK6-R | GAAGGCCTTTGCTGATATTCTGGATTGA (SEQ ID NO: 56) |
| | MYB46-EYFP_m46_F | AAAAAGCAGGCTATGAGGAAGCCAGAGGTAGCCAT (SEQ ID NO: 57) |
| | MYB46-EYFP_M46_R | AGAAAGCTGGGTTTATGCTTTGTTTGAAGTTGAAGT (SEQ ID NO: 58) |
| | EYFP-MYB46_M46_F | AAAAAGCAGGCTCCATGAGGAAGCCAGAGGTAGCCAT (SEQ ID NO: 59) |
| | EYFP-MYB46_M46_R | AGAAAGCTGGGTTCATATGCTTTGTTTGAAGTTGA (SEQ ID NO: 60) |
| | CAMPK6-EYFP_F | AAAAAGCAGGCTATGGACGGTG GTTCA GGTCA (SEQ ID NO: 61) |
| | CAMPK6-EYFP_R | AGAAAGCTGGGTTTTGCTGATATTCTGG ATTGAAAGCA (SEQ ID NO: 62) |
| | EYFP-CAMPK6_F | AAAAAGCAGGCTCCATGGACGGTG GTT CAGGTCA (SEQ ID NO: 63) |
| | EYFP-CAMPK6_R | AGAAAGCTGGGTTTGCTGATATTCTGGA TTGAAAGCATGA (SEQ ID NO: 64) |
| | MYB72-F | CATGCCATGGCCATGATGATGAGGAAA CCGGA (SEQ ID NO: 65) |
| | MYB83-R | CCCCCGGGATCGACTTGGAAATCAAGGAA (SEQ ID NO: 66) |
| Muta-genesis | CAMPK6-F | TGAGAGTGGTTTCATGACTGCATATGT TGT (SEQ ID NO: 67) |
| | CAMPK6-R | ACAACATATGCAGTCATGAAACCACT CTCA (SEQ ID NO: 68) |
| | MYB46$^{S138R}$-F | ACTCATCCTCAAGACCCAACACAGCA AGCG (SEQ ID NO: 69) |
| | MYB46$^{S138R}$-R | CGCTTGCTGTGTTGGGTCTTGAGGATGAGT (SEQ ID NO: 70) |
| | MYB46$^{T199R}$-F | GCAATGACGATTTTAGACCTTATGTAG ATG (SEQ ID NO: 71) |
| | MYB46$^{T199R}$-R | CATCTACATAAGGTCTAAAATCGTCAT TGC (SEQ ID NO: 72) |
| | MYB46$^{S138E}$-F | ACTCATCCTCAGAACCCAACACAGCAA GCG (SEQ ID NO: 73) |
| | MYB46$^{S138E}$-R | CGCTTGCTGTGTTGGGTTCTGAGGATGAGT (SEQ ID NO: 74) |
| | MYB46$^{T199D}$-F | GCAATGACGATTTTGACCCTTATGTAGATG (SEQ ID NO: 75) |
| | MYB46$^{T199D}$-R | CATCTACATAAGGGTCAAAATCGTCATTGC (SEQ ID NO: 76) |
| qRT-PCR | 4C11-F | AGGTTCCTTTGCAAAACCTAACGA (SEQ ID NO: 77) |
| | 4C11-R | CGATAAGAGTGGTGAAATCTGGTGC (SEQ ID NO: 78) |
| | PAL4-F | GGCGGTGCACTTCAAAATGA (SEQ ID NO: 79) |
| | PAL4-R | GAGAATCTCGAAGCGTATACCGGA (SEQ ID NO: 80) |
| | ACTIN2-F | ATGTGGATCTCCAAGGCCGA (SEQ ID NO: 81) |
| | ACTIN2-R | ACACACAAGTGCATCATAGAAAC GAAA (SEQ ID NO: 82) |
| | PP2A-F | TAACGTGGCCAAAATGATGC (SEQ ID NO: 83) |
| | PP2A-R | GTTCTCCACAACCGCTTGGT (SEQ ID NO: 84) |
| | MYB46-q-F | ATCGGACATCTTCTTTAGCCTTTTCTT (SEQ ID NO: 85) |
| | MYB46-q-R | CTCAAGCGTGGCGCTTTCT (SEQ ID NO: 86) |

To understand the mechanisms underlying the MPK6-mediated negative regulation of MYB46, the stability of MYB46 protein was examined in the presence of a constitutively activate a form of MPK6$^{D218G, E222A}$; CAMPK6).

An MYB46-GFP (men fluorescence protein) fusion protein construct (p35S::MYB46-GFP) was expressed in AMPs with or without a CAMPK6-YFP (yellow fluorescence protein) fusion protein construct (p35S::CAMPK6-YFP).

Figure 2A:
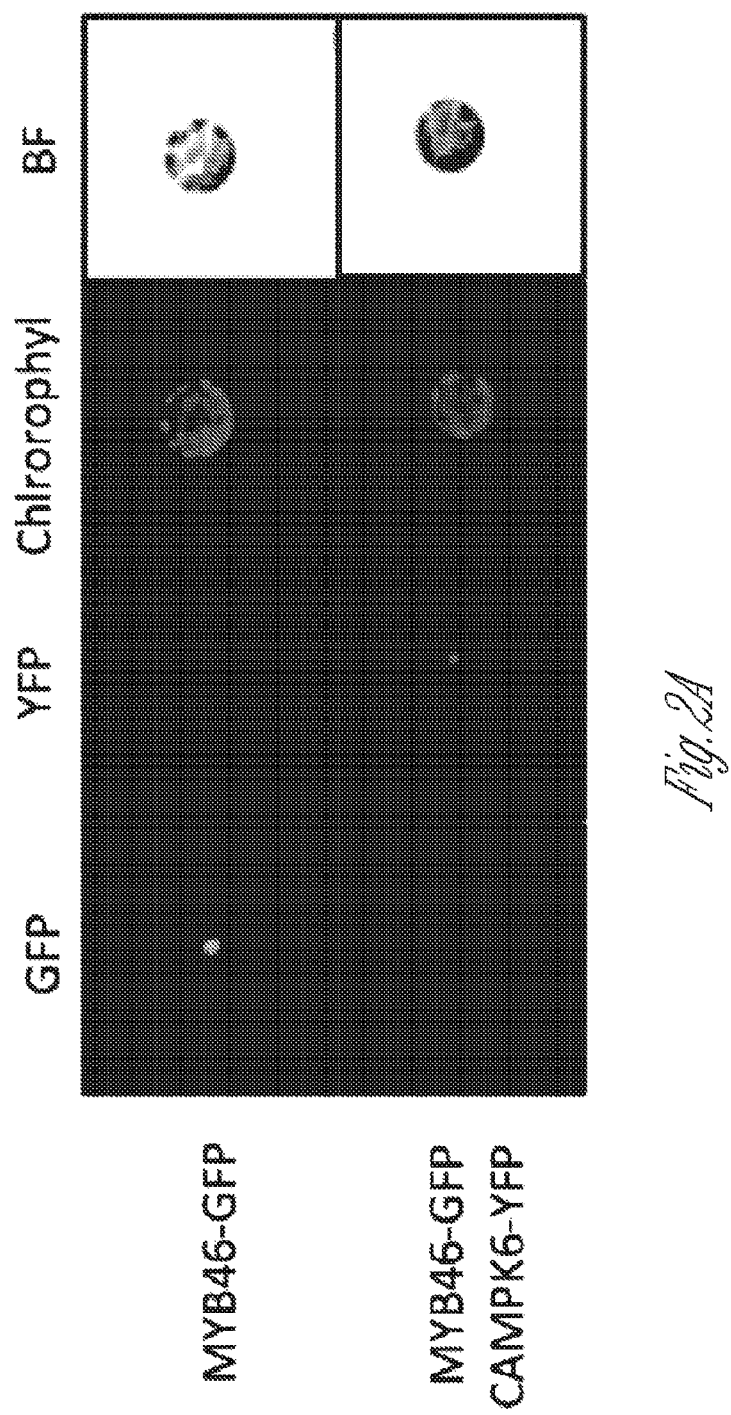
FIG. 2A-2F illustrate that MYB46 protein stability is negatively affected by a constitutively active form MPK6 (CAMPK6); in other words, the activated MPK6 (CAMPK6) negatively regulates MYB46 activity.

As shown in FIG. 2A the GFP signal was detected in the MYB46 alone treatment but the signal disappeared with CAMPK6 co-expression. These results indicate that the MYB46 was degraded when co-expressed with CAMPK6.

Figure 2B:
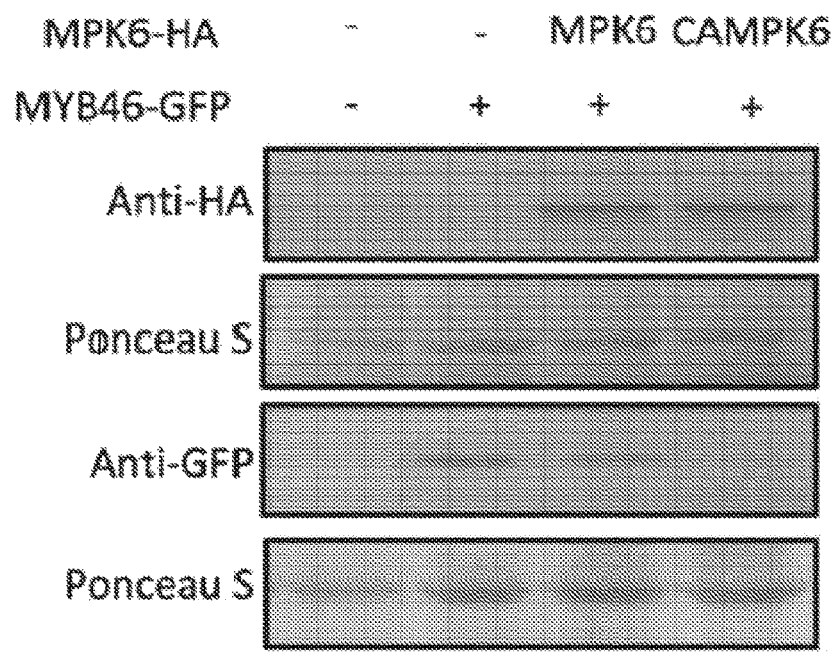

Such observations were confirmed by protein blot analysis of MYB46-GFP fusion proteins expressed in AMPs with or without CAMPK6. As shown in FIG. 2B, MYB46 protein levels were significantly decreased in the presence of CAMPK6.

Figure 2C:
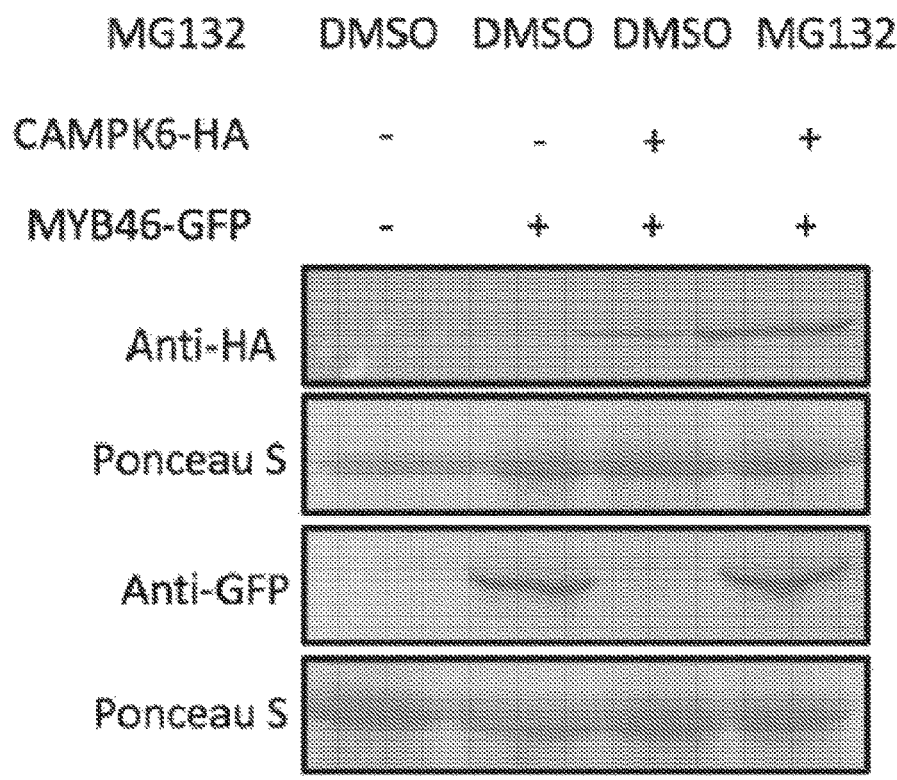
Figures 2D, 2E:
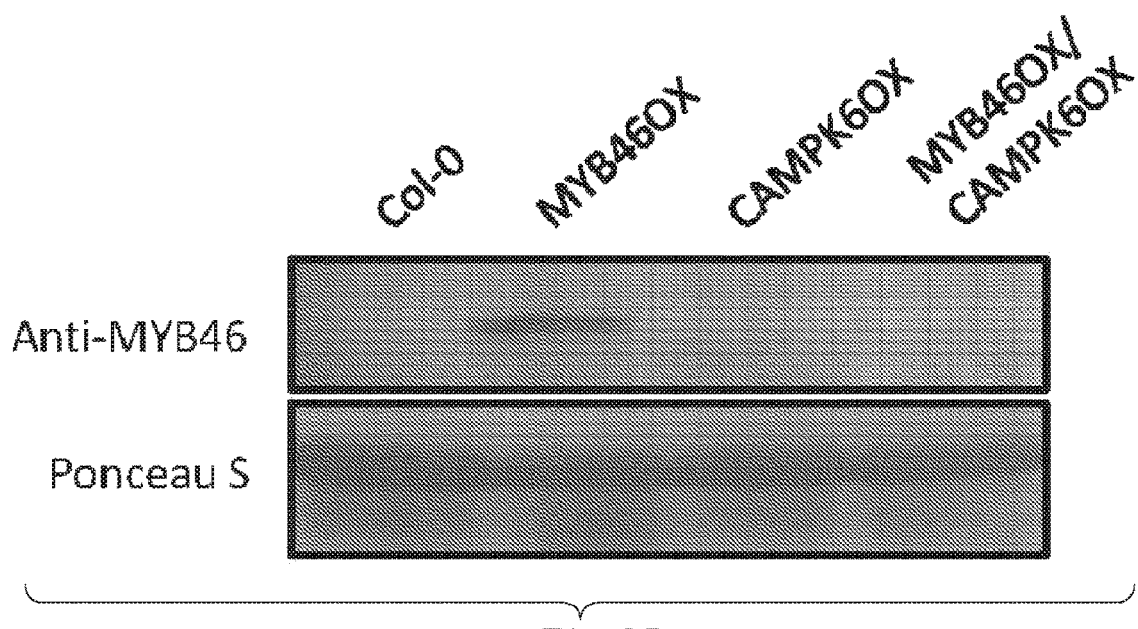
Figure 2F:
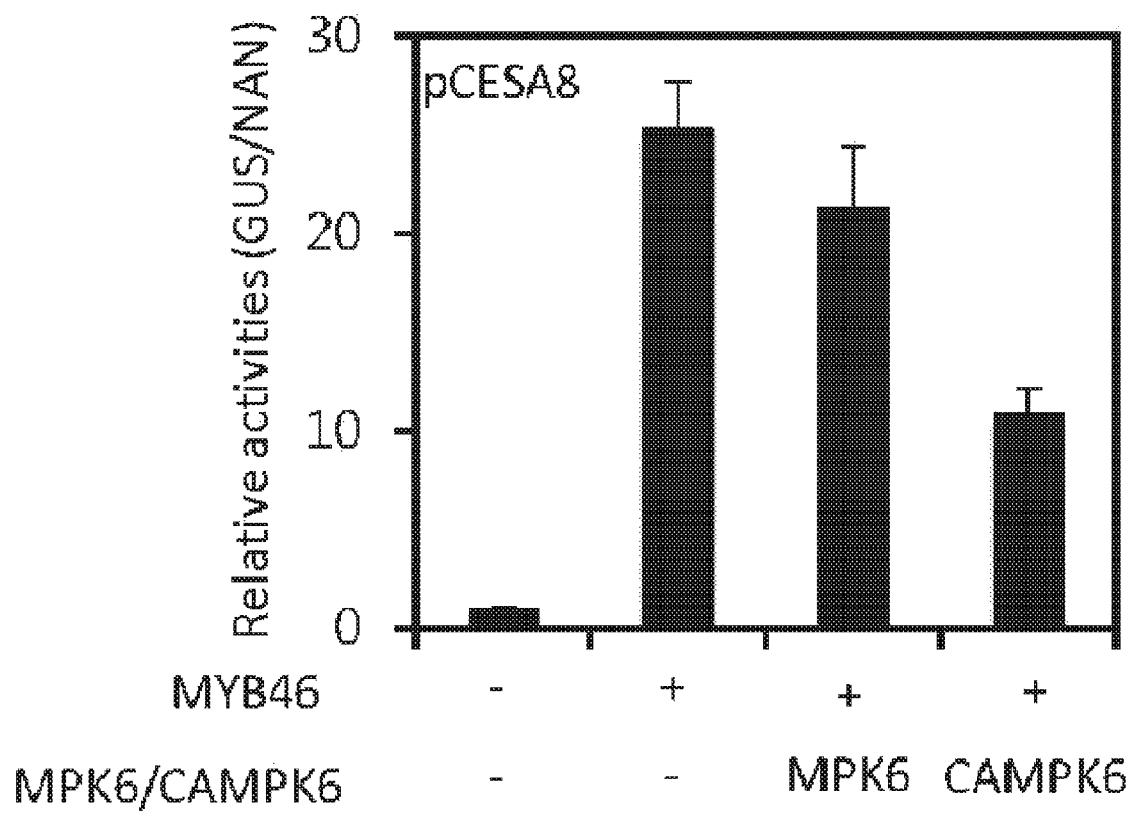

However, MYB46 protein level was not changed with co-expression of an inactive form of MPK6 (FIG. 2E-2F). MYB46 protein degradation was also not observed with addition of a proteasome inhibitor MG132 (FIG. 2C), indicating that the active form of MPK6 (CAMPK6) degrades MYB46 protein through a proteasomal degradation pathway. This CAMPK6-mediated degradation of MYB46 was further confirmed in transgenic Arabidopsis plants that overexpress MYB46 with or without CAMPK6 overexpression. Protein blot analysis using anti-MYB46 antibodies clearly showed that the level of MYB46 protein was decreased by CAMPK6 (FIG. 2D).

Example 3: MPK6-Mediated Phosphorylation of MYB46 Negatively Regulates its Function This Example illustrates that MPK6-mediated degradation negatively affects the function of MYB46, and that phosphorylation of MYB46 leads to such degradation.

A transient transcription activity assay (TAA) was used to test whether MPK6-mediated degradation would negatively affect the function of MYB46, using methods described by Kim et al. (2013). Various promoter sequences were used as targets of MYB46, including are CESA4 (cellulose synthase A4), CESA7, CESA8, CCoAOMT (caffeoyl-CoA O-methyltransferase), and phenylalanine ammonia lyase 4 (PAL4), to drive a GUS reporter gene.

Figure 3B:
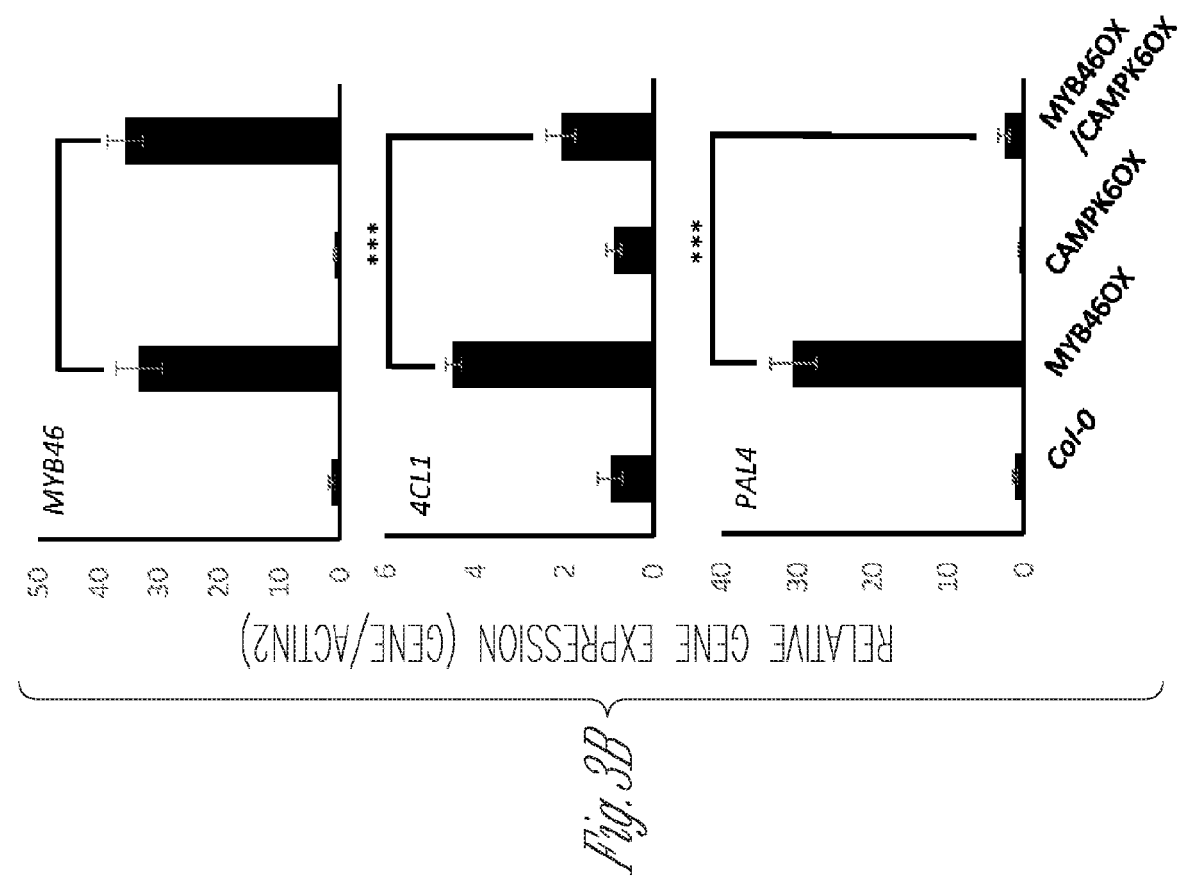
FIG. 3A-3E illustrate that MPK6 negatively regulates MYB46 function.
Figure 3A:
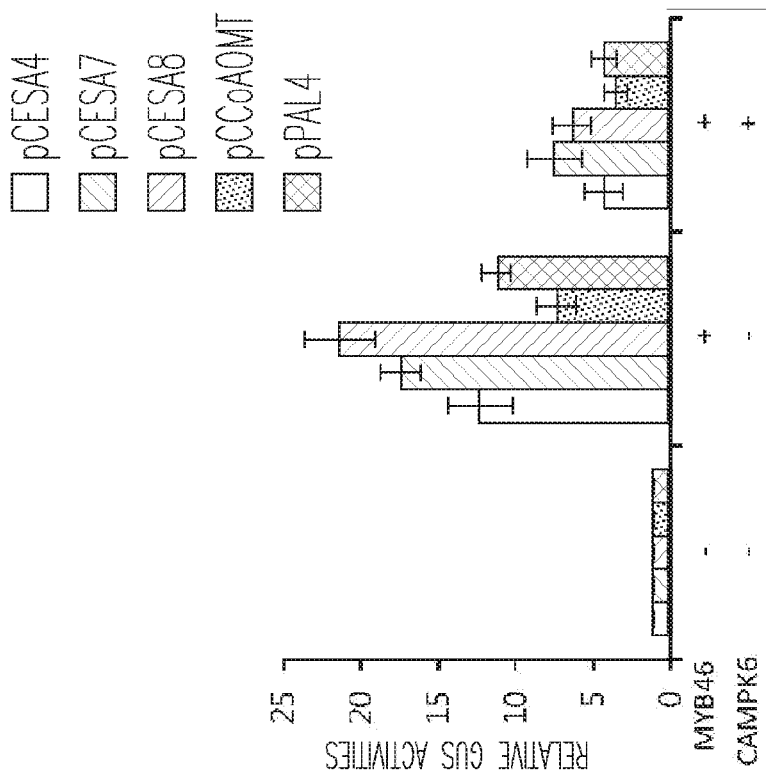

As shown in FIG. 3B, when co-expressed with 35S CaMV promoter-driven MYB46 (p35S::MYB46), the GUS activity was dramatically increased in all of the test constructs with MYB46 overexpression (p35S::MYB46 wt). However, GUS activity was significantly decreased when p35S::MYB46 wt was co-expressed with 35S CaMV promoter-driven CAMPK6 (p35S::CAMPK6), a constitutively active form of MPK6 indicating that activated MPK6 (CAMPK6) negatively regulates MYB46 activity.

Figure 3C:
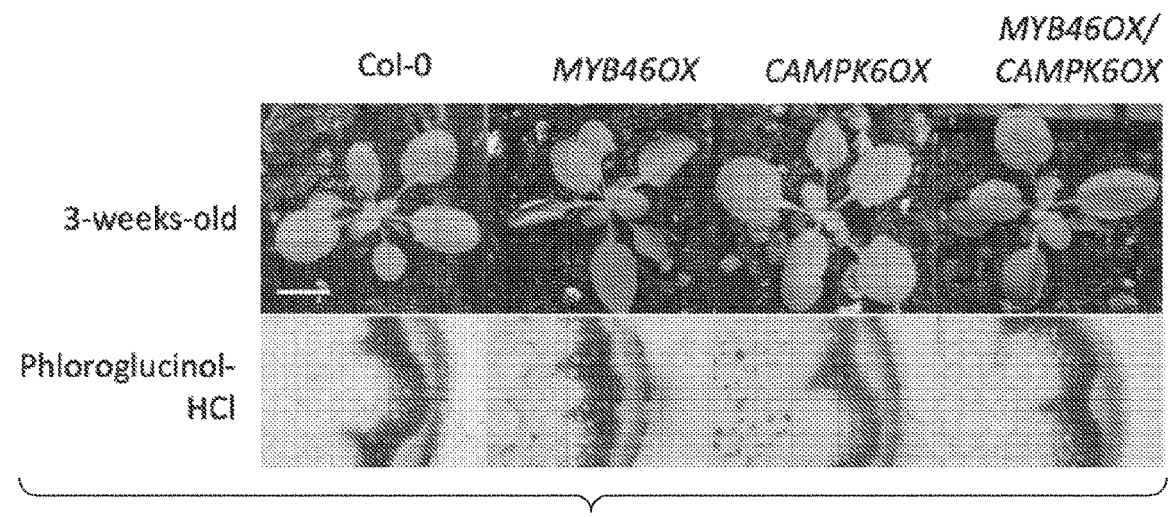

To further confirm this finding in planta, transgenic plants expressing p35S::MYB46, p35S::CAMPK6, or p35S::MYB46/p35S::CAMPK6 were produced. Expression of MYB46 and its two downstream target genes, 4-coumarate:coenzyme A ligase 1 (4CL1) and PAM, were significantly increased in the plants expressing p35S::MYB46 or compared to Col-0 control plants. However, even though MYB46 gene expression in p35S::MYB46/p35S::CAMPK6 was similar with p35S::MYB46, MYB46 target genes, 4CL1 and PAL4 were significantly reduced in the plants (FIG. 3B). This observation was further confirmed by phloroglucinol-HCl staining, which detects aldehyde groups contained in lignin and results in red staining that is indicative of the presence of lignin. Leaf curling and ectopic secondary wall biosynthesis, which is a phenotype of MYB46 overexpression (Ko et al., 2009), were clearly shown in the MYB46 overexpression plants. However, this phenotype was reverted back to wild type in the plants expressing CAMPK6 (FIG. 3C). Likewise, ectopic lignification of stem epidermal cells observed in p35S::MYB46 plants disappeared in the plants expressing CAMPK6.

Figure 3D:
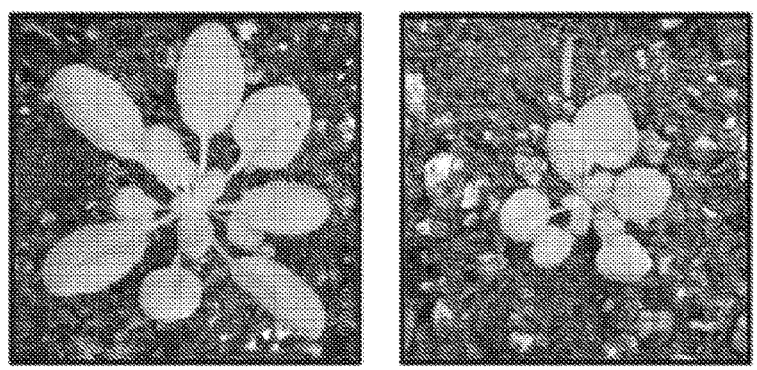
Figure 3E:
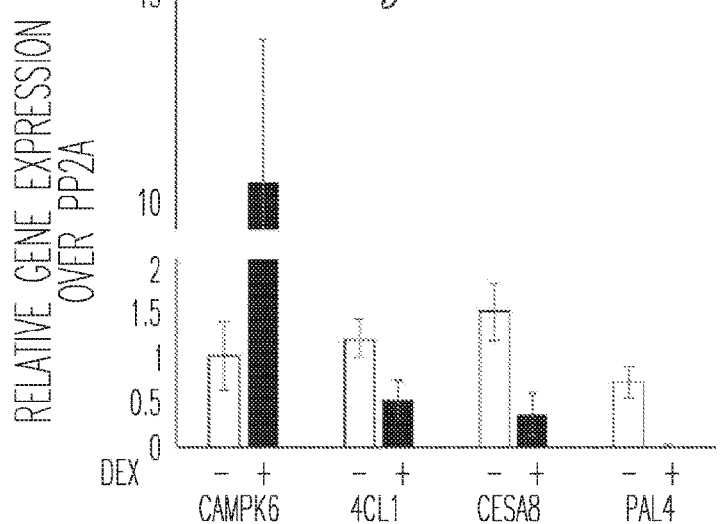

MYB46 has a functional homolog in MYB83. To further confirm the MPK6-mediated negative regulation of MYB46 function, transgenic Arabidopsis plants were created that express a dexamethasone (DEX)-inducible CAMPK6 in myb83 background (pDEX::CAMPK6/myb83). With DEX treatment, the pDEX::CAMPK6/myb83 plants showed stunted growth (FIG. 3D), which is a typical phenotype of myb46/myb83 double knockout mutants. This observation indicates that effective knockdown of MYB46 as occurred by CAMPK6. Expression of MYB46 target genes was significantly decreased with DEX treatment (FIG. 3E).

These data demonstrate that MPK6-mediated phosphorylation negatively regulates MYB46 activity.

Example 4: MPK6 Phosphorylation Target Sites in MYB46

This Example illustrates which amino acids are phosphorylated in MYB46.

MYB46 has two putative MPK phosphorylation sites, a serine at position 138 (S138) and a threonine at position 199 (T199), To test the functionality of such phosphorylation sites, these sites were modified by replacement of the serine and threonine residues with arginine, to generate modified MYB46 proteins that were either singly non-phosphorable with either S138 or T199 replaced by arginine (S138R or T199R), or that were doubly non-phosphorable with both S138 and T199 replaced by arginine (S138R/T199R).

Figure 4A:
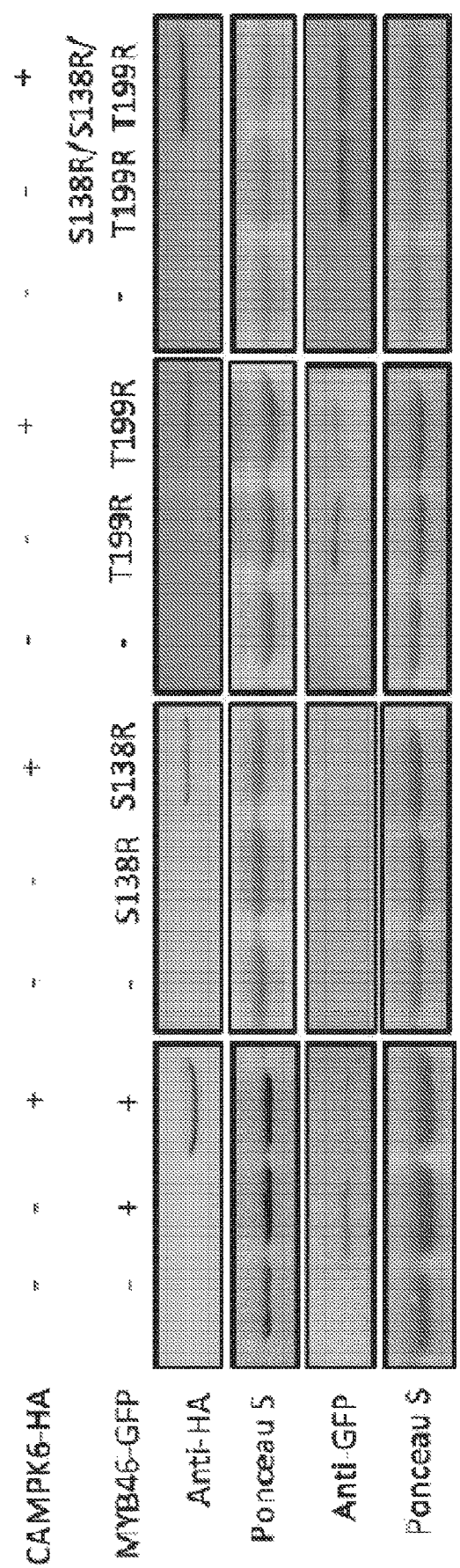
FIG. 4A-4G illustrates where the MPK6 target phosphorylation sites are in MYB46.

To assess whether these modified MYB46 mutants were subject to MPK6-mediated degradation, protein blot analysis was first performed. As shown in FIG. 4A, both of the single mutant proteins, MYB46$^{S138R}$ and MYB46$^{T199R}$, were degraded when co-expressed with CAMPK6 in AMPs. However, the double mutant MYB46$^{S138/T199R}$ was not affected by degradation (FIG. 4A). This result was further confirmed by co-expressing CAMPK6-YFP and MYB46-GFP fusion proteins in AMPs. The GFP signal was used to indicate the presence of MYB46 fusion proteins.

Figure 4B:
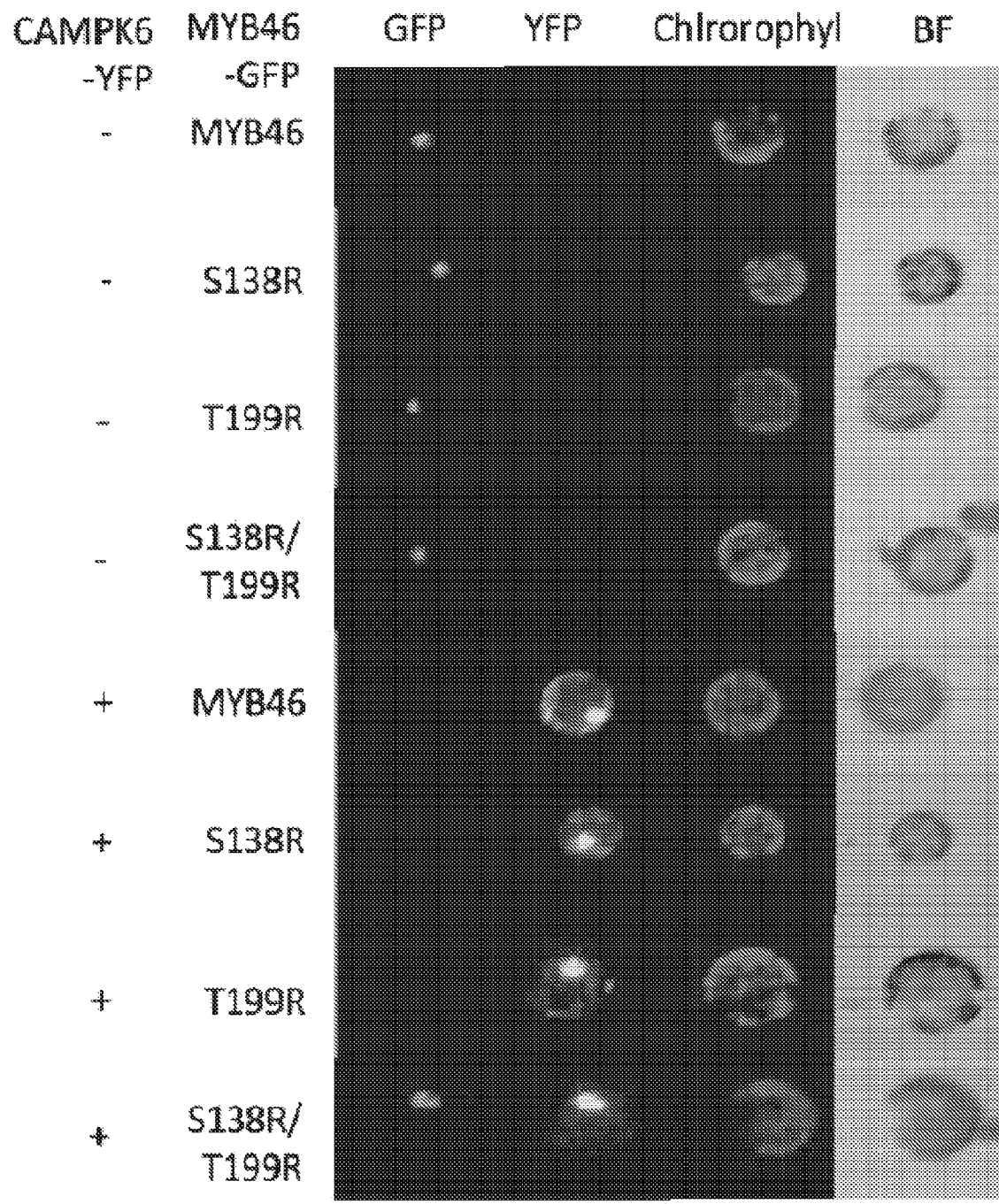

GFP signal was detected when the wild-type (p35S::MYB46-GFP), single mutant MYB46 (p35S:MYB46$^{S138R}$-GFP, p35S::MYB46$^{T199R}$-GFP), and double mutant MYB46 (p35S:MYB46$^{S138R/T199R}$-GFP) fusion proteins were expressed without p35S::CAMPK6-YFP co-expression (FIG. 4B). The GFP signal was not detected when wild type p35S::MYB46-GFP and single mutant, p35S:MYB46$^{S138R}$-GFP, or p35S::MYB46$^{T199R}$-GFP was co-expressed with p35S::CAMPK6-YFP, indicating that these MYB46 fusion proteins were degraded. However, consistent with the protein blot analysis result, GFP signal was detected from the MYB46 double mutant, p35S::MYB46$^{S138R/T199R}$-GFP, even in the presence of p35S::CAMPK6-YFP (FIG. 4B).

These data indicate that phosphorylation at either one of the target MYB46 sites was sufficient for the MPK6-mediated degradation of MYB46.

Figure 4C:
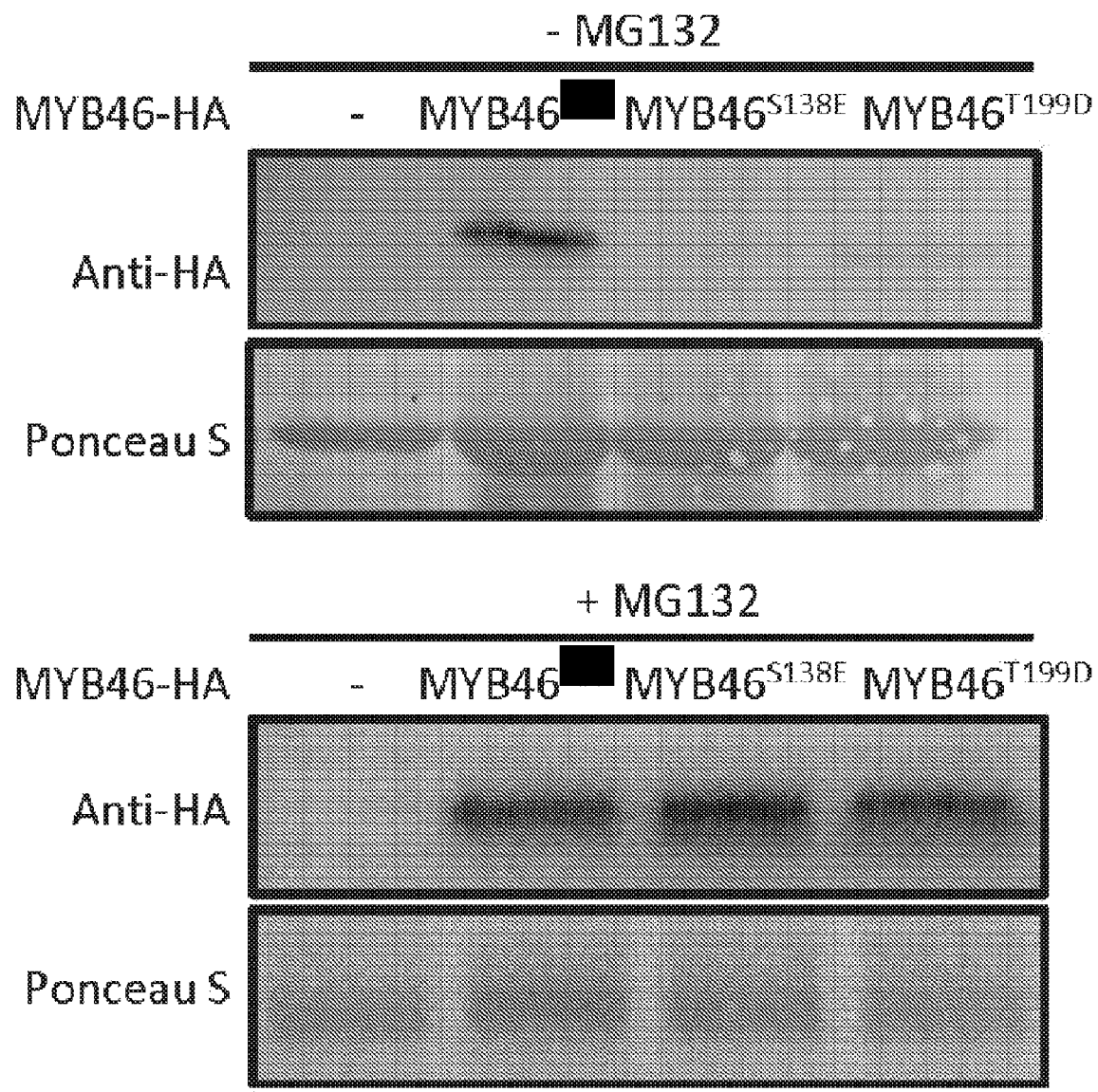

The functional significance of the two phosphorylation sites was further tested by introducing phosphomimic aspartic acid or glutamic acid substitutions into the S138 and T199 sites. Phosphomimic mutation at either of the two sites (MYB46$^{S138D}$ or MYB46$^{T199E}$) resulted in degradation of MYB46 protein (FIG. 4C, 4E). These results confirm that phosphorylation of either of the two target sites leads to degradation of MYB46. However, such MYB46 degradation was not observed in the presence of proteasome inhibitor MG132 (FIG. 4C), further confirming this phosphorylation-dependent degradation of MYB46 occurs through a proteasomal degradation pathway. In addition, substitution of lysine with arginine at a putative ubiquitination site of MYB46 (K156R) prevented degradation of the mutant MYB46$^{S138D}$ or MYB46$^{T199E}$ protein (FIG. 4G), further confirming that this phosphorylation-dependent degradation of MYB46 is through the proteasomal degradation pathway.

The inventors hypothesized that the two MPK6 phosphorylation sites play significant role in the regulation of MYB46 function. To test this hypothesis MYB46 phosphorylation site mutants were co-expressed with a GUS construct driven by CESA8 promoter (pCESA8::GUS), with or without CAMPK6 in AMPs.

Figure 4D:
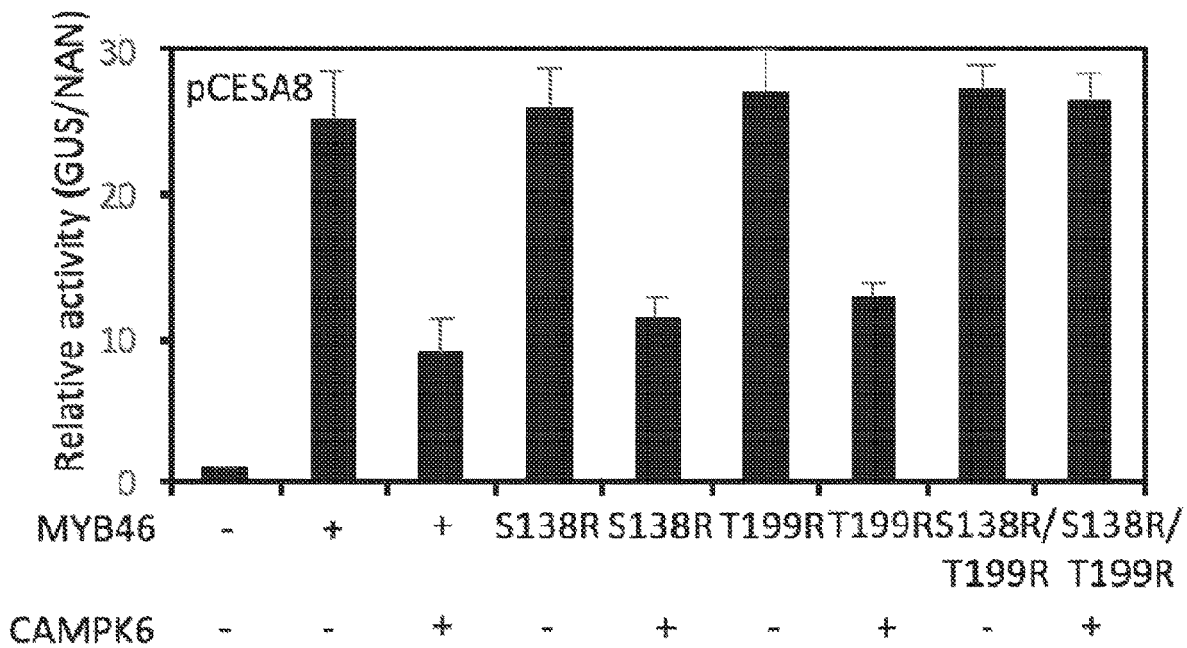
Figure 4E:
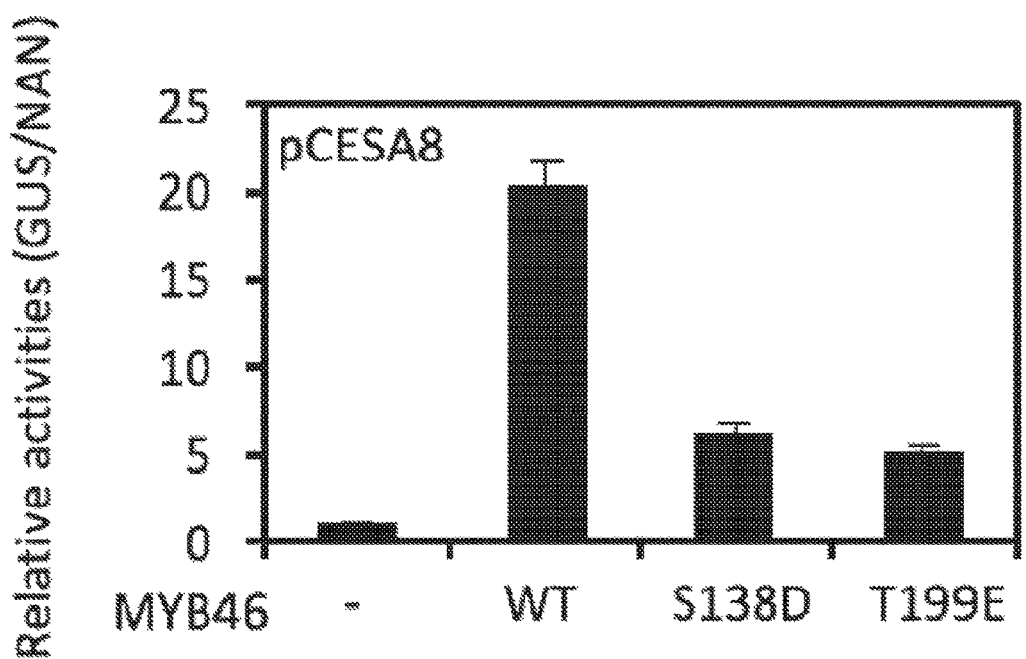

As shown in FIG. 4D, GUS activity was significantly increased by the expression of wild-type (MYB46$^{wt}$) or non-phosphorable mutants of MYB46 (MYB46$^{S138R}$, MYB46$^{T199R}$, MYB46$^{S138R/T199E}$. Such GUS activity was significantly reduced when these wildtype or single mutant MYB46 proteins were expressed in the presence of CAMPK6 (FIG. 4D-4E). However, GUS activity was not reduced when the double mutant (MYB46$^{S138R/T199R}$) was expressed, even in the presence of CAMPK6 co-expression (FIG. 4D). The phosphomimic replacement of serine or threonine with aspartic acid or glutamic acid at either of the two phosphorylation sites resulted in a significant reduction in MYB46 activity (FIG. 4E).

Figure 4F:
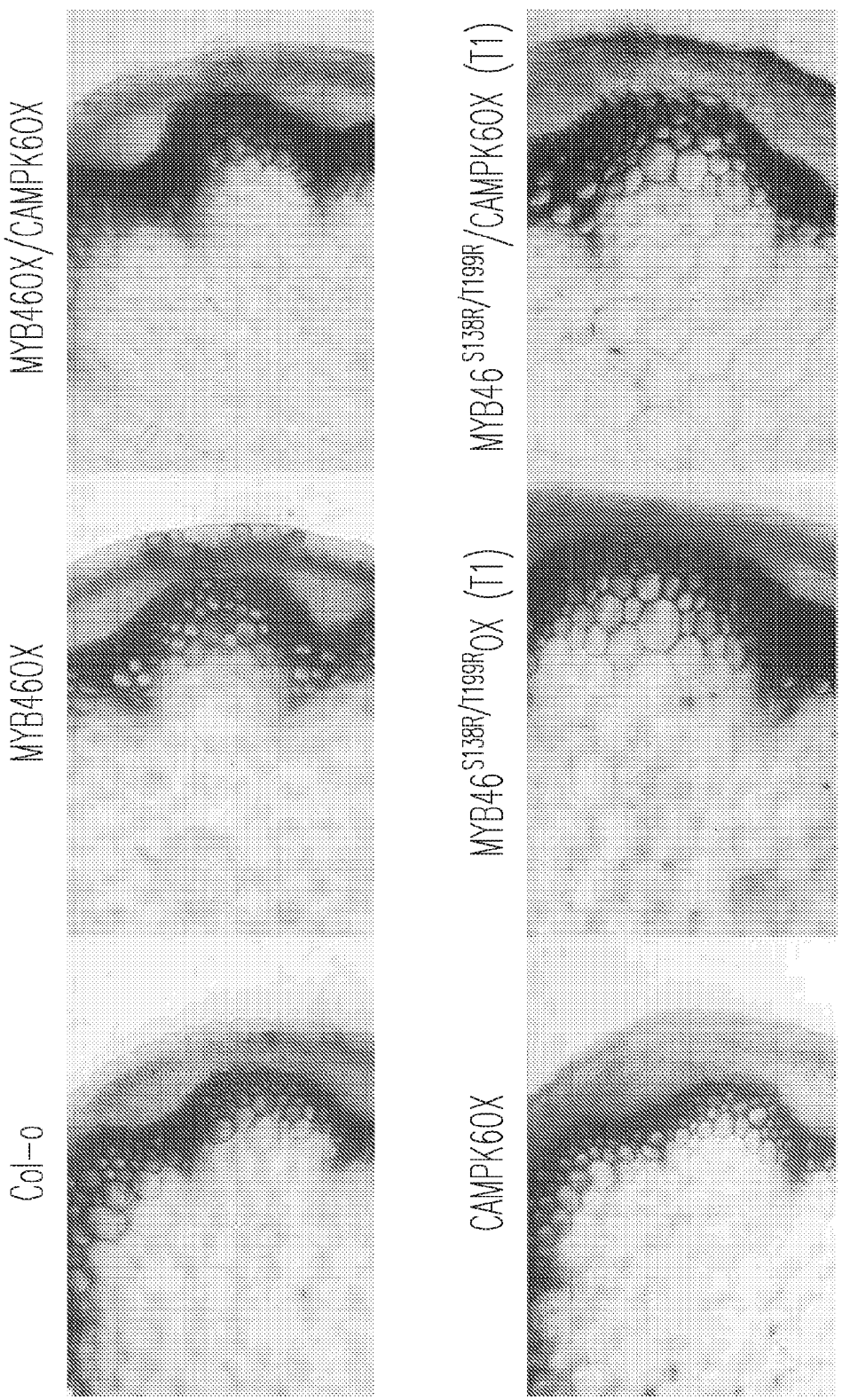
Figure 4G:
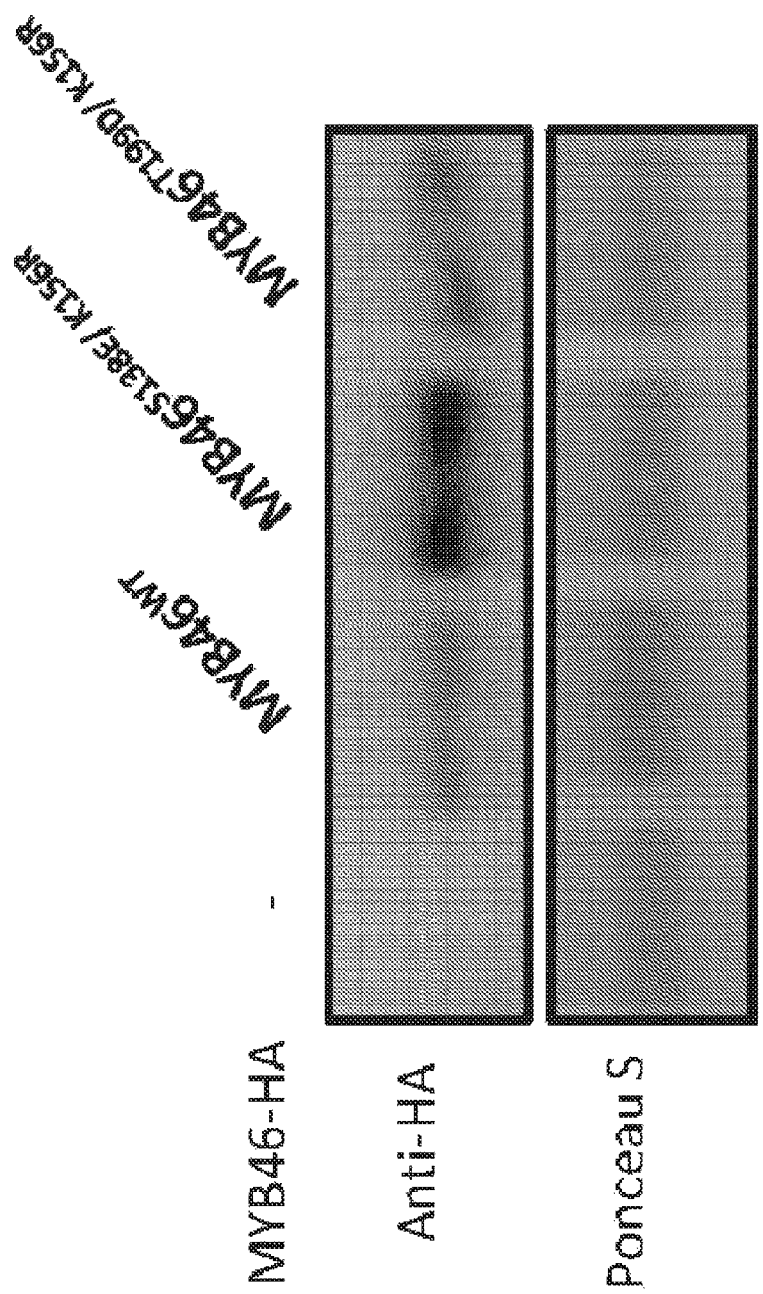

To further confirm these results, transgenic *Arabidopsis* plants were produced that overexpressed MYB46$^{wt}$ or the double mutant, MYB46$^{S138R/T199R}$, with or without CAMPK6. The transgenic plants overexpressing wild-type MYB46 (p35S::MYB46$^{wt}$) or with double non-phosphorable mutations (p35S:: MYB46$^{S138R/T199R}$) showed ectopic lignification in the epidermal cells (a phenotype of constitutive MYB46 overexpression) without CAMPK6 co-expression. However, such ectopic lignification disappeared in the wild type p35S::MYB46W transgenic plants when CAMPK6 was co-expressed (FIG. 4F). In contrast, the double non-phosphorable. MYB46$^{S138R/T199R}$ mutant continued to exhibit ectopic lignification (FIG. 4F). Hence, ectopic lignification by overexpression of MYB46$^{S138R/T199R}$ is not reduced by CAMPK6. These results illustrate that MPK6 negatively regulates MYB46 function through phosphorylation-dependent degradation of MYB46.

Example 5: Salt Stress Negatively Regulates MYB46 Protein Stability Via MPK6

Since MPK6 is activated by salt stress, the inventors then investigated the effect of salt stress on MYB46 protein stability and its function.

Figure 5A:
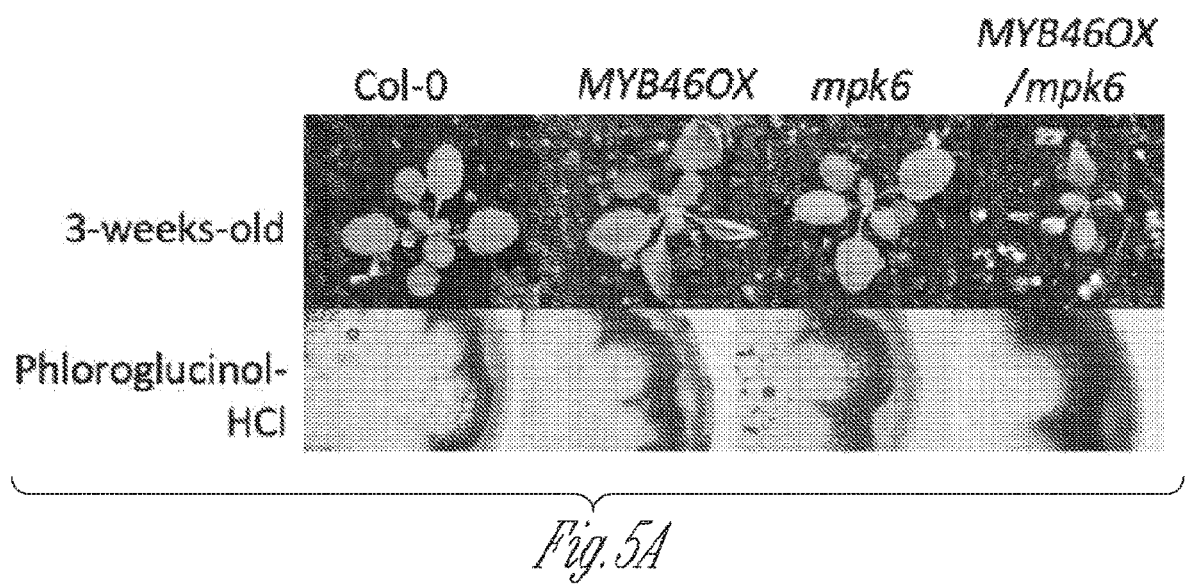
FIG. 5A-5E illustrate that salt stress negatively regulates MYB46 protein stability through MPK6.

Transgenic plants were generated that constitutively overexpressed MYB46 (p35S::MYB46; referred to as MYB46OX) in *Arabidopsis* Col-0 and in a MPK6 knock-out mutant mpk6 line (Yoo et al., 2008). Under normal growth conditions, both MYB46OX and MYB46OX/mpk6 plants exhibited typical MYB46 overexpression phenotypes, including upward curling of the leaves and ectopic lignification in epidermal cells, while mpk6 mutant plants grew normally (FIG. 5A).

Figure 5B:
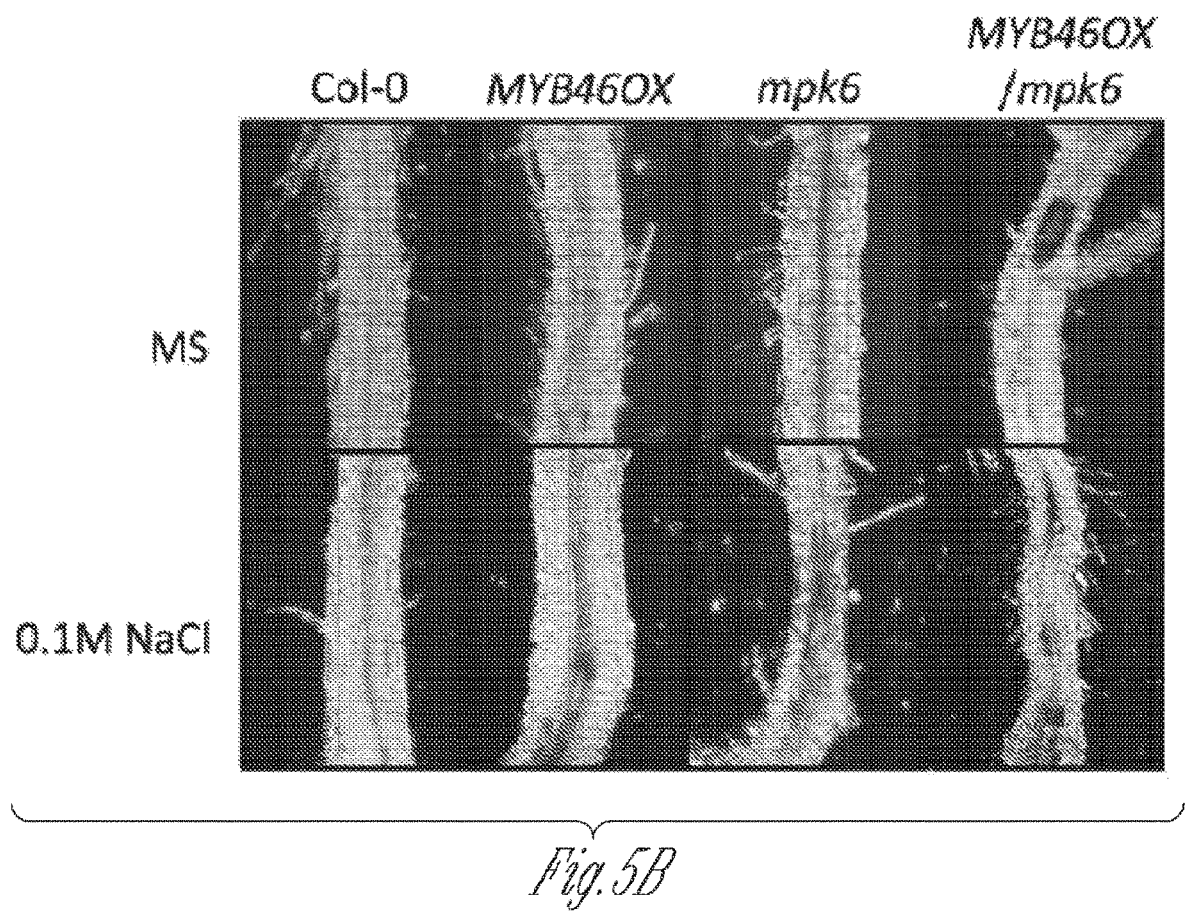
Figure 5C:
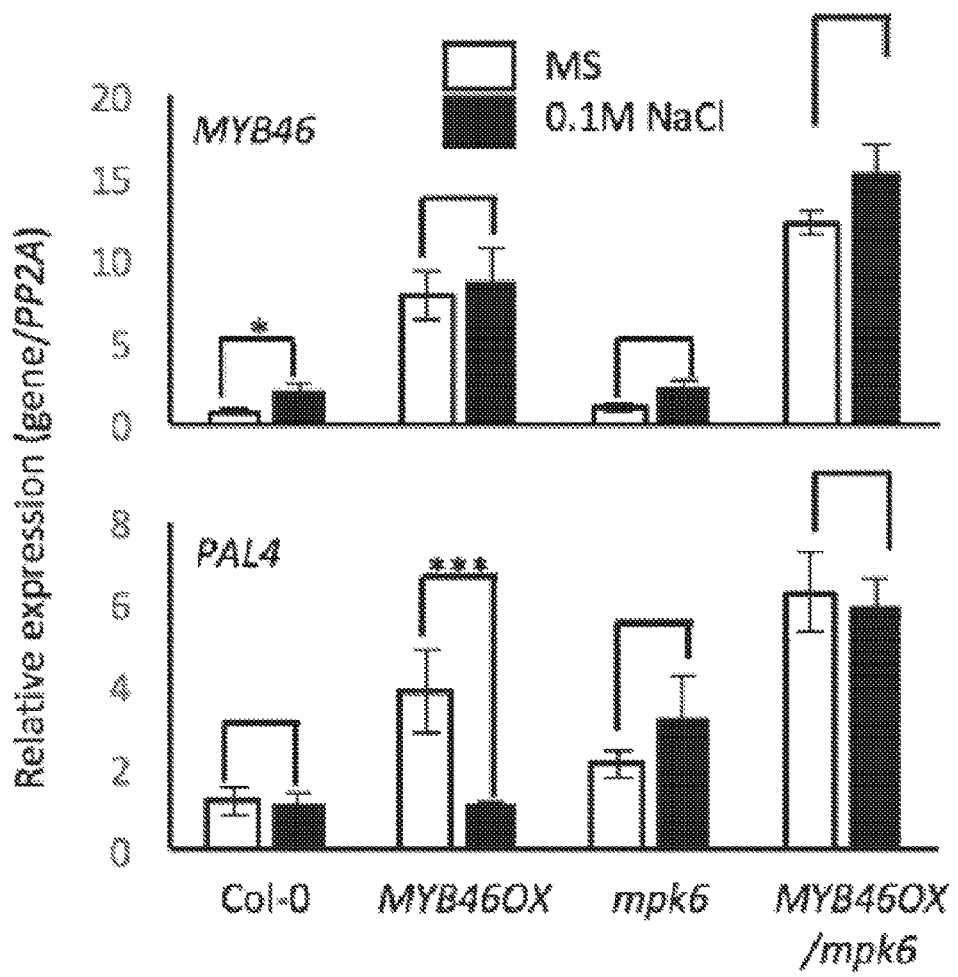

When treated with 0.1M NaCl for 72 hr, lignin staining was reduced in MYB46OX *Arabidopsis* Col-0 plants but not in either the mpk6 or MYB46OK/mpk6 plants (FIG. 5B). Significant increases in MYB46 gene expression were observed in Col-0 wild-type and mpk6 mutant plants after NaCl treatment, but not in the plants constitutively overexpressing MYB46 (i.e., MYB46OX) (FIG. 5C).

Despite the salt stress-induced upregulation of MYB46 expression, the transcription of a direct MYB46-target gene, PAL4, was significantly reduced in the MYB46OX plants. However, such reduction of the transcript level was not observed in the mpk6 mutant plants, indicating posttranscriptional regulation of MYB46 activity by salt treatment.

Figure 5D:
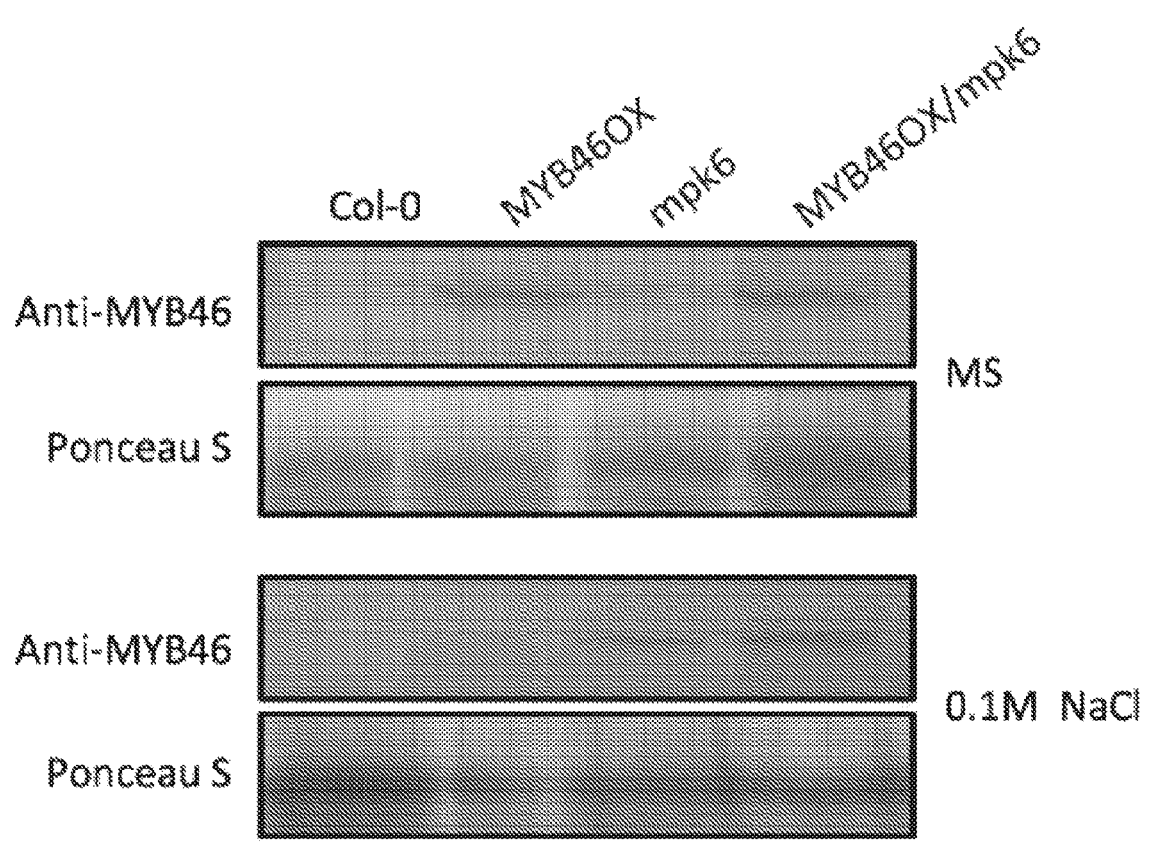
Figure 5H:
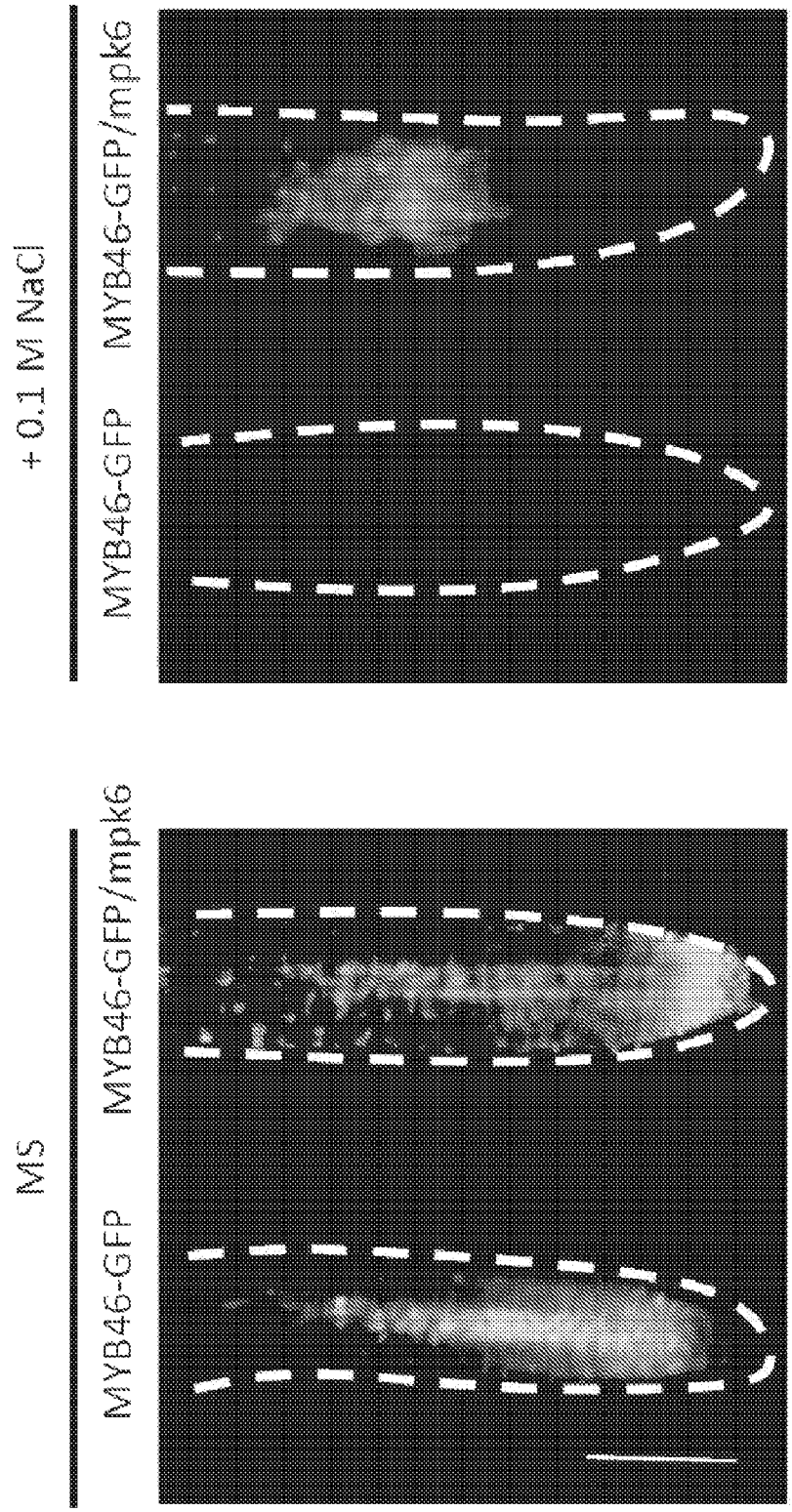

The inventors hypothesized that the salt-induced negative regulation of MYB46 function was caused by MPK6-mediated degradation of MYB46. To test this hypothesis, protein blot analysis was performed of the transgenic plants using anti-MYB46 antibodies. As shown in FIG. 5D, the MYB46 protein was detected in both MYB46OX and MYB46/mpk6 plants. However, the MYB46 protein was degraded with salt treatment in MYB46OX plants, but not in MYB46lmpk6 plants (FIG. 5D). These results indicate that the salt stress-induced negative regulation of MYB46 function is due to phosphorylation-dependent degradation of MYB46.

This observation was further confirmed in transgenic Arabidopsis plants expressing the MYB46-GFP fusion protein (35S::MYB46-GFP). When the 35S::MYB46-GFP plants were treated with 0. M NaCl for 72 hours, GFP signal disappeared in the roots of the transgenic plants expressing the MYB46-GFP in wild-type Col-0 background (FIG. 5E). However, the GFP signal was detectable even with salt stress treatment in the roots of the MYB46-GFP transgenic plants in a mpk6 knockout mutant background (FIG. 5E). These results indicate that MPK6-mediated degradation of MYB46 protein had been abated in the mpk6 knockout mutant transgenic plants.

Example 6: MYB83, a Homolog of MYB46, is not Regulated by CAMPK6

MYB83, a R2R3-type MYB transcription factor transcription, is a functional homolog of MYB46 (MacCarthy et al., 2009), It has two putative phosphorylation target sites, 5147 and 5195.

A sequence for an *Arabidopsis thaliana* MYB83 is shown below as SEQ ID NO:87.

```
  1 MMMRKPDITT IRDKGKPNHA CGGNNNYPKL RKGLWSPDED

41 EKLIRYMLTN GQGCWSDIAR NAGLLRCGKS CRLRWINYLR

81 PDLKRGSFSP QEEDLIFHLH SILGNRWSQI ATRLPGRTDN

121 EIKNFWNSTL KKRLKNNSNN NTSSGSSPNN SNSNSLDPRD

161 QHVDMGGNST SLMDDYHHDE NMMTVGNTMR MDSSSPFNVG

201 PMVNSVGLNQ LYDPLMISVP DNGYHQMGNT VNVFSVNGLG

241 DYGNTILDPI SKRVSVEGDD WFIPPSENTN VIACSTSNNL

281 NLQALDPCFN SKNLCHSESF KVGNVLGIEN GSWEIENPKI

321 GDWDLDGLID NNSSFPFLDF QVD
```

Figure 6B:
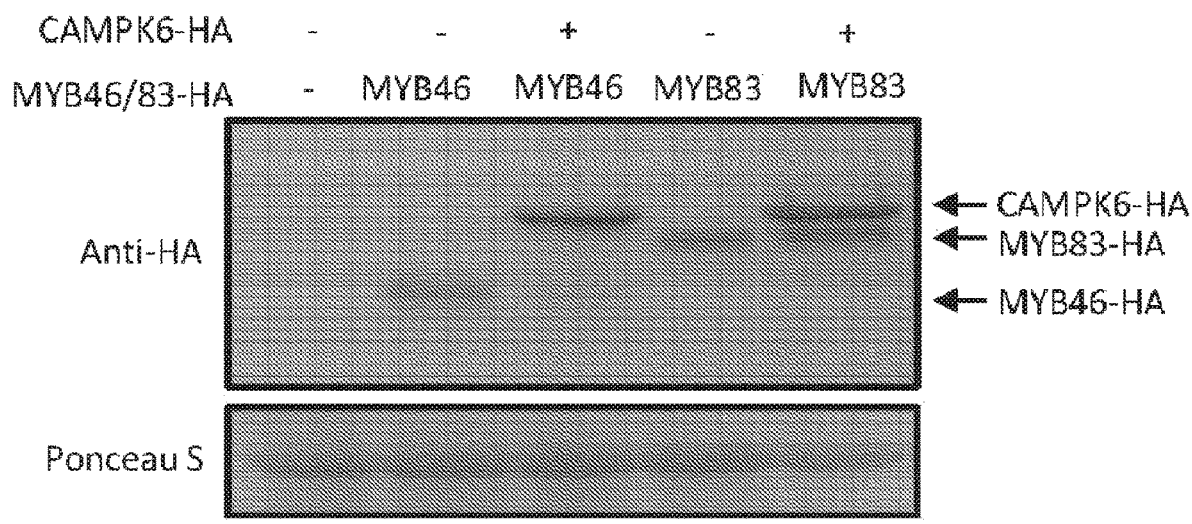

Unlike MYB46, MYB83 does not have a MPK binding motif (FIG. 6A). The inventors hypothesized that MYB83 is not a substrate for MPK6, and tested this hypothesis by investigating whether MYB83 is degraded by MPK6. As illustrated in FIG. 6E, MYB83 may have phosphorylation target sites (as predicted by Eukaryotic Linear Motif).

Protein blot analysis was performed of MYB46-HA or MYB83-HA fusion proteins that had been expressed in AMPs with or without CAMPK6 co-expression. As shown in FIG. 6B, the MYB83 protein level was not changed regardless of CAMPK6 co-expression while the MYB46 protein was degraded in the presence of CAMPK6. These results indicate that MYB83 was not a substrate for MPK6.

Figure 6C:
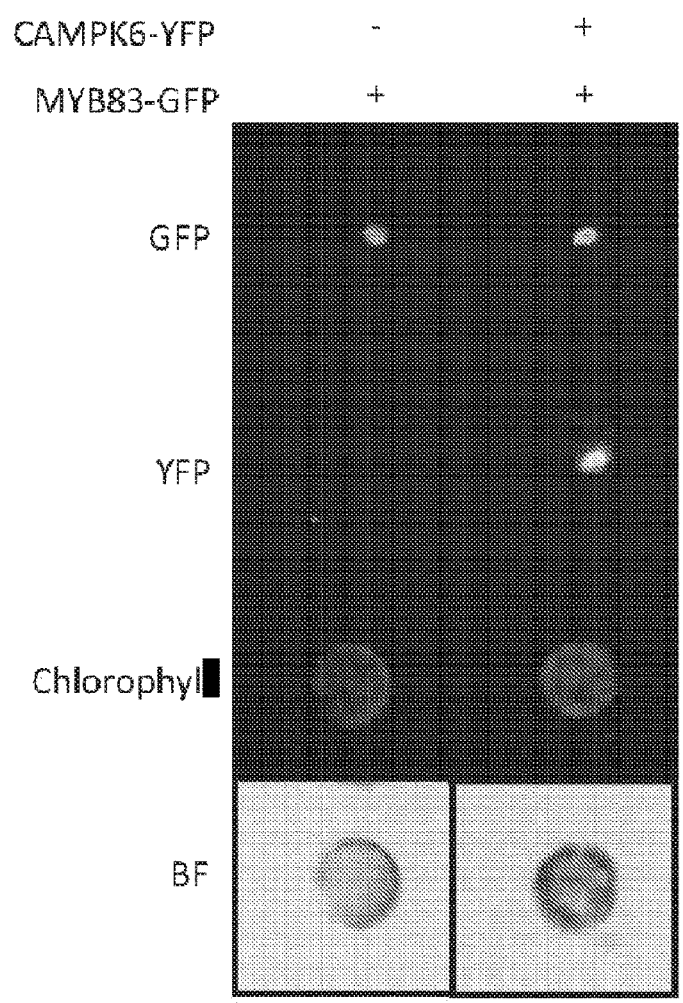

This observation was confirmed by expressing an MYB83-GFP fusion protein construct (p35S::MYB83-GFP) in AMPs with or without expression of a CAMPK6-YFP fusion protein construct (p35S::CAMPK6-YFP), As shown in FIG. 6C, a GFP signal was detected in for MYB83 regardless of CAMPK6 co-expression.

Figure 6D:
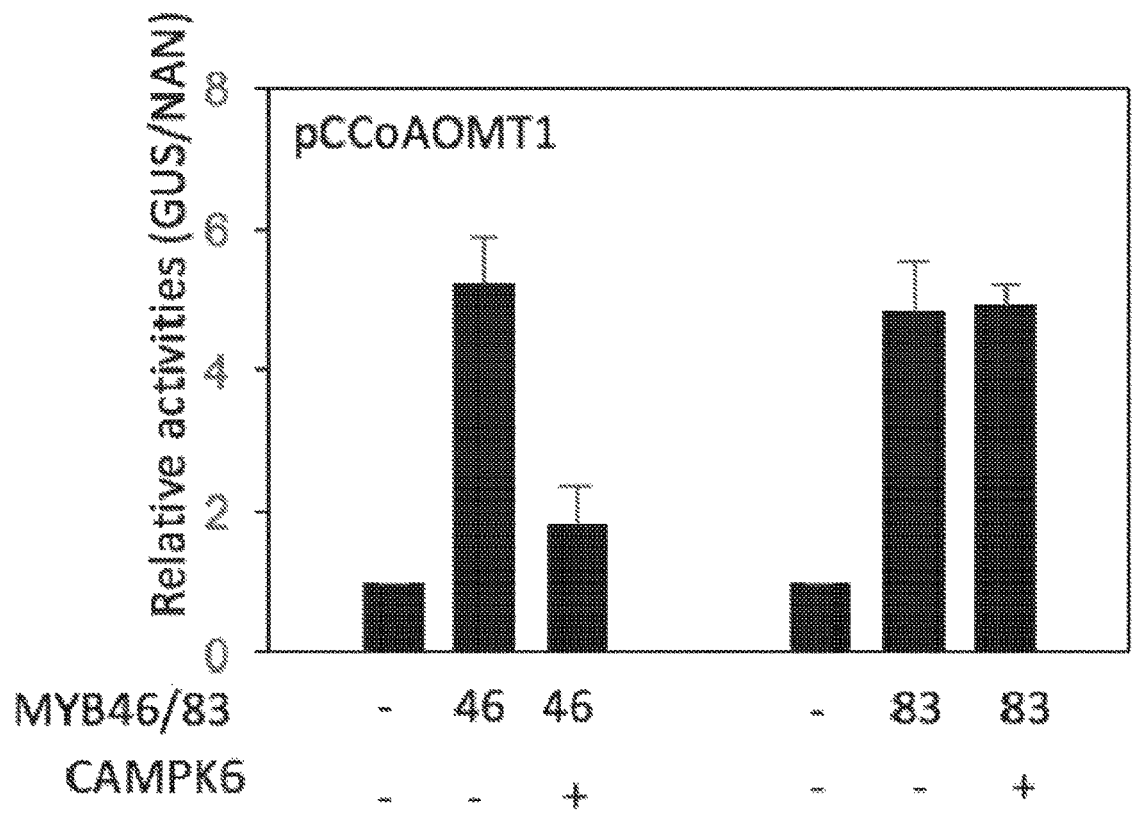
Figure 6E:
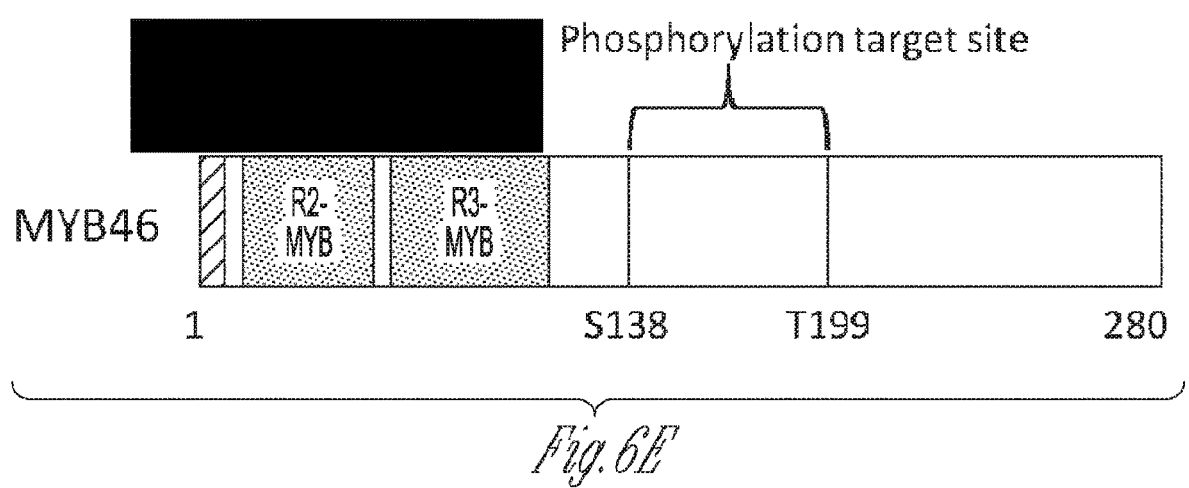

Since MYB83 protein stability was not affected by MPK6, the inventors hypothesized that MYB83 function is not regulated by CAMPK6. To test this hypothesis, a GUS reporter gene driven by the promoter of CCoAOMT, which is a direct target of both MYB46 and MYB83 (MacCarthy et al., 2009), was used in transient activation assay performed in AMPs. As shown in FIG. 6D, GUS expression was significantly increased by either MYB46 or MYB83 expression without CAMPK6 co-expression. However, the MYB46-induced GUS expression was significantly reduced when CAMPK6 was also expressed (FIG. 6D). Such a decrease in GUS expression was not observed when MYB83 was used, even when CAMPK6 was co-expressed (FIG. 6D).

While MYB46 protein is degraded by MPK6-mediated phosphorylation, MYB83 appears not to be subject to MPK6-mediated degradation (FIG. 6). MYB83 does not have a MPK docking domain (FIG. 6A). Hence, while the MYB46 protein has the following N-terminal the region MRKPEVAIAA (SEQ ID NO:88), with the MPK docking domain identified in bold and with underlining, the MYB83 N-terminus has the sequence: MMMRKPDITTI (SEQ ID NO:89), which has no MPK docking domain. Introduction of the MPK docking domain of MYB46 into the N-terminal of MYB83 (to generate a mutant MYB83 with the following N-terminal sequence: MMMRKPEVAITTI, SEQ ID NO:90) did not change MYB83 protein stability when CAMPK6 was co-expressed.

These results indicate that MYB83 is not regulated by MPK6, which conclusion is consistent with the fact that MYB83 protein is not degraded by MPK6.

REFERENCES

Berriri S, et al., (2012) Constitutively Active Mitogen-Activated Protein Kinase Versions Reveal Functions of *Arabidopsis* MPK4 in Pathogen Defense Signaling. *Plant Cell* 24(10):4281-4293.

vis R J (1993) The mitogen-activated protein kinase signal transduction pathway. *J Biol Chem* 268:14553-14556.

Enders T A, Frick E M, & Strader L C (2017) An *Arabidopsis* kinase cascade influences auxin-responsive cell expansion. *Plant J* 92(1):68-81.

Endo H. et al., Multiple classes of transcription factors regulate the expression of VASCULAR-RELATED NAC-DOMAIN7, a master switch of xylem vessel differentiation. Plant and Cell Physiology 56(2): 242-254 (2014).

Feilner T. et al., High throughput identification of potential *Arabidopsis* mitogen-activated protein kinases substrates. *Molecular & Cellular Proteomics* 4(10), 1558-1568 (2005).

Geng F., Wenzel S., Tansey W.-P., Ubiquitin and proteasomes in transcription. *Annual Review of Biochemistry* 81, 177-201 (2012).

Guan Y. et al., Two mitogen-activated protein kinases, MPK3 and MPK6, are required for 473 funicular guidance of pollen tubes in *Arabidopsis*. *Plant physiology* pp-113 14).

Ichimura K, Mizoguchi T, Yoshida R, Yuasa T, & Shinozaki K (2000) Various abiotic stresses vapidly activate *Arabidopsis* MAP kinases ATMPK4 and ATMPK6. *Plant J* 24(5):655-665.

Im J. H, Yoo S. D. Transient Expression in *Arabidopsis* Leaf Mesophyll Protoplast System for Cell-Based Functional Analysis of MAPK Cascades Signaling. In: G. Komis, J. Šamaj, Plant MAP Kinases. Methods in Molecular Biology 524 (Methods and Protocols), Humana Press, New York, NY Eds. (Springer, 2014). Vol: 1171.

Jia W, et al. Mitogen-Activated Protein Kinase Cascade MKK7-MPK6 Plays Important Roles in Plant Development and Regulates Shoot Branching by Phosphorylating PIN1 in *Arabidopsis*. *PLoS Biol* 14(9):e1002550 (2016).

Jeong E.-Y., Seo P.-J., Woo J.-C., Park C.-M., AKIN10 delays flowering by inactivating 494 IDD8 transcription factor through protein phosphorylation in *Arabidopsis*. BMC Plant Biology 15(1): 110 (2015).

Kawamoto N. et al., Calcium-dependent protein kinases responsible for the phosphorylation of a bZIP transcription factor ED crucial for the florigen complex formation. Scientific reports 5, srep 08341 (2015).

Kim S H, et al. Phosphorylation of the transcriptional repressor MYB15 by mitogen-activated protein kinase 6 is required for freezing tolerance in *Arabidopsis*. *Nucleic Acids Res* 45(11):6613-6627 (2017).

Kim W C, et al. (2013) MYB46 directly regulates the gene expression of secondary wall-associated cellulose synthases in *Arabidopsis*. *Plant J* 73(1):26-36.

Kim W C, Kim J Y, Ko J H, Kim J, & Han K H (2013) Transcription factor MYB46 is an obligate component of the transcriptional regulatory complex for functional expression of secondary wall-associated cellulose synthases in *Arabidopsis thaliana*. *Plant Physiol* 170(15): 1374-1378.

Kim W C, et al. (2014) Transcription factors that directly regulate the expression of CSLA9 encoding mannan synthase in *Arabidopsis thaliana*. *Plant Mol Biol* 84(4-5):577-587.

Kim W C, Kim J Y, Ko J H, Kang H, & Han K H (2014) Identification of direct targets of transcription factor MYB46 provides insights into the transcriptional regulation of secondary wall biosynthesis. *Plant Mol Biol* 85(6): 589-599.

Kirby J., Kavanagh T.-A., NAN fusions: a synthetic sialidase reporter gene as a sensitive and versatile partner for GUS. The Plant Journal 32(3): 391-400 (2002).

Ko J H, Kim W C, & Han K H (2009) Ectopic expression of MYB46 identifies transcriptional regulatory genes involved in secondary wall biosynthesis in *Arabidopsis*. *Plant J* 60(4):649-665.

Ko J H, Jeon H W, Kim W C, Kim J Y, & Han K H (2014) The MYB46/MYB83-mediated transcriptional regulatory programme is a gatekeeper of secondary wall biosynthesis. *Ann Bot* 114(6):1099-1107.

Ko J.-H. et al., MYB46-mediated transcriptional regulation of secondary wall biosynthesis, Molecular Plant 5(5): 961-963 (2012).

K. Kurashima et al., Identification of sites required for down-regulation of Na+/H+ exchanger NHE3 activity by cAMP-dependent protein kinase phosphorylation dependent and independent mechanisms. Journal of Biological Chemistry 272(45): 469 28672-28679 (1997).

Lampard G R, MacAlister C A, Bergmann D C (2008) *Arabidopsis* Stomatal initiation Is Controlled by MAPK-Mediated Regulation of the hHLH SPEECHLESS. Science 322:1113-1116. doi: 10.1126/science.1162263

Lee Y, Lee H-S, Lee J-S, Kim S-K, Kim S-H (2008) Hormone- and light-regulated nucleocytoplasmic transport in plants: current status. J Exp Bot 59:3229-3245. doi: 10.1093/jxb/ern200

Lee D. H., Goldberg A. L., Proteasome inhibitors: valuable new tools for cell biologists. Trends in Cell Biology 8(10):397-403 (1998).

Lerouxel O., Cavalier D.-M., Liepman A.-H., Keegstra K., Biosynthesis of plant cell wall polysaccharides a complex process. Current opinion in plant biology 9(6), 621-630 (2006).

Liu Y & Zhang S (2004) Phosphorylation of 1-aminocyclopropane-1-carboxylic acid synthase by MPK6, a stress-responsive mitogen-activated protein kinase, induces ethylene biosynthesis in *Arabidopsis*. *Plant Cell* 16(12)3386-3399.

Luan S (2002) Tyrosine phosphorylation in plant cell signaling. Proc Natl Acad. Sci USA 99:11567-11569. doi: 10.1073/pnas.182417599

Mao G. et al., Phosphorylation of a WRKY transcription factor by two pathogen responsive MAPKs drives phytoalexin biosynthesis in *Arabidopsis*. Plant Cell 23(4): 1639-1653 (2011).

Meng X Z, et al. (2013) Phosphorylation of an ERF Transcription Factor by *Arabidopsis* MPK3/MPK6 Regulates Plant Defense Gene Induction and Fungal Resistance. Plant Cell 25(3):1126-1142.

Mao G H, et al. (2011) Phosphorylation of a WRKY Transcription Factor by Two Pathogen-Responsive MAPKs Drives Phytoalexin Biosynthesis in *Arabidopsis*. *Plant Cell* 23(4):1639-1653.

McCarthy R.-L. Zhong R., Ye Z.-H., MYB83 is a direct target of SND1 and acts redundantly with MYB46 in the regulation of secondary cell wall biosynthesis in *Arabidopsis*. *Plant and Cell Physiology* 50(11): 1950-1964 (2009).

Morse A M, Whetten R W, Dubos C, & Campbell M M (2009) Post-translational modification of an R2R3-MYB transcription factor by a MAP Kinase during xylem development. New Phytol 183(4):1001-1013.

K. Ohashi-Ito, Y. Oda, H. Fukuda, *Arabidopsis* VASCULAR-RELATED NAC DOMAIN6 directly regulates the genes that govern programmed cell death and secondary wall formation during xylem differentiation. Plant Cell 22(10): 3461-3473 (2010).

Patzlaff A, al. (2003) Characterisation of a pine MYB that regulates lignification. *Plant J* 36(6):743-754.

Pahl H L, Baeuerle P A (1996) Control of gene expression by proteolysis. Curr Opin Cell Biol 8:340-347.

A. Pitzschke, S. Datta, H. Persak, Salt stress in *Arabidopsis*: lipid transfer protein AZI1 and its control by mitogen-activated protein kinase MPK3. *Molecular plant* 7(4), 722-738 (2014).

Popescu S.-C. et al., MAPK target networks in *Arabidopsis thaliana* revealed using functional protein microarrays. *Genes & Development* 23(1): 80-92 (2009).

Poizat C., Puri P.-L., Bai Y., Kedes L., Phosphorylation-dependent degradation of p300 by doxorubicin-activated p38 mitogen-activated protein kinase in cardiac cells. Molecular and cellular biology 25(7): 2673-2687 (2005).

Qiu J L., et al. (2008) *Arabidopsis* ogen-activated protein kinase kinases MKK1 and MKK2 have overlapping functions in defense signaling mediated by MEKK1, MPK4 and MKS1. *Plant Physiol* 148(11:212-222.

Ramirez V, et al. (2011) MYB46 modulates disease susceptibility to *Botrytis cinerea* in *Arabidopsis*. *Plant Physiol* 155(4):1920-1935.

Raes J, Rohde A, Christensen J H, Van de Peer Y, & Boerjan W (2003) Genome-w characterization of the lignification toolbox in *Arabidopsis*. *Plant Physiol* 133(3):1051-1071.

Santner A, Estelle M (2009) Recent advances and emerging trends in plant hormone signalling. Nature 459:1071-1078. doi:10.1038/nature08122

Sharrocks A D, Yang S H, Galanis A (2000) Docking domains and substrate-specificity determination for MAP kinases. Trends in Biochemical Sciences 25:448-453.

Takahashi F, et al. (2007) The mitogen-activated protein kinase cascade MKK3-MPK6 is an important part of the jasmonate signal transduction pathway in *Arabidopsis*. *Plant Cell* 19(3):805-818.

Taylor-Teeples M, et al. (2015) An *Arabidopsis* gene regulatory network for secondary cell wall synthesis. *Nature* 517(7536):571-U307.

Taylor-Teeples M, et al. (2015) An *Arabidopsis* gene regulatory network for secondary cell wall synthesis. *Nature* 517(7536):571-575.

Teige M, et al. (2004) The MKK2 pathway mediates cold and salt stress signaling in *Arabidopsis*. *Mol Cell* 15(1): 141-152.

Tootle T L, Rebay I (2005) Post-translational modifications influence transcription factor activity: A view from the EIS superfamily. *Bioessays* 27:285-298. doi: 10.1002/bies.20198

H. Wang et al., Stomatal development and patterning are 475 regulated by environmentally responsive mitogen-activated protein kinases in *Arabidopsis*. *The Plant Cell* 19(1), 63-47'7 73 (2007).

Whitmarsh A J, Davis R J (2000) Regulation of transcription factor function by phosphorylation. Cellular and Molecular Life Sciences 57:1172-1183. doi: 10,1007/P1.00000757

Wu Y., Cosgrove D.-J., Adaptation of roots to low water potentials by changes in cell 446 wall extensibility and cell wall proteins. Journal of experimental botany 51(350), 1543-447 1553 (2000).

Yamaguchi M. et al., VASCULAR-RELATED NAC-DOMAIN 7 directly regulates the expression of a broad range of genes for xylem vessel formation. *The Plant Journal* 66(4): 579-590(2011).

Yoo S D, Cho Y H, Tena G, Xiong Y, & Sheen J (2008) Dual control of nuclear EIN3 by bifurcate MAPK cascades in C2H4 signalling. *Nature* 451(7180):789-U781, Yu L J, et al. (2010) Phosphatidic acid mediates salt stress response by regulation of MPK6 in *Arabidopsis thaliana*. *New Phytol* 88(3):762-773.

Zhai Q. et al., Phosphorylation-coupled proteolysis of the transcription factor MYC2 is important for jasmonate-signaled plant immunity. *PLoS genetics* 9(4): e1003422 (2013).

Zhao C, Wang P, Si T, Hsu C-C, Wang 1, Zayed O, Yu Z, Zhu Y, Dong i, Tao W A, Zhu J-K (2017) MAP Kinase Cascades Regulate the Cold Response by Modulating ICE1 Protein Stability. Dev Cell 43:618-629.e5. doi: 10.10167j.devce1.2017.09.024

Zhong R Q & Ye Z H (2012) MYB46 and MYB83 Bind to the SMRE Sites and Directly Activate a Suite of Transcription Factors and Secondary Wall Biosynthetic Genes. *Plant Cell Physiol* 53(2)368-380.

Zhong R., Richardson E.-A., Ye Z.-14., The MYB46 transcription factor is a direct target of SND1 and regulates secondary wall biosynthesis in *Arabidopsis. The Plant Cell* 19(9): 2776-2792 (2007).

All patents and publications referenced or mentioned herein are indicative of the levels of skill of those skilled in the art to which the invention pertains, and each such referenced patent or publication is hereby specifically incorporated by reference to the same extent as if it had been incorporated by reference in its entirety individually or set forth herein in its entirety. Applicants reserve the right to physically incorporate into this specification any and all materials and information from any such cited patents or publications.

The following statements of the invention are intended to describe and summarize various embodiments of the invention according to the foregoing description in the specification.

Statements

1. A modified MYB46 polypeptide comprising replacements of at least one serine phosphorylation site and at least one threonine phosphorylation site with replacement amino acids that are not serine, threonine, aspartic acid, or glutamic acid.
2. The modified MYB46 polypeptide of statement 1, wherein the replacement amino acids are selected from arginine, lysine, glycine, proline, alanine, leucine, isoleucine, valine, phenylalanine, tryptophan, cysteine, methionine, histidine, asparagine, glutamine, or tyrosine.
3. The modified MYB46 polypeptide of statement 1 or 2, wherein the replacement amino acids are selected from arginine, lysine, glycine, proline, alanine, leucine, isoleucine, valine, phenylalanine, tryptophan, cysteine, methionine, or histidine.
4. The modified MYB46 polypeptide of statement 1, wherein the replacement amino acids are each arginine.
5. The modified MYB46 polypeptide of statement 1-3 or 4, wherein the at least one serine phosphorylation site and at least one threonine phosphorylation site are within amino acid sequence SEQ ID NO:1, 3, 7, 11, 13, 15, 17, 19, 20, 24, 27, 30, 35, 38, 39, 40, 41, 42, 45, 46, 47, or 48.
6. The modified MYB46 polypeptide of statement 1-4 or 5, wherein the modified MYB46 polypeptide has an increased half-life compared to a corresponding unmodified MYB46 polypeptide that has no replacements of serine or threonine residues.
7. The modified MYB46 polypeptide of statement 1-5 or 6, wherein the modified MYB46 polypeptide has an increase in half-life within a plant cell of at least about 10 minutes, at least about 30 minutes, at least about 1 hour, at least about 2 hours, at least about 4 hours, at least about 8 hours, at least about 10 hours, at least about 16 hours, about at least about 24 hours, at least about 30 hours, at least about 36 hours, about at least about 48 hours, at least about 1 day, at least about 2 days, or at least about 4 days compared to a corresponding unmodified MYB46 polypeptide that has no replacements of serine or threonine residues.
8. A nucleic acid encoding the modified MYB46 polypeptide of statement 1-6 or 7,
9. An expression cassette or expression vector comprising a heterologous promoter operably linked to the nucleic acid of statement 8.
10. The expression cassette of statement 9, wherein the heterologous promoter is a strong, weak, inducible, tissue specific, developmentally regulated or a combination thereof.
11. A plant, plant cell or seed comprising the modified MYB46 polypeptide of statement 1-6 or 7.
12. A plant, plant cell or seed comprising a heterologous nucleic encoding the modified MYB46 polypeptide of statement 1-6 or 7.
13. A plant, plant cell or seed comprising an expression cassette or expression vector having a heterologous promoter operably linked to the nucleic acid of statement 8,
14. The plant, plant cell or seed of statement 11, 12 or 13, which plant has increased biomass, fiber content, and/or structural strength compared to a wild type or parental plant without the modified MYB46 polypeptide.
15. The plant, plant cell or seed of statement 11-13 or 14, which plant has biomass, structural (e.g., tensile) strength, or fiber content that is by at least 3%, at least 5%, at least 7%, at least 10%, at least 15%, at least 20%, at least 25%, at least 30%, at least 40%, at least 50%, at least 60%, at least 70%, at least 80%, at least 85%, at least 95%, or at least 100%.
16. The plant, plant cell or seed of statement 11-14 or 15, which is a fiber-producing species.
17. The plant, plant cell or seed of statement 11-15 or 16, which is a cotton, flax, hemp, or wood species.
18. The plant, plant cell or seed of statement 11-16 or 17, which plant has biomass, structural (e.g., tensile) strength, or fiber content that is by at least 2-fold, or at least 3-fold., or at least 4-fold, or at least 5-fold, or at least 7-fold, or at least 10-fold,
19. A method comprising cultivating a seedling or seed having the modified MYB46 polypeptide of statement 1-6 or 7, to generate a plant having the modified MYB46 polypeptide.
20. A method comprising cultivating a seedling or seed having an expression cassette or expression vector having a heterologous promoter operably linked to nucleic acid segment encoding a modified MYB46 polypeptide having replacements of at least one serine phosphorylation site and at least one threonine phosphorylation site with replacement amino acids that are not serine, threonine, aspartic acid, or glutamic acid, to thereby generate a plant having the modified MYB46 polypeptide.
21. The method of statement 19 or 20 further comprising isolating biomass or fiber from the plant having the modified MYB46 polypeptide.
22. A method comprising transforming a host plant cell with an expression cassette or expression vector having a heterologous promoter operably linked to a nucleic acid segment encoding a modified MYB46 polypeptide having replacements of at least one serine phosphorylation site and at least one threonine phosphorylation site with replacement amino acids that are not serine, threonine, aspartic acid, or glutamic acid; and generating a seedling therefrom.
23. The method of statement 19-21 or 22, wherein the replacement amino acids are selected from arginine, lysine, glycine, proline, alanine, leucine, valine, phenylalanine, tryptophan, cysteine, methionine, histidine, asparagine, glutamine, or tyrosine.
24. The method of statement 19-22 or 23, wherein the replacement amino acids are selected from arginine, lysine, glycine, proline, alanine, leucine, isoleucine, valine, phenylalanine, tryptophan, cysteine, methionine, or histidine.

25. The method of statement 19-23 or 24, wherein the replacement amino acids are each arginine.

26. The method of statement 19-24 or 25, wherein the at least one serine phosphorylation site and at least one threonine phosphorylation site are within amino acid sequence SEQ NO:1, 3, 7, 11, 13, 15, 17, 19, 20, 24, 27, 30, 35, 38, 39, 40, 41, 42, 45, 46, 47, or 48.

27. The method of statement 19-25 or 26, wherein the modified MYB46 polypeptide has an increased half-life compared to a corresponding unmodified MYB46 polypeptide that has no replacements of serine or threonine residues.

28, The method of statement 19-26 or 27, wherein the modified MYB46 polypeptide has an increase in half-life within a plant cell of at least about 10 minutes, at least about 30 minutes, at least about 1 hour, at least about 2 hours, at least about 4 hours, at least about 8 hours, at least about 10 hours, at least about 16 hours, about at least about 24 hours, at least about 30 hours, at least about 36 hours, about at least about 48 hours, at least about 1 day, at least about 2 days, or at least about 4 days compared to a corresponding unmodified MYB46 polypeptide that has no replacements of serine or threonine residues.

The specific methods and compositions described herein are representative of preferred embodiments and are exemplary and not intended as limitations on the scope of the invention. Other objects, aspects, and embodiments will occur to those skilled in the art upon consideration of this specification and are encompassed within the spirit of the invention as defined by the scope of the claims. It will be readily apparent to one skilled in the art that varying substitutions and modifications may be made to the invention disclosed herein without departing from the scope and spirit of the invention.

The invention illustratively described herein suitably may be practiced in the absence of any element or elements, or limitation or limitations, which is not specifically disclosed herein as essential. The methods and processes illustratively described herein suitably may be practiced in differing orders of steps, and the methods and processes are not necessarily restricted to the orders of steps indicated herein or in the claims.

As used herein and in the appended claims, the singular forms "a" "an," and "the" include plural reference unless the context clearly dictates otherwise. Thus, for example, a reference to "a nucleic acid" or "a protein" or "a cell" includes a plurality of such nucleic acids, proteins, or cells (for example, a solution or dried preparation of nucleic acids or expression cassettes, a solution of proteins, or a population of cells), and so forth. In this document, the term "or" is used to refer to a nonexclusive or, such that "A or B" includes "A but not B," "B but not A," and "A and B," unless otherwise indicated.

Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims and statements of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein. In addition, where features or aspects of the invention are described in terms of Markush groups, those skilled in the art will recognize that the invention is also thereby described in terms of any individual member or subgroup of members of the Markush group.

What is claimed:

1. A modified MYB46 polypeptide comprising replacements of:
   (a) a serine phosphorylation site at residue S138 and a threonine phosphorylation site at residue T199, wherein the modified MYB46 polypeptide has at least 95% sequence identity to SEQ ID NO: 1;
   (b) a serine phosphorylation site S135 and a threonine phosphorylation site T191, wherein the modified MYB46 polypeptide has at least 95% sequence identity to SEQ ID NO: 3;
   (c) a serine phosphorylation site S139 and a glutamic acid phosphorylation site E140, wherein the modified MYB46 polypeptide has at least 95% sequence identity to SEQ ID NO: 7;
   (d) a serine phosphorylation site S138, wherein the modified MYB46 polypeptide has at least 95% sequence identity to SEQ ID NO: 11;
   (e) a serine phosphorylation site S138 and a threonine phosphorylation site T199, wherein the modified MYB46 polypeptide has at least 95% sequence identity to SEQ ID NO: 13;
   (f) a serine phosphorylation site S139 and a threonine phosphorylation site T200, wherein the modified MYB46 polypeptide has at least 95% sequence identity to SEQ ID NO: 15;
   (g) a serine phosphorylation site S139 and a threonine phosphorylation site T201, wherein the modified MYB46 polypeptide has at least 95% sequence identity to SEQ ID NO: 17;
   (h) a serine phosphorylation site S137 and a glutamic acid phosphorylation site E138, wherein the modified MYB46 polypeptide has at least 95% sequence identity to SEQ ID NO: 19;
   (i) a serine phosphorylation site S135, a threonine phosphorylation site T222, and an alanine phosphorylation site at A136, wherein the modified MYB46 polypeptide has at least 95% sequence identity to SEQ ID NO: 20;
   (j) a serine phosphorylation site S265, wherein the modified MYB46 polypeptide has at least 95% sequence identity to SEQ ID NO: 24;
   (k) a serine phosphorylation site S146, wherein the modified MYB46 polypeptide has at least 95% sequence identity to SEQ ID NO: 27;
   (l) serine phosphorylation sites S146 an S197, wherein the modified MYB46 polypeptide has at least 95% sequence identity to SEQ ID NO: 30;
   (m) a serine phosphorylation site S221, wherein the modified MYB46 polypeptide has at least 95% sequence identity to SEQ ID NO: 35;
   (n) a serine phosphorylation site S138, wherein the modified MYB46 polypeptide has at least 95% sequence identity to SEQ ID NO: 40;
   (o) a serine phosphorylation site S150, wherein the modified MYB46 polypeptide has at least 95% sequence identity to SEQ ID NO: 41;
   (p) serine phosphorylation sites S136, S137, and S213, wherein the modified MYB46 polypeptide has at least 95% sequence identity to SEQ ID NO: 42;
   (q) serine phosphorylation sites S138 and S139 and a glutamic acid phosphorylation site E141, wherein the modified MYB46 polypeptide has at least 95% sequence identity to SEQ ID NO:45;
   (r) a serine phosphorylation site S144, wherein the modified MYB46 polypeptide has at least 95% sequence identity to SEQ ID NO: 46;
   (s) a serine phosphorylation site S150, wherein the modified MYB46 polypeptide has at least 95% sequence identity to SEQ ID NO: 47; or
   (t) a serine phosphorylation site S145, wherein the modified MYB46 polypeptide has at least 95% sequence identity to SEQ ID NO: 48.

2. The modified MYB46 polypeptide of claim 1, wherein the replacement amino acids are selected from arginine, lysine, glycine, proline, alanine, leucine, isoleucine, valine, phenylalanine, tryptophan, cysteine, methionine, histidine, asparagine, glutamine, or tyrosine.

3. The modified MYB46 polypeptide of claim 1, wherein the replacement amino acids are selected from arginine, lysine, glycine, proline, alanine, leucine, isoleucine, valine, phenylalanine, tryptophan, cysteine, methionine, or histidine.

4. The modified MYB46 polypeptide of claim 1, wherein the replacement amino acids are each arginine.

5. The modified MYB46 polypeptide of claim 1, wherein the modified MYB46 polypeptide has an increased half-life compared to a corresponding unmodified MYB46 polypeptide that has no replacements of serine or threonine residues.

6. The modified MYB46 polypeptide of claim 1, wherein the modified MYB46 polypeptide has an increase in half-life within a plant cell of at least about 10 minutes, compared to a corresponding unmodified MYB46 polypeptide that has no replacements of serine or threonine residues.

7. A nucleic acid encoding the modified MYB46 polypeptide of claim 1.

8. An expression cassette or expression vector comprising a heterologous promoter operably linked to a nucleic acid encoding the modified MYB46 polypeptide of claim 1.

9. A plant, plant cell or seed comprising the modified MYB46 polypeptide of claim 1.

10. The plant, plant cell or seed of claim 9, comprising a heterologous nucleic acid encoding the modified MYB46 polypeptide.

11. The plant, plant cell or seed of claim 10, comprising an expression cassette or expression vector having a heterologous promoter operably linked to the nucleic acid.

12. The plant, plant cell or seed of claim 9, which plant has at least 3% increased biomass, fiber content, and/or structural strength compared to a wild type or parental plant without the modified MYB46 polypeptide.

13. The plant, plant cell or seed of claim 9, which is a fiber-producing species.

14. The plant, plant cell or seed of claim 9, which is a cotton, flax, hemp, or wood species.

15. A method comprising cultivating a seedling or seed having the modified MYB46 polypeptide of claim 1, to generate a plant having the modified MYB46 polypeptide.

16. The method of claim 15, comprising cultivating a seedling or seed having an expression cassette or expression vector having a heterologous promoter operably linked to nucleic acid segment encoding the modified MYB46 polypeptide.

17. The method of claim 15, further comprising isolating biomass or fiber from the plant having the modified MYB46 polypeptide.

18. A method comprising transforming a host plant cell with an expression cassette or expression vector having a heterologous promoter operably linked to a nucleic acid segment encoding a modified MYB46 polypeptide having replacements of:
  (a) a serine phosphorylation site at residue S138 and a threonine phosphorylation site at residue T199 in the amino acid sequence of SEQ ID NO: 1, wherein the modified MYB46 polypeptide has at least 95% sequence identity to SEQ ID NO: 1;
  (b) a serine phosphorylation site S135 and a threonine phosphorylation site T191, wherein the modified MYB46 polypeptide has at least 95% sequence identity to SEQ ID NO: 3;
  (c) a serine phosphorylation site S139 and a glutamic acid phosphorylation site E140, wherein the modified MYB46 polypeptide has at least 95% sequence identity to SEQ ID NO: 7;
  (d) a serine phosphorylation site S138, wherein the modified MYB46 polypeptide has at least 95% sequence identity to SEQ ID NO: 11;
  (e) a serine phosphorylation site S138 and a threonine phosphorylation site T199, wherein the modified MYB46 polypeptide has at least 95% sequence identity to SEQ ID NO: 13;
  (f) a serine phosphorylation site S139 and a threonine phosphorylation site T200, wherein the modified MYB46 polypeptide has at least 95% sequence identity to SEQ ID NO: 15;
  (g) a serine phosphorylation site S139 and a threonine phosphorylation site T201, wherein the modified MYB46 polypeptide has at least 95% sequence identity to SEQ ID NO: 17;
  (h) a serine phosphorylation site S137 and a glutamic acid phosphorylation site E138, wherein the modified MYB46 polypeptide has at least 95% sequence identity to SEQ ID NO: 19;
  (i) a serine phosphorylation site S135, a threonine phosphorylation site T222, and an alanine phosphorylation site at A136, wherein the modified MYB46 polypeptide has at least 95% sequence identity to SEQ ID NO: 20;
  (j) a serine phosphorylation site S265, wherein the modified MYB46 polypeptide has at least 95% sequence identity to SEQ ID NO: 24;
  (k) a serine phosphorylation site S146, wherein the modified MYB46 polypeptide has at least 95% sequence identity to SEQ ID NO: 27;
  (l) serine phosphorylation sites S146 an S197, wherein the modified MYB46 polypeptide has at least 95% sequence identity to SEQ ID NO: 30;
  (m) a serine phosphorylation site S221, wherein the modified MYB46 polypeptide has at least 95% sequence identity to SEQ ID NO: 35;
  (n) a serine phosphorylation site S138, wherein the modified MYB46 polypeptide has at least 95% sequence identity to SEQ ID NO: 40;
  (o) a serine phosphorylation site S150, wherein the modified MYB46 polypeptide has at least 95% sequence identity to SEQ ID NO: 41;
  (p) serine phosphorylation sites S136, S137, and S213, wherein the modified MYB46 polypeptide has at least 95% sequence identity to SEQ ID NO: 42;
  (q) serine phosphorylation sites S138 and S139 and a glutamic acid phosphorylation site E141, wherein the modified MYB46 polypeptide has at least 95% sequence identity to SEQ ID NO:45;
  (r) a serine phosphorylation site S144, wherein the modified MYB46 polypeptide has at least 95% sequence identity to SEQ ID NO: 46;
  (s) a serine phosphorylation site S150, wherein the modified MYB46 polypeptide has at least 95% sequence identity to SEQ ID NO: 47; or
  (t) a serine phosphorylation site S145, wherein the modified MYB46 polypeptide has at least 95% sequence identity to SEQ ID NO: 48.

19. The method of claim 18, wherein the replacement amino acids are selected from arginine, lysine, glycine, proline, alanine, leucine, isoleucine, valine, phenylalanine, tryptophan, cysteine, methionine, histidine, asparagine, glutamine, or tyrosine.

20. The method of claim 18, wherein the modified MYB46 polypeptide has an increased half-life compared to a corresponding unmodified MYB46 polypeptide that has no replacements of serine or threonine residues.

21. The modified MYB46 polypeptide of claim 1, wherein the MYB46 polypeptide having at least 95% sequence identity to SEQ ID NO: 1 has replacement amino acids that are not serine, threonine, aspartic acid, or glutamic acid at the serine phosphorylation site at residue S138 and the threonine phosphorylation site at residue T199.

22. The modified MYB46 polypeptide of claim 18, wherein the MYB46 polypeptide having at least 95% sequence identity to SEQ ID NO: 1 has replacement amino acids that are not serine, threonine, aspartic acid, or glutamic acid at the serine phosphorylation site at residue S138 and the threonine phosphorylation site at residue T199.

* * * * *

SEQUENCE LISTING

```
<160> NUMBER OF SEQ ID NOS: 90

<210> SEQ ID NO 1
<211> LENGTH: 280
<212> TYPE: PRT
<213> ORGANISM: Arabidopsis thaliana

<400> SEQUENCE: 1

Met Arg Lys Pro Glu Val Ala Ile Ala Ala Ser Thr His Gln Val Lys
1               5                   10                  15

Lys Met Lys Lys Gly Leu Trp Ser Pro Glu Glu Asp Ser Lys Leu Met
            20                  25                  30

Gln Tyr Met Leu Ser Asn Gly Gln Gly Cys Trp Ser Asp Val Ala Lys
        35                  40                  45

Asn Ala Gly Leu Gln Arg Cys Gly Lys Ser Cys Arg Leu Arg Trp Ile
    50                  55                  60
```

```
Asn Tyr Leu Arg Pro Asp Leu Lys Arg Gly Ala Phe Ser Pro Gln Glu
 65                  70                  75                  80

Glu Asp Leu Ile Ile Arg Phe His Ser Ile Leu Gly Asn Arg Trp Ser
                 85                  90                  95

Gln Ile Ala Ala Arg Leu Pro Gly Arg Thr Asp Asn Glu Ile Lys Asn
            100                 105                 110

Phe Trp Asn Ser Thr Ile Lys Lys Arg Leu Lys Lys Met Ser Asp Thr
        115                 120                 125

Ser Asn Leu Ile Asn Asn Ser Ser Ser Pro Asn Thr Ala Ser Asp
130                 135                 140

Ser Ser Ser Asn Ser Ala Ser Ser Leu Asp Ile Lys Asp Ile Ile Gly
145                 150                 155                 160

Ser Phe Met Ser Leu Gln Glu Gln Gly Phe Val Asn Pro Ser Leu Thr
                165                 170                 175

His Ile Gln Thr Asn Asn Pro Phe Pro Thr Gly Asn Met Ile Ser His
            180                 185                 190

Pro Cys Asn Asp Asp Phe Thr Pro Tyr Val Asp Gly Ile Tyr Gly Val
        195                 200                 205

Asn Ala Gly Val Gln Gly Glu Leu Tyr Phe Pro Pro Leu Glu Cys Glu
210                 215                 220

Glu Gly Asp Trp Tyr Asn Ala Asn Ile Asn Asn His Leu Asp Glu Leu
225                 230                 235                 240

Asn Thr Asn Gly Ser Gly Asn Ala Pro Glu Gly Met Arg Pro Val Glu
                245                 250                 255

Glu Phe Trp Asp Leu Asp Gln Leu Met Asn Thr Glu Val Pro Ser Phe
            260                 265                 270

Tyr Phe Asn Phe Lys Gln Ser Ile
        275                 280

<210> SEQ ID NO 2
<211> LENGTH: 1252
<212> TYPE: DNA
<213> ORGANISM: Arabidopsis thaliana

<400> SEQUENCE: 2
catcattctc ccttcatcaa gtcttctctc ttttctctct ctattataaa acaaacttca     60
ctcgttcaca tcaatggatc cttgagaaag acaaacaaat tgaagagaaa taataacaat    120
taactcaacc aaaaatatga ggaagccaga ggtagccatt gcagctagta ctcaccaagt    180
aaagaagatg aagaagggac tttggtctcc tgaggaagac tcaaagctga tgcaatacat    240
gttaagcaat ggacaaggat gttggagtga tgttgcgaaa aacgcaggac ttcaaagatg    300
tggcaaaagc tgccgtcttc gttggatcaa ctatcttcgt cctgacctca gcgtggcgc    360
tttctctcct caagaagagg atctcatcat tcgctttcat tccatcctcg gcaacaggtg    420
gtctcagatt gcagcacgat tgcctggtcg gaccgataac gagatcaaga atttctggaa    480
ctcaacaata aagaaaggc taagaagat gtccgatacc tccaacttaa tcaacaactc    540
atcctcatca cccaacacag caagcgattc ctcttctaat tccgcatctt ctttggatat    600
taaagacatt ataggaagct tcatgtcctt acaagaacaa ggcttcgtca accccttcctt    660
gacccacata caaaccaaca atccatttcc aacgggaaac atgatcagcc accgtgcaa    720
tgacgatttt acccccttatg tagatggtat ctatggagta aacgcagggg tacaagggga    780
actctacttc ccaccctttgg aatgtgaaga aggtgattgg tacaatgcaa atataaacaa    840
```

```
ccacttagac gagttgaaca ctaatggatc cggaaacgca cctgagggta tgagaccagt    900
ggaagaattt tgggaccttg accagttgat gaacactgag gttccttcgt tttacttcaa    960
cttcaaacaa agcatatgaa tatttttacg tcatcttatt cttttttcta ttgcggttta   1020
tactcaagat tcttagccac acacacataa atgcaaatat atatacattg ttagagagta   1080
ttttgtattt cgaataatct tttcgtacta gggcttgagc cttgaggtgc catgtaatga   1140
ttagtcaatg taaacatat atcctataat aaataaataa aagaaataat aagcacatac    1200
attctttaat ataacagggg caaacacttg aagaattttg taatcaagta gc            1252
```

<210> SEQ ID NO 3
<211> LENGTH: 290
<212> TYPE: PRT
<213> ORGANISM: Gossypium hirsutum

<400> SEQUENCE: 3

```
Met Met Arg Lys Pro Asn Asn Gly Ser Thr Ile Thr Thr Asn Asn
1               5                   10                  15

Lys Leu Arg Lys Gly Leu Trp Ser Pro Glu Glu Asp Asp Lys Leu Ile
            20                  25                  30

Asn Tyr Met Leu Thr Asn Gly Gln Gly Cys Trp Ser Asp Val Ala Arg
        35                  40                  45

Asn Ala Gly Leu Gln Arg Cys Gly Lys Ser Cys Arg Leu Arg Trp Ile
    50                  55                  60

Asn Tyr Leu Arg Pro Asp Leu Lys Arg Gly Ala Ile Ser Pro Glu Glu
65                  70                  75                  80

Glu Glu Leu Ile Val His Leu His Ser Ile Leu Gly Asn Arg Trp Ser
                85                  90                  95

Gln Ile Ala Ala Arg Leu Pro Gly Arg Thr Asp Asn Glu Ile Lys Asn
            100                 105                 110

Phe Trp Asn Ser Thr Ile Lys Lys Arg Leu Lys Asn Ser Ser Pro Asn
        115                 120                 125

Thr Ile Gly Ser Ser Thr Ser Asn Phe Asn Lys Asp Ser Asn Pro Val
    130                 135                 140

Gly Phe Ile Thr Met Glu Gln Gln Gly Val Leu Leu Pro Thr Tyr Ile
145                 150                 155                 160

Asp Leu Ser Ser Thr Ser Ser Asn Ser Ser Leu Gln Ser Thr Val Thr
                165                 170                 175

Asn Pro Gly Thr Ala Phe Gly Ala Thr Val Gly Tyr Phe Ala Thr Asn
            180                 185                 190

Val Asn Cys Met Tyr Gly Glu Asn Glu Met Leu Cys Gly Glu Glu Leu
        195                 200                 205

Tyr Met Pro Pro Leu Glu Thr Val Arg Glu Asn Leu Lys Ile Glu Asn
    210                 215                 220

Thr Phe Glu Ser Asp Ile Thr Thr Thr Thr Thr Asn Asn Asn Asn
225                 230                 235                 240

Asn Val Asp Cys Ser Met Lys Ser Glu Asn Val Met Thr Gly Ala Ala
                245                 250                 255

Val Gly Asn Phe Trp Leu Gly Glu Glu Ile Lys Val Gly Asp Trp Asn
            260                 265                 270

Leu Glu Asp Leu Met Lys Asp Val Ser Ser Phe Pro Phe Leu Asp Phe
        275                 280                 285

Gln Ser
    290
```

<210> SEQ ID NO 4
<211> LENGTH: 25
<212> TYPE: PRT
<213> ORGANISM: Arabidopsis thaliana

<400> SEQUENCE: 4

Phe Thr Pro Tyr Val Asp Gly Ile Tyr Gly Val Asn Ala Gly Val Gln
1               5                   10                  15

Gly Glu Leu Tyr Phe Pro Pro Leu Glu
            20                  25

<210> SEQ ID NO 5
<211> LENGTH: 26
<212> TYPE: PRT
<213> ORGANISM: Gossypium hirsutum

<400> SEQUENCE: 5

Phe Ala Thr Asn Val Asn Cys Met Tyr Gly Glu Asn Glu Met Leu Cys
1               5                   10                  15

Gly Glu Glu Leu Tyr Met Pro Pro Leu Glu
            20                  25

<210> SEQ ID NO 6
<211> LENGTH: 1196
<212> TYPE: DNA
<213> ORGANISM: Gossypium hirsutum

<400> SEQUENCE: 6
tcatcaccac catttccccc accatgaagc ctcctcctcc cttcttctat aaaatctcca      60
ctaatttcct tatgaccaaa aaaaaactcg tttataatat caacaaaaat aaacccaagt     120
ctttagttag ttcttaaatt ttcatctctt aggagatttt ttattatttt acatgatgag     180
gaagcctaac aatggtagca ctattactac tactaacaat aagcttagga aagggttatg     240
gtcacccgaa gaagatgata agctcatcaa ctatatgtta accaatggcc aaggttgttg     300
gagtgacgta gctcggaacg ccggcttgca acggtgcggc aagagttgcc gtctccgttg     360
gatcaattac ttgagacccg atctcaaacg aggtgccatt cgccagaaga agaagaact      420
aatcgtccat ttacattcta ttctcggcaa taggtggtct caaattgcgg ctcgcttgcc     480
tggtcgtacc gacaatgaaa taagaacctt tggaattcg acgataaaga aaaggctcaa      540
aaattcttca ccaaacacca tcggttcatc aacatcaaac tttaacaaag attccaatcc     600
agtcggcttc attacaatgg aacaacaagg tgttcttttg cctacgtaca tcgatttatc     660
gtcgacttca tccaattctt ccttgcaatc aaccgtcacg aaccccggga ctgcattcgg     720
tgccaccgtc gggtactttg cgacaaacgt caactgtatg tacggtgaaa acgagatgtt     780
atgtggggag gaactataca tgcctccttt agaaactgtt agagaaaacc ttaaaatcga     840
gaatacattc gaaagcgaca tcaccaccac caccaccaca aacaacaaca ataacgtaga     900
ttgcagtatg aaatcggaga acgtaatgac cggtgcggct gtcgggaatt tttggttagg     960
tgaagagatt aaagttggag actggaattt ggaggatttg atgaaagatg tttcttcttt    1020
tccatttctt gattttcaaa gttaaatata attaaaacat tttaggtcaa aattaaaaca    1080
ttaaaaaaaa accctagagt ccattaccaa aaaaaaaaac ccttaaaacc ttgtttgttt    1140
gatagtgaaa aaaggactac aaaattctca tagatttcga caatacttac aaaaaa       1196

<210> SEQ ID NO 7
<211> LENGTH: 321

<212> TYPE: PRT
<213> ORGANISM: Gossypium hirsutum

<400> SEQUENCE: 7

```
Met Met Arg Lys Pro Pro Ser Met Lys Gly Asn Asn Ser Asn Gly Thr
1               5                   10                  15

Asn Lys His Lys Lys Gly Leu Trp Ser Pro Glu Glu Asp Asp Lys Leu
            20                  25                  30

Val Thr Tyr Met Leu Thr Asn Gly Arg Gly Cys Trp Ser Asp Val Ala
        35                  40                  45

Arg Asn Ala Gly Leu Gln Arg Cys Gly Lys Ser Cys Arg Leu Arg Trp
    50                  55                  60

Ile Asn Tyr Leu Arg Pro Asp Leu Lys Arg Gly Ala Phe Ser Pro Gln
65                  70                  75                  80

Glu Gln Glu Leu Ile Val His Leu His Ser Ile Leu Gly Asn Arg Trp
                85                  90                  95

Ser Gln Ile Ala Ala Arg Leu Pro Gly Arg Thr Asp Asn Glu Ile Lys
            100                 105                 110

Asn Phe Trp Asn Ser Thr Ile Lys Lys Arg Leu Lys His Ser Ser Ser
        115                 120                 125

Thr Ala Ser His Asn Ala Ser Asp Ser Ser Glu Pro Asn Lys Asp
    130                 135                 140

Ala Met Ala Ala Gly Phe Met Thr Met Leu Glu Gln Glu Val Pro Pro
145                 150                 155                 160

Ile Tyr Leu Asp Leu Ser Ser Ala Trp Ser Asn Ser Phe Leu Gln Ser
                165                 170                 175

Met Val Leu Asn His Ser Gly Asn Ser Leu Pro Met Leu Gln His Gly
            180                 185                 190

Arg Asn Val Val Gly Ala Val Gly Tyr Phe Asp Pro Ala Gly Ser Cys
        195                 200                 205

Val Thr Gln Ala Glu Val Asn Gly Asp Ser Ser Leu Gly Leu Ser Glu
    210                 215                 220

Ile Phe Gly Ser Val Asp Asn Gly Ile Glu Arg Glu Leu Tyr Val Pro
225                 230                 235                 240

Pro Leu Glu Ser Ile Gly Lys Asp Leu Lys Thr Glu Asn Ser Val Asp
                245                 250                 255

Gly Asn Ile Asn Asn Gly Phe Asn Ile Ile Asn Thr Ser Gly Val Arg
            260                 265                 270

Ser Asp Asn Asn Asn Met Ser Lys Asn Met Asp Ser Asp Val
        275                 280                 285

Gly Ser Phe Trp Ile Gly Glu Glu Leu Lys Val Gly Glu Trp Asp Met
    290                 295                 300

Glu Asn Leu Met Lys Asp Val Ser Ser Phe Pro Phe Leu Asp Phe Gln
305                 310                 315                 320

Ser
```

<210> SEQ ID NO 8
<211> LENGTH: 1369
<212> TYPE: DNA
<213> ORGANISM: Gossypium hirsutum

<400> SEQUENCE: 8

```
cgttgtctac ttagacccat caaccaactc tctttctctc tcctttcttc cctgtattct      60
aagcaaaccc cacaaccatc agcatcatca tgagcaccat ttccgctcca tgaagccttc     120
```

```
tcctttctct ctcttttcct cttttagttc caatctataa agcgtgccca ctaatctata      180
tgatcaaact agttaggatc aacaaaaata acccaccaag attatttatt gtggttgttg      240
gataggatcc aaggcttatc tctcaattaa tttctccctt aggagatatt ggtttgatga      300
tgaggaagcc tccatccatg aagggtaaca atagtaatgg gaccaataag cataagaaag      360
ggttatggtc gccagaggaa gacgacaagc tcgtcaccta tatgctaaca aatggccggg      420
gttgttggag tgacgtggct agaaatgctg gcctgcagag gtgtggcaag agctgccggc      480
ttcgatggat aaattatctc agacccgatc tcaaacgagg cgcgttttcg cctcaggaac      540
aagagcttat cgtccattta cactccattc ttggcaacag gtggtctcaa atagcggctc      600
gcctacctgg tcgtacggac aatgaaataa agaacttttg gaattcaaca ataaagaaaa      660
ggctaaagca ttcatcatct actgcctcac ataacgccag tgattcatcg tcggagccta      720
acaaagatgc catggcggca gggttcatga cgatgcttga caagaggtt ccgccaattt      780 acctggattt atcatcggct tggtcgaatt ctttcttgca atccatggtc cttaaccatt      840
ccggcaactc tttaccgatg ctccagcatg gcagaaacgt tgttgggct gtcggatact       900 ttgatccggc aggctcatgc gtgacacagg ctgaggtgaa cggggacagt tccttgggtg      960
aaagtgagat atttggaagt gttgataatg ggatagaaag ggagttatat gtgcctccgt      1020
tagaaagcat tgggaaagac cttaaaactg aaaactcagt tgatgggaac atcaacaacg      1080
gtttcaatat cataaatact agcggtgtta gaagcgacaa caataataac atgtcgaaaa      1140
acatggacag cgacgacgtt gggagttttt ggataggaga ggagctaaaa gttggagaat      1200
gggacatgga aaatttgatg aaagatgttt cttcctttcc ttttcttgat ttccaaagct      1260
gaaaatagtt aattctaaac tttagttata attataaacc tccaatatat atatatatcc      1320
atgtatttga acaactttg gaaggaaca tctcaaggaa tgttattga                    1369
```

<210> SEQ ID NO 9
<211> LENGTH: 7
<212> TYPE: PRT
<213> ORGANISM: Arabidopsis thaliana

<400> SEQUENCE: 9

Arg Lys Pro Glu Val Ala Ile
1               5

<210> SEQ ID NO 10

<400> SEQUENCE: 10

000

<210> SEQ ID NO 11
<211> LENGTH: 332
<212> TYPE: PRT
<213> ORGANISM: Populus trichocarpa

<400> SEQUENCE: 11

Met Arg Lys Pro Glu Ala Ser Gly Lys Asn Asn Val Asn Asn Ile Asn
1               5                   10                  15

Lys Phe Arg Lys Gly Leu Trp Ser Pro Glu Asp Asp Lys Leu Met
            20                  25                  30

Asn Tyr Met Leu Asn Asn Gly Gln Gly Cys Trp Ser Asp Val Ala Arg
        35                  40                  45

Asn Ala Gly Leu Gln Arg Cys Gly Lys Ser Cys Arg Leu Arg Trp Ile
    50                  55                  60

Asn Tyr Leu Arg Pro Asp Leu Lys Arg Gly Ala Phe Ser Pro Gln Glu
 65                  70                  75                  80

Glu Glu Met Ile Ile His Leu His Ser Leu Leu Gly Asn Arg Trp Ser
             85                  90                  95

Gln Ile Ala Ala Arg Leu Pro Gly Arg Thr Asp Asn Glu Ile Lys Asn
            100                 105                 110

Phe Trp Asn Ser Thr Ile Lys Lys Arg Leu Lys Asn Leu Gln Ser Ser
        115                 120                 125

Asn Ala Ser Pro Asn Thr Ser Asp Ser Ser Glu Pro Ser Lys Asp
130                 135                 140

Val Met Gly Gly Leu Met Ser Thr Met Gln Gln Gly Ile Phe Ser
145                 150                 155                 160

Met Asn Met Asp Pro Ser Met Ser Ser Ser Ser Leu Ala Thr Ser
                165                 170                 175

Met Lys Ala Met Ile Leu Asn Thr Met Met Asp Pro Leu Leu Pro Met
            180                 185                 190

Leu Asp Tyr Asp His Gly Leu Asn Met Tyr Gly Gly Ala Ser Gly Tyr
        195                 200                 205

Glu Ser Ile Thr Ala Pro Pro Cys Met Ala Gln Val Gly Val Leu Asn
    210                 215                 220

Ser Gly Asp His Gly Phe Tyr Gly Glu Gly Ile Phe Glu Gly Ile Asn
225                 230                 235                 240

Val Glu Ile Pro Pro Leu Glu Ser Val Ser Cys Met Glu Glu Asn Ala
                245                 250                 255

Lys Thr Gln Asn Ile Gln Asp Asn Thr Asp Lys Tyr Ser Tyr Ser
            260                 265                 270

Ser Pro Val Asn Ser Leu Tyr His Lys Asn Cys Asn Ile Thr Ser Asn
        275                 280                 285

Asn Lys Thr Asp Ser Ile Ala Ala Asp Gln Met Gly Asn Leu Trp His
    290                 295                 300

Gly Ser Glu Glu Leu Lys Val Gly Glu Trp Asp Leu Glu Glu Leu Met
305                 310                 315                 320

Lys Asp Val Ser Ala Phe Pro Phe Leu Asp Phe Gln
            325                 330

<210> SEQ ID NO 12
<211> LENGTH: 1471
<212> TYPE: DNA
<213> ORGANISM: Populus trichocarpa

<400> SEQUENCE: 12
ctctctcttt ctttcctata ttctaagcaa taccccacaa ccatcatcaa aatcatgatc      60
atcaagccca ctctaccaag cctcctcttt ctctttctta taatctgcca ctctataaag     120
tcttaactaa tcgacatcaa accagttggg aagagatata gatcaccttt ctagtgacag     180
gatccaaagg ctctcagaat gaggaagcca gaggcctctg ggaagaacaa cgttaataac     240
attaacaagt tcagaaaggg cttgtggtca ccagaggaag atgacaagct catgaactac     300
atgctaaaca atggacaagg ttgctggagt gatgtggcaa ggaatgctgg tttgcagcga     360
tgcggcaaga gttgccggct tcgttggatt aattacttga ggcctgatct caagagaggt     420
gcattttcac cccaagaaga agagatgatc atccatttgc attcccttct cggcaatagg     480
tggtctcaaa ttgcggctcg cttgccagga agaacggaca tgaaatcaa gattttttgg      540 aattcaacaa taagaagag attaaagaat ctgcagtcat ccaacgcatc accaaacaca      600

```
agtgattcct cctcggagcc tagcaaagat gtcatgggag ggttgatgtc gaccatgcaa    660
gaacaaggca ttttctccat gaacatggat ccttcaatgt catcttcgtc atcgttagca    720
acctccatga aagcaatgat tctaaatacc atgatggatc cattactacc tatgcttgat    780
tatgatcatg gcctaaacat gtatggcggt gcaagtgggt acgaatccat taccgcacca    840
ccatgcatgg ctcaagttgg agtccttaac agtggtgatc atggttttta tggggaaggg    900
atctttgaag gtattaatgt tgagattcct cctttagaga gtgtaagctg catggaggaa    960
aatgcaaaaa cccagaatat acaggataac aacactgaca agtactcata tagtagtcct   1020
gtgaatagtc tttaccacaa aaactgcaac atcactagta ataacaagac agatagcata   1080
gctgctgatc agatggggaa cttatggcac ggatcagaag agttaaaagt gggggagtgg   1140
gacttggaag agttgatgaa agatgtttcg gcctttccat tccttgattt ccaatgatcg   1200
ttgaataaat ggtttcccaa tacacataat ttttcaagtt tagatcggcc ttgccacata   1260
ttcacccttc aaatactgtt atcactcaac ccttgtattg atctatcctt tttcgtcaag   1320
aaacttagca atttcatgta tagttccgat gaggtacagg aagcatggaa taaaggtcag   1380
gagagttata cattaattag tgaccaaaca tttcttgtac gtaaatttat gtaccttatg   1440
atattattgc aatttcgatc gccattaatt a                                  1471
```

<210> SEQ ID NO 13
<211> LENGTH: 280
<212> TYPE: PRT
<213> ORGANISM: Arabidopsis lyrata

<400> SEQUENCE: 13

```
Met Arg Lys Pro Glu Val Ala Ile Ala Ala Ser Thr His Gln Val Lys
1               5                   10                  15

Lys Met Lys Lys Gly Leu Trp Ser Pro Glu Glu Asp Ser Lys Leu Met
            20                  25                  30

Gln Tyr Met Leu Ser Asn Gly Gln Gly Cys Trp Ser Asp Val Ala Lys
        35                  40                  45

Asn Ala Gly Leu Gln Arg Cys Gly Lys Ser Cys Arg Leu Arg Trp Ile
    50                  55                  60

Asn Tyr Leu Arg Pro Asp Leu Lys Arg Gly Ala Phe Ser Pro Gln Glu
65                  70                  75                  80

Glu Asp Leu Ile Ile Arg Phe His Ser Ile Leu Gly Asn Arg Trp Ser
                85                  90                  95

Gln Ile Ala Ala Arg Leu Pro Gly Arg Thr Asp Asn Glu Ile Lys Asn
            100                 105                 110

Phe Trp Asn Ser Thr Ile Lys Lys Arg Leu Lys Lys Met Ser Asp Thr
        115                 120                 125

Ser Asn Leu Ile Asn Asn Ser Ser Ser Pro Asn Thr Thr Ser Asp
    130                 135                 140

Thr Ser Ser Asn Ser Ala Ser Ser Leu Asp Leu Lys Asp Ile Ile Gly
145                 150                 155                 160

Ser Phe Met Ser Leu Gln Glu Gln Gly Phe Val Asn Pro Ser Leu Thr
                165                 170                 175

His Ile Pro Ser Asn Asn Pro Phe Pro Ala Ala Asn Met Thr Ser His
            180                 185                 190

Pro Cys Asn Asp Asp Phe Thr Pro Tyr Val Asp Gly Ile Tyr Gly Val
        195                 200                 205
```

```
Asn Ala Gly Val Gln Gly Asp Leu Tyr Phe Pro Pro Leu Glu Cys Glu
        210                 215                 220

Glu Gly Asp Trp Tyr Asn Ala Asn Ile Asn Asn His Leu Asp Glu Leu
225                 230                 235                 240

Asn Thr Asn Gly Ser Gly Asn Ala Pro Asp Ser Met Arg Pro Val Glu
                245                 250                 255

Glu Phe Trp Asp Leu Asp Gln Leu Met Asn Thr Glu Val Pro Ser Phe
            260                 265                 270

Tyr Phe Asn Phe Lys Gln Ser Ile
            275                 280

<210> SEQ ID NO 14
<211> LENGTH: 1238
<212> TYPE: DNA
<213> ORGANISM: Arabidopsis lyrata

<400> SEQUENCE: 14
aaaccataca accatcccct tctcatcatc atcattctcc cttcatcaag tcttctctct      60
tttctctccc tattataaaa taaacttcac tcgttcacat caatggatcc ttgcagaaat     120
acaaacacat tgaagagaaa taataacaat taactcaact aaaaaaatga ggaaaccaga     180
ggtagccatt gcagctagta ctcatcaagt aaagaagatg aagaagggtc tttggtctcc     240
ggaggaagac tcaaagctta tgcaatacat gttaagcaat ggacaaggat gttggagcga     300
tgttgcgaaa aacgcaggtc ttcaaagatg tggcaaaagc tgccgtcttc gttggatcaa     360
ctatcttcgt cctgacctca agcgtggtgc tttctctcct caagaagagg atctcatcat     420
tcgctttcat tccatcctcg gcaacaggtg gtctcagatt gcagcacgat tgcctggtcg     480
gaccgacaat gagatcaaga attttttgga ctcaacaata aagaaaaggc taaagaagat     540
gtctgataca tccaatctca tcaacaactc atcctcatca cccaacacaa caagtgacac     600
ctcttctaat tccgcctctt ctttggatct taaagacatt ataggaagct tcatgtcttt     660
acaagaacaa ggcttcgtca cccttccttg acccacata ccaagcaaca atccatttcc      720
agcggcaaac atgaccagcc acccgtgcaa tgacgatttc acaccttatg tagatggtat     780
ctatggagta aacgcagggg tacaagggga cctctatttt ccacctttgg aatgtgaaga     840
aggtgattgg tacaatgcaa atattaacaa ccacttagac gagttgaaca ctaatggatc     900
tggaaacgca cctgacagta tgagaccagt ggaagaattt tgggaccttg accagttgat     960
gaacactgag gttccttcgt tttacttcaa cttcaaacaa agcatatgaa tttttacatc    1020
atcttatttt tttttctgct gctgatttat actcaagatt cttagccaca cacataaatg    1080
caaatatata tacattgtta ttgatagatg aaagcttaga gagtattttg tatttcgaat    1140
aacgttttcg cactagggct tgaggtgccg tgtgtaatga tagtcaatgt aaaacatata    1200
taatataata aaaagaaat aataataata aacacata                             1238

<210> SEQ ID NO 15
<211> LENGTH: 284
<212> TYPE: PRT
<213> ORGANISM: Camelina sativa

<400> SEQUENCE: 15

Met Arg Lys Pro Glu Val Ala Ile Ala Ala Ala Thr Thr His Gln Val
1               5                   10                  15

Lys Lys Met Lys Lys Gly Leu Trp Ser Pro Glu Glu Asp Ser Lys Leu
            20                  25                  30
```

```
Met Gln Tyr Met Leu Ser Asn Gly Gln Gly Cys Trp Ser Asp Val Ala
            35                  40                  45
Lys Asn Ala Gly Leu Gln Arg Cys Gly Lys Ser Cys Arg Leu Arg Trp
 50                  55                  60
Ile Asn Tyr Leu Arg Pro Asp Leu Lys Arg Gly Ala Phe Ser Pro Gln
 65                  70                  75                  80
Glu Glu Asp Leu Ile Ile Arg Phe His Ser Ile Leu Gly Asn Arg Trp
                 85                  90                  95
Ser Gln Ile Ala Ala Arg Leu Pro Gly Arg Thr Asp Asn Glu Ile Lys
            100                 105                 110
Asn Phe Trp Asn Ser Thr Ile Lys Lys Arg Leu Lys Lys Met Ser Asp
            115                 120                 125
Thr Ser Asn Leu Ile Asn Asn Ser Ser Ser Pro Asn Thr Thr Ser
130                 135                 140
Asp Ser Ser Ser Asn Ser Thr Ser Ser Leu Glu Leu Lys Asp Ile Ile
145                 150                 155                 160
Gly Ser Phe Met Thr Leu Gln Glu Gln Gly Phe Ile Asn Pro Ser Leu
                165                 170                 175
Thr Gln Ile Pro Thr Asn Asn Pro Phe Pro Ala Pro Asn Met Ile Ser
            180                 185                 190
His Pro Cys Asn Asp Asp Phe Thr Pro Tyr Leu Asp Gly Ile Tyr Gly
            195                 200                 205
Val Asn Thr Gly Val Gln Gly Glu Leu Tyr Phe Pro Pro Leu Glu Cys
            210                 215                 220
Glu Glu Gly Asp Trp Tyr Asn Thr Asn Ile Asn Asn His Leu Asp
225                 230                 235                 240
Glu Leu Asn Thr Asn Gly Ser Gly Asn Ala Pro Glu Ser Met Ile Arg
                245                 250                 255
Pro Val Glu Glu Leu Trp Asp Leu Asp Gln Leu Met Met Asn Thr Glu
            260                 265                 270
Val Pro Ser Phe Tyr Phe Asn Phe Lys Gln Ser Ile
            275                 280

<210> SEQ ID NO 16
<211> LENGTH: 1027
<212> TYPE: DNA
<213> ORGANISM: Camelina sativa

<400> SEQUENCE: 16 aatgagcct tgagaaagac aaacaaatca aagagaaaca attaactcaa ccaaaaaaaa    60
aaaatgagga accagaggt agccattgca gcagccacta ctcatcaagt aaagaagatg   120 aagaaggac tttggtctcc ggaggaagac tcaaagctga tgcaatacat gctaagcaat   180
gggcaaggat gttggagcga tgtcgcgaaa aacgcaggcc ttcaaagatg tggcaaaagc   240
tgccgtcttc gttggatcaa ctatcttcgt cctgacctca agcgtggagc tttctctcct   300
caagaagagg atctcatcat tcgctttcat tccatcctcg gcaacaggtg gtctcagatt   360
gcagcacgat tgcctggtcg gactgacaac gagatcaaga ttttttggaa ctcaacaata   420
aagaaaaggc taagaagat gtcggataca tccaatctca tcaacaactc atcttcatcg   480
cccaacacaa caagcgactc tcttctctaat tcgacctcct ctttggagct taagacatt   540 ataggaagct tcatgacctt acaagaacaa ggattcatca cccttccctt gactcagata   600
ccaaccaaca atccattccc cgcgccaaac atgatcagcc accgtgcaa tgatgatttt   660
```

```
acccccatacc tagatggtat ctatggtgta aacacagggg tacaagggga actttacttt      720
ccaccgttgg aatgtgaaga aggtgattgg tacaatacaa atattaacaa caaccactta      780
gacgagttga acactaatgg atctggaaac gcacctgaga gtatgatcag accagtggaa      840
gaattatggg accttgacca gttgatgatg aacactgagg ttccttcgtt ttacttcaac      900
ttcaaacaaa gcatatgaaa ttttttacgtc atcttattct ttttttcttc tgttgcggat      960
ttatactcaa gagtcagcat gcacactcac acacacataa atgcaaatat atatatacat     1020
tgttata                                                               1027
```

<210> SEQ ID NO 17
<211> LENGTH: 285
<212> TYPE: PRT
<213> ORGANISM: Camelina sativa

<400> SEQUENCE: 17

```
Met Arg Lys Pro Glu Val Ala Ile Ala Ala Ala Thr Thr His Gln Val
1               5                   10                  15

Lys Lys Met Lys Lys Gly Leu Trp Ser Pro Glu Asp Ser Lys Leu
            20                  25                  30

Met Gln Tyr Met Leu Ser Asn Gly Gln Gly Cys Trp Ser Asp Val Ala
        35                  40                  45

Lys Asn Ala Gly Leu Gln Arg Cys Gly Lys Ser Cys Arg Leu Arg Trp
    50                  55                  60

Ile Asn Tyr Leu Arg Pro Asp Leu Lys Arg Gly Ala Phe Ser Pro Gln
65                  70                  75                  80

Glu Glu Asp Leu Ile Ile Arg Phe His Ser Ile Leu Gly Asn Arg Trp
                85                  90                  95

Ser Gln Ile Ala Ala Arg Leu Pro Gly Arg Thr Asp Asn Glu Ile Lys
            100                 105                 110

Asn Phe Trp Asn Ser Thr Ile Lys Lys Arg Leu Lys Lys Met Ser Asp
        115                 120                 125

Thr Ser Asn Leu Ile Asn Asn Ser Ser Ser Pro Asn Asn Thr Thr
    130                 135                 140

Ser Asp Ser Ser Ser Asn Ser Thr Ser Ser Leu Glu Leu Lys Asp Ile
145                 150                 155                 160

Ile Gly Ser Phe Met Ser Leu Gln Glu Gln Gly Phe Ile Asn Pro Ser
                165                 170                 175

Leu Thr Gln Ile Pro Thr Asn Asn Pro Phe Pro Ala Pro Asn Met Ile
            180                 185                 190

Ser His Pro Cys Asn Asp Asp Phe Thr Pro Tyr Val Asp Gly Ile Tyr
        195                 200                 205

Gly Val Asn Thr Gly Val Gln Gly Glu Leu Tyr Phe Pro Pro Leu Glu
    210                 215                 220

Cys Glu Glu Gly Asp Trp Tyr Asn Thr Asn Ile Asn Asn His Leu
225                 230                 235                 240

Asp Glu Leu Asn Thr Asn Gly Ser Gly Asn Ala Pro Glu Ser Met Ile
                245                 250                 255

Arg Pro Val Glu Glu Leu Trp Asp Leu Asp Gln Leu Met Met Asn Thr
            260                 265                 270

Glu Val Pro Ser Phe Tyr Phe Asn Phe Lys Gln Ser Ile
        275                 280                 285
```

<210> SEQ ID NO 18
<211> LENGTH: 1016

<212> TYPE: DNA
<213> ORGANISM: Camelina sativa

<400> SEQUENCE: 18

```
aagacaaaac aaaacaaaga gaaacaatca acttaaccaa aaaaaaaata tgaggaaacc      60
agaggtagcc attgcagcag ccactactca tcaagtaaag aagatgaaga agggactttg     120
gtctccagag gaagactcaa agctgatgca atacatgcta agcaatgggc aaggatgttg     180
gagcgatgtc gcaaaaaacg caggccttca agatgtggc aaaagctgcc gtcttcgttg      240
gattaactat cttcgtcctg acctcaagcg tggagctttc tctcctcaag agaggatct      300
catcattcgc tttcattcca tcctcggcaa caggtggtct cagattgcag cacgattgcc     360
tggtcggact gacaacgaga tcaagaattt ttggaactca acaataaaga aaaggctaaa     420
gaagatgtcg gatacatcca atctcatcaa caactcatct tcatcgccca ataacacaac     480
aagcgactcc tcttctaatt ccacctcttc tttggagctt aaagacatta taggaagctt     540
catgtcctta caagaacaag gattcatcaa cccttcctta actcagatac caaccaacaa     600
tccattcccc gcgccaaaca tgatcagcca cccgtgcaac gatgatttta ccccatatgt     660
agatggtatc tatggtgtaa acacagggt acaaggggaa ctttactttc caccactgga      720
atgtgaagaa ggtgattggt acaatacaaa tattaacaac aaccacttag acgagttgaa     780
cactaatgga tctggaaacg cacctgagag tatgatcaga ccagtggaag aattatggga     840
ccttgaccag ttgatgatga acactgaggt tccttcgttt tacttcaact tcaaacaaag     900
catatgaaat ttttacgtca tcttattctt tttttcttct gttgcggatt tatactcaag     960
agtcagcatg cacactcaca cacacataaa tgcaaatata tatatacatt gttata        1016
```

<210> SEQ ID NO 19
<211> LENGTH: 327
<212> TYPE: PRT
<213> ORGANISM: Hevea brasiliensis

<400> SEQUENCE: 19

```
Met Arg Lys Pro Glu Ala Ser Gly Lys Asn Asn Asn Asn Asn Lys
1               5                   10                  15

Leu Arg Lys Gly Leu Trp Ser Pro Glu Glu Asp Asp Lys Leu Met Asn
            20                  25                  30

Tyr Met Leu Asn Asn Gly Gln Gly Cys Trp Ser Asp Val Ala Arg Asn
        35                  40                  45

Ala Gly Leu Gln Arg Cys Gly Lys Ser Cys Arg Leu Arg Trp Ile Asn
    50                  55                  60

Tyr Leu Arg Pro Asp Leu Lys Arg Gly Ala Phe Ser Pro Gln Glu Glu
65                  70                  75                  80

Glu Leu Ile Ile His Leu His Ser Leu Leu Gly Asn Arg Trp Ser Gln
                85                  90                  95

Ile Ala Ala Arg Leu Pro Gly Arg Thr Asp Asn Glu Ile Lys Asn Phe
            100                 105                 110

Trp Asn Ser Thr Ile Lys Lys Arg Leu Lys Asn Leu Ser Ser Ser Ala
        115                 120                 125

Ser Pro Asn Thr Ser Asn Ser Ser Glu Pro Ser Lys Glu Val Ala
    130                 135                 140

Ala Ala Leu Gly Glu Gly Phe Ile Ser Met Gln Glu Gln Ser Met Thr
145                 150                 155                 160

Pro Met Tyr Ile Tyr Pro Ser Leu Ser Ser Ser Ser Ser Asn Thr
                165                 170                 175
```

-continued

```
Ser Met Gln Ala Met Phe Leu Asn Gln Met Met Asp Pro Leu Pro Thr
            180                 185                 190

Phe Asp His Gly Leu Ser Thr Cys Gly Ala Ser Val Tyr Phe Asn Asn
            195                 200                 205

Asp Ala Pro Pro Cys Met Thr His Ile Gly Val Ser Gly Asp Asp Ile
210                 215                 220

Tyr Gly Asn Gln Gly Ile Leu Gly Gly Val Asn Ile Gly Ile Glu Gly
225                 230                 235                 240

Glu Leu His Ile Pro Pro Leu Glu Ser Ile Ser Ile Glu Glu Asn Ala
            245                 250                 255

Lys Thr Glu Asp Met Tyr Gly Ser Asn Asn Lys Tyr Pro Tyr Ser
            260                 265                 270

Asn Val Asn Arg Ile Asn Ser Asn Cys Asn Asn Thr Lys Ala Glu
            275                 280                 285

Ser Met Thr Thr Gly Val Gly Arg Gln Gly Glu Glu Leu Lys Val Gly
            290                 295                 300

Asp Trp Asp Leu Glu Glu Leu Met Lys Asp Val Ser Ser Phe Pro Phe
305                 310                 315                 320

Leu Asp Ile Phe Gln Ala Glu
                325
```

<210> SEQ ID NO 20
<211> LENGTH: 314
<212> TYPE: PRT
<213> ORGANISM: Pinus taeda

<400> SEQUENCE: 20

```
Met Ser Cys Thr Thr Gly Gly Leu Ser Ser Pro Val Ser Lys Pro Lys
1               5                   10                  15

Leu Arg Lys Gly Leu Trp Ser Pro Glu Glu Asp Asp Lys Leu Ile Asn
            20                  25                  30

Tyr Met Met Lys Asn Gly Gln Gly Cys Trp Ser Asp Val Ala Lys Gln
            35                  40                  45

Ala Gly Leu Gln Arg Cys Gly Lys Ser Cys Arg Leu Arg Trp Ile Asn
        50                  55                  60

Tyr Leu Arg Pro Asp Leu Lys Arg Gly Ala Phe Ser Pro Gln Glu Glu
65                  70                  75                  80

His Trp Ile Ile His Leu His Ser Ile Leu Gly Asn Arg Trp Ser Gln
            85                  90                  95

Ile Ala Ala Arg Leu Pro Gly Arg Thr Asp Asn Glu Ile Lys Asn Phe
            100                 105                 110

Trp Asn Ser Cys Ile Lys Lys Lys Leu Lys His Leu Ser Ala Ser Thr
            115                 120                 125

Asn Asn Ser Lys Ser Ile Ser Ala Pro Asn Arg Thr Ser Thr Met Asn
        130                 135                 140

Ser Ser Ile Thr Pro Phe Ser Glu Ser Ser Ala Glu Pro Leu Glu Val
145                 150                 155                 160

Met Ala Thr Arg Tyr Gln Pro Ser Asn Ala Phe Asn His Glu Val Pro
            165                 170                 175

Thr Ala Glu Asn Gln Phe Cys Ile Pro Asp Val Leu Ala Leu Arg His
            180                 185                 190

Glu Gln Val Gln Ser Gln Asn Gln Phe Ser Ile Asp Gln Asp Ser Ala
            195                 200                 205
```

```
Thr Asn Asn Leu Ile Ser His Leu Trp Asn Ser Asn Ser Thr Ala Val
    210                 215                 220
Ser Ser His Glu Ser Phe Ser His Ala Phe Met Ser Pro Gly Leu Gln
225                 230                 235                 240
Thr Gln Gly His Val Val Lys Thr Pro Ile Lys Pro Cys Asp Gln Ile
                245                 250                 255
Ser Trp Ser Thr Pro Leu Thr Arg Glu Ala Ala Gly Ser His Ala Cys
            260                 265                 270
Asn Tyr Ser Leu Gly Cys Asn Ile Pro Ala Leu Val Glu Ser Glu Thr
        275                 280                 285
Leu Lys Glu Lys Phe Lys Asn Asp Ala Gly Asp Gln Ile Asn Glu Asn
    290                 295                 300
Glu Ile Met Tyr Leu Pro Arg His Leu Leu
305                 310
```

<210> SEQ ID NO 21
<211> LENGTH: 945
<212> TYPE: DNA
<213> ORGANISM: Pinus taeda

<400> SEQUENCE: 21

```
atgagctgca caacaggagg actctcctct cccgtctcca aacccaagct aaggaaaggc    60
ctctggtcgc ctgaggagga tgataaactc atcaactaca tgatgaaaaa cggccagggt   120
tgctggagcg atgtcgccaa gcaagctggt ctgcagagat gcggaaaaag ctgtaggctg   180
aggtggatta actatttaag gcccgacctc aaacgcggtg cattttcacc ccaggaagaa   240
cattggatca tacacttgca ttccattctc ggcaacaggt ggtctcagat gcagcccgg    300
ttgcccggac gtacggacaa cgagatcaag aatttctgga actcctgcat aaagaagaag   360
ttgaaacacc tttcggcctc caccaacaac agtaaatcta tctctgcacc taatcgtacc   420
agtaccatga attcatcgat cacgcccttt tctgaatcgt ctgccgagcc attggaggtc   480
atggcaacaa ggtatcagcc atcgaatgct tttaatcatg aagtgcccac tgcagaaaat   540
cagttttgta ttccggatgt attggcgtta agacatgagc aagtacagag tcagaatcaa   600
ttttcaattg atcaggactc ggccaccaac aacctcattt cccacctgtg gaattccaat   660
tctacagctg tttcttctca tgagagcttc tcccatgcct tcatgtctcc gggtctgcaa   720
acgcaaggcc atgttgtaaa gactccaatt aaaccatgcg atcaaatctc gtggagtaca   780
ccactgactc gtgaagctgc tgggtctcat gcctgcaatt actctcttgg ctgcaacatc   840
cctgctcttg ttgagagcga gacactgaaa gaaaaattca gaatgatgc aggcgatcag    900
attaatgaaa atgagatcat gtatcttcca cggcatcttc tgtga                  945
```

<210> SEQ ID NO 22
<211> LENGTH: 14
<212> TYPE: PRT
<213> ORGANISM: Arabidopsis thaliana

<400> SEQUENCE: 22

```
Thr Gly Asn Met Ile Ser His Pro Cys Asn Asp Asp Phe Thr
1               5                   10
```

<210> SEQ ID NO 23
<211> LENGTH: 14
<212> TYPE: PRT
<213> ORGANISM: Pinus taeda

<400> SEQUENCE: 23

Thr Asn Asn Leu Ile Ser His Leu Trp Asn Ser Asn Ser Thr
1               5                   10

<210> SEQ ID NO 24
<211> LENGTH: 349
<212> TYPE: PRT
<213> ORGANISM: Eucalyptus grandis

<400> SEQUENCE: 24

Met Ala Arg Ser Ser Cys Asn Gln Lys Leu Arg Lys Gly Leu Trp Ser
1               5                   10                  15

Pro Glu Glu Asp Glu Lys Leu Phe Asn Tyr Ile Ser Arg His Gly Leu
                20                  25                  30

Gly Cys Trp Ser Ser Val Pro Lys Leu Ala Gly Leu Gln Arg Cys Gly
            35                  40                  45

Lys Ser Cys Arg Leu Arg Trp Ile Asn Tyr Leu Arg Pro Asp Leu Lys
        50                  55                  60

Arg Gly Met Phe Ser Gln Gln Glu Asp Leu Ile Ile Thr Leu His
65                  70                  75                  80

Ala Ala Leu Gly Asn Arg Trp Ala Gln Ile Ala Thr Gln Leu Pro Gly
                85                  90                  95

Arg Thr Asp Asn Glu Ile Lys Asn Phe Trp Asn Ser Tyr Val Arg Lys
            100                 105                 110

Lys Leu Thr Lys Gln Gly Ile Asp Pro Val Thr His Lys Pro Leu Arg
        115                 120                 125

Glu Leu Asn Ser Met Ser Asn Cys Val Glu Ile Glu Ala Ala Gln
130                 135                 140

Ala Leu Gln Glu Phe Lys Gly Ser Arg Asp Ile Ser Ser Leu Arg Ala
145                 150                 155                 160

Lys Glu Pro Ala Phe Pro Ile Asp Gly Met His Gly Gly Pro Met Glu
                165                 170                 175

Ser Pro Val Gly Glu Val Phe Leu Asn Arg Ala Leu Phe Asp Pro Ser
            180                 185                 190

Ser Ser Leu Glu Phe His Asn Ala Ile Asn Pro Val Leu His Gly Ala
        195                 200                 205

Lys Ser Arg Leu Val Asp Pro Gly Tyr Phe Glu Met Asn Ala Ala Pro
210                 215                 220

Phe Ser Ser Val Ser Ser Met Glu Ile Asp His Glu Asn Lys Asn
225                 230                 235                 240

Thr Ser Gly Asn Leu Val Ser Arg Met Ser Cys Leu Phe Phe His Glu
                245                 250                 255

Ala Lys Lys Tyr Cys Ser Asn Ser Asn Asn Ile Ser Asn Asn Thr
            260                 265                 270

Glu Phe Gln Leu Asn Ser Ala Ala Glu Asn Lys Asp Leu Pro Trp Ala
        275                 280                 285

Asp Asp Glu Glu Leu Asp Pro Leu His Gln Phe Gln Val Asn Val Thr
290                 295                 300

Gly Ser Glu Asp Leu Lys Ser Ile Ser Trp Gln Glu Glu His Leu Leu
305                 310                 315                 320

Ala His Ala Ala Val Asp Phe His Gly Asn His Pro Ser Met Ser Leu
                325                 330                 335

Ser Asp Asp Gln Ile Leu Gln Ala His Phe Asn Ile Phe
            340                 345

<210> SEQ ID NO 25
<211> LENGTH: 24
<212> TYPE: PRT
<213> ORGANISM: Arabidopsis thaliana

<400> SEQUENCE: 25

Ser Ser Ser Ser Pro Asn Thr Ala Ser Asp Ser Ser Asn Ser Ala
1               5                   10                  15
Ser Ser Leu Asp Ile Lys Asp Ile
            20

<210> SEQ ID NO 26
<211> LENGTH: 24
<212> TYPE: PRT
<213> ORGANISM: Eucalyptus grandis

<400> SEQUENCE: 26

Ser Asn Ser Ser Asn Asn Ile Ser Asn Asn Thr Glu Phe Gln Leu Asn
1               5                   10                  15
Ser Ala Ala Glu Asn Lys Asp Leu
            20

<210> SEQ ID NO 27
<211> LENGTH: 409
<212> TYPE: PRT
<213> ORGANISM: Oryza sativa

<400> SEQUENCE: 27

Met Arg Lys Pro Asp Cys Gly Gly Gly Gly Ala Ala Lys Gly Gly
1               5                   10                  15

Gly Val Leu Gly Val Ala Gly Gly Asn Ala Ala Val Val Gly Gly
                20                  25                  30

Lys Val Arg Lys Gly Leu Trp Ser Pro Glu Glu Asp Glu Lys Leu Val
            35                  40                      45

Ala Tyr Met Leu Arg Ser Gly Gln Gly Ser Trp Ser Asp Val Ala Arg
        50                  55                      60

Asn Ala Gly Leu Gln Arg Cys Gly Lys Ser Cys Arg Leu Arg Trp Ile
65                  70                  75                  80

Asn Tyr Leu Arg Pro Asp Leu Lys Arg Gly Ala Phe Ser Pro Gln Glu
                85                  90                      95

Glu Asp Leu Ile Val Asn Leu His Ala Ile Leu Gly Asn Arg Trp Ser
            100                 105                     110

Gln Ile Ala Ala Arg Leu Pro Gly Arg Thr Asp Asn Glu Ile Lys Asn
        115                 120                     125

Phe Trp Asn Ser Thr Ile Lys Lys Arg Leu Lys Ile Ser Ser Ser Ser
130                 135                 140

Ala Ser Pro Ala Thr Thr Thr Asp Cys Ala Ser Pro Glu His Lys
            145                 150                 155                 160

Leu Gly Ala Val Val Asp Leu Ala Gly Gly Gly Ala Thr Asp Asp
                165                 170                     175

Val Val Val Gly Thr Ala Asn Ala Ala Met Lys Ser Met Trp Val Asp
            180                 185                     190

Ser Ser Ser Ser Ser Ser Ser Ser Ser Met Gln Ser Arg Pro
        195                 200                     205

Ser Ile Met Ala Ala Ala Ala Gly Arg Ser Tyr Gly Gly Leu Leu
            210                 215                 220

```
Pro Leu Pro Asp Gln Val Cys Gly Val Asp Thr Ser Pro Pro Pro
225                 230                 235                 240

Phe Phe His Asp His Ser Ile Ser Ile Lys Gln Ala Tyr Tyr Gly Ser
            245                 250                 255

Thr Gly Ala His His His His Ala Ile Ala Thr Met Asp Gly Ser
        260                 265                 270

Ser Leu Ile Gly Asp His His His Ser Ser Ile Leu Phe Gly
        275                 280                 285

Gly Ala Ser Val Pro Pro Leu Leu Asp His Gln Thr Ile Leu Asp Asp
        290                 295                 300

Asp Asp Asp His Pro Asn Lys Thr Gly Ser Asn Thr Thr Ala Ala Thr
305                 310                 315                 320

Leu Ser Ser Asn Ile Thr Asp Asn Ser Asn Ser Asn Lys Asn Asn Ser
                325                 330                 335

Asp Asn Asn Asn Asn Ile Ser Ser Ser Cys Cys Ile Ser Leu Met Asn
                340                 345                 350

Ser Ser Ser Asn Met Ile Tyr Trp Glu Gly His His Gln Gln Gln Gln
                355                 360                 365

Gln Gln His Gln Met Leu Gln Gln Gln Gln His Met Ser Arg Asn
        370                 375                 380

Val Met Gly Glu Trp Asp Leu Glu Glu Leu Met Lys Asp Val Ser Ser
385                 390                 395                 400

Leu Pro Phe Leu Asp Phe Gln Val Glu
                405

<210> SEQ ID NO 28
<211> LENGTH: 16
<212> TYPE: PRT
<213> ORGANISM: Arabidopsis thaliana

<400> SEQUENCE: 28

Ile Asn Asn Ser Ser Ser Ser Pro Asn Thr Ala Ser Asp Ser Ser Ser
1               5                   10                  15

<210> SEQ ID NO 29
<211> LENGTH: 16
<212> TYPE: PRT
<213> ORGANISM: Oryza sativa

<400> SEQUENCE: 29

Ile Ser Ser Ser Ser Ala Ser Pro Ala Thr Thr Thr Asp Cys Ala Ser
1               5                   10                  15

<210> SEQ ID NO 30
<211> LENGTH: 409
<212> TYPE: PRT
<213> ORGANISM: Zea mays

<400> SEQUENCE: 30

Met Arg Lys Pro Asp Cys Gly Gly Gly Gly Ala Ala Lys Gly Gly
1               5                   10                  15

Gly Val Leu Gly Val Ala Gly Gly Asn Asn Ala Ala Val Val Gly Gly
            20                  25                  30

Lys Val Arg Lys Gly Leu Trp Ser Pro Glu Glu Asp Glu Lys Leu Val
        35                  40                  45

Ala Tyr Met Leu Arg Ser Gly Gln Gly Ser Trp Ser Asp Val Ala Arg
50                  55                  60
```

```
Asn Ala Gly Leu Gln Arg Cys Gly Lys Ser Cys Arg Leu Arg Trp Ile
 65                  70                  75                  80

Asn Tyr Leu Arg Pro Asp Leu Lys Arg Gly Ala Phe Ser Pro Gln Glu
             85                  90                  95

Glu Asp Leu Ile Val Asn Leu His Ala Ile Leu Gly Asn Arg Trp Ser
            100                 105                 110

Gln Ile Ala Ala Arg Leu Pro Gly Arg Thr Asp Asn Glu Ile Lys Asn
            115                 120                 125

Phe Trp Asn Ser Thr Ile Lys Lys Arg Leu Lys Ile Ser Ser Ser Ser
130                 135                 140

Ala Ser Pro Ala Thr Thr Thr Asp Cys Ala Ser Pro Pro Glu His Lys
145                 150                 155                 160

Leu Gly Ala Val Val Asp Leu Ala Gly Gly Gly Ala Thr Asp Asp
                165                 170                 175

Val Val Val Gly Thr Ala Asn Ala Ala Met Lys Ser Met Trp Val Asp
                180                 185                 190

Ser Ser Ser Ser Ser Ser Ser Ser Ser Met Gln Ser Arg Pro
            195                 200                 205

Ser Ile Met Ala Ala Ala Ala Gly Arg Ser Tyr Gly Gly Leu Leu
210                 215                 220

Pro Leu Pro Asp Gln Val Cys Gly Val Asp Thr Ser Pro Pro Pro
225                 230                 235                 240

Phe Phe His Asp His Ser Ile Ser Ile Lys Gln Ala Tyr Tyr Gly Ser
                245                 250                 255

Thr Gly Ala His His His His Ala Ile Ala Thr Met Asp Gly Ser
            260                 265                 270

Ser Leu Ile Gly Asp His His His Ser Ser Ser Ile Leu Phe Gly
        275                 280                 285

Gly Ala Ser Val Pro Pro Leu Leu Asp His Gln Thr Ile Leu Asp Asp
            290                 295                 300

Asp Asp Asp His Pro Asn Lys Thr Gly Ser Asn Thr Thr Ala Ala Thr
305                 310                 315                 320

Leu Ser Ser Asn Ile Thr Asp Asn Ser Asn Ser Asn Lys Asn Asn Ser
                325                 330                 335

Asp Asn Asn Asn Ile Ser Ser Ser Cys Cys Ile Ser Leu Met Asn
            340                 345                 350

Ser Ser Ser Asn Met Ile Tyr Trp Glu Gly His His Gln Gln Gln
            355                 360                 365

Gln Gln His Gln Met Leu Gln Gln Gln Gln His Met Ser Arg Asn
    370                 375                 380

Val Met Gly Glu Trp Asp Leu Glu Glu Leu Met Lys Asp Val Ser Ser
385                 390                 395                 400

Leu Pro Phe Leu Asp Phe Gln Val Glu
                405

<210> SEQ ID NO 31
<211> LENGTH: 16
<212> TYPE: PRT
<213> ORGANISM: Arabidopsis thaliana

<400> SEQUENCE: 31

Ile Asn Asn Ser Ser Ser Ser Pro Asn Thr Ala Ser Asp Ser Ser
1               5                  10                  15

<210> SEQ ID NO 32
```

```
<211> LENGTH: 16
<212> TYPE: PRT
<213> ORGANISM: Zea mays

<400> SEQUENCE: 32

Ile Ser Ser Ser Ala Ser Pro Ala Thr Thr Thr Asp Cys Ala Ser
1               5                   10                  15

<210> SEQ ID NO 33
<211> LENGTH: 16
<212> TYPE: PRT
<213> ORGANISM: Arabidopsis thaliana

<400> SEQUENCE: 33

Ile Asn Asn Ser Ser Ser Ser Pro Asn Thr Ala Ser Asp Ser Ser Ser
1               5                   10                  15

<210> SEQ ID NO 34
<211> LENGTH: 16
<212> TYPE: PRT
<213> ORGANISM: Zea mays

<400> SEQUENCE: 34

Val Asp Ser Ser Ser Ser Ser Ser Ser Ser Ser Ser Met Gln Ser
1               5                   10                  15

<210> SEQ ID NO 35
<211> LENGTH: 264
<212> TYPE: PRT
<213> ORGANISM: Populus trichocarpa

<400> SEQUENCE: 35

Met Ser Trp Gly Val Met Ala Gly Gln Leu Ala Trp Gly Gly Leu Ile
1               5                   10                  15

Glu Glu Gly Trp Arg Lys Gly Pro Trp Thr Ala Glu Glu Asp Arg Leu
                20                  25                  30

Leu Ile Glu Tyr Val Arg Leu His Gly Asp Gly Arg Trp Ser Ser Val
            35                  40                  45

Ala Arg Leu Ala Gly Leu Lys Arg Asn Gly Lys Ser Cys Arg Leu Arg
        50                  55                  60

Trp Val Asn Tyr Leu Arg Pro Asp Leu Lys Arg Gly Gln Ile Thr Pro
65                  70                  75                  80

His Glu Glu Ser Ile Ile Val Glu Leu His Ala Arg Trp Gly Asn Arg
                85                  90                  95

Trp Ser Thr Ile Ala Arg Ser Leu Pro Gly Arg Thr Asp Asn Glu Ile
            100                 105                 110

Lys Asn Tyr Trp Arg Thr His Phe Lys Lys Ala Lys Leu Ser Pro
        115                 120                 125

Asp Asn Ser Asp Lys Ala Arg Thr Arg His Leu Lys Arg Gln Gln Phe
130                 135                 140

Gln Gln Gln Gln Gln Leu Gln Arg Gln Gln Gln Gln Thr Gln His
145                 150                 155                 160

Gln Gln Pro Leu Gln Ile Asn Gln Leu Asp Met Arg Lys Ile Val Ser
                165                 170                 175

Leu Leu Asp Glu Asn Glu Asp Lys Ala Pro Cys Thr Pro Gln Met Arg
            180                 185                 190

Gln Glu Met Ala Pro His Ala Ile Tyr Pro Asn Thr Ile Glu Glu His
        195                 200                 205
```

```
Val Leu Leu Tyr Asn Met Phe Asn Val Asn Asn Ala Ser Val Pro Glu
    210                 215                 220

Ala Ser Asn Glu Asp Ile Leu Trp Asp Gly Leu Trp Asn Leu Asp Asp
225                 230                 235                 240

Leu His Gly Asn Leu Gly Val Ala Cys Ala Thr Ser Lys Ala Ser Met
                245                 250                 255

Gln Asn Leu Val Ala Pro Phe Cys
            260

<210> SEQ ID NO 36
<211> LENGTH: 15
<212> TYPE: PRT
<213> ORGANISM: Arabidopsis thaliana

<400> SEQUENCE: 36

Asn Leu Ile Asn Asn Ser Ser Ser Pro Asn Thr Ala Ser Asp
1               5                   10                  15

<210> SEQ ID NO 37
<211> LENGTH: 15
<212> TYPE: PRT
<213> ORGANISM: Populus trichocarpa

<400> SEQUENCE: 37

Asn Met Phe Asn Val Asn Asn Ala Ser Val Pro Glu Ala Ser Asn
1               5                   10                  15

<210> SEQ ID NO 38
<211> LENGTH: 185
<212> TYPE: PRT
<213> ORGANISM: Populus trichocarpa

<400> SEQUENCE: 38

Met Arg Lys Pro Cys Cys Asp Lys Gln Tyr Thr Asn Lys Gly Ala Trp
1               5                   10                  15

Ser Gln Gln Glu Asp Gln Lys Leu Ile Asp Tyr Ile Gln Lys His Gly
            20                  25                  30

Glu Gly Cys Trp Arg Ser Leu Pro Gln Ala Ala Gly Leu Leu Arg Cys
        35                  40                  45

Gly Lys Ser Cys Arg Leu Arg Trp Arg Asn Tyr Leu Arg Pro Asp Leu
    50                  55                  60

Lys Arg Asp Gly Phe Gly Glu Asp Glu Glu Asp Leu Ile Ile Arg Leu
65                  70                  75                  80

His Ala Leu Leu Gly Asn Arg Trp Ser Leu Ile Ala Gly Arg Leu Pro
                85                  90                  95

Gly Arg Thr Asp Asn Glu Val Lys Asn Tyr Trp Asn Ser His Ile Arg
            100                 105                 110

Lys Lys Leu Glu Ser Ser His Arg Asn Thr Gly Phe Thr Arg Leu Arg
        115                 120                 125

Ala Glu Ile Ser Ser Ala Ala Arg Ser Lys Arg Gln Ala Asn Val Pro
    130                 135                 140

Glu Thr Gln Val Phe Asp Ser Asn Gly Gly Lys Pro Glu Pro Ser Asn
145                 150                 155                 160

Lys Ser Ser Ser Asp Ile Asn Leu Asp Leu Thr Leu Ser Ile Pro Ser
                165                 170                 175

Lys Lys Leu Glu Ser Ser Asp Glu Asn
            180                 185
```

<210> SEQ ID NO 39
<211> LENGTH: 321
<212> TYPE: PRT
<213> ORGANISM: Populus trichocarpa

<400> SEQUENCE: 39

Met Gly Arg Gln Pro Cys Cys Asp Lys Val Gly Leu Lys Lys Gly Pro
1               5                   10                  15

Trp Thr Ser Asp Glu Asp Lys Lys Leu Ile Thr Phe Ile Leu Ala Asn
            20                  25                  30

Gly Gln Cys Cys Trp Arg Ala Val Pro Lys Leu Ala Gly Leu Leu Arg
        35                  40                  45

Cys Gly Lys Ser Cys Arg Leu Arg Trp Thr Asn Tyr Leu Arg Pro Asp
50                  55                  60

Leu Lys Arg Gly Leu Leu Ser Glu Tyr Glu Lys Met Val Ile Asp
65                  70                  75                  80

Leu His Ala Gln Leu Gly Asn Arg Trp Ser Lys Ile Ala Ser His Leu
                85                  90                  95

Pro Gly Arg Thr Asp Asn Glu Ile Lys Asn His Trp Asn Thr His Ile
            100                 105                 110

Lys Lys Lys Leu Arg Lys Met Gly Ile Asp Pro Leu Thr His Lys Pro
        115                 120                 125

Leu Ser Thr Ile Glu Thr Pro Pro Ser Pro Pro Gln Gln Glu Val
130                 135                 140

Gln Val Gln Glu Lys Ile Gln Glu Ile Glu Gln Ala Val Gln Gln
145                 150                 155                 160

Ser Cys Ser Pro Asn Ile Val Ser Glu Leu Asp Gln Asn Lys Glu Pro
                165                 170                 175

Glu Thr Ser Leu Arg Ser Thr Val Thr Gln Glu Glu Ile Asn Asn
            180                 185                 190

Met Ala Ala Ser Thr Tyr Gly Thr Met Glu Gln Thr Asp Gly Phe Cys
        195                 200                 205

Ile Asp Glu Val Pro Leu Ile Glu Pro His Glu Ile Leu Val Pro Cys
210                 215                 220

Gly Leu Ser Pro Ser Ser Thr Pro Ala Pro Thr Ser Ser Ser Ser Ser
225                 230                 235                 240

Ser Thr Ser Ser Ser Ser Ser Tyr Gly Ser Asn Asn Ile Leu Glu
                245                 250                 255

Asp Leu Leu Leu Pro Asp Phe Glu Trp Pro Ile Asn Asn Val Asp Ile
            260                 265                 270

Gly Leu Trp Gly Asp Tyr Leu Asn Ser Trp Asp Val Leu Ile Ser Asp
        275                 280                 285

Ala Val Gly Asp Trp Lys Gln Thr Thr Met Phe Asp Pro Pro Leu Asn
290                 295                 300

Gln Cys Ser Arg Met Ile Leu Asp Gln Asp Ser Trp Thr Asn Gly Leu
305                 310                 315                 320

Leu

<210> SEQ ID NO 40
<211> LENGTH: 332
<212> TYPE: PRT
<213> ORGANISM: Populus trichocarpa

<400> SEQUENCE: 40

| Met | Arg | Lys | Pro | Glu | Ala | Ser | Gly | Lys | Asn | Asn | Val | Asn | Asn | Ile | Asn |
|---|---|---|---|---|---|---|---|---|---|---|---|---|---|---|---|
| 1 | | | | 5 | | | | | 10 | | | | | 15 | |

| Lys | Phe | Arg | Lys | Gly | Leu | Trp | Ser | Pro | Glu | Glu | Asp | Asp | Lys | Leu | Met |
|---|---|---|---|---|---|---|---|---|---|---|---|---|---|---|---|
| | | | 20 | | | | | 25 | | | | | 30 | | |

| Asn | Tyr | Met | Leu | Asn | Asn | Gly | Gln | Gly | Cys | Trp | Ser | Asp | Val | Ala | Arg |
|---|---|---|---|---|---|---|---|---|---|---|---|---|---|---|---|
| | | | 35 | | | | | 40 | | | | | 45 | | |

| Asn | Ala | Gly | Leu | Gln | Arg | Cys | Gly | Lys | Ser | Cys | Arg | Leu | Arg | Trp | Ile |
|---|---|---|---|---|---|---|---|---|---|---|---|---|---|---|---|
| | 50 | | | | | 55 | | | | | 60 | | | | |

| Asn | Tyr | Leu | Arg | Pro | Asp | Leu | Lys | Arg | Gly | Ala | Phe | Ser | Pro | Gln | Glu |
|---|---|---|---|---|---|---|---|---|---|---|---|---|---|---|---|
| 65 | | | | | 70 | | | | | 75 | | | | | 80 |

| Glu | Glu | Met | Ile | Ile | His | Leu | His | Ser | Leu | Leu | Gly | Asn | Arg | Trp | Ser |
|---|---|---|---|---|---|---|---|---|---|---|---|---|---|---|---|
| | | | | 85 | | | | | 90 | | | | | 95 | |

| Gln | Ile | Ala | Ala | Arg | Leu | Pro | Gly | Arg | Thr | Asp | Asn | Glu | Ile | Lys | Asn |
|---|---|---|---|---|---|---|---|---|---|---|---|---|---|---|---|
| | | | 100 | | | | | 105 | | | | | 110 | | |

| Phe | Trp | Asn | Ser | Thr | Ile | Lys | Lys | Arg | Leu | Lys | Asn | Leu | Gln | Ser | Ser |
|---|---|---|---|---|---|---|---|---|---|---|---|---|---|---|---|
| | | | 115 | | | | | 120 | | | | | 125 | | |

| Asn | Ala | Ser | Pro | Asn | Thr | Ser | Asp | Ser | Ser | Ser | Glu | Pro | Ser | Lys | Asp |
|---|---|---|---|---|---|---|---|---|---|---|---|---|---|---|---|
| | 130 | | | | | 135 | | | | | 140 | | | | |

| Val | Met | Gly | Gly | Leu | Met | Ser | Thr | Met | Gln | Glu | Gln | Gly | Ile | Phe | Ser |
|---|---|---|---|---|---|---|---|---|---|---|---|---|---|---|---|
| 145 | | | | | 150 | | | | | 155 | | | | | 160 |

| Met | Asn | Met | Asp | Pro | Ser | Met | Ser | Ser | Ser | Ser | Leu | Ala | Thr | Ser |
|---|---|---|---|---|---|---|---|---|---|---|---|---|---|---|
| | | | | 165 | | | | | 170 | | | | | 175 |

| Met | Lys | Ala | Met | Ile | Leu | Asn | Thr | Met | Met | Asp | Pro | Leu | Leu | Pro | Met |
|---|---|---|---|---|---|---|---|---|---|---|---|---|---|---|---|
| | | | 180 | | | | | 185 | | | | | 190 | | |

| Leu | Asp | Tyr | Asp | His | Gly | Leu | Asn | Met | Tyr | Gly | Gly | Ala | Ser | Gly | Tyr |
|---|---|---|---|---|---|---|---|---|---|---|---|---|---|---|---|
| | | | 195 | | | | | 200 | | | | | 205 | | |

| Glu | Ser | Ile | Thr | Ala | Pro | Pro | Cys | Met | Ala | Gln | Val | Gly | Val | Leu | Asn |
|---|---|---|---|---|---|---|---|---|---|---|---|---|---|---|---|
| | 210 | | | | | 215 | | | | | 220 | | | | |

| Ser | Gly | Asp | His | Gly | Phe | Tyr | Gly | Glu | Gly | Ile | Phe | Glu | Gly | Ile | Asn |
|---|---|---|---|---|---|---|---|---|---|---|---|---|---|---|---|
| 225 | | | | | 230 | | | | | 235 | | | | | 240 |

| Val | Glu | Ile | Pro | Pro | Leu | Glu | Ser | Val | Ser | Cys | Met | Glu | Glu | Asn | Ala |
|---|---|---|---|---|---|---|---|---|---|---|---|---|---|---|---|
| | | | | 245 | | | | | 250 | | | | | 255 | |

| Lys | Thr | Gln | Asn | Ile | Gln | Asp | Asn | Thr | Asp | Lys | Tyr | Ser | Tyr | Ser |
|---|---|---|---|---|---|---|---|---|---|---|---|---|---|---|
| | | | 260 | | | | | 265 | | | | | 270 | |

| Ser | Pro | Val | Asn | Ser | Leu | Tyr | His | Lys | Asn | Cys | Asn | Ile | Thr | Ser | Asn |
|---|---|---|---|---|---|---|---|---|---|---|---|---|---|---|---|
| | | 275 | | | | | 280 | | | | | 285 | | | |

| Asn | Lys | Thr | Asp | Ser | Ile | Ala | Ala | Asp | Gln | Met | Gly | Asn | Leu | Trp | His |
|---|---|---|---|---|---|---|---|---|---|---|---|---|---|---|---|
| | 290 | | | | | 295 | | | | | 300 | | | | |

| Gly | Ser | Glu | Glu | Leu | Lys | Val | Gly | Glu | Trp | Asp | Leu | Glu | Glu | Leu | Met |
|---|---|---|---|---|---|---|---|---|---|---|---|---|---|---|---|
| 305 | | | | | 310 | | | | | 315 | | | | | 320 |

| Lys | Asp | Val | Ser | Ala | Phe | Pro | Phe | Leu | Asp | Phe | Gln |
|---|---|---|---|---|---|---|---|---|---|---|---|
| | | | | 325 | | | | | 330 | | |

<210> SEQ ID NO 41
<211> LENGTH: 332
<212> TYPE: PRT
<213> ORGANISM: Vitis vinifera

<400> SEQUENCE: 41

| Met | Arg | Lys | Pro | Asp | Leu | Met | Gly | Lys | Asp | Arg | Val | Leu | Ile | Asn | Asn |
|---|---|---|---|---|---|---|---|---|---|---|---|---|---|---|---|
| 1 | | | | 5 | | | | | 10 | | | | | 15 | |

| Asn | Ile | Ala | Asn | Asn | Asn | Asn | Lys | Asn | Asn | Asn | Asn | Lys | Leu | Arg | Lys |
|---|---|---|---|---|---|---|---|---|---|---|---|---|---|---|---|
| | | | 20 | | | | | 25 | | | | | 30 | | |

Gly Leu Trp Ser Pro Glu Glu Asp Glu Lys Leu Met Ser Tyr Met Leu
            35                  40                  45

Arg Asn Gly Gln Gly Cys Trp Ser Asp Ile Ala Arg Asn Ala Gly Leu
 50                  55                  60

Gln Arg Cys Gly Lys Ser Cys Arg Leu Arg Trp Ile Asn Tyr Leu Arg
 65                  70                  75                  80

Pro Asp Leu Lys Arg Gly Ala Phe Ser Pro Gln Glu Glu Leu Ile
                85                  90                  95

Ile His Leu His Ser Ile Leu Gly Asn Arg Trp Ser Gln Ile Ala Ala
            100                 105                 110

Arg Leu Pro Gly Arg Thr Asp Asn Glu Ile Lys Asn Phe Trp Asn Ser
            115                 120                 125

Thr Ile Lys Lys Arg Leu Lys Asn Ser Leu Gln Thr His Ser Pro Asn
130                 135                 140

Asp Cys His Asp Ser Ser Leu Glu Pro Arg Val Val Asp Asn Ile
145                 150                 155                 160

Asn Ala Met Gly Met Gly Val Gly Gly Ser Ser Gly Met Leu Leu Ser
                165                 170                 175

Met His Glu His Glu Met Met Asn Met Tyr Met Asp Ser Ser Ser Ser
            180                 185                 190

Ser Phe Ser Ser Met Asn Thr Met Leu Thr Ser Asn His Leu Asp Asn
            195                 200                 205

Pro Phe Pro Leu Leu Asp Asn Arg His Asp Gln Met Val Phe Ser Leu
            210                 215                 220

Pro Asn Cys Met Ala Lys Pro Glu Met Thr Asp Glu Phe Asp Gly Arg
225                 230                 235                 240

Tyr Gly Val Thr Gly Gly Asn Met Gly Val Glu Arg Glu Ile Ser
                245                 250                 255

Ile Pro Gly Ser Gln Ser Asn Ser Thr Thr Glu Glu Asn Asn Gly Ala
                260                 265                 270

Thr Gln Asn Glu Tyr Tyr Thr Ile Asp Met Lys Asn Asn Ser Lys
            275                 280                 285

Val Glu Glu Ser Asp Asn Ile Phe Gly Val Gly Asn His Trp Gln Gly
            290                 295                 300

Glu Asn Met Gly Ile Gly Glu Trp Asp Leu Glu Gly Leu Leu Glu Asn
305                 310                 315                 320

Ala Ser Ser Phe Pro Phe Leu Asp Phe Gln Leu Gln
                325                 330

<210> SEQ ID NO 42
<211> LENGTH: 332
<212> TYPE: PRT
<213> ORGANISM: Medicago truncatula

<400> SEQUENCE: 42

Met Arg Lys Pro Asp Ile Ala Ser Gly Lys Asn Asn Thr Asn Asn Lys
1               5                   10                  15

Leu Arg Lys Gly Leu Trp Ser Pro Glu Asp Glu Lys Leu Met Asn
            20                  25                  30

Tyr Met Leu Asn Ser Gly Gln Gly Cys Trp Ser Asp Val Ala Arg Asn
            35                  40                  45

Ala Gly Leu Gln Arg Cys Gly Lys Ser Cys Arg Leu Arg Trp Ile Asn
 50                  55                  60

Tyr Leu Arg Pro Asp Leu Lys Arg Gly Ala Phe Ser Pro Gln Glu Glu
65                  70                  75                  80

Glu His Ile Ile His Leu His Ser Leu Leu Gly Asn Arg Trp Ser Gln
                85                  90                  95

Ile Ala Ala Arg Leu Pro Gly Arg Thr Asp Asn Glu Ile Lys Asn Phe
            100                 105                 110

Trp Asn Ser Thr Ile Lys Lys Arg Leu Lys Asn Met Ser Leu Asn Thr
        115                 120                 125

Ser Pro Asn Ala Ser Asp Glu Ser Ser Tyr Asp Pro Asn Lys Asp His
130                 135                 140

Asn Met Gly Gly Phe Ile Thr Ser Ser Thr Gln Asp Gln Gln His Ile
145                 150                 155                 160

Asp Asn His Phe Met Pro Met Phe Asn Thr Ser Ser Pro Ser Pro Pro
                165                 170                 175

Thr Met Gln Asn Thr Val Phe Asn Thr Ile Met Ser Gly Ser Gly Cys
            180                 185                 190

Gly Phe Phe Asn Asn Ser Thr Thr Gly Thr Tyr Leu Ser Gln Asn Asn
        195                 200                 205

His Asp Ser Lys Ser Phe Tyr Leu Glu Lys Val Phe Gly Ser Val Asn
210                 215                 220

Ile Ile Asn Gly Val Glu Gly Asp Glu Met Glu Ile Tyr Asn Val Pro
225                 230                 235                 240

Pro Leu Glu Ser Val Asn Ser Thr Ile Thr Ser Glu His Ser Val Lys
                245                 250                 255

Met Glu Asn Ala Cys Asn Gly Glu Asp Gly Asn Tyr Asn Ser Ser Tyr
            260                 265                 270

Asn Phe Asp Asp Ile Asn Asn Ile Val Ile Asn Asn Cys Asn Val Val
        275                 280                 285

Ser Lys Arg Ser Glu Asn Arg Val Asp Asp Glu Val Glu Asn Leu Phe
290                 295                 300

His Gly Asp Leu Ser Val Gly Asp Trp Asn Leu Glu Asp Leu Met Lys
305                 310                 315                 320

Asp Val Ser Ser Phe Pro Phe Leu Asp Phe Ser Asn
                325                 330

<210> SEQ ID NO 43
<211> LENGTH: 26
<212> TYPE: PRT
<213> ORGANISM: Arabidopsis thaliana

<400> SEQUENCE: 43

Asn Pro Phe Pro Thr Gly Asn Met Ile Ser His Pro Cys Asn Asp Asp
1               5                   10                  15

Phe Thr Pro Tyr Val Asp Gly Ile Tyr Gly
            20                  25

<210> SEQ ID NO 44
<211> LENGTH: 26
<212> TYPE: PRT
<213> ORGANISM: Medicago truncatula

<400> SEQUENCE: 44

Asn Asn Ser Thr Thr Gly Thr Tyr Leu Ser Gln Asn Asn His Asp Ser
1               5                   10                  15

Lys Ser Phe Tyr Leu Glu Lys Val Phe Gly
            20                  25

<210> SEQ ID NO 45
<211> LENGTH: 336
<212> TYPE: PRT
<213> ORGANISM: Glycine max

<400> SEQUENCE: 45

| Met | Arg | Lys | Pro | Glu | Val | Ser | Gly | Asn | Asn | Asn | Asn | Asn | Asn | Ile |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Asn | Asn | Lys | Leu | Arg | Lys | Gly | Leu | Trp | Ser | Pro | Glu | Glu | Asp | Lys |
|-----|-----|-----|-----|-----|-----|-----|-----|-----|-----|-----|-----|-----|-----|-----|
|     |     |     | 20  |     |     |     |     | 25  |     |     |     |     | 30  |     |

| Leu | Met | Asn | Tyr | Met | Leu | Asn | Ser | Gly | Gln | Gly | Cys | Trp | Ser | Asp | Val |
|-----|-----|-----|-----|-----|-----|-----|-----|-----|-----|-----|-----|-----|-----|-----|-----|
|     |     | 35  |     |     |     |     | 40  |     |     |     |     | 45  |     |     |     |

| Ala | Arg | Asn | Ala | Gly | Leu | Gln | Arg | Cys | Gly | Lys | Ser | Cys | Arg | Leu | Arg |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Trp | Ile | Asn | Tyr | Leu | Arg | Pro | Asp | Leu | Lys | Arg | Gly | Ala | Phe | Ser | Gln |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Gln | Glu | Glu | Leu | Ile | Ile | His | Leu | His | Ser | Leu | Leu | Gly | Asn | Arg |
|-----|-----|-----|-----|-----|-----|-----|-----|-----|-----|-----|-----|-----|-----|-----|
|     |     |     |     | 85  |     |     |     |     | 90  |     |     |     |     | 95  |

| Trp | Ser | Gln | Ile | Ala | Ala | Arg | Leu | Pro | Gly | Arg | Thr | Asp | Asn | Glu | Ile |
|-----|-----|-----|-----|-----|-----|-----|-----|-----|-----|-----|-----|-----|-----|-----|-----|
|     |     |     | 100 |     |     |     |     | 105 |     |     |     |     | 110 |     |     |

| Lys | Asn | Phe | Trp | Asn | Ser | Thr | Ile | Lys | Lys | Arg | Leu | Lys | Asn | Met | Ser |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Ser | Asn | Thr | Ser | Pro | Asn | Gly | Ser | Glu | Ser | Ser | Tyr | Glu | Pro | Asn | Asn |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Arg | Asp | Leu | Asn | Met | Ala | Gly | Phe | Thr | Thr | Ser | Asn | Thr | Gln | Asp | Gln |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Gln | His | Ala | Asp | Phe | Met | Pro | Met | Phe | Asn | Ser | Ser | Gln | Ser | Pro |
|-----|-----|-----|-----|-----|-----|-----|-----|-----|-----|-----|-----|-----|-----|-----|
|     |     |     |     | 165 |     |     |     |     | 170 |     |     |     |     | 175 |

| Ser | Met | His | Ala | Met | Val | Leu | Asn | Ser | Ile | Ile | Asp | Arg | Leu | Pro | Met |
|-----|-----|-----|-----|-----|-----|-----|-----|-----|-----|-----|-----|-----|-----|-----|-----|
|     |     |     | 180 |     |     |     |     | 185 |     |     |     |     | 190 |     |     |

| Leu | Glu | His | Gly | Leu | Asn | Met | Pro | Cys | Ser | Gly | Gly | Phe | Phe | Asn | Ser |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Thr | Gly | Pro | Cys | Phe | Ser | Ser | Gln | Ser | Gly | Val | Asp | Asn | Lys | Gly |
|-----|-----|-----|-----|-----|-----|-----|-----|-----|-----|-----|-----|-----|-----|-----|
|     | 210 |     |     |     |     | 215 |     |     |     |     | 220 |     |     |     |

| Ile | Tyr | Leu | Glu | Asn | Gly | Gly | Val | Phe | Gly | Ser | Val | Asn | Ile | Gly | Ala |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

| Glu | Gly | Asp | Val | Tyr | Val | Pro | Pro | Leu | Glu | Ser | Val | Ser | Thr | Thr | Ser |
|-----|-----|-----|-----|-----|-----|-----|-----|-----|-----|-----|-----|-----|-----|-----|-----|
|     |     |     |     | 245 |     |     |     |     | 250 |     |     |     |     | 255 |     |

| Asp | His | Asn | Leu | Lys | Val | Glu | Ser | Thr | Cys | Asn | Thr | Asp | Thr | Asn | Asn |
|-----|-----|-----|-----|-----|-----|-----|-----|-----|-----|-----|-----|-----|-----|-----|-----|
|     |     |     | 260 |     |     |     |     | 265 |     |     |     |     | 270 |     |     |

| Ser | Tyr | Phe | Asp | Asp | Ile | Asn | Ser | Ile | Leu | Leu | Asn | Asn | Cys | Asn | Ile |
|-----|-----|-----|-----|-----|-----|-----|-----|-----|-----|-----|-----|-----|-----|-----|-----|
|     |     | 275 |     |     |     |     | 280 |     |     |     |     | 285 |     |     |     |

| Asn | Ser | Asn | Asn | Lys | Arg | Ala | Glu | Asn | Arg | Ala | Gly | Gly | Val | Glu | Asn |
|-----|-----|-----|-----|-----|-----|-----|-----|-----|-----|-----|-----|-----|-----|-----|-----|
|     | 290 |     |     |     |     | 295 |     |     |     |     | 300 |     |     |     |     |

| Leu | Phe | Gln | Glu | Glu | Leu | Thr | Ile | Gly | Glu | Trp | Asp | Leu | Glu | Glu | Leu |
|-----|-----|-----|-----|-----|-----|-----|-----|-----|-----|-----|-----|-----|-----|-----|-----|
| 305 |     |     |     |     | 310 |     |     |     |     | 315 |     |     |     |     | 320 |

| Met | Lys | Asp | Val | Ser | Ser | Phe | Pro | Phe | Leu | Asp | Phe | Asn | Ile | Gln |
|-----|-----|-----|-----|-----|-----|-----|-----|-----|-----|-----|-----|-----|-----|-----|
|     |     |     |     | 325 |     |     |     |     | 330 |     |     |     |     | 335 |

<210> SEQ ID NO 46
<211> LENGTH: 418
<212> TYPE: PRT
<213> ORGANISM: Sorghum bicolor

<400> SEQUENCE: 46

```
Met Arg Lys Pro Glu Cys Pro Ala Ala Asn Ser Gly Asn Ala Gly
1               5                   10                  15

Gly Ala Ala Ala Thr Lys Leu Arg Lys Gly Leu Trp Ser Pro Glu
                20                  25                  30

Glu Asp Glu Arg Leu Val Ala Tyr Met Leu Arg Ser Gly Gln Gly Ser
            35                  40                  45

Trp Ser Asp Val Ala Arg Asn Ala Gly Leu Gln Arg Cys Gly Lys Ser
50                      55                  60

Cys Arg Leu Arg Trp Ile Asn Tyr Leu Arg Pro Asp Leu Lys Arg Gly
65                  70                  75                  80

Ala Phe Ser Pro Gln Glu Glu Leu Ile Val Ser Leu His Ala Ile
                85                  90                  95

Leu Gly Asn Arg Trp Ser Gln Ile Ala Ala Arg Leu Pro Gly Arg Thr
                100                 105                 110

Asp Asn Glu Ile Lys Asn Phe Trp Asn Ser Thr Ile Lys Lys Arg Leu
            115                 120                 125

Lys Asn Thr Ser Ala Thr Ser Ser Pro Ala Ala Thr Glu Cys Ala Ser
130                 135                 140

Pro Glu Pro Asn Asn Lys Val Ala Ala Gly Ser Cys Pro Asp Leu Ala
145                 150                 155                 160

Gly Leu Asp His Gln Asp Gly His His His His His Leu Met
                165                 170                 175

Thr Thr Thr Thr Thr Gly Leu Trp Met Val Asp Ser Ser Ser Cys
                180                 185                 190

Thr Ser Ser Thr Ser Pro Met His Gln Arg Gln Pro Pro Thr Thr
            195                 200                 205

Ala Ile Met Ala Ala Ala Ala Val Ala Ala Thr Arg Ser Tyr Gly Gly
            210                 215                 220

Leu Val Pro Phe Pro Asp Gln Leu Arg Gly Val Met Ala Asp Ala Ser
225                 230                 235                 240

Pro Pro Gly Arg Phe Phe His Gly His Ala Ala Pro Phe Lys His
                245                 250                 255

Gln Val Ala Ala Leu His His Gly Gly Phe Tyr Gly Ser Thr Pro Pro
                260                 265                 270

His His His Gly Met Met Ala Thr Met Glu Gly Gly Gly Cys Phe Met
        275                 280                 285

Arg Gly Glu Asp Met Phe Val Gly Val Val Pro Pro Leu Leu Asp Pro
290                 295                 300

Met Ser Ala Ala Ala Gln Glu Gln Glu Gln Gly Gln Gln Gly Leu Met
305                 310                 315                 320

Ala Ser Ser Gly Ser Asn Asn Ala Lys Asn Asn Asn Ser Asn Asn
                325                 330                 335

Thr Thr Glu Thr Thr Thr Thr Thr Leu Ser Asn Asn Glu Ser Asn
            340                 345                 350

Ile Thr Glu Asn Asn Thr Asn Thr Lys Asp Asn Ile Asn Thr Ile Ser
            355                 360                 365

Gln Val Asn Asn Gly Ser Asn Val Ala Ala Val Phe Trp Glu Gly Ala
    370                 375                 380

His Gln Gln Tyr Met Ser Arg Asn Val Met His Gly Glu Trp Asp Leu
385                 390                 395                 400
```

Glu Glu Leu Met Lys Asp Val Ser Ser Leu Pro Phe Leu Asp Phe Gln
            405                 410                 415

Val Glu

<210> SEQ ID NO 47
<211> LENGTH: 388
<212> TYPE: PRT
<213> ORGANISM: Hordeum vulgare

<400> SEQUENCE: 47

Met Arg Lys Pro Val Glu Cys Pro Ala Thr Lys Cys Ser Gly Gly Val
1               5                   10                  15

Ala Pro Gly Asn Ser Asn Val Ala Ala Ala Ala Lys Leu Arg Lys
            20                  25                  30

Gly Leu Trp Ser Pro Glu Glu Asp Glu Arg Leu Val Ala Tyr Met Leu
            35                  40                  45

Arg Ser Gly Gln Gly Ser Trp Ser Asp Val Ala Arg Asn Ala Gly Leu
        50                  55                  60

Gln Arg Cys Gly Lys Ser Cys Arg Leu Arg Trp Ile Asn Tyr Leu Arg
65                  70                  75                  80

Pro Asp Leu Lys Arg Gly Ala Phe Ser Pro His Glu Glu Asp Leu Ile
                85                  90                  95

Val Asn Leu His Ala Ile Leu Gly Asn Arg Trp Ser Gln Ile Ala Ala
            100                 105                 110

Arg Leu Pro Gly Arg Thr Asp Asn Glu Ile Lys Asn Phe Trp Asn Ser
        115                 120                 125

Thr Ile Lys Lys Arg Leu Lys Met Asn Ser Ala Ala Ser Ser Pro Ala
130                 135                 140

Thr Thr Glu Cys Ala Ser Pro Pro Glu Pro Asn Leu Asp Gly Gly Ser
145                 150                 155                 160

Ala Ser Cys Leu Asp Leu Thr Ser Gln Glu Asp Gly Ser His His Ala
                165                 170                 175

Met Lys Ser Met Trp Met Asp Ser Ser Ser Ser Ser Ser Ser Ser Ser
            180                 185                 190

Ser Met Gln Gln Gly Ser Arg Pro Ser Thr Met Ala Pro Ala Ala Asn
        195                 200                 205

Arg Gly Tyr Gly Gly Leu Leu Leu Pro Leu Pro Asp Gln Val Cys Gly
    210                 215                 220

Val Ala Pro Ser Thr His Thr Ser Leu Pro Pro Phe Phe Gln Asp His
225                 230                 235                 240

Ser Ser Phe Lys Gln Val Ser Pro Leu Arg Thr Gly Tyr Tyr Pro
                245                 250                 255

His Gly Met Ala Met Glu Gly Ala Gly Gly Cys Phe Met Gly Glu Glu
            260                 265                 270

Ala Val Gly Gly Gly Glu Arg Ser Val Val Phe Asn Val Pro Pro
        275                 280                 285

Leu Leu Glu Pro Met Ala Val Ala Leu Gln Asp Gln Thr Leu Met Ala
290                 295                 300

Ser Thr Gly Asn Ser Asn Asn Asn His Arg Asn Thr Asn Ser Thr Ala
305                 310                 315                 320

Glu Gly Thr Thr Leu Ser Ser Lys Asn Gly Cys Asn Ile Asn Asp Asp
                325                 330                 335

Asn Thr Ser Lys Asn Asn Ile Asn Ser Val Val Ser Tyr Trp Glu Gln
            340                 345                 350

His Gly Gln Gln Gln His Met Ser Arg Asn Val Val Met Gly Glu Trp
        355                 360                 365

Asp Leu Glu Glu Leu Met Lys Asp Val Ser Cys Leu Pro Phe Leu Asp
    370                 375                 380

Phe Gln Val Glu
385

<210> SEQ ID NO 48
<211> LENGTH: 272
<212> TYPE: PRT
<213> ORGANISM: Brachypodium distachyon

<400> SEQUENCE: 48

Met Gly Ala Glu Ala Glu Cys Asp Arg Ile Lys Gly Pro Trp Ser Pro
1               5                   10                  15

Glu Glu Asp Glu Ala Leu Arg Arg Leu Val Glu Arg His Gly Ala Arg
            20                  25                  30

Asn Trp Thr Ala Ile Gly Arg Gly Ile Pro Gly Arg Ser Gly Lys Ser
        35                  40                  45

Cys Arg Leu Arg Trp Cys Asn Gln Leu Ser Pro Gln Val Glu Arg Arg
    50                  55                  60

Pro Phe Thr Ala Glu Glu Asp Ala Ser Ile Leu Arg Ala His Ala Arg
65              70                  75                  80

Leu Gly Asn Arg Trp Ala Ala Ile Ala Arg Leu Leu Pro Gly Arg Thr
                85                  90                  95

Asp Asn Ala Val Lys Asn His Trp Asn Ser Ser Leu Lys Arg Lys Leu
            100                 105                 110

Ala Thr Ala Thr Ala Ala Trp Glu Gly Asp Ala Val Ser Gly Asp Gly
        115                 120                 125

Ser Gly Ser Gly Gly Glu Ser Glu Pro Pro Arg Pro Cys Lys Arg Ala
130                 135                 140

Ser Pro Gly Pro Gly Pro Glu Ser Pro Thr Gly Ser Asp Arg Ser Glu
145                 150                 155                 160

Leu Ser His Gly Ser Gly Gln Val Phe Arg Pro Val Pro Arg Ala Gly
                165                 170                 175

Gly Phe Asp Ala Ile Ile Ser Ala Asp Val Val Arg Pro Pro Pro Pro
            180                 185                 190

Arg Pro Glu Glu Asp Pro Leu Thr Ser Leu Ser Leu Ser Leu Pro Gly
        195                 200                 205

Leu Asp Gln Gly Phe His His Asp Ser Ala Arg Ser His Phe Gln Glu
    210                 215                 220

Leu Ser Pro Ser Pro Arg Ser Pro Ser Pro Pro Ala Gln Pro Ala
225                 230                 235                 240

Tyr Pro Phe Ser Gly Asp Leu Val Ala Ala Met Gln Glu Met Ile Arg
                245                 250                 255

Ala Glu Val Arg Tyr Tyr Leu Leu Ser Ser Asp Glu Val Gly Met Gly
            260                 265                 270

<210> SEQ ID NO 49
<211> LENGTH: 16
<212> TYPE: PRT
<213> ORGANISM: Arabidopsis thaliana

<400> SEQUENCE: 49

Ser Ser Pro Asn Thr Ala Ser Asp Ser Ser Asn Ser Ala Ser Ser
1               5                   10                  15

<210> SEQ ID NO 50
<211> LENGTH: 16
<212> TYPE: PRT
<213> ORGANISM: Brachypodium distachyon

<400> SEQUENCE: 50

Ala Ser Pro Gly Pro Gly Pro Glu Ser Pro Thr Gly Ser Asp Arg Ser
1               5                   10                  15

<210> SEQ ID NO 51
<211> LENGTH: 1025
<212> TYPE: DNA
<213> ORGANISM: Artificial Sequence
<220> FEATURE:
<223> OTHER INFORMATION: A synthetic promoter sequence

<400> SEQUENCE: 51

```
ttccccctttt tggttcaatg cctttttattc ttccaaaatt atttcatatt ttgtatccgg      60
aggacatatt tgtttcaaaa ggtgtcagaa atcaaagcc cattgaaaat atataaacat       120
atatagatat aaaaactcaa gggttcattc caaatataa gaacaaactg attgaattaa       180
tttgttattt taagaacact gtctatatgt ttatatagtg ggaggtagtg tttttttaaat     240 catatactaa cttattataa aaataaatca taaaaaagga acctcaagca tccctggta      300 agctcgtatg taggaatact cggagatcaa atgtccgaat gtcaaatgtt aaggcaagtg     360
aaatatccct gacttttag caagcaaatt gttgagtagc taaaatgaat tatttaata       420 tttttaaatc attttaatat attaatatta aaaaaaatta atatttttt ttaatacatt      480 ttcaataaca aacactttaa aatataatct ttgtcacact cttaaacagt aacagcagaa     540
agcatatgtg agtgatatag ctatagttgc tgtttgacac ggacaatctc catctaaatt    600
catgaataat aaagttttgc ctacacaccc acttgaaatc tcctcctagt tttcctgatt    660
tgccatgcta actacaagaa caagatgcta gctagtatct tgttctgtct ctcgctctct    720
ctctatctct ccagttgata gttgatagtt gatagttgat agctgatacc ctcccacctt    780
tcccagaaag atgattgagg aactagtcac tgtgttcgtg taactaatac tgttcatggc    840
acctaacttg atcctctctt caccagacca ctataaaaac cctatctgtc ctcctcataa    900
tcatatcact acacccaaca cttctgcaag cacaactcca ttcaagaaca tcaagagtat    960
aggccgccgc tgcaacaaaa cagcactcct agctacttca agatgaggcc acaatctttc   1020
atctt                                                                 1025
```

<210> SEQ ID NO 52
<211> LENGTH: 1940
<212> TYPE: DNA
<213> ORGANISM: Artificial Sequence
<220> FEATURE:
<223> OTHER INFORMATION: A synthetic promoter sequence

<400> SEQUENCE: 52

```
ggggcagatg ataccttgat acttggacta ggaatattca aaggagaaaa tattgatgtg      60
tatatttgta cttaattatg cacatctctt tcactttatg ctgtaagctg gcagtataca     120
acacaagaac ggtctttata ctttgattt cttttctcat aagaaggtag ataattggct      180
tttaactgaa atgaatattg cttcagttag agaatatatc aagtatcgta aagggcaccc    240
caaattctta cagcctcgtg atgcacgttt tgttcttcaa atctagggg aaattcatta     300 atttgaaggt cggatctgta ggtagagttt ccttttctt tttaatggaa tttgatgaaa     360
```

```
gatactgtag caataattta aaaggaaatt aaggaagttc ccgggttttg atggggtttt    420
tctcgaacta attgcggatt aacctgagtt tttgaacgga ttataccaaa taaatttctt    480
cttatattta ttgaaattta gtctaatcta aatcccgggt tattctatcc attaaataat    540
gaagtaagtt taaaaaaaaa gagtaataaa agacattaaa gacgaactat ttatgtggga    600
agtagacaat tccatgtaag aaatttgtgt tgtcattttt tttattaaat tgctctctct    660 ttttttaacag gaatgctata atacagggac atttattaat tcagctcaat aatcttttgg    720
attaatttta ttttcttgg aacaaggggc tgttaccaaa tatggagcac tgtgcttgtg    780
tcatgcatgt aggtaagggg ggaaaaaact aaggaattta gctgagaaag aggttgtcaa    840
tttactgtga tagataggtt ccttgcttta catgagaagt ctacgtgaag aaatggaatt    900
atatatttgg ttggacattg gctctcttaa tatttattaa ttattattcc attttatcct    960
gtgatattaa acctaactcc tcttgaataa tcgggttgaa ttgatattta attaacttga    1020
tatatcaagt atcaaaactt aatttgatat tttaaaaat aatattgttt tgatttttt    1080 taaatattga tttagattat tttttataat ttgaatcata gttagataaa ttttgagtta    1140
ggttttataa ttattatttt attagtttct ttcttattta tgttttcaa tattaaggag    1200 tttatacatt agctttgttc acactctagg ttgacattgg agctgaaata tctctctcta    1260
tgaggtggtg aaatagctct cacgcatcag attgccccat ctccactcaa ccctaactag    1320
ccatgattaa tattttattt ctttttttaa aaaaaaatta ttaatcttta aaacttattt    1380
caagaagaaa aacatgactt tggacggagt aaaaaggacc ctaaaactac atttattgtc    1440
ctacgagttt tcataagcat cccatttaca taagcacacc accaaactta agatccaagc    1500
aaccctaaaa ttttccttc tttgcaacat actactacta ctgcattttt ggaaattaca    1560
ccatattttg attttttagg tatacttttc tctctctctc tctctctctc tctctcctga    1620
gaaaggacaa agaggtggta gggggagggg gggaggagag gagaggagag tgtgcatgtt    1680
gtctcatgca aaagtggagg agaatttaat tccttccta ccctaaagat caagagctat    1740
ctatgtcttg aagagagaca atacatgctt tagaaggaga caaattgctt ttccttcttt    1800
tcttttaagc ccttcgtgtc tctcttccac acacacacac gcatcataca tagtctttgt    1860
ctattttggg agtagcagtt gtcgagggag agagcaagaa agaaaggtgt gcaatatatg    1920
ggcataagag gaaaccaaag                                                1940

<210> SEQ ID NO 53
<211> LENGTH: 29
<212> TYPE: DNA
<213> ORGANISM: Artificial Sequence
<220> FEATURE:
<223> OTHER INFORMATION: A synthetic primer sequence

<400> SEQUENCE: 53
catgccatgg caaggaagcc agaggtagc                                       29

<210> SEQ ID NO 54
<211> LENGTH: 28
<212> TYPE: DNA
<213> ORGANISM: Artificial Sequence
<220> FEATURE:
<223> OTHER INFORMATION: A synthetic primer sequence

<400> SEQUENCE: 54
gaaggcctta tgctttgttt gaagttga                                        28
```

<210> SEQ ID NO 55
<211> LENGTH: 28
<212> TYPE: DNA
<213> ORGANISM: Artificial Sequence
<220> FEATURE:
<223> OTHER INFORMATION: A synthetic primer sequence

<400> SEQUENCE: 55
cgggatccat ggacggtggt tcaggtca                                       28

<210> SEQ ID NO 56
<211> LENGTH: 28
<212> TYPE: DNA
<213> ORGANISM: Artificial Sequence
<220> FEATURE:
<223> OTHER INFORMATION: A synthetic primer sequence

<400> SEQUENCE: 56
gaaggccttt gctgatattc tggattga                                       28

<210> SEQ ID NO 57
<211> LENGTH: 35
<212> TYPE: DNA
<213> ORGANISM: Artificial Sequence
<220> FEATURE:
<223> OTHER INFORMATION: A synthetic primer sequence

<400> SEQUENCE: 57
aaaaagcagg ctatgaggaa gccagaggta gccat                               35

<210> SEQ ID NO 58
<211> LENGTH: 36
<212> TYPE: DNA
<213> ORGANISM: Artificial Sequence
<220> FEATURE:
<223> OTHER INFORMATION: A synthetic primer sequence

<400> SEQUENCE: 58
agaaagctgg gtttatgctt tgtttgaagt tgaagt                              36

<210> SEQ ID NO 59
<211> LENGTH: 37
<212> TYPE: DNA
<213> ORGANISM: Artificial Sequence
<220> FEATURE:
<223> OTHER INFORMATION: A synthetic primer sequence

<400> SEQUENCE: 59
aaaaagcagg ctccatgagg aagccagagg tagccat                             37

<210> SEQ ID NO 60
<211> LENGTH: 35
<212> TYPE: DNA
<213> ORGANISM: Artificial Sequence
<220> FEATURE:
<223> OTHER INFORMATION: A synthetic primer sequence

<400> SEQUENCE: 60
agaaagctgg gttcatatgc tttgtttgaa gttga                               35

<210> SEQ ID NO 61
<211> LENGTH: 32
<212> TYPE: DNA
<213> ORGANISM: Artificial Sequence
<220> FEATURE:
<223> OTHER INFORMATION: A synthetic primer sequence

```
<400> SEQUENCE: 61
aaaaagcagg ctatggacgg tggttcaggt ca                                    32

<210> SEQ ID NO 62
<211> LENGTH: 38
<212> TYPE: DNA
<213> ORGANISM: Artificial Sequence
<220> FEATURE:
<223> OTHER INFORMATION: A synthetic primer sequence

<400> SEQUENCE: 62
agaaagctgg gttttgctga tattctggat tgaaagca                              38

<210> SEQ ID NO 63
<211> LENGTH: 34
<212> TYPE: DNA
<213> ORGANISM: Artificial Sequence
<220> FEATURE:
<223> OTHER INFORMATION: A synthetic primer sequence

<400> SEQUENCE: 63
aaaaagcagg ctccatggac ggtggttcag gtca                                  34

<210> SEQ ID NO 64
<211> LENGTH: 40
<212> TYPE: DNA
<213> ORGANISM: Artificial Sequence
<220> FEATURE:
<223> OTHER INFORMATION: A synthetic primer sequence

<400> SEQUENCE: 64
agaaagctgg gtttgctgat attctggatt gaaagcatga                            40

<210> SEQ ID NO 65
<211> LENGTH: 32
<212> TYPE: DNA
<213> ORGANISM: Artificial Sequence
<220> FEATURE:
<223> OTHER INFORMATION: A synthetic primer sequence

<400> SEQUENCE: 65
catgccatgg ccatgatgat gaggaaaccg ga                                    32

<210> SEQ ID NO 66
<211> LENGTH: 29
<212> TYPE: DNA
<213> ORGANISM: Artificial Sequence
<220> FEATURE:
<223> OTHER INFORMATION: A synthetic primer sequence

<400> SEQUENCE: 66
cccccgggat cgacttggaa atcaaggaa                                        29

<210> SEQ ID NO 67
<211> LENGTH: 30
<212> TYPE: DNA
<213> ORGANISM: Artificial Sequence
<220> FEATURE:
<223> OTHER INFORMATION: A synthetic primer sequence

<400> SEQUENCE: 67
tgagagtggt ttcatgactg catatgttgt                                       30

<210> SEQ ID NO 68
```

```
<211> LENGTH: 30
<212> TYPE: DNA
<213> ORGANISM: Artificial Sequence
<220> FEATURE:
<223> OTHER INFORMATION: A synthetic primer sequence

<400> SEQUENCE: 68
acaacatatg cagtcatgaa accactctca                                    30

<210> SEQ ID NO 69
<211> LENGTH: 30
<212> TYPE: DNA
<213> ORGANISM: Artificial Sequence
<220> FEATURE:
<223> OTHER INFORMATION: A synthetic primer sequence

<400> SEQUENCE: 69
actcatcctc aagacccaac acagcaagcg                                    30

<210> SEQ ID NO 70
<211> LENGTH: 30
<212> TYPE: DNA
<213> ORGANISM: Artificial Sequence
<220> FEATURE:
<223> OTHER INFORMATION: A synthetic primer sequence

<400> SEQUENCE: 70
cgcttgctgt gttgggtctt gaggatgagt                                    30

<210> SEQ ID NO 71
<211> LENGTH: 30
<212> TYPE: DNA
<213> ORGANISM: Artificial Sequence
<220> FEATURE:
<223> OTHER INFORMATION: A synthetic primer sequence

<400> SEQUENCE: 71
gcaatgacga ttttagacct tatgtagatg                                    30

<210> SEQ ID NO 72
<211> LENGTH: 30
<212> TYPE: DNA
<213> ORGANISM: Artificial Sequence
<220> FEATURE:
<223> OTHER INFORMATION: A synthetic primer sequence

<400> SEQUENCE: 72
catctacata aggtctaaaa tcgtcattgc                                    30

<210> SEQ ID NO 73
<211> LENGTH: 30
<212> TYPE: DNA
<213> ORGANISM: Artificial Sequence
<220> FEATURE:
<223> OTHER INFORMATION: A synthetic primer sequence

<400> SEQUENCE: 73
actcatcctc agaacccaac acagcaagcg                                    30

<210> SEQ ID NO 74
<211> LENGTH: 30
<212> TYPE: DNA
<213> ORGANISM: Artificial Sequence
<220> FEATURE:
<223> OTHER INFORMATION: A synthetic primer sequence
```

<400> SEQUENCE: 74
cgcttgctgt gttgggttct gaggatgagt                                30

<210> SEQ ID NO 75
<211> LENGTH: 30
<212> TYPE: DNA
<213> ORGANISM: Artificial Sequence
<220> FEATURE:
<223> OTHER INFORMATION: A synthetic primer sequence

<400> SEQUENCE: 75
gcaatgacga ttttgaccct tatgtagatg                                30

<210> SEQ ID NO 76
<211> LENGTH: 30
<212> TYPE: DNA
<213> ORGANISM: Artificial Sequence
<220> FEATURE:
<223> OTHER INFORMATION: A synthetic primer sequence

<400> SEQUENCE: 76
catctacata agggtcaaaa tcgtcattgc                                30

<210> SEQ ID NO 77
<211> LENGTH: 24
<212> TYPE: DNA
<213> ORGANISM: Artificial Sequence
<220> FEATURE:
<223> OTHER INFORMATION: A synthetic primer sequence

<400> SEQUENCE: 77
aggttccttt gcaaaaccta acga                                      24

<210> SEQ ID NO 78
<211> LENGTH: 25
<212> TYPE: DNA
<213> ORGANISM: Artificial Sequence
<220> FEATURE:
<223> OTHER INFORMATION: A synthetic primer sequence

<400> SEQUENCE: 78
cgataagagt ggtgaaatct ggtgc                                     25

<210> SEQ ID NO 79
<211> LENGTH: 20
<212> TYPE: DNA
<213> ORGANISM: Artificial Sequence
<220> FEATURE:
<223> OTHER INFORMATION: A synthetic primer sequence

<400> SEQUENCE: 79
ggcggtgcac ttcaaaatga                                           20

<210> SEQ ID NO 80
<211> LENGTH: 24
<212> TYPE: DNA
<213> ORGANISM: Artificial Sequence
<220> FEATURE:
<223> OTHER INFORMATION: A synthetic primer sequence

<400> SEQUENCE: 80
gagaatctcg aagcgtatac cgga                                      24

<210> SEQ ID NO 81

```
<211> LENGTH: 20
<212> TYPE: DNA
<213> ORGANISM: Artificial Sequence
<220> FEATURE:
<223> OTHER INFORMATION: A synthetic primer sequence

<400> SEQUENCE: 81
atgtggatct ccaaggccga                                            20

<210> SEQ ID NO 82
<211> LENGTH: 27
<212> TYPE: DNA
<213> ORGANISM: Artificial Sequence
<220> FEATURE:
<223> OTHER INFORMATION: A synthetic primer sequence

<400> SEQUENCE: 82
acacacaagt gcatcataga aacgaaa                                    27

<210> SEQ ID NO 83
<211> LENGTH: 20
<212> TYPE: DNA
<213> ORGANISM: Artificial Sequence
<220> FEATURE:
<223> OTHER INFORMATION: A synthetic primer sequence

<400> SEQUENCE: 83
taacgtggcc aaaatgatgc                                            20

<210> SEQ ID NO 84
<211> LENGTH: 20
<212> TYPE: DNA
<213> ORGANISM: Artificial Sequence
<220> FEATURE:
<223> OTHER INFORMATION: A synthetic primer sequence

<400> SEQUENCE: 84
gttctccaca accgcttggt                                            20

<210> SEQ ID NO 85
<211> LENGTH: 27
<212> TYPE: DNA
<213> ORGANISM: Artificial Sequence
<220> FEATURE:
<223> OTHER INFORMATION: A synthetic primer sequence

<400> SEQUENCE: 85
atcggacatc ttctttagcc ttttctt                                    27

<210> SEQ ID NO 86
<211> LENGTH: 19
<212> TYPE: DNA
<213> ORGANISM: Artificial Sequence
<220> FEATURE:
<223> OTHER INFORMATION: A synthetic primer sequence

<400> SEQUENCE: 86
ctcaagcgtg gcgctttct                                             19

<210> SEQ ID NO 87
<211> LENGTH: 343
<212> TYPE: PRT
<213> ORGANISM: Arabidopsis thaliana
```

<400> SEQUENCE: 87

```
Met Met Met Arg Lys Pro Asp Ile Thr Thr Ile Arg Asp Lys Gly Lys
1               5                   10                  15

Pro Asn His Ala Cys Gly Gly Asn Asn Asn Lys Pro Lys Leu Arg Lys
            20                  25                  30

Gly Leu Trp Ser Pro Asp Glu Asp Glu Lys Leu Ile Arg Tyr Met Leu
        35                  40                  45

Thr Asn Gly Gln Gly Cys Trp Ser Asp Ile Ala Arg Asn Ala Gly Leu
    50                  55                  60

Leu Arg Cys Gly Lys Ser Cys Arg Leu Arg Trp Ile Asn Tyr Leu Arg
65                  70                  75                  80

Pro Asp Leu Lys Arg Gly Ser Phe Ser Pro Gln Glu Asp Leu Ile
                85                  90                  95

Phe His Leu His Ser Ile Leu Gly Asn Arg Trp Ser Gln Ile Ala Thr
                100                 105                 110

Arg Leu Pro Gly Arg Thr Asp Asn Glu Ile Lys Asn Phe Trp Asn Ser
            115                 120                 125

Thr Leu Lys Lys Arg Leu Lys Asn Asn Ser Asn Asn Thr Ser Ser
130                 135                 140

Gly Ser Ser Pro Asn Asn Ser Asn Ser Asn Leu Asp Pro Arg Asp
145                 150                 155                 160

Gln His Val Asp Met Gly Gly Asn Ser Thr Ser Leu Met Asp Asp Tyr
                165                 170                 175

His His Asp Glu Asn Met Met Thr Val Gly Asn Thr Met Arg Met Asp
            180                 185                 190

Ser Ser Ser Pro Phe Asn Val Gly Pro Met Val Asn Ser Val Gly Leu
            195                 200                 205

Asn Gln Leu Tyr Asp Pro Leu Met Ile Ser Val Pro Asp Asn Gly Tyr
            210                 215                 220

His Gln Met Gly Asn Thr Val Asn Val Phe Ser Val Asn Gly Leu Gly
225                 230                 235                 240

Asp Tyr Gly Asn Thr Ile Leu Asp Pro Ile Ser Lys Arg Val Ser Val
                245                 250                 255

Glu Gly Asp Asp Trp Phe Ile Pro Pro Ser Glu Asn Thr Asn Val Ile
            260                 265                 270

Ala Cys Ser Thr Ser Asn Asn Leu Asn Leu Gln Ala Leu Asp Pro Cys
                275                 280                 285

Phe Asn Ser Lys Asn Leu Cys His Ser Glu Ser Phe Lys Val Gly Asn
            290                 295                 300

Val Leu Gly Ile Glu Asn Gly Ser Trp Glu Ile Glu Asn Pro Lys Ile
305                 310                 315                 320

Gly Asp Trp Asp Leu Asp Gly Leu Ile Asp Asn Asn Ser Ser Phe Pro
                325                 330                 335

Phe Leu Asp Phe Gln Val Asp
            340
```

<210> SEQ ID NO 88
<211> LENGTH: 10
<212> TYPE: PRT
<213> ORGANISM: Arabidopsis thaliana

<400> SEQUENCE: 88

```
Met Arg Lys Pro Glu Val Ala Ile Ala Ala
1               5                   10
```

```
<210> SEQ ID NO 89
<211> LENGTH: 11
<212> TYPE: PRT
<213> ORGANISM: Arabidopsis thaliana

<400> SEQUENCE: 89

Met Met Met Arg Lys Pro Asp Ile Thr Thr Ile
1               5                   10

<210> SEQ ID NO 90
<211> LENGTH: 13
<212> TYPE: PRT
<213> ORGANISM: Arabidopsis thaliana

<400> SEQUENCE: 90

Met Met Met Arg Lys Pro Glu Val Ala Ile Thr Thr Ile
1               5                   10
```